(12) United States Patent
Chen et al.

(10) Patent No.: US 9,834,545 B2
(45) Date of Patent: Dec. 5, 2017

(54) MODULATORS OF CHEMOKINE RECEPTORS

(71) Applicant: CHEMOCENTRYX, INC., Mountain View, CA (US)

(72) Inventors: Xi Chen, E. Palo Alto, CA (US); Dean R. Dragoli, Los Altos, CA (US); Junfa Fan, Palo Alto, CA (US); Jaroslaw Kalisiak, Mountain View, CA (US); Antoni Krasinski, Sunnyvale, CA (US); Manmohan Reddy Leleti, San Jose, CA (US); Venkat Mali, Cupertino, CA (US); Jeffrey McMahon, San Francisco, CA (US); Rajinder Singh, Belmont, CA (US); Hiroko Tanaka, Mountain View, CA (US); Ju Yang, Palo Alto, CA (US); Chao Yu, Sunnyvale, CA (US); Penglie Zhang, Foster City, CA (US)

(73) Assignee: CHEMOCENTRYX, INC., Mountain View, CA (US)

( * ) Notice: Subject to any disclaimer, the term of this patent is extended or adjusted under 35 U.S.C. 154(b) by 0 days.

(21) Appl. No.: 15/353,889

(22) Filed: Nov. 17, 2016

(65) Prior Publication Data
US 2017/0144997 A1    May 25, 2017

Related U.S. Application Data

(60) Provisional application No. 62/257,389, filed on Nov. 19, 2015, provisional application No. 62/277,711, filed on Jan. 12, 2016.

(51) Int. Cl.
| | | |
|---|---|---|
| C07D 405/14 | (2006.01) |
| A61K 31/506 | (2006.01) |
| A61K 31/4155 | (2006.01) |
| A61K 31/4439 | (2006.01) |
| A61K 31/454 | (2006.01) |
| A61K 31/341 | (2006.01) |
| A61K 31/4035 | (2006.01) |
| A61K 45/06 | (2006.01) |
| C07D 209/46 | (2006.01) |
| C07D 307/52 | (2006.01) |
| C07D 405/12 | (2006.01) |
| A61K 31/4725 | (2006.01) |

(52) U.S. Cl.
CPC .......... *C07D 405/14* (2013.01); *A61K 31/341* (2013.01); *A61K 31/4035* (2013.01); *A61K 31/4155* (2013.01); *A61K 31/4439* (2013.01); *A61K 31/454* (2013.01); *A61K 31/4725* (2013.01); *A61K 31/506* (2013.01); *A61K 45/06* (2013.01); *C07D 209/46* (2013.01); *C07D 307/52* (2013.01); *C07D 405/12* (2013.01)

(58) Field of Classification Search
None
See application file for complete search history.

(56) References Cited

U.S. PATENT DOCUMENTS

| | | |
|---|---|---|
| 6,166,050 A | 12/2000 | Lombardo et al. |
| 2003/0204085 A1 | 10/2003 | Taveras et al. |
| 2004/0097547 A1 | 5/2004 | Taveras et al. |
| 2004/0106794 A1 | 6/2004 | Taveras et al. |
| 2004/0147559 A1 | 7/2004 | Taveras et al. |
| 2004/0209946 A1 | 10/2004 | Yin et al. |
| 2008/0261917 A1 | 10/2008 | Willems et al. |
| 2009/0306079 A1 | 12/2009 | Taveras et al. |
| 2010/0029670 A1 | 2/2010 | Baettig et al. |
| 2010/0267712 A1 | 10/2010 | Heemskerk et al. |
| 2011/0086842 A1 | 4/2011 | Stadtmueller et al. |
| 2011/0213029 A1 | 9/2011 | Taveras et al. |
| 2013/0231393 A1 | 9/2013 | Aubert |
| 2014/0296254 A1 | 10/2014 | Musicki et al. |
| 2014/0309208 A1 | 10/2014 | Musicki et al. |
| 2015/0087675 A1 | 3/2015 | Musicki et al. |
| 2017/0144996 A1 | 5/2017 | Chen et al. |

FOREIGN PATENT DOCUMENTS

| | | |
|---|---|---|
| WO | 01/64208 A1 | 9/2001 |
| WO | 01/92202 A1 | 12/2001 |
| WO | 02/057230 A1 | 7/2002 |
| WO | 02/067919 A1 | 9/2002 |
| WO | 02/076926 A1 | 10/2002 |
| WO | 02/083624 A1 | 10/2002 |
| WO | 03/080053 A1 | 10/2003 |
| WO | 2004/011418 A1 | 2/2004 |
| WO | 2005/075447 A1 | 8/2005 |
| WO | 2006/021544 A1 | 3/2006 |

(Continued)

OTHER PUBLICATIONS

Aki, Cynthia et al., "Diaminocyclobutenediones as potent and orally available CXCR2 receptor antagonists: SAR in the phenolic amide region," *Bioorganic & Medicinal Chemistry Letters* (available online May 18, 2009); 19:4446-4449.

(Continued)

*Primary Examiner* — Brian J Davis
(74) *Attorney, Agent, or Firm* — Mintz Levin Cohn Ferris Glovsky and Popeo PC

(57) ABSTRACT

Compounds are provided as chemokine inhibitors having the structure:

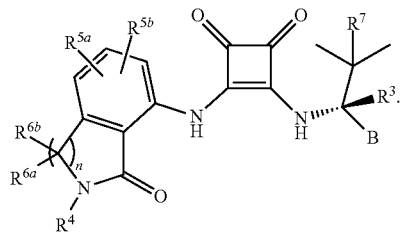

33 Claims, 38 Drawing Sheets

(56) References Cited

FOREIGN PATENT DOCUMENTS

| | | |
|---|---|---|
| WO | 2008/005570 A1 | 1/2008 |
| WO | 2008/109178 A1 | 9/2008 |
| WO | 2008/109179 A1 | 9/2008 |
| WO | 2008/148790 A1 | 12/2008 |
| WO | 2009/005801 A1 | 1/2009 |
| WO | 2009/005802 A1 | 1/2009 |
| WO | 2009/012375 A2 | 1/2009 |
| WO | 2009/073683 A2 | 6/2009 |
| WO | 2009/156421 A1 | 12/2009 |
| WO | 2010/0045303 A2 | 4/2010 |
| WO | 2010/063802 A1 | 6/2010 |
| WO | 2010/091543 A1 | 8/2010 |
| WO | 2010/131145 A1 | 11/2010 |
| WO | 2010/131147 A1 | 11/2010 |
| WO | 2012/001076 A1 | 1/2012 |
| WO | 2012/080456 A1 | 6/2012 |
| WO | 2012/080457 A1 | 6/2012 |
| WO | 2013/030803 A1 | 3/2013 |
| WO | 2013/061002 A1 | 5/2013 |
| WO | 2013/061004 A1 | 5/2013 |
| WO | 2013/061005 A1 | 5/2013 |
| WO | 2013/174947 A1 | 11/2013 |
| WO | 2016/079049 A1 | 5/2016 |

OTHER PUBLICATIONS

Asadollahi, Tahereh et al., "QSAR Models for CXCR2 Receptor Antagonists Based on the Genetic Algorithm for Data Preprocessing Prior to Application of the PLS Linear Regression Method and Design of the New Compounds Using *In Silico* Virtual Screening," *Molecules* (Feb. 25, 2011); 16:1928-1955.

Biju, Purakkattle et al., "3,4-Diamino-2,5-thiadiazole-1-oxides as potent CXCR2/CXCR1 antagonists," *Bioorganic & Medicinal Chemistry Letters* (2008; available online Oct. 30, 2007); 18:228-231.

Biju, Purakkattle et al., "Fluoroalkyl α side chain containing 3,4-diamino-cyclobutenediones as potent and orally bioavailable CXCR2-CXCR1 dual antagonists," *Bioorganic & Medicinal Chemistry Letters* (available online Jan. 15, 2009); 19:1431-1433.

Biju, Purakkattle et al., "3,4-Diamino-1,2,5-thiadizole as potent and selective CXCR2 antagonists," *Bioorganic & Medicinal Chemistry Letters* (available online Jan. 15, 2009); 19:1434-1437.

Busch-Petersen, Jakob et al., "Phenol-containing antagonists of the CXCR2 receptor," *Expert Opin. Ther. Patents* (published online May 26, 2008); 18(6):629-637.

Chao, Jianhua et al., "C(4)-alkyl substituted furanyl cyclobutenediones as potent, orally bioavailable CXCR2 and CXCR1 receptor antagonists," *Bioorganic & Medicinal Chemistry Letters* (available online Apr. 10, 2007); 17:3778-3783.

Dwyer, Michael P. et al., "Discovery of 2-Hydrozy-*N*,*N*-dimethyl-3-12-[[(*R*)-1-(5-methylfuran-2-yl)propyl]amino]-3,4-dioxo-cyclobut-1-enylamino)benzamide (SCH 527123): A Potent, Orally Bioavailable CXCR2/CXCR1 Receptor Antagonist," *J. Med. Chem.* (Aug. 9, 2006); 49(26):7603-7606.

Ebsworth, Karen et al., "Chemokine Receptor Inhibition as a Novel Therapeutic Approach for Psoriasis," *Poster No. 521* ChemoCentryx, Inc., Mountain View, CA (May 12, 2016); 2 pages.

Gunda, Shravan Kumar et al., "Structural investigations of CXCR2 receptor antagonists by CoMFA, CoMSIA and flexible docking studies," *Acta Pharm* (Jul. 17, 2012); 62:287-304.

Lai, Gaifa et al., "Synthesis and structure-activity relationships of new disubstiuted phenyl-containing 3,4-diamino-3-cyclobutene-1,2-diones as CXCR2 receptor antagonists," *Bioorganic & Medicinal Chemistry Letters* (available online Feb. 10, 2008); 18:1864-1868.

Liu, Shilan et al., "Design, synthesis, and evaluation of novel 3-amino-4-hydrazine-cyclobut-3-ene-1,2-diones as potent and selective CXCR2 chemokine receptor antagonists," *Bioorganic & Medicinal Chemistry Letters* (available online Aug. 7, 2009); 19:5741-5745.

McCleland, Brent W. et al., "Comparison of *N*,*N*'-diarylsquaramides and *N*,*N*'-diarylureas as antagonists of the CXCR2 chemokine receptor," *Bioorganic & Medicinal Chemistry Letters* (2007; available online Dec. 23, 2006); 17:1713-1717.

Merritt, J. Robert et al., "Synthesis and structure-activity relationships of 3,4-diaminocyclobut-3-ene-1,2-dione CXCR2 antagonists," *Bioorganic & Medicinal Chemistry Letters* (available online May 11, 2006); 16:4107-4110.

Wijtmans, Maikel et al., "Therapeutic targeting of chemokine receptors by small molecules," *Drug Discovery Today: Technologies* (2012; http://dx.doi.org/10.1016/j.ddtec.2012.03.004); 9(4):e229-e236.

Yu, Younong et al., "Synthesis and structure-activity relationships of heteroaryl substituted-3,4-diamino-3-cyclobut-3-ene-1,2-dione CXCR2/CXCR1 receptor antagonists," *Bioorganic & Medicinal Chemistry Letters* (available online Jan. 11, 2008); 18:1318-1322.

Zhang, Shuang et al., "Comparative Analysis of Pharmacophore Features and Quantitative Structure-Activity Relationships for CD38 Covalent and Non-covalent Inhibitors," *Chemical Biology & Drug Design* (Dec. 2015; first published Jul. 14, 2015); 86(6):1411-1424.

Zhou, Yi et al., "Design, Synthesis and Biological Evaluation of Noncovalent Inhibitors of Human CD38 NADase," *ChemMedChem* (Feb. 6, 2012); 7(2):223-228.

International Search Report and Written Opinion corresponding to PCT Application No. PCT/US2016/062417 dated Jan. 12, 2017, 12 pages.

International Search Report and Written Opinion corresponding to PCT Application No. PCT/US2016/062427 dated Feb. 21, 2017; 9 pages.

Barbosa, Maria Leticia de Castro et al., "Therapeutic approaches for tumor necrosis factor inhibition," Brazilian Journal of Pharmaceutical Sciences (Jul./Sep. 2011; accepted for pub May 25, 2011); 47:427-446.

Nieuwenhuis, S. A. M. et al., "Structure of the $Y_D$ Tyrosine Radical in Photosystem II. Determination of the Orientation of the Phenoxyl Ring by Enantioselective Deuteration of the Methylene Group," *J. Am. Chem. Soc.* (Jan. 16, 1998); 120:829-830.

FIGURE 1A
| | | CCR6 IC$_{50}$ | CXCR2 IC$_{50}$ |
|---|---|---|---|
| 1.000 | 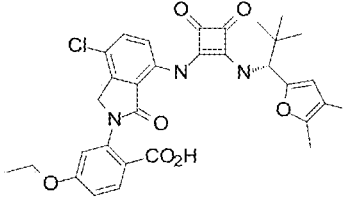 | +++ | +++ |
| 1.001 | 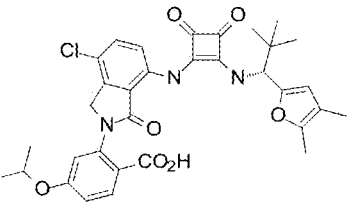 | +++ | +++ |
| 1.002 | 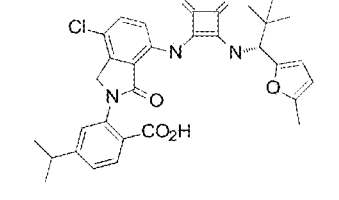 | +++ | +++ |
| 1.003 | 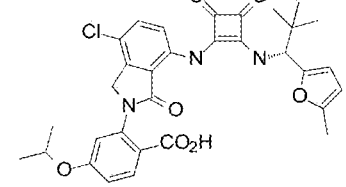 | +++ | +++ |

FIGURE 1B
| | | CCR6 IC$_{50}$ | CXCR2 IC$_{50}$ |
|---|---|---|---|
| 1.004 | 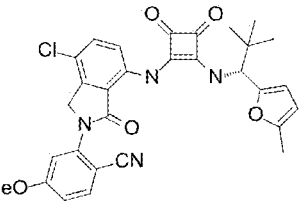 | ++ | +++ |
| 1.005 | 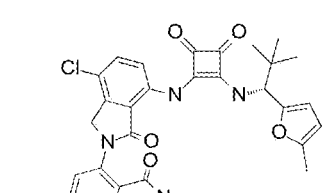 | +++ | +++ |
| 1.006 | 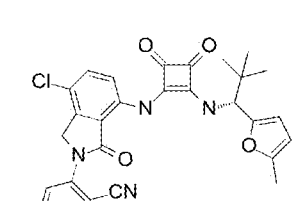 | + | ++ |
| 1.007 | 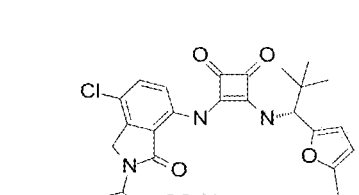 | +++ | +++ |
| 1.008 | 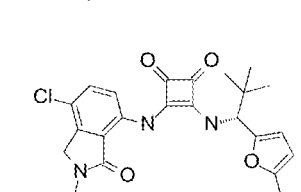 | +++ | ++ |

FIGURE 1C
| | | CCR6 IC$_{50}$ | CXCR2 IC$_{50}$ |
|---|---|---|---|
| 1.009 | 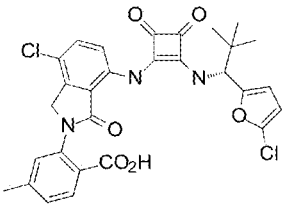 | +++ | ++ |
| 1.010 | 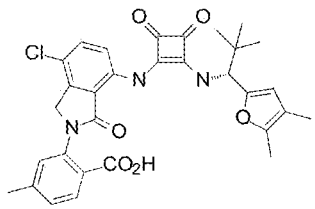 | +++ | +++ |
| 1.011 | 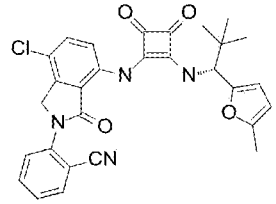 | +++ | +++ |
| 1.012 | 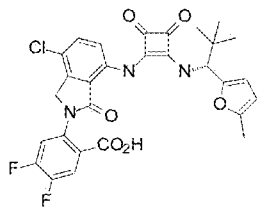 | +++ | ++ |
| 1.013 | 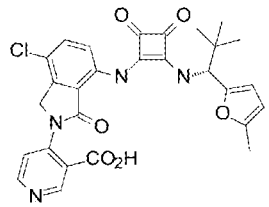 | + | + |

FIGURE 1D

| | | CCR6 IC$_{50}$ | CXCR2 IC$_{50}$ |
|---|---|---|---|
| 1.014 | | +++ | +++ |
| 1.015 | | +++ | ++ |
| 1.016 | | ++ | ++ |
| 1.017 | | +++ | ++ |
| 1.018 | | +++ | +++ |

FIGURE 1E
| | | CCR6 IC$_{50}$ | CXCR2 IC$_{50}$ |
|---|---|---|---|
| 1.019 | 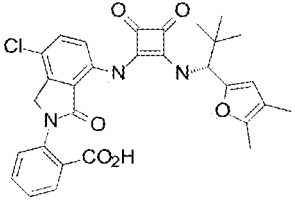 | +++ | +++ |
| 1.020 | 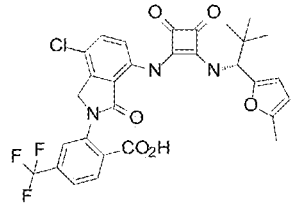 | +++ | ++ |
| 1.021 | 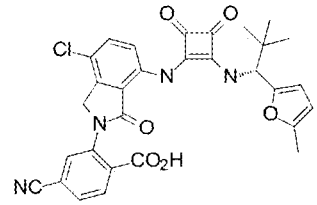 | + | + |
| 1.022 | 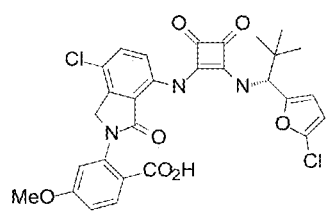 | +++ | +++ |
| 1.023 | 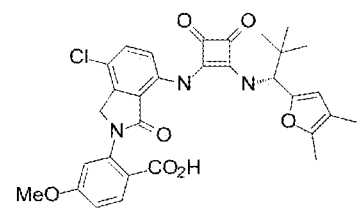 | +++ | +++ |

FIGURE 1F
| | | CCR6 IC$_{50}$ | CXCR2 IC$_{50}$ |
|---|---|---|---|
| 1.024 | 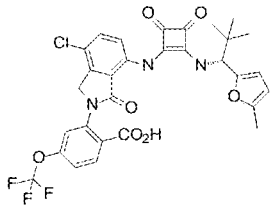 | +++ | ++ |
| 1.025 | 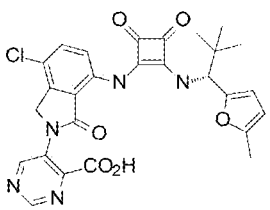 | + | + |
| 1.026 | 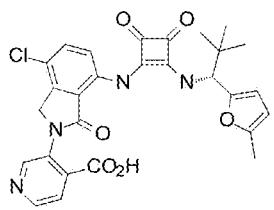 | +++ | + |
| 1.027 | 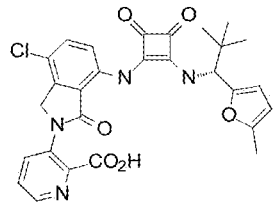 | +++ | + |
| 1.028 | 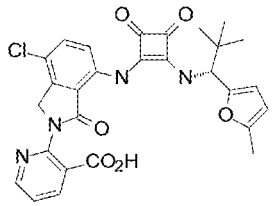 | +++ | ++ |

FIGURE 1G

| | | CCR6 IC$_{50}$ | CXCR2 IC$_{50}$ |
|---|---|---|---|
| 1.029 | | +++ | ++ |
| 1.030 | | +++ | ++ |
| 1.031 | | +++ | ++ |
| 1.032 | | +++ | ++ |
| 1.033 | | +++ | ++ |

FIGURE 1H
| | | CCR6 IC$_{50}$ | CXCR2 IC$_{50}$ |
|---|---|---|---|
| 1.034 | 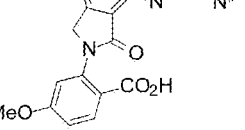 | +++ | ++ |
| 1.035 | 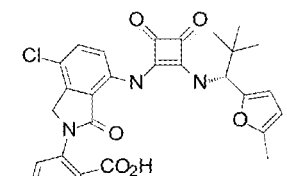 | +++ | ++ |
| 1.036 | 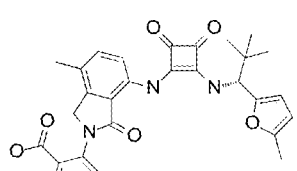 | ++ | ++ |
| 1.037 | 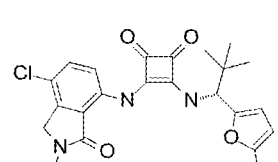 | +++ | ++ |
| 1.038 | 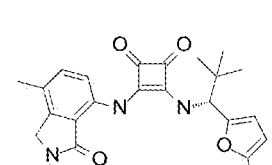 | +++ | ++ |

FIGURE 1I

| | | CCR6 IC$_{50}$ | CXCR2 IC$_{50}$ |
|---|---|---|---|
| 1.039 | | + | + |
| 1.040 | | +++ | ++ |
| 1.041 | | +++ | ++ |
| 1.042 | | +++ | ++ |
| 1.043 | | +++ | ++ |

FIGURE 1J

| | | CCR6 IC$_{50}$ | CXCR2 IC$_{50}$ |
|---|---|---|---|
| 1.044 | | +++ | ++ |
| 1.045 | | +++ | + |
| 1.046 | | +++ | + |
| 1.047 | | +++ | ++ |
| 1.048 | | +++ | + |

FIGURE 1K

| | | CCR6 IC$_{50}$ | CXCR2 IC$_{50}$ |
|---|---|---|---|
| 1.049 | | +++ | ++ |
| 1.050 | | +++ | ++ |
| 1.051 | | +++ | ++ |
| 1.052 | | +++ | ++ |
| 1.053 | | +++ | ++ |

FIGURE 1L

| | | CCR6 IC$_{50}$ | CXCR2 IC$_{50}$ |
|---|---|---|---|
| 1.054 | | +++ | + |
| 1.055 | | +++ | ++ |
| 1.056 | | +++ | ++ |
| 1.057 | | + | +++ |
| 1.058 | | +++ | + |

FIGURE 1M
| | | CCR6 IC$_{50}$ | CXCR2 IC$_{50}$ |
|---|---|---|---|
| 1.059 | 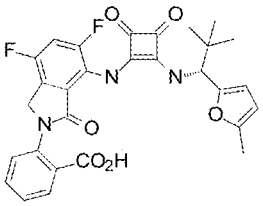 | +++ | + |
| 1.060 | 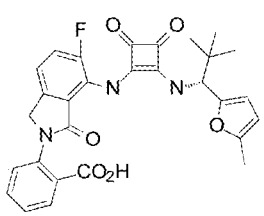 | ++ | + |
| 1.061 | 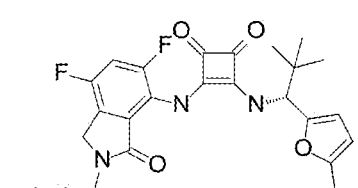 | +++ | + |
| 1.062 | 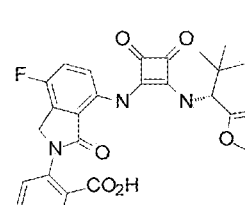 | +++ | ++ |
| 1.063 | 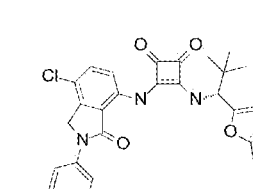 | +++ | +++ |

FIGURE 1N

| | | CCR6 IC$_{50}$ | CXCR2 IC$_{50}$ |
|---|---|---|---|
| 1.064 | | +++ | ++ |
| 1.065 | | +++ | ++ |
| 1.066 | | +++ | ++ |
| 1.067 | | ++ | +++ |
| 1.068 | | +++ | +++ |

FIGURE 10

| | | CCR6 IC$_{50}$ | CXCR2 IC$_{50}$ |
|---|---|---|---|
| 1.069 | | ++ | +++ |
| 1.070 | | ++ | + |
| 1.071 | | +++ | +++ |
| 1.072 | | + | + |
| 1.073 | | +++ | +++ |

FIGURE 1P

| | | CCR6 IC$_{50}$ | CXCR2 IC$_{50}$ |
|---|---|---|---|
| 1.074 | | +++ | +++ |
| 1.075 | | +++ | +++ |
| 1.076 | | +++ | +++ |
| 1.077 | | +++ | +++ |
| 1.078 | | ++ | +++ |

FIGURE 1Q

| | | CCR6 IC$_{50}$ | CXCR2 IC$_{50}$ |
|---|---|---|---|
| 1.079 | | +++ | +++ |
| 1.080 | | +++ | ++ |
| 1.081 | | +++ | +++ |
| 1.082 | | +++ | +++ |
| 1.083 | | +++ | +++ |

FIGURE 1R

| | | CCR6 IC$_{50}$ | CXCR2 IC$_{50}$ |
|---|---|---|---|
| 1.084 | | +++ | +++ |
| 1.085 | | +++ | +++ |
| 1.086 | | ++ | +++ |
| 1.087 | | +++ | +++ |
| 1.088 | | +++ | +++ |

FIGURE 1S
| | | CCR6 IC$_{50}$ | CXCR2 IC$_{50}$ |
|---|---|---|---|
| 1.089 | 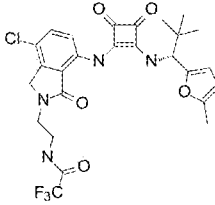 | ++ | +++ |
| 1.090 | 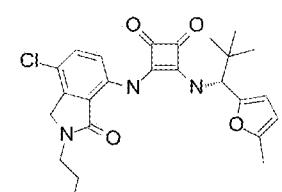 | ++ | +++ |
| 1.091 | 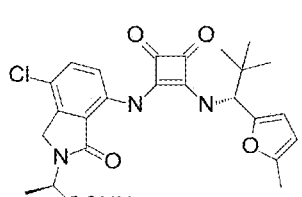 | ++ | +++ |
| 1.092 | 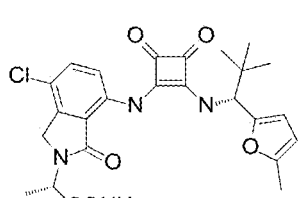 | +++ | +++ |
| 1.093 | 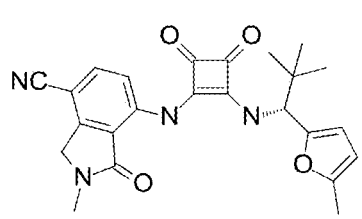 | ++ | + |

FIGURE 1T

| | Structure | CCR6 IC$_{50}$ | CXCR2 IC$_{50}$ |
|---|---|---|---|
| 1.094 | | ++ | ++ |
| 1.095 | | +++ | ++ |
| 1.096 | | +++ | ++ |
| 1.097 | | +++ | ++ |
| 1.098 | | +++ | +++ |

FIGURE 1U

| | | CCR6 IC$_{50}$ | CXCR2 IC$_{50}$ |
|---|---|---|---|
| 1.099 | | ++ | + |
| 1.100 | | + | +++ |
| 1.101 | | ++ | +++ |
| 1.102 | | ++ | +++ |
| 1.103 | | ++ | + |

FIGURE 1V

| | | CCR6 IC$_{50}$ | CXCR2 IC$_{50}$ |
|---|---|---|---|
| 1.104 | | +++ | +++ |
| 1.105 | | ++ | ++ |
| 1.106 | | +++ | ++ |
| 1.107 | | +++ | +++ |
| 1.108 | | +++ | +++ |

FIGURE 1W

| | | CCR6 IC$_{50}$ | CXCR2 IC$_{50}$ |
|---|---|---|---|
| 1.109 | | +++ | +++ |
| 1.110 | | ++ | +++ |
| 1.111 | | +++ | +++ |
| 1.112 | | +++ | +++ |
| 1.113 | | +++ | +++ |

FIGURE 1X

| | | CCR6 IC$_{50}$ | CXCR2 IC$_{50}$ |
|---|---|---|---|
| 1.114 | | +++ | +++ |
| 1.115 | | +++ | +++ |
| 1.116 | | +++ | ++ |
| 1.117 | | +++ | +++ |
| 1.118 | | ++ | ++ |

FIGURE 1Y

|  |  | CCR6 IC$_{50}$ | CXCR2 IC$_{50}$ |
|---|---|---|---|
| 1.119 |  | ++ | + |
| 1.120 |  | +++ | +++ |
| 1.121 |  | +++ | +++ |
| 1.122 |  | +++ | +++ |
| 1.123 |  | +++ | +++ |

FIGURE 1Z

| | | CCR6 IC$_{50}$ | CXCR2 IC$_{50}$ |
|---|---|---|---|
| 1.124 | | +++ | +++ |
| 1.125 | | +++ | +++ |
| 1.126 | | +++ | ++ |
| 1.127 | | +++ | +++ |
| 1.128 | | +++ | +++ |

FIGURE 1AA
| | | CCR6 IC$_{50}$ | CXCR2 IC$_{50}$ |
|---|---|---|---|
| 1.129 | 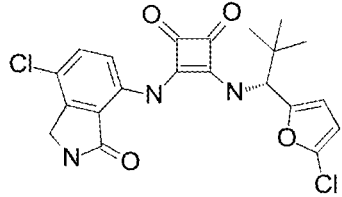 | +++ | +++ |
| 1.130 | 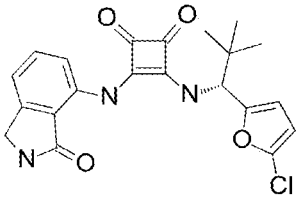 | +++ | +++ |
| 1.131 | 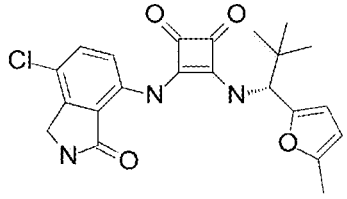 | +++ | +++ |
| 1.132 | 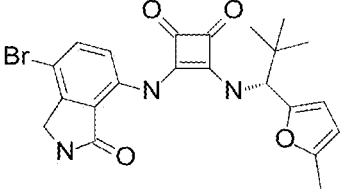 | +++ | +++ |
| 1.133 | 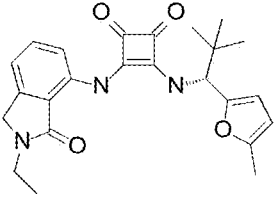 | +++ | +++ |

FIGURE 1AB
| | | CCR6 IC$_{50}$ | CXCR2 IC$_{50}$ |
|---|---|---|---|
| 1.134 | 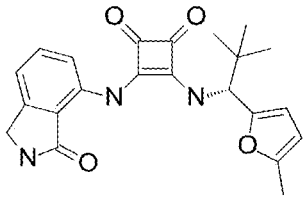 | +++ | +++ |
| 1.135 | 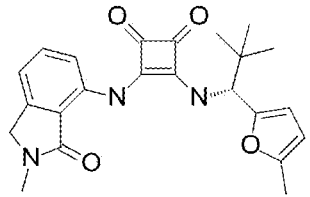 | +++ | +++ |
| 1.136 | 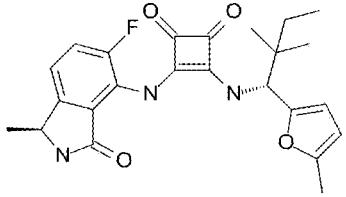 | +++ | +++ |
| 1.137 | 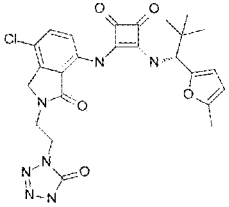 | +++ | |
| 1.138 | 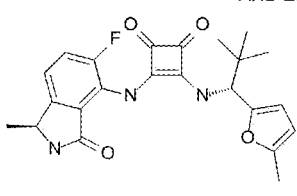 | +++ | +++ |
AND Enantiomer FIGURE 1AI
| 1.175 | 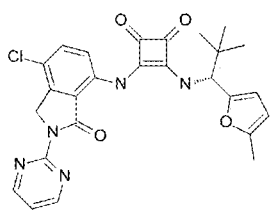 | +++ | +++ |
| 1.176 | 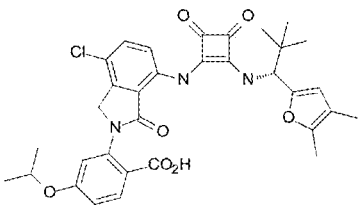 | +++ | +++ |
| 1.177 | 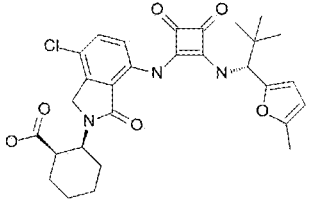 | +++ | + |
| 1.178 | 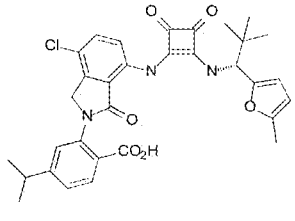 | +++ | ++ |
| 1.179 | 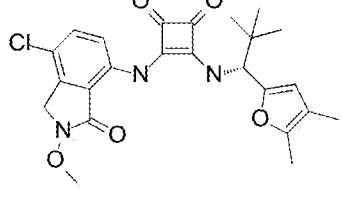 | +++ | +++ |
| 1.180 | 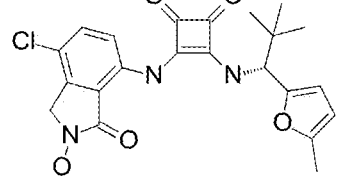 | +++ | +++ |

Compound 1.023 in the IL-23 Induced ear swelling model

PASI score in mice treated with Compound 1.129 in the imiquimod induced psoriasis model Thickness, erythema and scaling scores ≥3 in mice treated with Compound 1.129 compared to vehicle treated mice in the imiquimod induced psoriasis model

MODULATORS OF CHEMOKINE RECEPTORS

CROSS-REFERENCES TO RELATED APPLICATIONS

This application is an application claiming benefit under 35 U.S.C. §119(e) of U.S. Provisional Application No. 62/257,389 filed Nov. 19, 2015, and U.S. Provisional Application No. 62/277,711 filed Jan. 12, 2016, each of which is herein incorporated by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Chemokines are chemotactic cytokines that are released by a wide variety of cells to attract macrophages, lymphocytes, eosinophils, basophils and neutrophils to sites of inflammation (reviewed in Schall, *Cytokine,* 3:165-183 (1991), Schall, et al., *Curr Opin. Immunol.* 6:865-873 (1994) and Murphy, *Rev. Immun.,* 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin upregulation, formation of bioactive lipids (e.g., leukotrienes) and respiratory burst, which is associated with leukocyte activation. Thus, the chemokines are early triggers of the inflammatory response, causing inflammatory mediator release, chemotaxis and extravasation to sites of infection or inflammation.

There are two main classes of chemokines, CXC (alpha) and CC (beta), depending on whether the first two cysteines are separated by a single amino acid (C-X-C) or are adjacent (C-C). The alpha-chemokines, such as CXCL1 (GROα) and CXCL8 (interleukin-8, IL-8) are chemotactic primarily for neutrophils, whereas beta-chemokines, such as CCL5 (RANTES) and CCL20 (LARC, MIP-3α), are chemotactic for T cells, B cells, macrophages, eosinophils and basophils (Deng, et al., *Nature,* 381:661-666 (1996)). The chemokines bind specific cell-surface receptors belonging to the family of G-protein-coupled seven-transmembrane-domain proteins (reviewed in Horuk, *Trends Pharm. Sci.,* 15:159-165 (1994)) which are termed "chemokine receptors."

On binding their cognate ligands, chemokine receptors transduce an intracellular signal through the associated trimeric G protein, resulting in a rapid increase in intracellular calcium concentration. There are at least eleven human chemokine receptors that bind or respond to beta-chemokines and at least seven human chemokine receptors that bind to the alpha chemokines. Additionally CX3CR1 (fractalkine receptor) can bind to the fractalkine chemokine, which is distinguished by a series of three amino acids between the first two cysteines. Chemokine receptors, have been implicated as being important mediators of inflammatory and immunoregulatory disorders and diseases, including asthma and allergic diseases, as well as autoimmune pathologies such as rheumatoid arthritis and atherosclerosis.

The chemokine receptor CCR6 is known to be expressed by memory (but not naïve) CD4 T cells, IL17-secreting αβ T cells, IL17-secreting γδ T cells, regulatory T cells, B cells and dendritic cells. Its only known ligand is CCL20 (MIP-3α, LARC), for which it shows strong binding. It is expressed on approximately 30-60% of adult peripheral blood effector/memory CD4+ T cells. CCR6 is involved in leukocyte homing to inflamed tissue, particularly the skin, lungs and gut; and is co-expressed on a subset of T cells that have a skin homing phenotype (i.e., T cells that express the cutaneous lymphocyte antigen (CLA) and CCR4). Thus CCR6 may be an important player in skin pathologies in which leukocytes participate.

CCR6 expression has been linked to psoriasis. In humans, a large majority of IL17-expressing skin-homing CD4 T cells in the peripheral blood express CCR6 (Homey, et. al., *JI,* 2000). IL17 secreting cells are central agents in several inflammatory diseases. T cells, such as γδ T cells and TH17 T cells produce IL17 after activation. The pathogenic effects of IL17 have been associated with human diseases such as rheumatoid arthritis (Patel D D et. al., *Ann Rheum Dis* 2013), multiple sclerosis (Zepp J, Wu L, and X Li *Trends Immunol* 2011), and psoriasis (Martin D A et. al., *J Invest Dermatol* 2012). Evidence strongly linking IL17 with psoriasis include gene wide association studies that show strong association between psoriasis and genes upstream (IL-23) or downstream (NFκb) of IL17 signaling pathways as well as efficacy in targeting IL17 in a clinical setting (Martin D A et. al., *J. Invest Dermat.* 2012; Papp et. al., *NEJM,* 2012; Papp et. al., *NEJM,* 2012). In addition to enhanced CCL20-mediated chemotaxis, CCR6+ T cells isolated from psoriatic patients preferentially secrete IL-17A, IL22, and TNFα when compared to healthy controls (Kagami, et. al., *J. Invest. Dermatol.,* 2010). Lastly, ccl20 mRNA was up-regulated in lesional psoriatic skin samples (Homey, et. al., *JI,* 2000; Dieu-Nosjean, et. al., *JEM,* 2000). In mice, CCR6 knock-out mice were protected from IL-23 driven psoriasis (Hedrick M. N. et. al. *JCI,* 2009). Thus, a multitude of evidence in both mice and men suggest a protective role for CCR6 blockade in psoriasis and psoriasis-like models.

CCR6 is also expressed by dendritic cells at critical stages during their development, and is important for their migration through tissues (Sozzani et al, *J Leuk Biol,* 66:1, 1999). Dendritic cells are responsible for presenting antigens to T cells within lymph nodes, and thus inhibition of dendritic cell trafficking can have a dampening effect on T cell mediated inflammatory responses (Banchereau and Steinman, *Nature,* 392:245, 1998).

CCR6 is expressed by B cells, and it has recently been demonstrated that CCR6-mediated B cell migration is required for B cells to engage is memory responses to soluble antigen (Elgueta et al., *J Immunol,* 194:505, 2015). Inhibiting such B cell migration via CCR6 blockade can therefore potentially dampen B cell mediated (and therefore antibody-mediated) inflammatory responses in disorders such as lupus, rheumatoid arthritis and pemphigus.

CCR6 is often expressed by colorectal cancer (CRC) cells. High expression of this receptor is associated with poor outcome for CRC patients, and CCR6 itself has been proposed to contribute to migration of CRC cells leading to metastasis (Liu J. et. al. *PLOSone* 20149 (6):e101137).

Chemokines that bind to a separate receptor, CXCR2, promote the accumulation and activation of neutrophils. These chemokines are implicated in a wide range of acute and chronic inflammatory disorders such as psoriasis, rheumatoid arthritis, radiation-induced fibrotic lung disease, autoimmune bullous dermatoses (AIBD), chronic obstructive pulmonary disease (COPD) and ozone-induced airway inflammation (see, Baggiolini et al., *FEBS Lett.* 307:97 (1992); Miller et al., *Crit. Rev. Immunol.* 12:17 (1992); Oppenheim et al., *Annu. Rev. Immunol.* 9: 617 (1991); Seitz et al., *J Clin. Invest.* 87: 463 (1991); Miller et al., *Ann. Rev. Respir. Dis.* 146:427 (1992); and Donnely et al., *Lancet* 341: 643 (1993), Fox & Haston, *Radiation Oncology*, 85:215 (2013), Hirose et al., *J Genet. Syndr. Genet. Ther.* S3:005 (2013), Miller et al., *Eur. J Drug Metab. Pharmacokinet.* 39:173 (2014), Lazaar et al., *Br. J Clin. Pharmacol.*, 72:282 (2011)).

In addition to inflammatory disorders, some of the CXCR2 ligand chemokines including CXCL1, CXCL2, CXCL3, and CXCL5 have been implicated in the induction of tumor angiogenesis (Strieter et al. *JBC* 270: 27348-27357 (1995)). Some CXCR2 ligand chemokines are exacerbating agents during ischemic stroke (Connell et al., Neurosci. Lett., 15:30111 (2015). Their angiogenic activity is possibly due to the activation of CXCR2 expressed on the surface of vascular endothelial cells (ECs) in surrounding vessels by the chemokines.

Many types of tumors are known to produce CXCR2 ligand chemokines. The production of these chemokines correlates with a more aggressive phenotype (Inoue et al. *Clin Cancer Res* 6:2104-2119 (2000)) and poor prognosis (Yoneda et. al. *J Nat Cancer Inst* 90:447-454 (1998)). As the chemokines are potent chemotactic factors for EC chemotaxis, they probably induce chemotaxis of endothelial cells toward their site of production in the tumor. This may be a critical step in the induction of tumor angiogenesis. Inhibitors of CXCR2 will inhibit the angiogenic activity of the ELR-CXC chemokines and therefore block the tumor growth. This anti-tumor activity has been demonstrated for antibodies to CXCL8 (Arenberg et al. *J Clin Invest* 97:2792-2802 (1996)), ENA-78 (Arenberg et al. *J Clin Invest* 102: 465-72 (1998)), and CXCL1 (Haghnegahdar et al. *J. Leukoc Biology* 67:53-62 (2000)).

Many tumor cells express CXCR2 and tumor cells may stimulate their own growth by secreting ELR-CXC chemokines. Thus, in addition to decreasing angiogenesis within tumors, CXCR2 inhibitors may directly inhibit the growth of tumor cells.

CXCR2 is often expressed by myeloid-derived suppressor cells (MDSC) within the microenvironment of tumors. MDSC are implicated in the suppression of tumor immune responses, and migration of MDSC in response to CXCR2 ligand chemokines is most likely responsible for attracting these cells into tumors (Marvel and Gabrilovich, *J. Clin. Invest.* 13:1 (2015) and Mackall et al., *Sci. Trans. Med.* 6:237 (2014)). Thus, CXCR2 inhibitors may reverse suppressive processes and thereby allow immune cells to more effectively reject the tumor. In fact, blocking the activation of CXC-chemokine receptors has proven useful as a combination therapy with checkpoint inhibitors in suppressing tumor growth, suggesting that CXCR2 blockade may also enhance tumor rejection in combination with other anti-tumor therapies, including but not limited to vaccines or traditional cytotoxic chemotherapies (see Highfill et al., *Science Translational Medicine*, 6:237 (2014)).

The activities of CCR6 and CXCR2 have each been associated with poor outcome in certain cancer types including CRC, although each is likely to work through a different, potentially complementary, mechanism (Nandi et al., *PLoS One*, 9:e97566, 2014; Liu et al, *PLoS One*, 9:e101137, 2014; Cheluvappa, *Int J Colorectal Dis*, 29:1181, 2014; Zhang, *Biomed Pharmacother.* 69:242, 2014; Lee et al, *Int J Cancer*, 135:232, 2014; Wang and DuBois, *Oncoimmunology*, 29:e28581, 2014; Wu et al, Int J Clin Exp Med, 8:5883, 2015).

In view of the clinical importance of CCR6 and CXCR2, the identification of compounds that modulate the function of one or both of these two receptors represent an attractive avenue into the development of new therapeutic agents. Such compounds and methods for their use are provided herein.

BRIEF SUMMARY OF THE INVENTION

Described herein are compounds having formula (A):

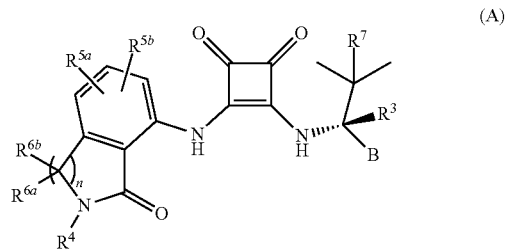

wherein $R^3$, $R^4$, $R^{5a}$, $R^{5b}$, $R^{6a}$, $R^{6b}$, $R^7$, B and the subscript n, have the meanings provided in the Detailed Description below. The compounds have utility in the treatment of diseases or conditions modulated at least in part by CCR6 and can also be used in the treatment of diseases or conditions modulated at least in part by CXCR2.

Pharmaceutical compositions of the compounds of formula (A) are also provided.

Further provided in the present disclosure preparative methods for the synthesis of compounds of formula (A), as well as selected intermediates useful in the preparation.

DETAILED DESCRIPTION OF THE INVENTION

Figure 1A:
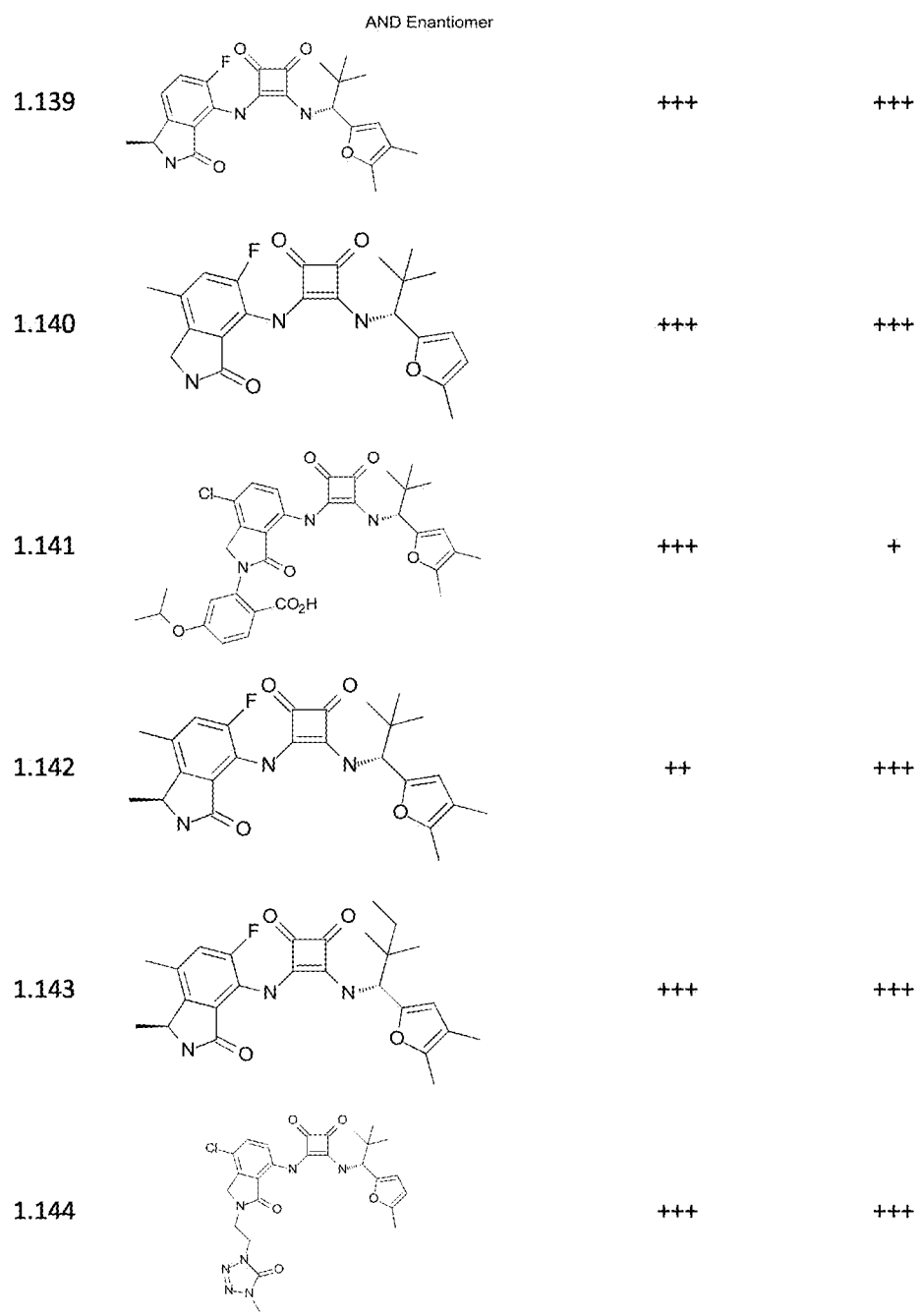
FIG. 1A-1AJ provides structures and biological activity for compounds described herein.
Figure 1A:
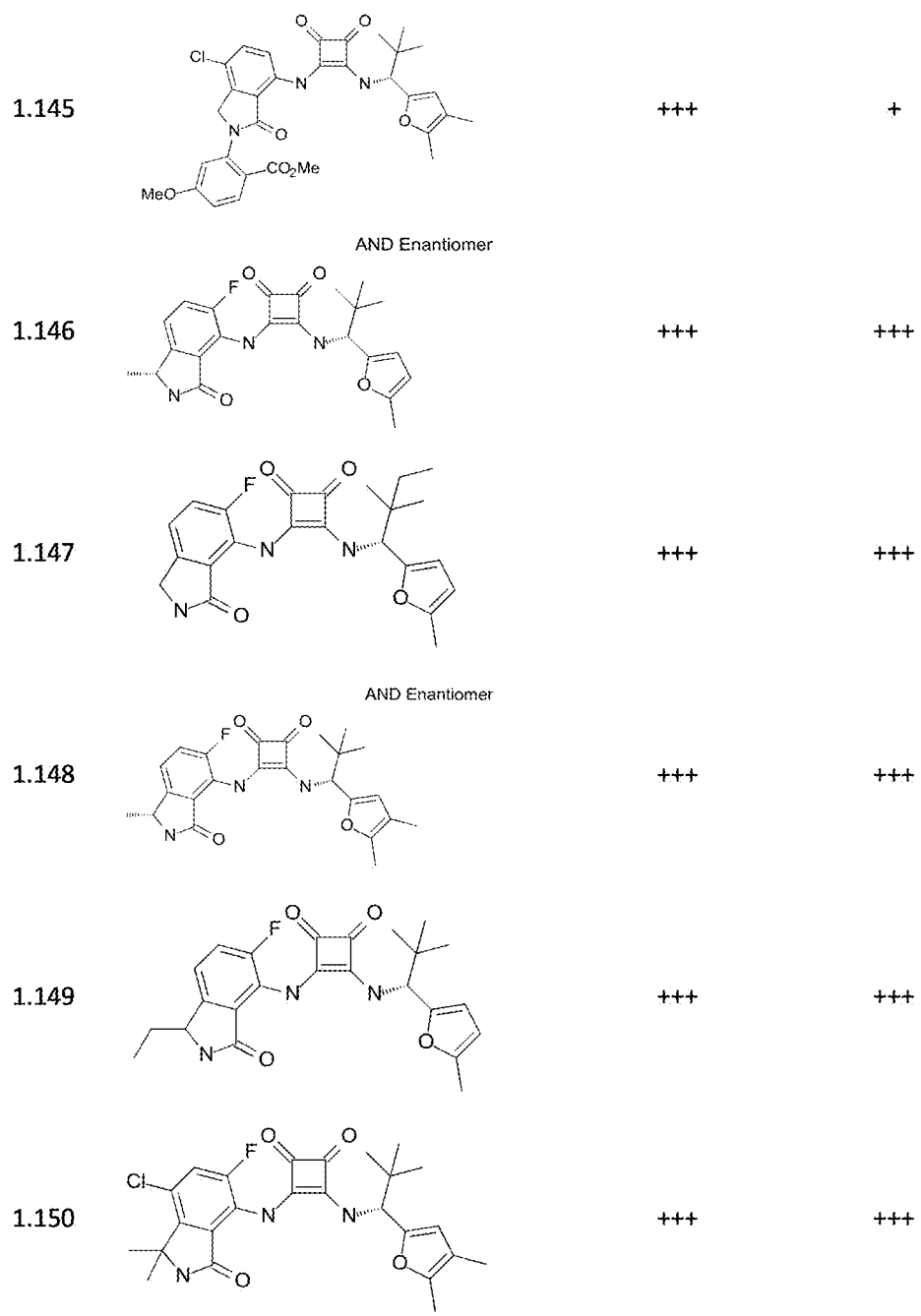
Figure 1A:
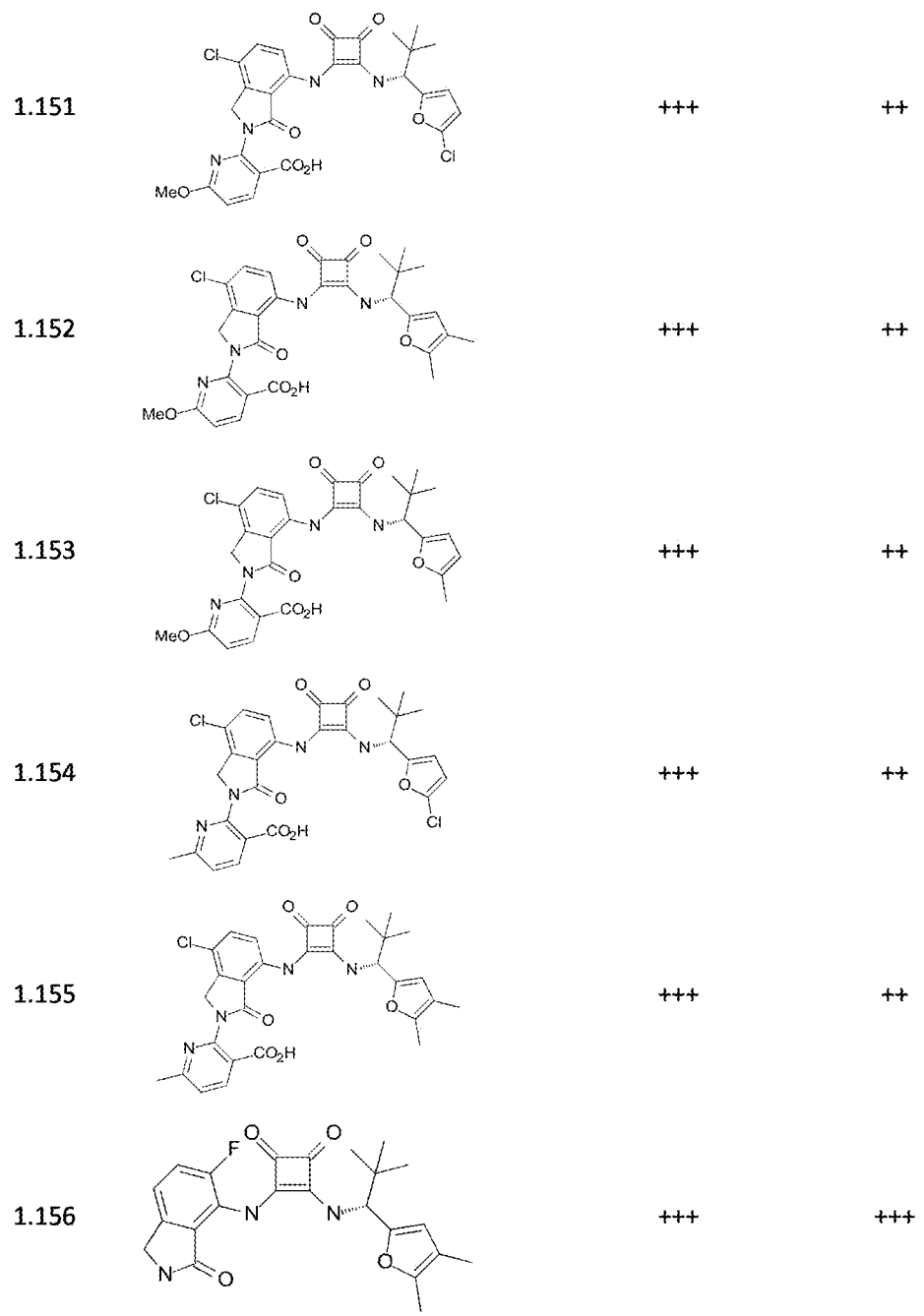
Figure 1A:
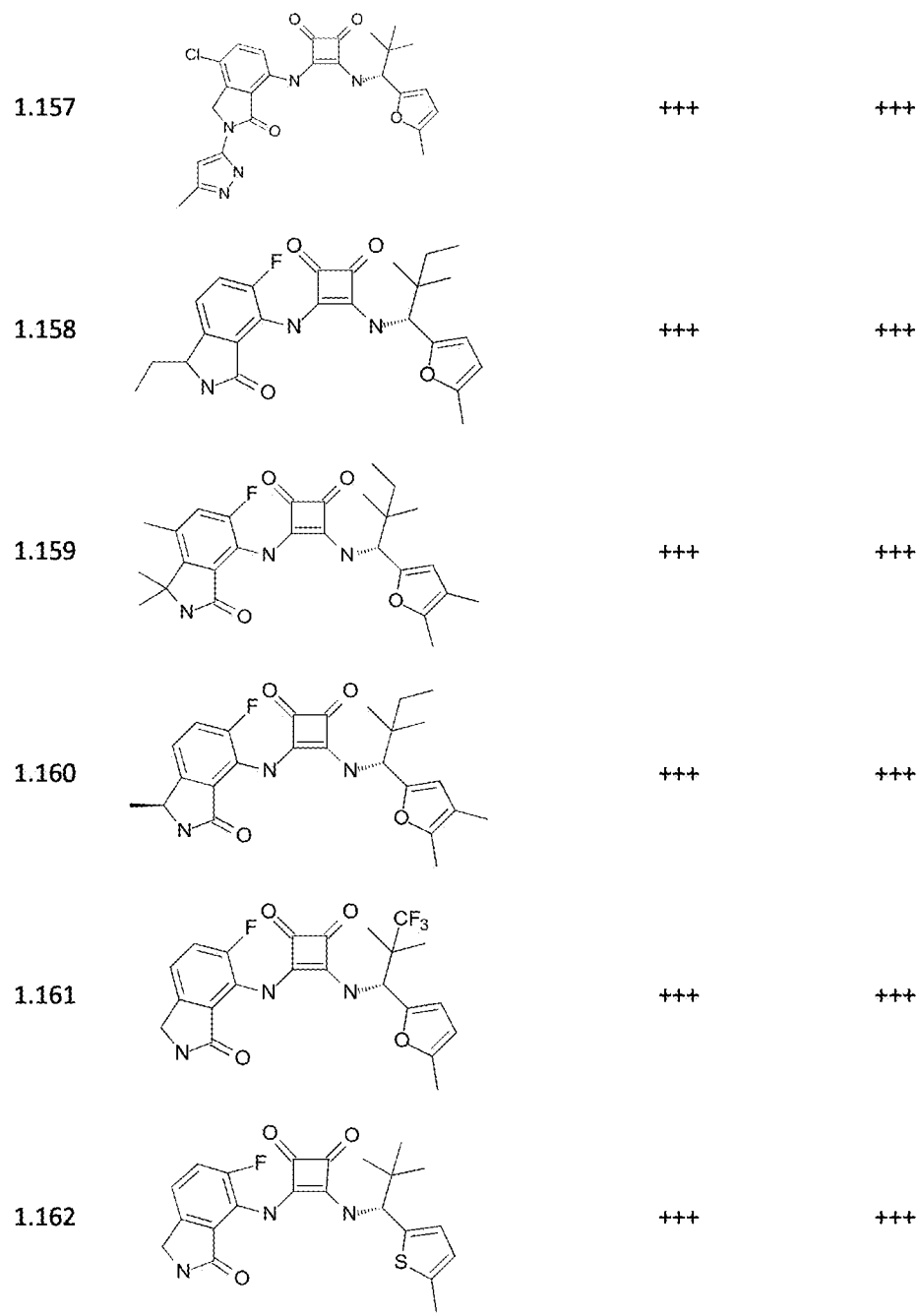
Figure 1A:
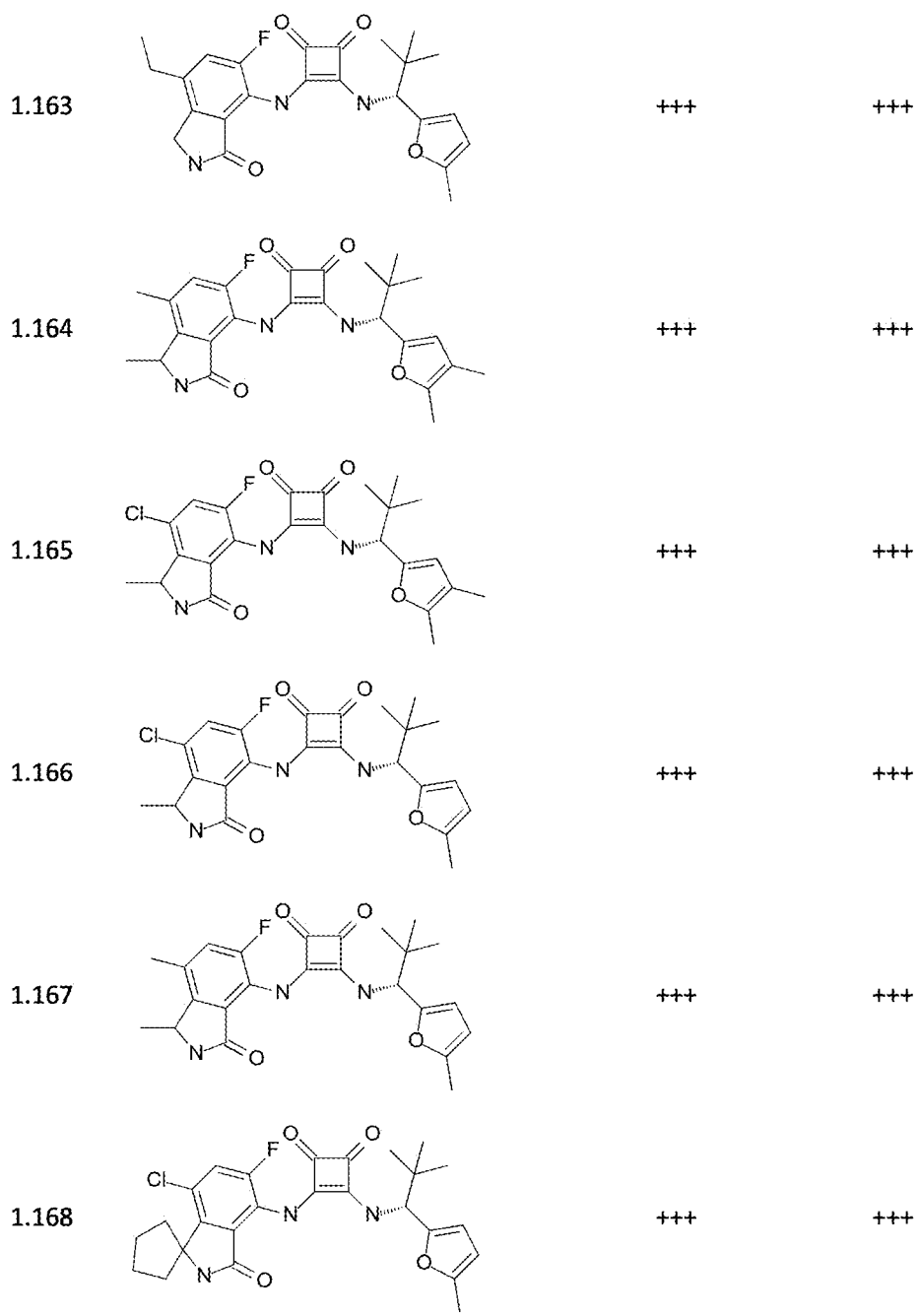
Figure 1A:
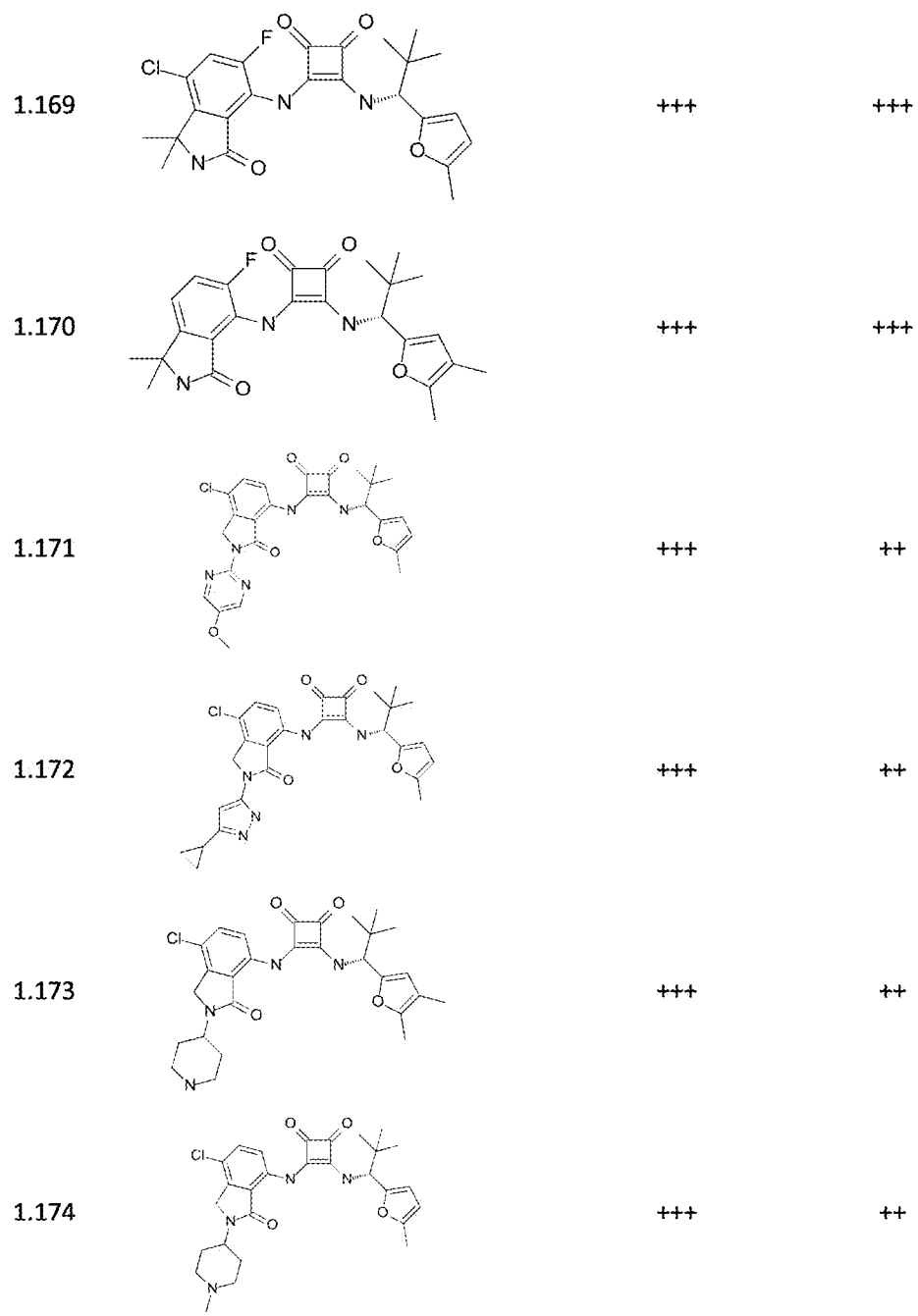
Figure 1A:
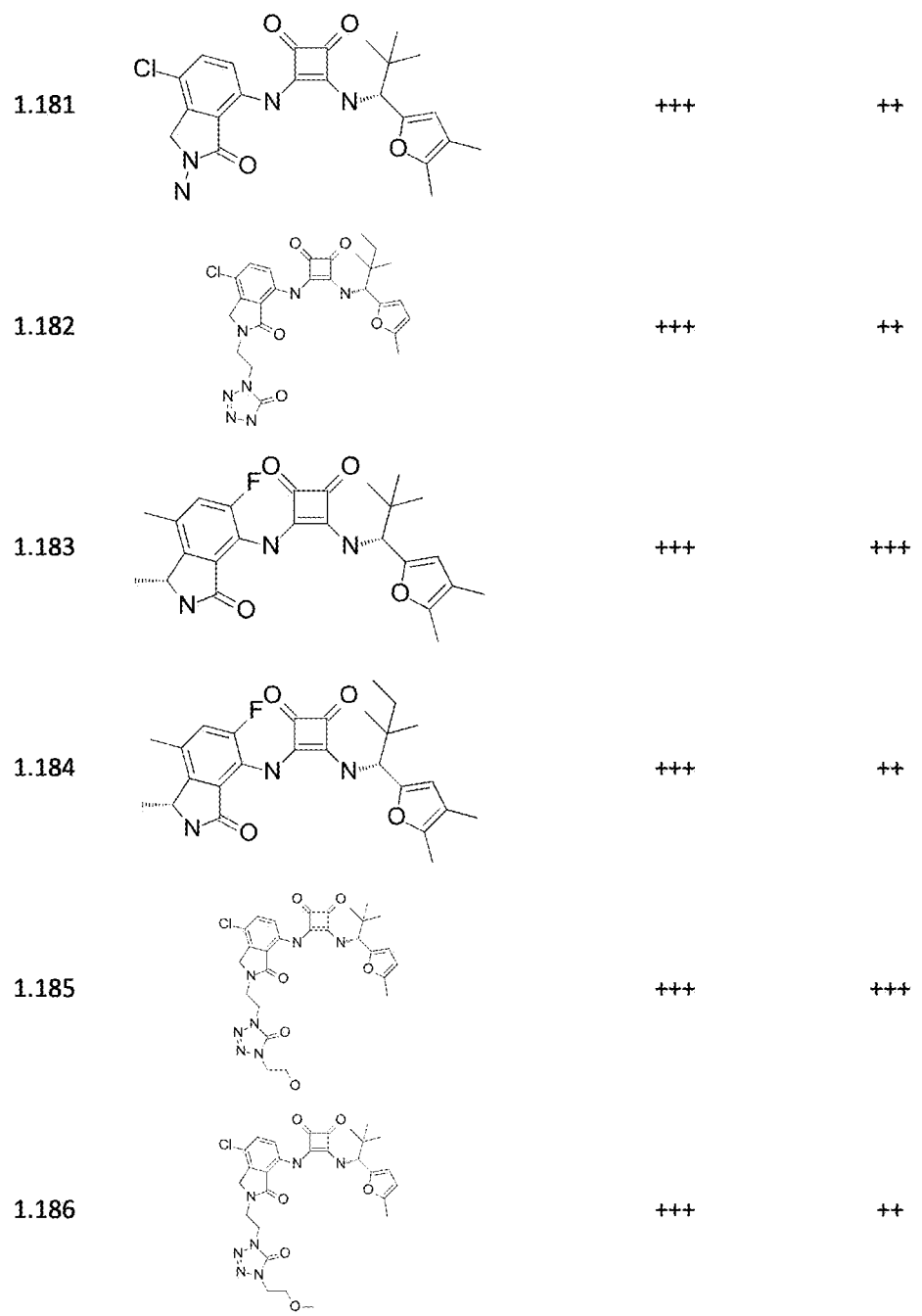

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present invention derives from the discovery that compounds of formula (A), (A1), (A2), (I) and (Ia1) act as potent antagonists of the CCR6 receptor and/or the CXCR2 receptor. The compounds have in vivo anti-inflammatory activity and have superior pharmacokinetic properties. Accordingly, the compounds provided herein are useful in pharmaceutical compositions, methods for the treatment of CCR6-mediated diseases and/or CXCR2-mediated diseases, and as controls in assays for the identification of CCR6 and/or CXCR2 antagonists.

Abbreviations and Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothio- phene, quinuclidine, and the like. A cycloheteroalkyl group can be attached to the remainder of the molecule through a ring carbon or a heteroatom.

As used herein, a wavy line, "〰", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

When a variable (e. g., $R^1$ or $R^a$) occurs more than one time in any compound or substituent, its definition on each occurrence is independent of its definition at every other occurrence. Additionally, combinations of substituents and/or variables are permissible only if such combinations result in stable compounds.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an antagonist of CCR6 and/or CXCR2, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an antagonist of CCR6 and/or CXCR2, or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an antagonist of CCR6 and/or CXCR2, or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an antagonist of CCR6 and/or CXCR2 (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CCR6 and/or CXCR2, either directly or indirectly. A modulator may act alone, or it may use a cofactor, e.g., a protein, metal ion, or small molecule.

The "activity" of a molecule may describe or refer to the binding of the molecule to a receptor; to catalytic activity; to the ability to stimulate gene expression or cell signaling, differentiation, or maturation; to antigenic activity; to the modulation of activities of other molecules; and the like.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content of the composition. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

Compounds

Provided herein are compounds compound having Formula (I):

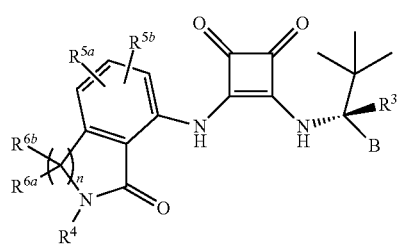

(I)

or any salts, solvates, hydrates, N-oxides, tautomers or rotamers thereof, wherein B is selected from the group consisting of furanyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;

$R^3$ is a member selected from H and D;

$R^4$ is a member selected from H, $C_{1-8}$ alkyl, and Y; wherein the $C_{1-8}$ alkyl is optionally substituted with halogen, —CN, —$CO_2R^a$, —$CONR^aR^b$, —$C(O)R^a$, $OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$ and Y, wherein each $R^a$ and $R^b$ is independently selected from hydrogen, $C_{1-4}$ alkyl, $C_{1-4}$ hydroxyalkyl and $C_{1-4}$ haloalkyl, $R^c$ is selected from $C_{1-4}$ alkyl, $C_{1-4}$ hydroxyalkyl and $C_{1-4}$ haloalkyl, and Y is a 5 or 6 membered aryl or heteroaryl group optionally substituted with from one to four substituents selected from halogen, —CN, —$C_{1-4}$ alkyl, —$C_{1-4}$ alkoxy, —$C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$;

$R^{5a}$ and $R^{5b}$ are each members independently selected from H, halogen, $C_{1-4}$ alkyl, $C_{1-4}$ alkoxy, $CO_2H$ and CN;

$R^{6a}$ and $R^{6b}$ are each members independently selected from H, $C_{1-4}$ alkyl, $C_{1-4}$ hydroxyalkyl and $C_{1-4}$ haloalkyl; or optionally $R^{6a}$ and $R^{6b}$ are taken together to form oxo (=O); and the subscript n is 1 or 2.

In some embodiments, the compound of formula I is a compound wherein B is furanyl or oxazolyl, which is which is optionally substituted with $R^{1a}$ and $R^{1b}$, which are independently selected from the group consisting of halogen, CN, $C_{1-4}$ alkyl, $C_{1-4}$ alkoxy and $C_{1-4}$ haloalkyl. Within this group of embodiments, certain selected embodiments are those wherein $R^{1a}$ is $CH_3$. In other selected embodiments, $R^3$ is H. In still other selected embodiments, each of $R^{5a}$ and $R^{5b}$ is independently selected from H, Cl and F. In yet other selected embodiments, each of $R^{6a}$ and $R^{6b}$ is independently selected from H and $C_{1-4}$ alkyl. In other selected embodiments, $R^4$ is Y. In still other selected embodiments, $R^4$ is selected from H and optionally substituted aryl or heteroaryl groups. In particular embodiments, $R^{1a}$ is selected from $CH_3$ and Cl; and $R^{1b}$ is absent or is $CH_3$.

In one group of selected embodiments, compounds are provided having the formula (Ia1):

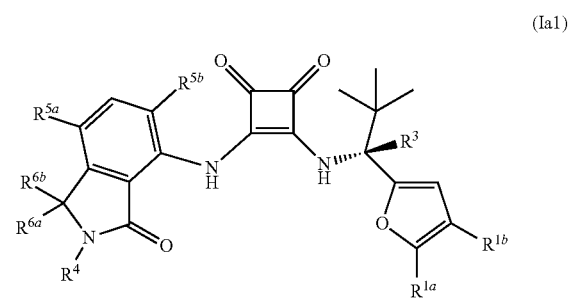

(Ia1)

or a pharmaceutically acceptable salt, solvate or hydrate, thereof, wherein $R^{1a}$ is selected from $CH_3$ and Cl; $R^{1b}$ is absent (replaced by H) or is $CH_3$; $R^3$ is H or D; $R^4$ is H or an optionally substituted aryl or heteroaryl group; $R^{5a}$ and $R^{5b}$ are each independently selected from H, F, Cl, Br and $CH_3$; and $R^{6a}$ and $R^{6b}$ are each independently selected from H and $CH_3$.

In certain embodiments, compounds of formula (Ia1) are provided wherein $R^{1a}$ is $CH_3$; $R^{1b}$ is absent (replaced by H) or is $CH_3$; $R^3$ is H or D; $R^4$ is H or an optionally substituted aryl or heteroaryl group; $R^{5a}$ is H or Cl or Br; $R^{5b}$ is H or F; and $R^{6a}$ and $R^{6b}$ are each H; or a pharmaceutically acceptable salt, solvate or hydrate, thereof.

In some selected embodiments, compounds of formula (I) are provided that are selected from those compounds in FIG. 1.

Also provided herein are compounds compound having Formula (A):

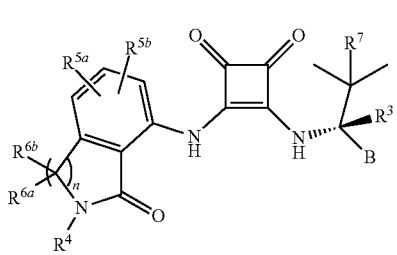

(A)

wherein
  B is selected from the group consisting of furanyl, thiophenyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;
  $R^3$ is a member selected from the group consisting of H and D;
  $R^4$ is a member selected from the group consisting of H, $C_{1-8}$ alkyl, OH, $-NR^aR^b$, $-C_{1-4}$ alkoxy, and Y; wherein the $C_{1-8}$ alkyl is optionally substituted with halogen, $-CN$, $-CO_2R^a$, $-CONR^aR^b$, $-C(O)R^a$, $OC(O)NR^aR^b$, $-NR^aC(O)R^b$, $-NR^aC(O)_2R^c$, $-NR^aC(O)NR^aR^b$, $-NR^aR^b$, $-OR^a$, $-S(O)_2NR^aR^b$, $-NR^aS(O)_2R^b$ and Y, wherein Y is a 4 to 8 membered cycloheteroalkyl group or a 3 to 8 membered cycloalkyl group or a 5- or 6-membered aryl or heteroaryl group any of which is optionally substituted with from 1 to four substituents selected from halogen, oxo, $-CN$, $-C_{1-6}$ alkyl, $-C_{1-6}$ alkoxy, $-C_{1-6}$ hydroxyalkyl, $-C_{1-6}$ haloalkyl, $O-C_{1-6}$ haloalkyl, $-C_{1-4}$alkyl-O-$C_{1-4}$ alkyl, $-C_{1-6}$ alkyl-$NR^aR^b$, $-C_{1-6}$ alkyl-$CO_2H$, $-C_{1-6}$ alkyl-$CO_2R^a$, $-C_{1-6}$ alkyl-$CONR^aR^b$, $-C_{1-6}$ alkyl-$C(O)R^a$, $-C_{1-6}$ alkyl-$OC(O)NR^aR^b$, $-C_{1-6}$ alkyl-$NR^aC(O)R^b$, $-C_{1-6}$ alkyl-$NR^aC(O)_2R^c$, $-C_{1-6}$ alkyl-$NR^aC(O)NR^aR^b$, $-C_{1-6}$ alkyl-$OR^a$, $-C_{1-6}$ alkyl-$S(O)_2NR^aR^b$, $-C_{1-6}$ alkyl-$NR^aS(O)_2R^b$, $-CO_2R^a$, $-CONR^aR^b$, $-C(O)R^a$, $-OC(O)NR^aR^b$, $-NR^aC(O)R^b$, $-NR^aC(O)_2R^c$, $-NR^aC(O)NR^aR^b$, $-NR^aR^b$, $-OR^a$, $-S(O)_2NR^aR^b$, $-NR^aS(O)_2R^b$, $-CH_2CO_2R^a$; each $R^a$ and $R^b$ is independently selected from hydrogen, $C_{1-4}$ alkyl, $C_{1-4}$ hydroxyalkyl and $C_{1-4}$ haloalkyl, and $R^c$ is selected from $C_{1-4}$ alkyl, $C_{1-4}$ hydroxyalkyl and $C_{1-4}$ haloalkyl; and wherein the 4 to 8 membered cycloheteroalkyl group and the 3 to 8 membered cycloalkyl group may additionally be optionally substituted with oxo;
  $R^{5a}$ and $R^{5b}$ are each members independently selected from the group consisting of H, halogen, $C_{1-4}$ alkyl, $-C_{1-4}$ haloalkyl, $O-C_{1-4}$ haloalkyl, $C_{1-4}$ alkoxy, $CO_2H$ and CN;
  $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O) or a 4 to 6 membered cycloheteroalkyl group or a 3 to 6 membered cycloalkyl group;
  $R^7$ is a member selected from the group consisting of methyl, ethyl and $C_{1-2}$ haloalkyl; and
  the subscript n is 1 or 2;
  or any pharmaceutically acceptable salts, solvates, hydrates, N-oxides, tautomers or rotamers thereof.

In some embodiments, B is selected from the group consisting of:

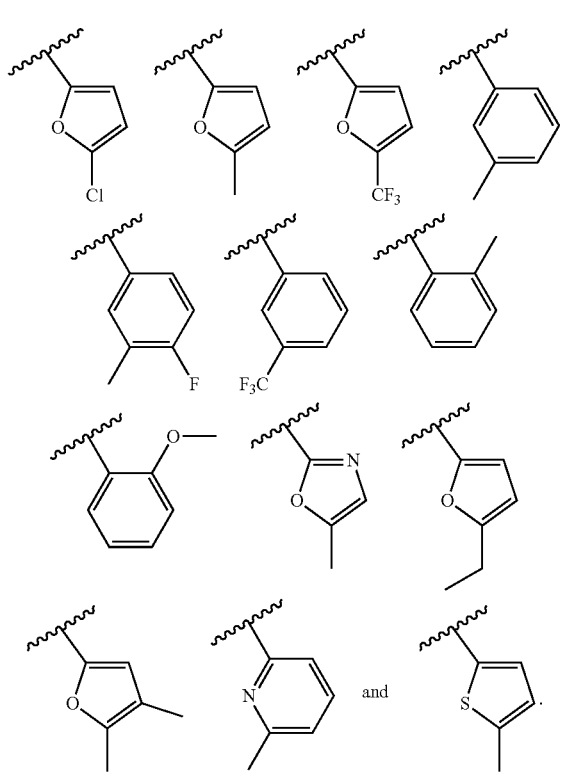

In some embodiments, B is selected from the group consisting of:

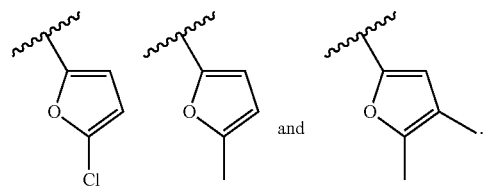

In some embodiments, B is furanyl or oxazolyl, each of which is optionally substituted with $R^{1a}$ and $R^{1b}$, which are independently selected from the group consisting of halogen, CN, $C_{1-4}$ alkyl, $C_{1-4}$ alkoxy and $C_{1-4}$ haloalkyl.

In some embodiments, B is furanyl substituted with $R^{1a}$ which is $CH_3$ or Cl and optionally substituted with $R^{1b}$ which is $CH_3$.

In some embodiments, $R^3$ is H.

In some embodiments, each of $R^{5a}$ and $R^{5b}$ is independently selected from the group consisting of H, $CH_3$, Cl and F.

In some embodiments,
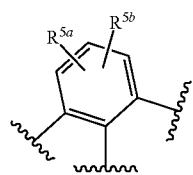
is selected from the group consisting of:
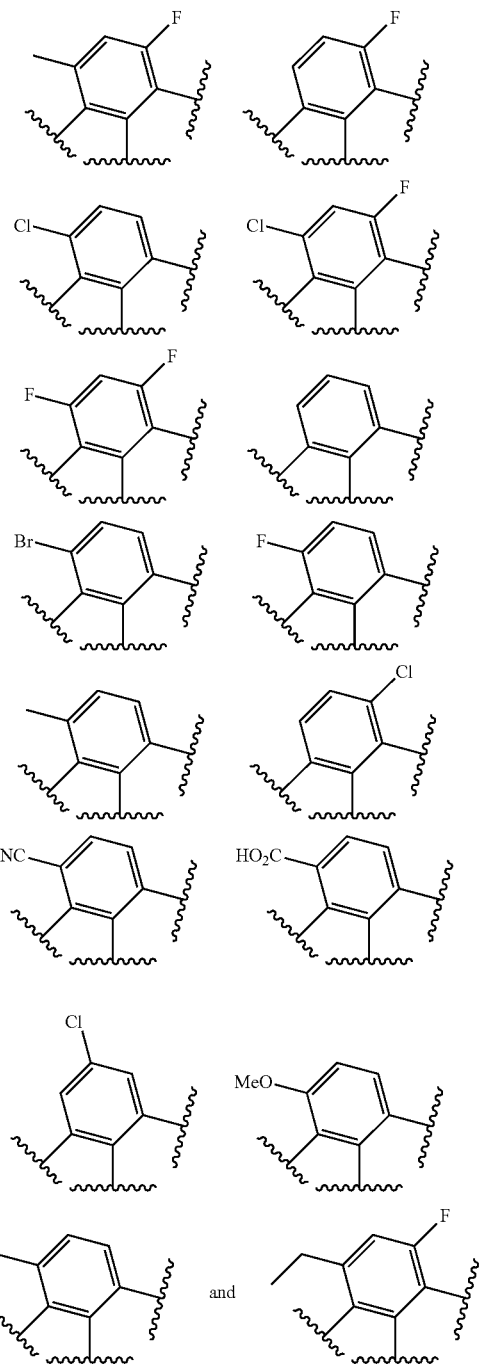
In some embodiments,
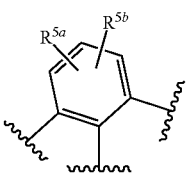
is selected from the group consisting of:
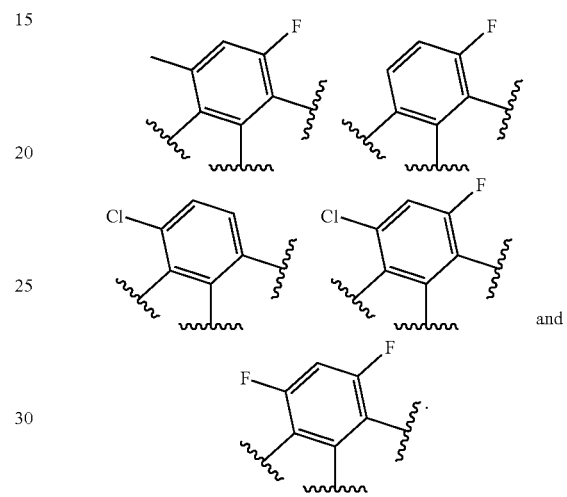
and
In some embodiments, each of $R^{6a}$ and $R^{6b}$ is independently selected from the group consisting of H and $C_{1-2}$ alkyl.
In some embodiments,
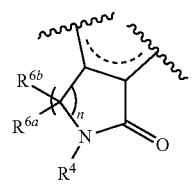
is independently selected from the group consisting of
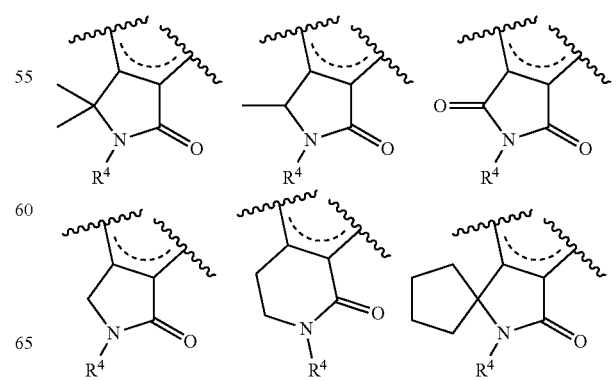

-continued

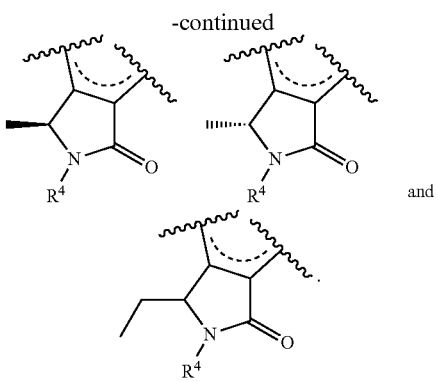

In some embodiments,

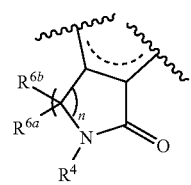

is independently selected from the group consisting of

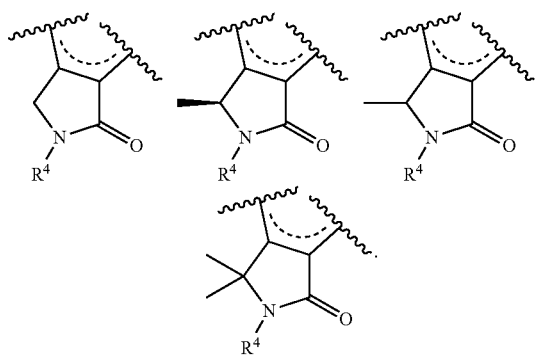

In some embodiments, $R^4$ is H, $C_{1-3}$ alkyl or Y, wherein the $C_{1-3}$ alkyl is substituted with tetrazolyl or tetrazolonyl, wherein the tetrazolyl or tetrazolonyl is optionally substituted with $C_{1-6}$ alkyl, $C_{1-6}$ hydroxyalkyl, or $C_{1-4}$alkyl-O—$C_{1-4}$ alkyl wherein Y is selected from the group consisting of pyridinyl, pyrazolyl, and phenyl wherein the pyridinyl, pyrazolyl, and phenyl have from one to three substituents each of which is independently selected from —$C_{1-4}$ alkyl, —$C_{1-4}$ alkoxy and —$CO_2H$.

In some embodiments, $R^4$ is H.

In some embodiments, $R^4$ is $C_{1-6}$ alkyl wherein the $C_{1-6}$ alkyl is substituted with tetrazolyl or tetrazolonyl, wherein the tetrazolyl or tetrazolonyl is optionally substituted with —$C_{1-6}$ alkyl, —$C_{1-6}$ alkoxy, —$C_{1-6}$ hydroxyalkyl, —$C_{1-6}$ haloalkyl, O—$C_{1-6}$ haloalkyl, —$C_{1-4}$ alkyl-O—$C_{1-4}$ alkyl, —$C_{1-6}$ alkyl-NR$^a$R$^b$, —$C_{1-6}$ alkyl-$CO_2H$, —$C_{1-6}$ alkyl-$CO_2R^a$, —$C_{1-6}$ alkyl-CONR$^a$R$^b$, —$C_{1-6}$ alkyl-C(O)R$^a$, —$C_{1-6}$ alkyl-OC(O)NR$^a$R$^b$, —$C_{1-6}$ alkyl-NR$^a$C(O)R$^b$, —$C_{1-6}$ alkyl-NR$^a$C(O)$_2$R$^c$, —$C_{1-6}$ alkyl-NR$^a$C(O)NR$^a$R$^b$, —$C_{1-6}$ alkyl-OR$^a$, —$C_{1-6}$ alkyl-S(O)$_2$NR$^a$R$^b$, or —$C_{1-6}$ alkyl-NR$^a$S(O)$_2$R$^b$.

In some embodiments, $R^4$ is $C_{1-3}$ alkyl wherein the $C_{1-3}$ alkyl is substituted with tetrazolyl or tetrazolonyl, wherein the tetrazolyl or tetrazolonyl is optionally substituted with —$C_{1-6}$ alkyl, —$C_{1-6}$ alkoxy, —$C_{1-6}$ hydroxyalkyl, —$C_{1-6}$ haloalkyl, —$C_{1-4}$alkyl-O—$C_{1-4}$ alkyl, —$C_{1-6}$ alkyl-NR$^a$R$^b$, or —$C_{1-6}$ alkyl-$CO_2H$.

In some embodiments, $R^4$ is $C_{1-3}$ alkyl wherein the $C_{1-3}$ alkyl is substituted with tetrazolyl or tetrazolonyl, wherein the tetrazolyl or tetrazolonyl is optionally substituted with $C_{1-3}$ alkyl, $C_{1-3}$ hydroxyalkyl, or $C_{1-3}$alkyl-O—$C_{1-3}$alkyl.

In some embodiments, $R^4$ is selected from the group consisting of pyridinyl, pyrazolyl, and phenyl wherein the pyridinyl, pyrazolyl, and phenyl have from one to three substituents each of which is independently selected from —$C_{1-4}$ alkyl, —$C_{1-4}$ alkoxy and —$CO_2H$.

In some embodiments, $R^4$ is $C_{1-3}$ alkyl substituted with tetrazolyl or tetrazolonyl, wherein the tetrazolyl or tetrazolonyl is optionally substituted with $C_{1-3}$ alkyl.

In some embodiments, $R^4$ is selected from the group consisting of:

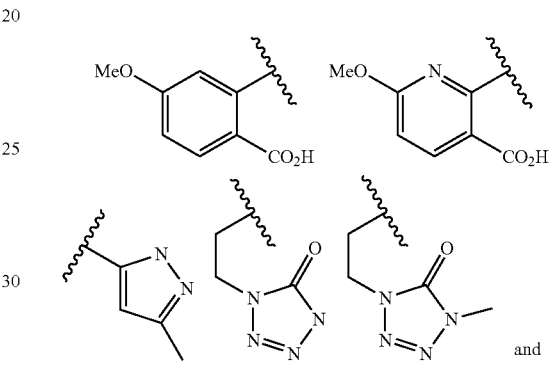

and H.

In some embodiments, $R^7$ is selected from the group consisting of methyl, ethyl and $CF_3$. In some embodiments, $R^7$ is methyl.

In some embodiments, a compound of formula (A1) is provided:

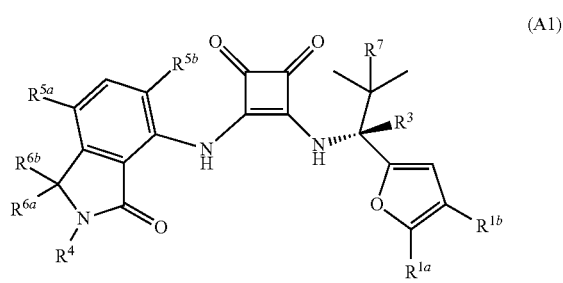

(A1)

wherein $R^{1a}$ is selected from $CH_3$ and Cl; $R^{1b}$ is absent or is $CH_3$; $R^3$ is H or D; $R^4$ is H or Y; $R^{5a}$ and $R^{5b}$ are each independently selected from H, F, Cl, Br and $CH_3$; $R^{6a}$ and $R^{6b}$ are each independently selected from H and $CH_3$; and $R^7$ is methyl or ethyl; or a pharmaceutically acceptable salt, solvate or hydrate, thereof.

In some embodiments, $R^{1a}$ is $CH_3$; $R^{1b}$ is absent or is $CH_3$; $R^3$ is H or D; $R^4$ is H; $R^{5a}$ is H, F, Me or Cl or Br; $R^{5b}$ is H or F; $R^{6a}$ and $R^{6b}$ are each H; and $R^7$ is methyl or ethyl; or a pharmaceutically acceptable salt, solvate or hydrate, thereof.

In some embodiments, the compound is substantially free of other isomers at the carbon atom bearing $R^3$.

In some embodiments, $R^4$ is Y.

In some embodiments, a compound of formula (A2) is provided:

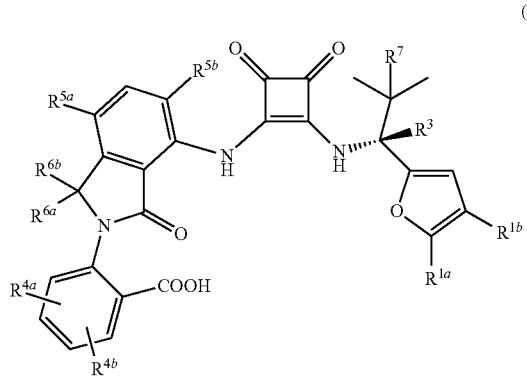

(A2)

wherein $R^{1a}$ is selected from $CH_3$ and Cl; $R^{1b}$ is H or $CH_3$; $R^3$ is H or D; $R^{4a}$ and $R^{4b}$ are independently selected from halogen, —CN, —$C_{1-4}$ alkyl, —$C_{1-4}$ alkoxy, —$C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$, and $R^a$ and $R^b$ are independently selected from hydrogen, $C_{1-4}$ alkyl, $C_{1-4}$ hydroxyalkyl and $C_{1-4}$ haloalkyl; $R^{5a}$ and $R^{5b}$ are each independently selected from H, F, Cl, Br and $CH_3$; $R^{6a}$ and $R^{6b}$ are each independently selected from H and $CH_3$; and $R^7$ is selected from the group consisting of methyl, ethyl and $C_{1-2}$ haloalkyl; or a pharmaceutically acceptable salt, solvate or hydrate, thereof.

In some embodiments, a compound, or a pharmaceutically acceptable salt thereof, is provided, selected from the group consisting of:

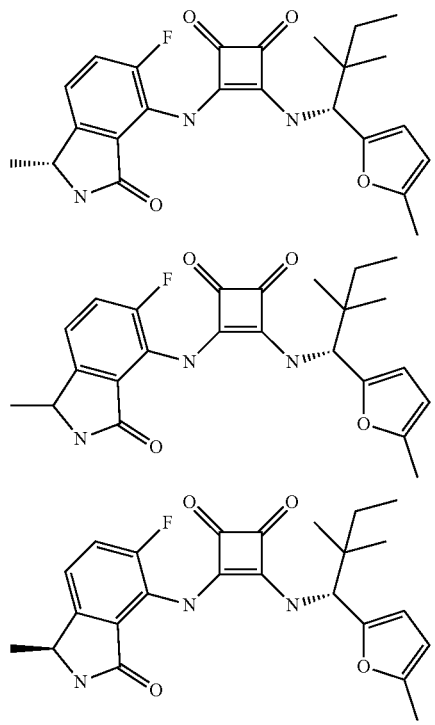

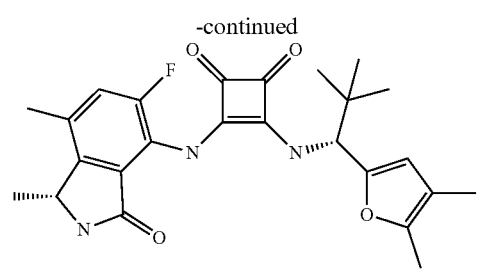

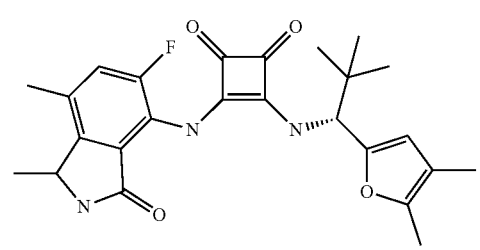

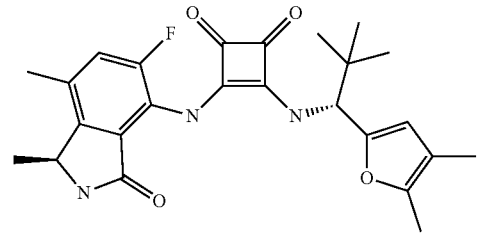

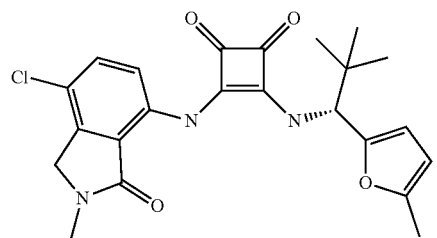

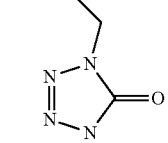

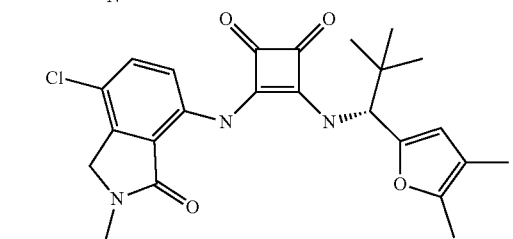

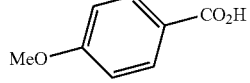

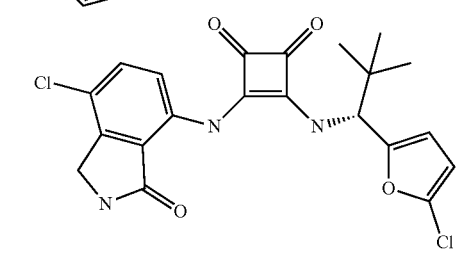

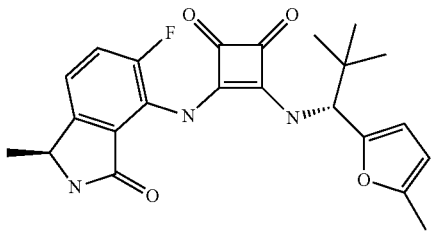
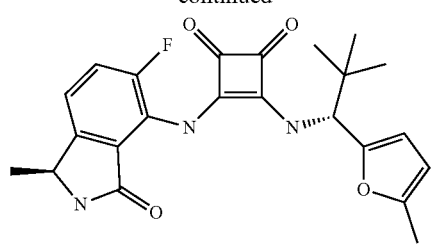
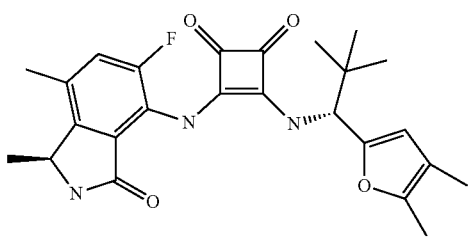
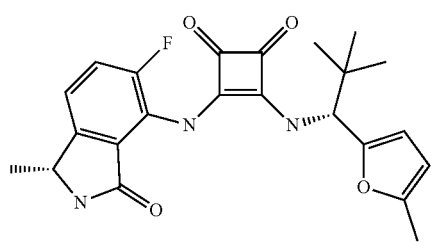
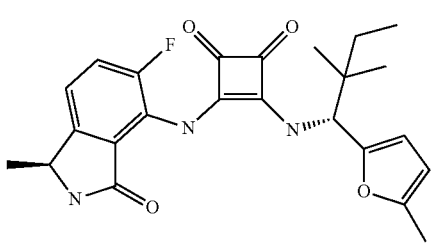
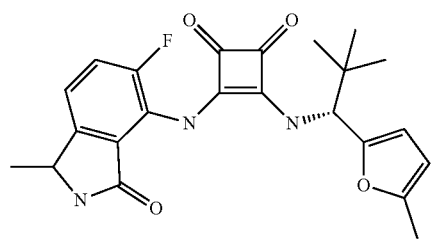
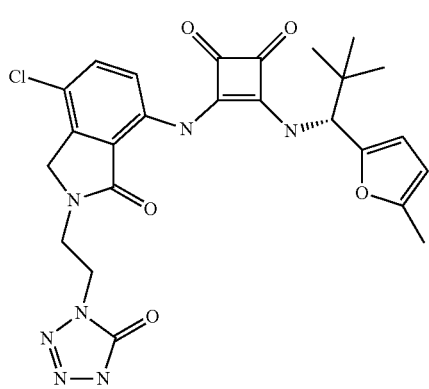
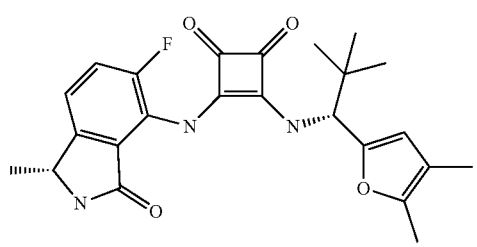
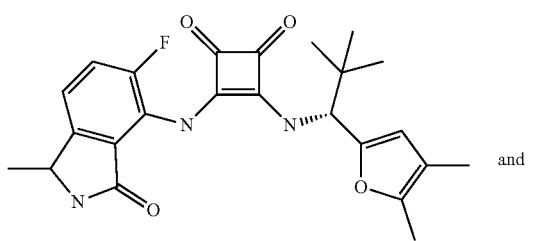
and
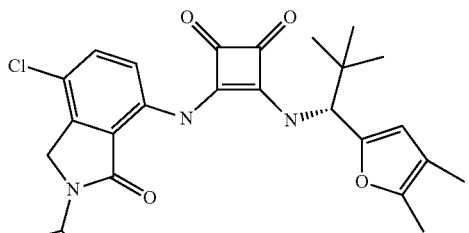
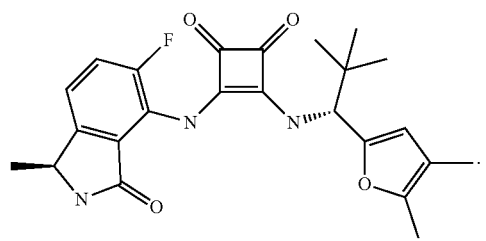
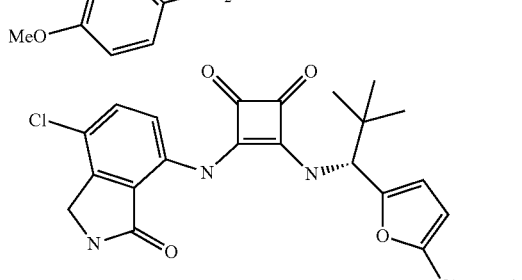
and
In some embodiments, a compound, or a pharmaceutically acceptable salt thereof, is provided, selected from the group consisting of:

-continued

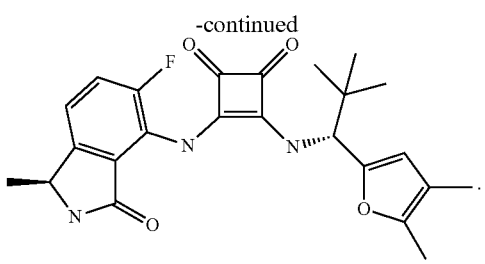

In some embodiments, a compound, or a pharmaceutically acceptable salt thereof, is provided, selected from the group consisting of:

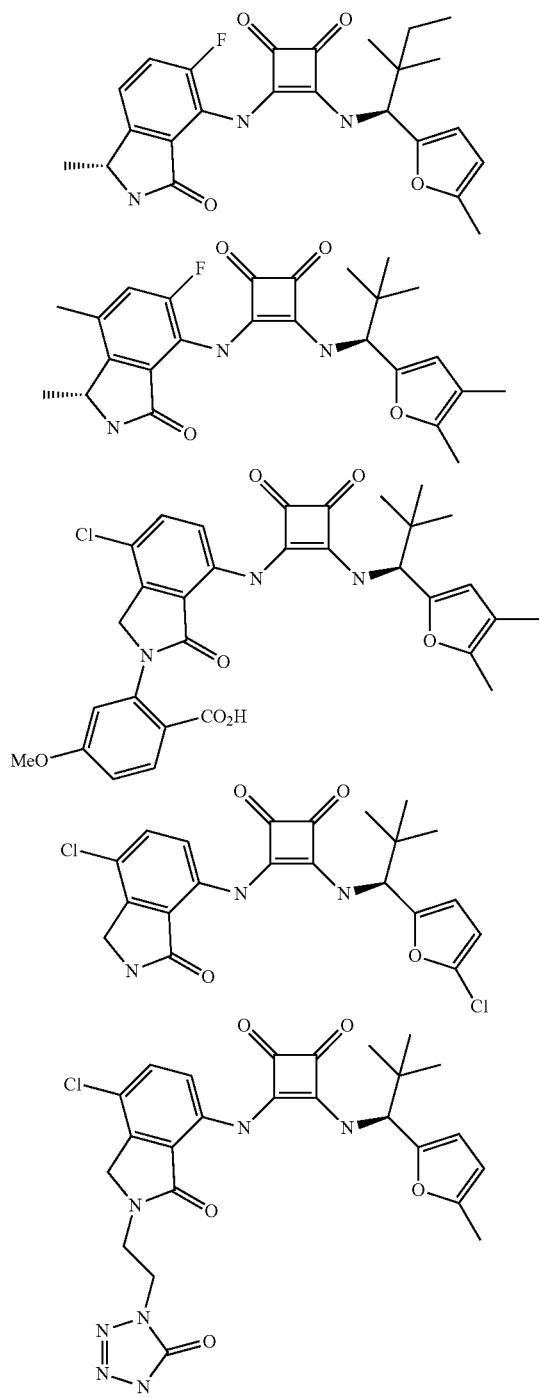

-continued

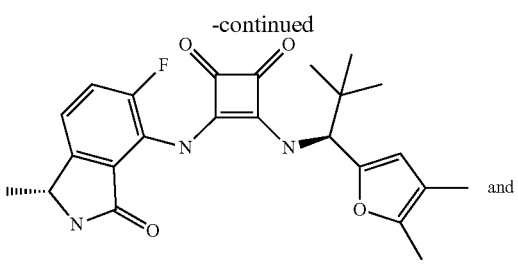

and

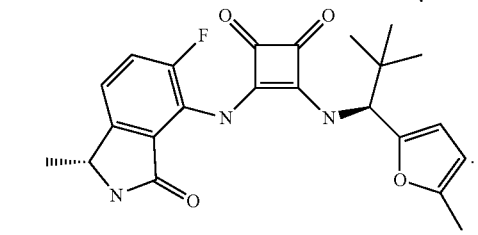

.

Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

Pharmaceutical Compositions

In addition the compounds provided above, the compositions for modulating CCR6 and/or CXCR2 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and/or coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sinai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacryl-amide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

In some embodiments, a pharmaceutical composition comprising a compound of the present disclosure is provided. In some embodiments, the pharmaceutical composition further comprises one or more additional therapeutic agents. In some embodiments, the one or more additional therapeutic agent is selected from the group consisting of cytotoxic chemotherapy, anti-cancer or anti-tumor vaccines, anti-immunocytokine therapies, immunocytokine therapies, chimeric antigen receptor (CAR) T cell receptors, gene transfer therapy, checkpoint inhibitors, corticosteroids, retinoid-like agents, antineoplastics, and interferons analogs. In some embodiments, the one or more additional therapeutic agent is selected from the group consisting of a TNF alpha ligand inhibitor, a TNF binding agent, an IL-1 ligand inhibitor; an IL-6 ligand inhibitor, an IL-8 ligand inhibitor; an IL-17 antagonist, a calcineurin inhibitor, a TNF antagonist, a Retinoic acid receptor gamma antagonist, an IL-17A ligand inhibitor; an IL-17F ligand inhibitor, a RIP-1 kinase inhibitor, a sphingosine-1-phosphate receptor-1 antagonist, a sphingosine-1-phosphate receptor-1 modulator, a Rho associated protein kinase 2 inhibitor, an IL-12 antagonist; an IL-23 antagonist, a type II TNF receptor modulator, an IL-23A inhibitor, a PDE 4 inhibitor, a JAK tyrosine kinase inhibitor, a Jak1 tyrosine kinase inhibitor; a Jak3 tyrosine kinase inhibitor, a Histamine H1 receptor antagonist, a Retinoic acid receptor agonist, a membrane copper amine oxidase inhibitor, a PI3K modulator, a Phosphoinositide-3 kinase delta inhibitor, a mitochondrial 10 kDa heat shock protein stimulator, an adenosine A3 receptor agonist, a galectin-3 inhibitor, a F1F0 ATP synthase modulator, a GM-CSF ligand inhibitor, a vitamin D3 receptor agonist, a glucocorticoid agonist, a histamine H4 receptor antagonist, a CCR3 chemokine antagonist, an eotaxin ligand inhibitor, a Sphingosine-1-phosphate receptor-1 modulator, a phospholipase A2 inhibitor, a PDE 4 inhibitor, an albumin modulator, a TLR-7 antagonist, a TLR-8 antagonist a TLR-9 antagonist, a CD40 ligand receptor antagonist, a Src tyrosine kinase inhibitor, a tubulin binding agent, an interleukin-1 alpha ligand inhibitor, a histone deacetylase-1 inhibitor, a histone deacetylase-2 inhibitor, a histone deacetylase-3 inhibitor, a histone deacetylase-6 inhibitor, a nucleoside reverse transcriptase inhibitor, a nuclear factor kappa B inhibitor, a STAT-3 inhibitor, a parathyroid hormone ligand inhibitor; a vitamin D3 receptor agonist, a T cell surface glycoprotein CD28 stimulator, a histamine H4 receptor antagonist, a TGF beta agonist, a P-selectin glycoprotein ligand-1 stimulator, a DHFR inhibitor, a Retinoic acid receptor gamma modulator, a cytosolic phospholipase A2 inhibitor, a retinoid X receptor modulator, a beta-catenin inhibitor, a CREB binding protein inhibitor, a TrkA receptor antagonist, a T-cell differentiation antigen CD6 inhibitor, an ADP ribosyl cyclase-1 inhibitor, an Interleukin-1 beta ligand modulator; an insulin receptor substrate-1 inhibitor, a DHFR inhibitor, an IL-8 antagonist, a drug that blocks the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

Methods of Treating Diseases Modulated by CCR6 and/or CXCR2

In one aspect, the present invention provides methods of treating or preventing a CCR6-mediated condition or disease and/or a CXCR2-mediated condition or disease by administering to a subject having such a condition or disease, a therapeutically effective amount of any compound of the invention. Preferred compounds for use in the present methods are those compounds provided above as preferred embodiments, as well as compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR6-mediated condition or disease" and related phrases and terms refer to a condition or disease characterized by inappropriate, e.g., less than or greater than normal, CCR6 functional activity. Inappropriate CCR6 functional activity might arise as the result of CCR6 expression in cells which normally do not express CCR6, increased CCR6 expression (leading to, e.g., inflammatory and immunoregulatory disorders and diseases) or decreased CCR6 expression. Inappropriate CCR6 functional activity might also arise as the result of CCL20 secretion by cells which normally do not secrete CCL20, increased CCL20 expression (leading to, e.g., inflammatory and immunoregulatory disorders and diseases) or decreased CCL20 expression. A CCR6-mediated condition or disease may be completely or partially mediated by inappropriate CCR6 functional activity. However, a CCR6-mediated condition or disease is one in which modulation of CCR6 results in some effect on the underlying condition or disease (e.g., a CCR6 antagonist results in some improvement in patient well-being in at least some patients).

Similarly, the phrase "CXCR2-mediated condition or disease" and related phrases and terms refer to a condition or disease characterized by inappropriate, e.g., less than or greater than normal, CXCR2 functional activity. Inappropriate CXCR2 functional activity might arise as the result of CXCR2 expression in cells which normally do not express CXCR2, increased CXCR2 expression (leading to, e.g., inflammatory and immunoregulatory disorders and diseases) or decreased CXCR2 expression. A CXCR2-mediated condition or disease may be completely or partially mediated by inappropriate CXCR2 functional activity. However, a CXCR2-mediated condition or disease is one in which modulation of CXCR2 results in some effect on the underlying condition or disease (e.g., a CXCR2 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR6 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, Vitiligo (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic) as well as for instance Hashimoto's thyroiditis and Grave's disease, multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

Preferably, the present methods are directed to the treatment of diseases or conditions selected from allergic diseases, psoriasis, skin conditions such as atopic dermatitis and asthma and scleroderma.

In another group of embodiments, modulation of CCR6 dependent regulatory T cell trafficking may be modulated to treat diseases or conditions including cancers, infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Having regard to their inhibition of binding of CXCR2, compounds of the invention are useful in the treatment of conditions or diseases mediated by CXCR2, for example inflammatory or allergic conditions or diseases, particularly chronic obstructive pulmonary airways or lung disease (COPD, COAD or COLD), including chronic bronchitis or dyspnea associated therewith, emphysema, bronchiolitis obliterans syndrome and severe asthma.

Compounds of the present invention are further useful in the treatment of various diseases, such as cancer, e.g. colorectal cancer, ovarian cancer, prostate cancer, melanoma including metastatic melanoma, lung cancer, e.g. non-small cell lung cancer, renal cell carcinoma; tumor angiogenesis, ischemia/reperfusion injury, delayed graft function, osteoarthritis, myeloid metaplasia with myelofibrosis, Adenomyosis, contact hypersensitivity (skin). and in wound healing. Treatment in accordance with the invention may be symptomatic or prophylactic.

Prophylactic efficacy in the treatment of chronic bronchitis or COPD will be evidenced by reduced frequency or severity, will provide symptomatic relief and reduce disease progression, improvement in lung function. It may further be evidenced by reduced requirement for other, symptomatic therapy, i.e. therapy for or intended to restrict or abort symptomatic attack when it occurs, for example anti-inflammatory (e.g. corticosteroid) or bronchodilatory.

Other inflammatory or obstructive airways diseases and conditions to which the invention is applicable include acute lung injury (ALI), acute/adult respiratory distress syndrome (ARDS), idiopathic pulmonary fibrosis, fibroid lung, airway hyperresponsiveness, dyspnea, pulmonary fibrosis, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Compounds of the invention are also useful for treating respiratory viral infections, which exacerbate underlying chronic conditions such as asthma, chronic bronchitis, COPD, otitis media, and sinusitis. The respiratory viral infection treated may be associated with secondary bacterial infection, such as otitis media, sinusitis or pneumonia.

Compounds of the invention are also useful in the treatment of inflammatory conditions of the skin, for example psoriasis, atopic dermatitis, lupus erythematosus, and other inflammatory or allergic conditions of the skin.

Compounds of the invention may also be used for the treatment of other diseases or conditions, in particular diseases or conditions having an inflammatory component, for example, diseases affecting the nose including allergic rhinitis, e.g. atrophic, chronic, or seasonal rhinitis, inflammatory conditions of the gastrointestinal tract, for example inflammatory bowel disease such as ulcerative colitis and Crohn's disease, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

Compounds of the invention are also useful in the treatment of endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), Helicobacter pylori associated gastritis, and cancers, particularly the growth of ovarian cancer.

Compounds of the invention are also useful for treating symptoms caused by viral infection in a human which is caused by the human rhinovirus, other enterovirus, coronavirus, herpes viruses, influenza virus, parainfluenza virus, respiratory syncytial virus or an adenovirus. Compounds of the invention are also useful for treating pancreatitis.

The effectiveness of a compound of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med* 180:1135-40 (1994); Sekido et al, *Nature* 365:654-57 (1993); Modelska et al., *Am. J. Respir. Crit. Care. Med* 160:1450-56 (1999); and Laffon et al *Am. J. Respir. Crit. Care Med.* 160:1443-49 (1999).

In some embodiments, provided herein are methods for the treatment of a condition or disease mediated by CXCR2, for example an inflammatory or allergic condition, particularly an inflammatory or obstructive airways disease, which comprises administering to a subject, particularly a human subject, in need thereof an effective amount of a compound of formula (A), (A1), (A2), (I) or (Ia1) in a free or pharmaceutically acceptable salt form as hereinbefore described. In another aspect the invention provides the use of a compound of formula (A), (A1), (A2), (I) or (Ia1), in free or pharmaceutically acceptable salt form, as hereinbefore described for the manufacture of a medicament for the treatment of a condition or disease mediated by CXCR2, for example an inflammatory or allergic condition or disease, particularly an inflammatory or obstructive airways disease.

The compounds of formula (A), (A1), (A2), (I) and (Ia1) described herein are also useful as co-therapeutic compounds for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CCR6 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

The compounds of the present invention are accordingly useful in the prevention and treatment of a wide variety of inflammatory and immunoregulatory disorders and diseases.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non-sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide, (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®), (v) an antibody against CTLA-4, PD1, or PD-L1. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In some embodiments, a method of treating a CXCR2- and/or CCR6-mediated disease or condition in a subject in need thereof is provided, said method comprising administering an effective amount of a compound of the present disclosure or a pharmaceutically acceptable salt thereof, or a pharmaceutical composition comprising a compound of the present disclosure, to said subject. In some embodiments, the disease or condition is an acute or chronic inflammatory disorder. In some embodiments, the acute or chronic inflammatory disorder is psoriasis, dry eye disease, atherosclerosis, discoid lupus erythematosus, rheumatoid arthritis, lupus, radiation induced fibrotic lung disease, autoimmune bullous dermatosis (AIBD), chronic obstructive pulmonary disease, or ozone-induced airway inflammation. In some embodiments, the acute or chronic inflammatory disorder is psoriasis.

In some embodiments, the disease is a cancer. In some embodiments, the cancer is selected from the group consisting of cutaneous T-cell lymphoma, non-Hodgkin lymphoma, Mycosis fungoides, Pagetoid reticulosis, Sézary syndrome, Granulomatous slack skin, Lymphomatoid papulosis, Pityriasis lichenoides chronica, Pityriasis lichenoides et varioliformis acuta, CD30+ cutaneous T-cell lymphoma, Secondary cutaneous CD30+ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins Lymphoma (HL), Head and neck tumor; Squamous cell carcinoma, rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma. In some embodiments, the disease is colorectal cancer. In some embodiments, the disease is cutaneous T-cell lymphoma.

In some embodiments, the compound is used alone or in combination with one or more other anti-cancer therapies. In some embodiments, the compound is used in combination with one or more of a cytotoxic chemotherapy, an anti-cancer vaccine, an anti-tumor vaccine, an anti-immunocytokine therapy, an immunocytokine therapy, a checkpoint inhibitor, and a chimeric antigen receptor (CAR) T cell receptors, gene transfer therapy. In some embodiments, the compound is used in combination with at least a checkpoint inhibitor. In some embodiments, the compound is used in combination with one or more of a compound that blocks the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO). In some embodiments, the compound is used in combination with one or more of an agonist of OX40, GITR, 4-1BB, ICOS, STING or CD40.

In some embodiments, the compounds of the disclosure, or a pharmaceutically acceptable salt and/or a prodrug thereof, or compositions of the disclosure are administered to treat colorectal cancer, metastasis, advanced cutaneous T-cell lymphoma, pancreatic cancer, non-Hodgkin lymphoma, mycosis fungoides, pagetoid reticulosis, Sézary syndrome, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, lennert lymphoma, subcutaneous T-cell lymphoma, angiocentric lymphoma, blastic NK-cell lymphoma, B-cell Lymphomas, hodgkins Lymphoma (HL), dry eye disease, atherosclerosis, or discoid lupus erythematosus.

In some embodiments, the compounds of the disclosure, or a pharmaceutically acceptable salt and/or a prodrug thereof, or compositions of the disclosure are administered to treat insulin dependent diabetes, cystitis, islet cell transplant rejection; kidney transplant rejection; liver transplant rejection; lung transplant rejection, COPD, or influenza.

In some embodiments, the compounds of the disclosure, or a pharmaceutically acceptable salt and/or a prodrug thereof, or compositions of the disclosure are administered to treat melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and/or fibroma.

Combination Therapies

The compounds of the disclosure can be supplied alone or in conjunction with one or more other drugs. Possible combination partners can include, additional anti-angiogenic factors and/or chemotherapeutic agents (e.g., cytotoxic agents) or radiation, a cancer vaccine, an immunomodulatory agent, a checkpoint inhibitor, an anti-vascular agent, a signal transduction inhibitor, an antiproliferative agent, an apoptosis inducer, an alkylation agent, a nitrosourea agent, an antimetabolite, an anticancer antibiotic, a vegetable-origin alkaloid, a topoisomerase inhibitor, an hormone drug, an hormone antagonist, an aromatase inhibitor, a P-glycoprotein inhibitor, a platinum complex derivative, an anti-fibrotic agent, radiotherapy, a radiotherapeutic agent and a gene expression modulatory agent.

Examples of other therapeutic agents that may be combined with a compound or composition of the present disclosure, either administered separately or in the same pharmaceutical composition, include, but are not limited to: modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CR1, ChemR23, C5aR, C5a, and C5, or any combination thereof. In some embodiments, the modulator is an antagonist.

Examples of other therapeutic agents that may be combined with a compound or composition of the present disclosure, either administered separately or in the same pharmaceutical compositions, include, but are not limited to: a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, cytokines, vaccines, vaccine adjuvants, GM-CSF, M-CSF, G-CSF, interferon-a, beta, or gamma, IL-1, IL-2, IL-3, IL-12, Poly (I:C), CPG, cyclophosphamide, analogs of cyclophosphamide, anti-TGF and imatinib (Gleevac), a mitosis inhibitor, akinas inhibitor, paclitaxel, Sunitinib (Sutent), antiangiogenic agents, an aromatase inhibitor, letrozole, an A2a adenosine receptor (A2AR) antagonist, an adenosine receptor modulator, an A3 adenosine receptor modulator, an angiogenesis inhibitor, anthracyclines, oxaliplatin, doxorubicin, TLR4 antagonists, IL-18 antagonists, a Btk tyrosine kinase inhibitor, an Erbb2 tyrosine kinase receptor inhibitor; an Erbb4 tyrosine kinase receptor inhibitor, an mTOR inhibitor, a Thymidylate synthase inhibitor, an EGFR tyrosine kinase receptor inhibitor, an Epidermal growth factor antagonist, a Fyn tyrosine kinase inhibitor, a Kit tyrosine kinase inhibitor, a Lyn tyrosine kinase inhibitor, a NK cell receptor modulator, a PDGF receptor antagonist, a PARP inhibitor, a Poly ADP ribose polymerase inhibitor, a Poly ADP ribose polymerase 1 inhibitor, a Poly ADP ribose polymerase 2 inhibitor, a Poly ADP ribose polymerase 3 inhibitor, a Galactosyltransferase modulator, a Dihydropyrimidine dehydrogenase inhibitor, an Orotate phosphoribosyltransferase inhibitor, a Telomerase modulator, a Mucin 1 inhibitor, a Mucin inhibitor, a Secretin agonist, a TNF related apoptosis inducing ligand modulator, an IL17 gene stimulator, an Interleukin 17E ligand, a Neurokinin receptor agonist, a Cyclin G1 inhibitor, a checkpoint inhibitor, a PD-1 inhibitor, a PD-L1 inhibitor, a CTLA4 inhibitor, a Topoisomerase I inhibitor, an Alk-5 protein kinase inhibitor, a Connective tissue growth factor ligand inhibitor, a Notch-2 receptor antagonist, a Notch-3 receptor antagonist, a Hyaluronidase stimulator, a MEK-1 protein kinase inhibitor, a Phosphoinositide-3 kinase inhibitor, a MEK-2 protein kinase inhibitor, a GM-CSF receptor modulator; TNF alpha ligand modulator, a Mesothelin modulator, an Asparaginase stimulator, a CSF2 gene stimulator, a Caspase-3 stimulator; Caspase-9 stimulator, a PKN3 gene inhibitor, a Hedgehog protein inhibitor; Smoothened receptor antagonist, an AKT1 gene inhibitor, a DHFR inhibitor, a Thymidine kinase stimulator, a CD29 modulator, a Fibronectin modulator, an Interleukin-2 ligand, a Serine protease inhibitor, a D40LG gene stimulator; TNFSF9 gene stimulator, a 2 oxoglutarate dehydrogenase inhibitor, a TGF-beta type II receptor antagonist, an Erbb3 tyrosine kinase receptor inhibitor, a Cholecystokinin CCK2 receptor antagonist, a Wilms tumor protein modulator, a Ras GTPase modulator, an Histone deacetylase inhibitor, a Raf B protein kinase inhibitor, a Cyclin-dependent kinase 4 inhibitor A modulator, an Estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a TIGIT inhibitor, a NKG2A inhibitor, a GALS inhibitor, a LAG3 inhibitor, a PD-1H inhibitor, a PD96 inhibitor, a VISTA inhibitor, a KIR inhibitor, a 2B4 inhibitor, a CD160 inhibitor, a CD66e modulator, an Angiotensin II receptor antagonist, a Connective tissue growth factor ligand inhibitor, a Jak1 tyrosine kinase inhibitor, a Jak2 tyrosine kinase inhibitor, a dual Jak1/Jak2 tyrosine kinase inhibitor, an Angiotensin converting enzyme 2 stimulator, a Growth hormone receptor antagonist, a Galectin-3 inhibitor, a Checkpoint kinase 2 modulator, a Sodium glucose transporter-2 inhibitor, a Endothelin ET-A antagonist, a Mineralocorticoid receptor antagonist, an Endothelin ET-B antagonist, an Advanced glycosylation product receptor antagonist, an Adrenocorticotrophic hormone ligand, a Farnesoid X receptor agonist, a G-protein coupled bile acid receptor 1 agonist, an Aldose reductase inhibitor, a Xanthine oxidase inhibitor, a PPAR gamma agonist, a Prostanoid receptor antagonist, a FGF receptor antagonist, a PDGF receptor antagonist, a TGF beta antagonist, a P3 protein modulator, a p38 MAP kinase inhibitor, a VEGF-1 receptor antagonist, a Protein tyrosine phosphatase beta inhibitor, a Tek tyrosine kinase receptor stimulator, a PDE 5 inhibitor, a Mineralocorticoid receptor antagonist, an ACE inhibitor, a I-kappa B kinase inhibitor, a NFE2L2 gene stimulator, a Nuclear factor kappa B inhibitor, a STAT3 gene inhibitor, a NADPH oxidase 1 inhibitor, a NADPH oxidase 4 inhibitor, a PDE 4 inhibitor, a Renin inhibitor, a FURIN gene inhibitor, a MEKK-5 protein kinase inhibitor, a Membrane copper amine oxidase inhibitor, an Integrin alpha-V/beta-3 antagonist, an Insulin sensitizer, a Kallikrein 1 modulator, a Cyclooxygenase inhibitor, a Complement C3 modulator, a Tubulin binding agent, a Macrophage mannose receptor 1 modulator, a Phenylalanine hydroxylase stimulator, Denileukin diftitox, Bexarotene, Vorinostat, Romidepsin, Pralatrexate, prednisone, prednisolone, CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, CCX168-M1, bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, nab-paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX, KY-1003, olmesartan medoxomil, candesartan, PBI-4050, baricitinib, GSK-2586881, losartan, dapagliflozin propanediol, pegvisomant, GR-MD-02, canagliflozin, irbesartan, FG-3019, atrasentan, finerenone, sparsentan, bosentan, defibrotide, fimasartan, azeliragon, pyridoxamine, corticotropin, INT-767, epalrestat, topiroxostat, SER-150-DN, pirfenidone, VEGFR-1 mAb, AKB-9778, PF-489791, SHP-627, CS-3150, imidapril, perindopril, captopril, enalapril, lisinopril, Zofenopril, Lisinopril, Quinapril, Benazepril, Trandolapril, Cilazapril, Fosinopril, Ramipril, bardoxolone methyl, irbesartan+propagermanium, GKT-831, MT-3995, TAK-648, TAK-272, GS-4997, DW-1029M, ASP-8232, VPI-2690B, DM-199, rhein, PHN-033, GLY-230, and sapropterin, sulodexide, lirilumab, IPH-4102, IPH-2101, IMP-321, BMS-986016, MGD-013, LAG-525, durvalumab, monalizumab, MCLA-134, MBG-453, CA-170, AUPM-170, AUPM-327, resminostat, ipilimumab, BGB-A317, tremelimumab, REGN-2810, AZD-5069, masitinib, binimetinib, trametinib, ruxolitinib, dabrafenib, linaclotide, ipilimumab, apatinib, nintedanib, cabozantinib, pazopanib, belinostat, panitumumab, guadecitabine, vismodegib, vemurafenib, dasatinib, tremelimumab, bevacizumab, oxaliplatin, aflibercept, vandetanib, everolimus, thalidomide, veliparib, encorafenib, napabucasin, alpelisib, axitinib, cediranib, necitumumab, ramucirumab, irofulven, trifluridine+tipiracil, donafenib, pacritinib, pexastimogene devacirepvec, tivantinib, GNR-011, talaporfin, piclidenoson, decitabine, ganitumab, panobinostat, rintatolimod, polmacoxib, levofolinate, famitinib, votumumab, tivozanib, entinostat, plitidepsin, lefitolimod, OSE-2101, vitespen, TroVax, bromocriptine, midostaurin, fosbretabulin, fruquintinib, ganetespib, brivanib, anlotinib, L19-TNF-alpha, racotumomab, Novaferon, raltitrexed, enzastaurin, GM-CT-01, arcitumomab, denileukin diftitox, bexarotene, vorinostat, romidepsin, pralatrexate, prednisone, prednisolone or any combination thereof.

Examples of other therapeutic agents that may be combined with a compound or composition of the present disclosure, either administered separately or in the same pharmaceutical composition, include, but are not limited to: MP-1032, secukinumab, betamethasone, ciclosporin, certolizumab, certolizumab pegol, VTP-43742, bimekizumab, GSK-2982772, amiselimod, KD-025, ustekinumab, etanercept, guselkumab, apremilast, dimethyl fumarate+ethyl hydrogen fumarate calcium+ethyl hydrogen fumarate magnesium+ethyl hydrogen fumarate zinc, infliximab, risankizumab, ixekizumab, mometasone, brodalumab, adalimumab, tofacitinib, olopatadine, tazarotene, dimethyl fumarate, Trichuris suis ova, BTT-1023, voclosporin, seletalisib, INV-103, piclidenoson, GR-MD-02, PRX-167700, LYC-30937 EC, namilumab, LY-3074828, LEO-32731, acitretin, calcipotriol, WBI-1001, clobetasol propionate, betamethasone, ZPL-389, bertilimumab, AKP-11, ZPL-521, crisaborole, CLS-008, IMO-8400, bleselumab, calcipotriol, tildrakizumab, KX-01, 18C3, DSXS-1411, DLX-105, remetinostat, Prurisol, S-414114, GLG-801, inecalcitol, maxacalcitol+betamethasone, TAB-08, alefacept, ulobetasol, toreforant, calcipotriol, betamethasone dipropionate, tregalizumab, CJM-112, neihulizumab, betamethasone valerate, P-3072, P-3073, methotrexate, GSK2981278A, calcipotriol+betamethasone dipropionate, LEO-124249, AVX-001, calcipotriol+betamethasone dipropionate, dimethyl fumarate, halobetasol propionate+tazarotene, calcipotriol, calcipotriol+betamethasone, alitretinoin, DFD-06, rose bengal sodium, C-82, TU-2100, CT-327, pefcalcitol, fluocinonide, clobetasol propionate+tretinoin, GK-664-S, tazarotene+betamethasone, itolizumab, betamethasone valerate, IMO-3100, PUR-0110, LEO-29102, orilotimod, maxacalcitol, IR-502, myristyl nicotinate, aganirsen, methotrexate, mometasone furoate, BCG polysaccharide+nucleic acid injection, lithium succinate, orilotimod, LAS-41004, calcitriol, GMDP, mometasone furoate, MOL-4249, aminopterin, tacalcitol, dithranol, halometasone, anapsos, osimertinib, and AGEN-1884.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of Formula (A), (A1), (A2), (I) or (Ia1), or a pharmaceutically acceptable salt thereof, and instructions for its administration are provided. In one embodiment, kits comprising a compound of Formula (A), (A1), (A2), (I) and (Ia1), or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

General Synthetic Procedure

The embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in the scheme below, and the particular examples that follow. Schemes 1 and 2 are provided as further embodiment of the disclosure and illustrate general methods which were used to prepare compounds of the present disclosure including compounds of Formula (A), (A1), (A2), (I) and (Ia1), and which can be used to prepare additional compounds having the Formula (A), (A1), (A2), (I) and (Ia1). The methodology is compatible with a wide variety of functionalities.

Scheme 1

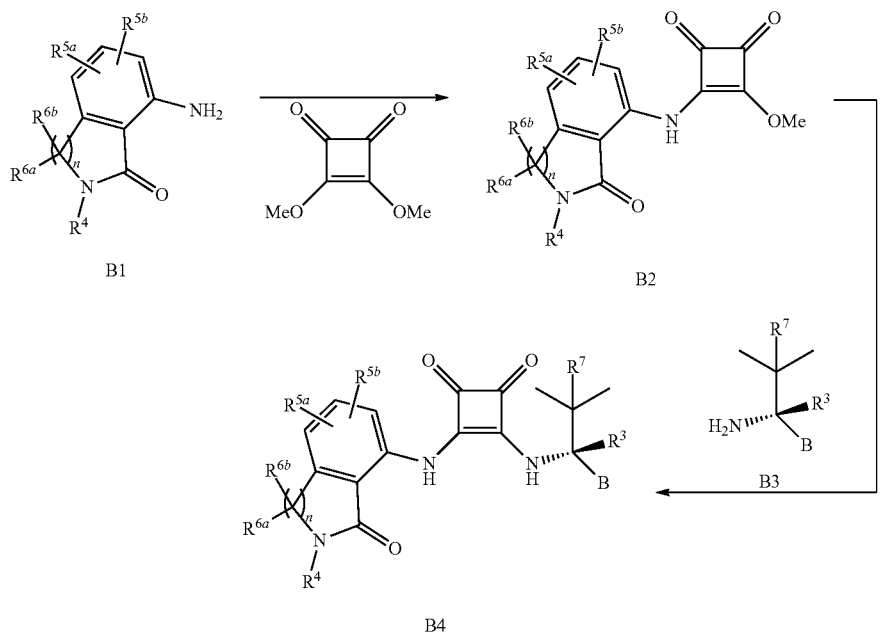

The amino group of B1 can be reacted with 3,4-dimethoxycyclobut-3-ene-1,2-dione to provide B2. B2 can then be reacted with the amino group of B3 to provide B4.

Scheme 2

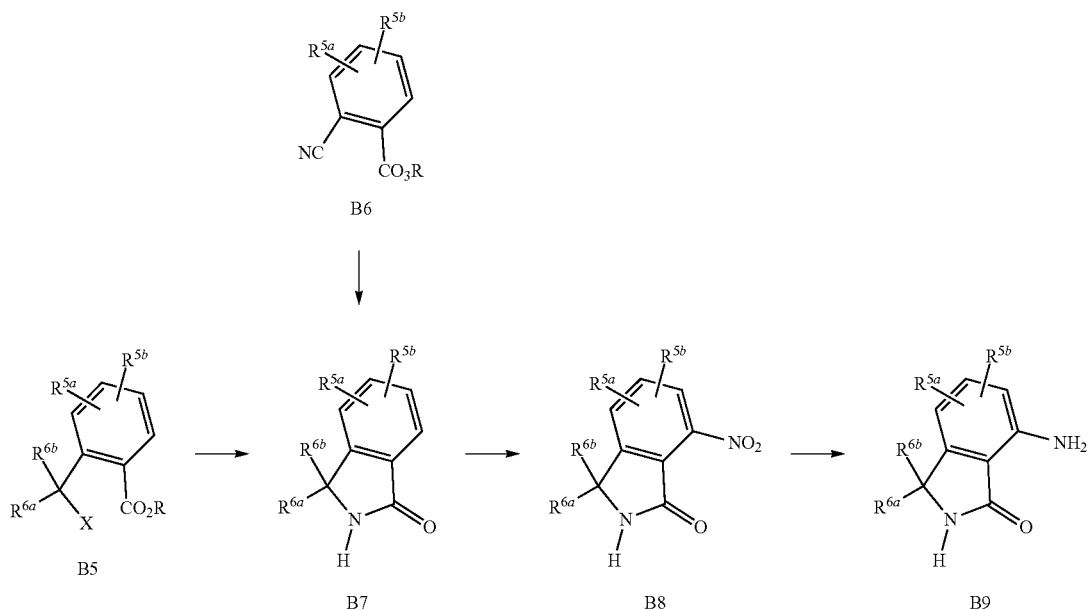

B7 can be obtained by reduction of the cyano group in B6, for example by hydrogenation, followed by cyclization. Alternatively, B5 (where X represents a leaving group such as a halogen or a tosylate and where R is an alkyl group), can be reacted with $NH_3$ to form the cyclized product B7. B7 can be reacted with $HNO_3$ to introduce the nitro group in presence of an acid such as sulfuric acid to give B8. Subsequent reduction of the nitro group in B8 by for example hydrogenation can provide B9.

EXAMPLES

The following examples are offered to illustrate, but not to limit the claimed invention.

Reagents and solvents used below can be obtained from commercial sources such as Aldrich Chemical Co. (Milwaukee, Wis., USA). ¹H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium(0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of 3-[[(1R)-2,2-dimethyl-1-(5-methyl-2-furyl)propyl]amino]-4-ethoxy-cyclobut-3-ene-1,2-dione

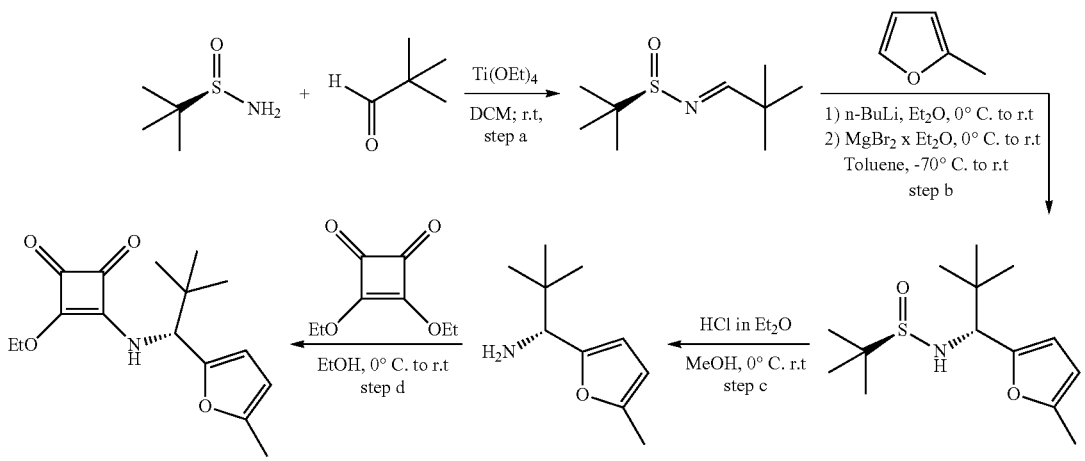

Step a:

To a 3-neck 5 L round bottom flask equipped with a mechanical stirrer were added (R)-2-methylpropane-2-sulfinamide (100 g, 0.825 mol), 2,2-dimethylpropanal (78.2 g, 0.907 mol), and titanium tetraethoxide (414.1 g, 1.815 mol) in dichloromethane (1.5 L). The reaction mixture was stirred at room temperature for 12 h, then sodium sulfate decahydrate (260 g) was added, followed by Celite (500 g). The mixture was stirred at room temperature for 5 h, filtered through Celite and rinsed with dichloromethane (1 L). The filtrate was concentrated in vacuo and dried under vacuum overnight to give [N(E),S(R)]—N-(2,2-dimethylpropylidene)-2-methyl-propane-2-sulfinamide (150 g, 96%) as a brown oil which was used in the next step without further purification. ¹H NMR (400 MHz, CD$_3$OD) δ 7.80 (s, 1H), 1.10 (s, 9H), 1.08 (s, 9H); MS: (ES) m/z calculated for C$_{19}$H$_{19}$NOS[M+H]$^+$ 190.1. found 190.1.

Step b:

A 1-L, 3 neck flask equipped with an addition funnel was charged with 2-methylfuran (31.1 mL, 345.1 mmol, 1.5 equiv.) and anhydrous Et$_2$O (300 mL) and then cooled in an ice bath. n-BuLi in hexanes (2.5 M, 120 mL, 299 mmol, 1.3 equiv) was added drop wise over approximately 35 min. The mixture was stirred at 0° C. for 30 min then at room temperature for 40 min, then it was again cooled to 0° C. Solid MgBr$_2$×Et$_2$O (77.2 g, 299.1 mmol, 1.3 equiv) was added and the mixture was stirred at 0° C. for 30 min, then at room temperature for 20 min.

In 5-L 3 neck flask equipped with mechanical stirring and internal thermometer, the imine from Step a (43.5 g, 230.1 mmol) was dissolved in anhydrous toluene (1.2 L) and this was cooled to an internal temperature of −70° C. The lithium salt solution from the above paragraph was added over 56 minutes, keeping the internal temperature between −70 to −67.8° C. After the addition, the reaction mixture was stirred at −70° C. for 1 h then at room temperature overnight. The reaction mixture was slowly quenched with saturated aqueous $NH_4Cl$ (400 mL) and water (400 mL), then stirred at room temperature for 15 min. The organic layer was separated and washed with brine (200 mL). The combined aqueous layers were extracted with ethyl acetate (300 mL). The organics were dried over $MgSO_4$, filtered and evaporated to give an orange oil. The crude product was dissolved in hexanes (500 mL) and allowed to crystallize at −20° C. overnight to give a yellow solid. The solid was filtered and the mother liquor was evaporated and crystallized again from hexanes (50 mL) to give the product (51.9 g, 83%) as the pure diastereomer. MS: (ES) m/z calculated for $C_{14}H_{26}NO_2S$ $[M+H]^+$ 272.2. found 272.2.

Step c:

The N-[(1R)-2,2-dimethyl-1-(5-methyl-2-furyl)propyl]-2-methyl-propane-2-sulfinamide from the previous step (51.9 g, 191.5 mmol) was dissolved in methanol (100 mL) and cooled in an ice-bath, then 2M HCl in ether (191.5 mL, 383.0 mmol, 2 equiv) was added. The cooling bath was removed and the reaction mixture was stirred at room temperature for 2 h. Solvents were removed in vacuo, and anhydrous ether (300 mL) was added to the residue. The resulting mixture was filtered. To the solid was added water (100 mL) and 1M aqueous NaOH (200 mL). The product was extracted with dichloromethane (3×100 mL) and the combined organic layers were dried over $MgSO_4$, filtered and evaporated to give a yellow oil (27.2 g, 85%). MS: (ES) m/z calculated for $C_{10}H_{15}O[(M-NH_3)+H]^+$ 151.1. found 151.1.

Step d:

3,4-Diethoxycyclobut-3-ene-1,2-dione (15.9 g, 93.5 mmol, 1.05 equiv) was dissolved in anhydrous ethanol (150 mL) and cooled in an ice-bath. Then a solution of (1R)-2,2-dimethyl-1-(5-methyl-2-furyl)propan-1-amine (14.9 g, 89.0 mmol) in anhydrous ethanol (50 mL) was added drop wise and the reaction mixture was stirred at room temperature overnight. The excess solvent was evaporated and the residue was stirred with hexanes (500 mL) until a solid precipitated. The solid was filtered, washed with hexanes (100 mL) and dried under high vacuum to afford the title compound (24.4 g, 94%). MS: (ES) m/z calculated for $C_{16}H_{22}NO_4[M+H]^+$ 292.1. found 292.1.

Example 2: Synthesis of 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]benzoic acid

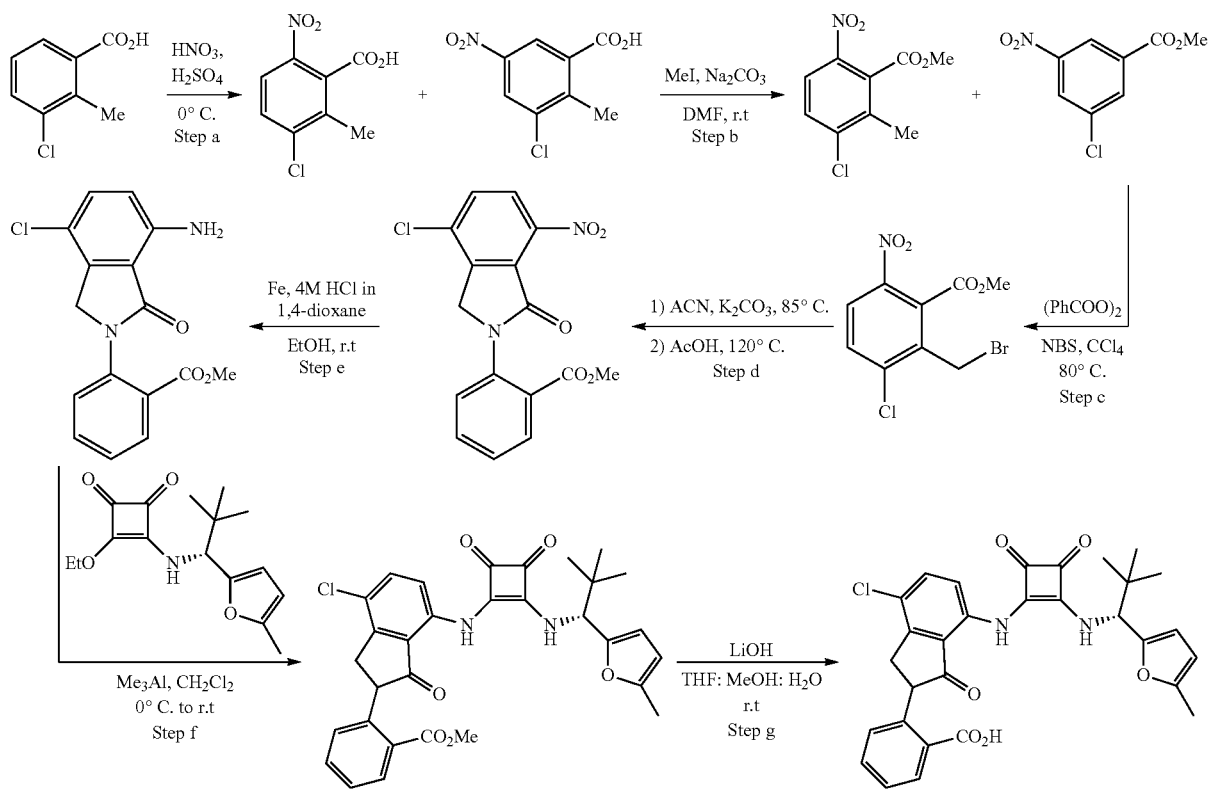

Step a:

A 4-L Erlenmeyer flask containing 3-chloro-2-methylbenzoic acid (100.0 g, 0.586 mole) in concentrated $H_2SO_4$ (500 mL) was cooled in an ice-bath. 70% $HNO_3$ (45.2 mL, 0.703 mole, 1.2 equiv.) was added drop-wise and reaction mixture was stirred at 0° C. for 2 h, then carefully quenched with ice and diluted to 4 L with cold water. A white solid was filtered, washed with water and dried under high vacuum (127 g, quant) to afford a mixture of 3-chloro-2-methyl-6-nitro-benzoic acid and 3-chloro-2-methyl-5-nitro-benzoic acid in 3:1 ratio. MS: (ES) m/z calculated for $C_8H_5ClNO_4$ [M−H]⁻ 214.0. found 214.0.

Step b:

The mixture of isomeric acids from the previous step (50 g, 232.0 mmol) was dissolved in anhydrous DMF (200 mL), anhydrous $Na_2CO_3$ (27.0 g, 255.2 mmol, 1.1 equiv.) was added, and the reaction was stirred at room temperature for 30 minutes. Methyl iodide (15.9 mL, 255.2 mmol, 1.1 equiv.) was added and stirring was continued at room temperature for 3 h. The reaction mixture was diluted with water (1.2 L) and the product was extracted using $Et_2O$ (3×250 mL). The combined organic layers were washed with brine (4×100 mL), dried over $MgSO_4$, filtered and evaporated to give a yellow oil (49.7 g, 93%).

Step c:

The mixture of isomeric esters from the previous step (49.7 g, 216.5 mmol) was dissolved in $CCl_4$ (400 mL) and N-bromosuccinimide (57.8 g, 324.7 mmol, 1.5 equiv.) was added followed by benzoyl peroxide (10.4 g, 43.2 mmol, 0.20 equiv). The reaction mixture was stirred under reflux overnight then cooled to room temperature and filtered. The filtrate was evaporated and the residue was purified by silica gel chromatography (100:0 to 9:1 Hex:EtOAc) to give yellow solid as a single isomer (44.1 g, 66%). ¹H NMR (400 MHz, $CDCl_3$) δ 8.07 (d, J=9.2 Hz, 1H), 7.65 (d, J=9.2 Hz, 1H), 4.63 (s, 2H), 4.01 (s, 3H).

Step d:

A suspension of the product from the previous step (616 mg, 2 mmol), methyl anthranilate (302 mg, 2 mmol) and $K_2CO_3$ (553 mg, 4 mmol) in anhydrous acetonitrile was heated to 85° C. in a closed 40 mL reaction vial overnight. The reaction was then cooled to room temperature, diluted with ethyl acetate and filtered. The filtrate was concentrated to afford the uncyclized crude product (800 mg). This crude product was dissolved in acetic acid (5 mL) and heated to 120° C. overnight to afford the cyclized product. It was diluted with ethyl acetate, washed with water and saturated aqueous $NaHCO_3$, then dried ($Na_2SO_4$), filtered, and concentrated. The residue was adsorbed on silica and purified by silica gel chromatography (0-50% ethyl acetate in hexanes) to afford the desired product (350 mg, 50%). MS: (ES) m/z calculated for $C_{16}H_{11}ClN_2O_5$[M+H]⁺ 347.0. found 347.0.

Step e:

To a stirred mixture of methyl 2-(4-chloro-7-nitro-1-oxo-isoindolin-2-yl)benzoate (347 mg, 1 mmol) in ethanol at room temperature was added iron powder (224 mg, 4 mmol), followed by 4 M HCl in dioxane (2 mL, 8 mmol). The reaction mixture was stirred at room temperature for 1 h then concentrated in vacuo. The residue was diluted with ethyl acetate and neutralized with saturated sodium bicarbonate solution and extracted with ethyl acetate (2×5 mL). The combined organic layers were dried ($Na_2SO_4$), filtered, and concentrated in vacuo. The crude product was purified by silica gel chromatography (0-100% ethyl acetate in hexanes) to afford methyl 2-(7-amino-4-chloro-1-oxo-isoindolin-2-yl)benzoate as a yellow powder (200 mg, 0.63 mmol, 63%). MS: (ES) m/z calculated for $C_{16}H_{13}ClN_2O_3$ [M+H]⁺ 317.0. found 317.0.

Step f:

A solution of methyl 2-(7-amino-4-chloro-1-oxo-isoindolin-2-yl)benzoate (109 mg, 0.34 mmol) and 3-[[(1R)-2,2-dimethyl-1-(5-methyl-2-furyl)propyl]amino]-4-ethoxy-cyclobut-3-ene-1,2-dione (100 mg, 0.34 mmol) in dichloromethane was stirred at 0° C. and a 2M solution of trimethylaluminium in toluene (0.68 mL, 1.36 mmol) was added. The solution was stirred at 0° C. for 1 hour, then warmed to room temperature and stirred for another hour. The reaction mixture was cooled to 0° C. and quenched with 5% hydrochloric acid solution and diluted with water then extracted with ethyl acetate (2×5 mL). The organic layers were dried ($Na_2SO_4$), filtered, and concentrated in vacuo. The crude product was purified by HPLC to afford methyl 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]benzoate as a yellow solid (65 mg, 0.12 mmol, 34%). MS: (ES) m/z calculated for $C_{30}H_{28}ClN_3O_6$ [M−H]⁺ 560.0. found 560.0.

Step g:

To a solution of methyl 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]benzoate (56 mg, 0.1 mmol) in tetrahydrofuran (1 mL) and methanol (0.1 mL) and water (0.1 mL) was added excess lithium hydroxide. The resulting mixture was stirred at room temperature for 1 h. The reaction was acidified with a 5% hydrochloric acid solution and extracted with ethyl acetate. The organic layers were dried ($Na_2SO_4$), filtered, and concentrated in vacuo. The crude product was purified by HPLC to afford 2-[4-chloro-7-[[2-[[(1R)-2,2-dimethyl-1-(5-methyl-2-furyl)propyl[amino]-3,4-dioxo-cyclobuten-1-yl]amino]-1-oxo-isoindolin-2-yl]benzoic acid as a yellow solid (30 mg, 0.05 mmol, 50%). ¹H NMR (400 MHz, DMSO-$d_6$) δ 9.89 (s, 1H), 9.06 (d, J=10 Hz, 1H), 7.85 (dd, J=7.6, 1.6 Hz, 1H), 7.65-7.41 (m, 5H), 6.10 (d, J=2.6 Hz, 1H), 5.95 (d, J=2.6 Hz, 1H), 5.03 (d, J=10.4 Hz, 1H), 4.80 (dd, J=20, 10 Hz, 2H), 2.20 (s, 3H), 0.87 (s, 9H). MS: (ES) m/z calculated for $C_{29}H_{26}ClN_3O_6$[M−H]⁻ 546.0. found 546.0.

Example 3: 3-[[(1R)-2,2-dimethyl-1-(5-methyl-2-furyl)propyl]amino]-4-[(5-fluoro-3-oxo-isoindolin-4-yl)amino]cyclobut-3-ene-1,2-dione

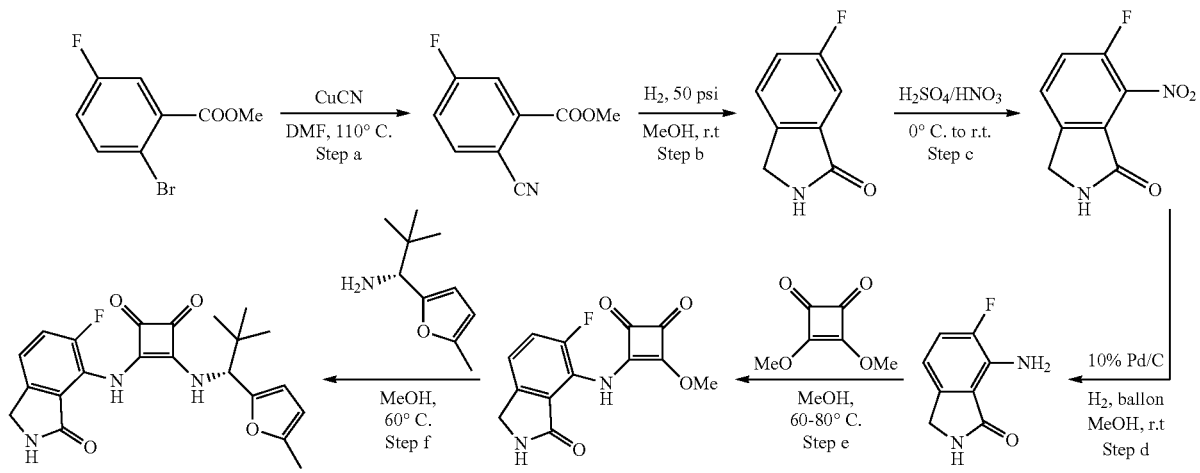

Step a:

A 500 mL round-bottom flask was charged with methyl 2-bromo-5-fluorobenzoate (48 g, 206 mmol), copper cyanide (37 g, 412 mmmol) and DMF (200 mL).

The mixture was heated at 110° C. overnight and then cooled to room temperature. Ether (1.5 L) and Celite (100 g) were added and the mixture was stirred at room temperature for 30 minutes. The solid was filtered and the filtrate was washed with brine (3×200 mL) and then dried over $MgSO_4$. The solvent was evaporated under reduced pressure to give the desired product as a colorless solid (31 g, 84%). MS: (ES) m/z calculated for $C_9H_7FNO_2[M+H]^+$ 180.1. found 180.1.

Step b:

To a solution of methyl 2-cyano-5-fluorobenzoate (10 g, 56 mmol) in methanol (200 mL) was added 10% Pd—C (1.0 g) at room temperature. The resulting mixture was stirred under a hydrogen (50 psi) atmosphere overnight. The reaction mixture was filtered through Celite and the filtrate was concentrated under reduced pressure to give the desired product as a colorless solid (8.0 g, 90%). MS: (ES) m/z calculated for $C_8H_7FNO$ $[M+H]^+$ 152. found 152.

Step c:

To a 0° C. suspension of 6-fluoroisoindoline-1-one (8.0 g, 5.3 mmol) in concentrated $H_2SO_4$ was added drop-wise a pre-cooled mixture of concentrated $H_2SO_4$ (26 mL) and nitric acid (6 mL) while keeping the reaction mixture below 5° C. After addition, the reaction mixture was slowly warmed to room temperature during overnight. Ice (50 g) was added to the mixture and the solid was collected and dried, then washed with MTBE (50 mL) and ethyl acetate (50 mL) to give the desired product as a light yellow solid (5.1 g, 50%). MS: (ES) m/z calculated for $C_8H_6FN_2O_3[M+H]^+$ 197.2. found 197.2.

Step d:

A solution of 6-fluoro-7-nitroisoindoline-1-one (11.3 g, 57 mmol) and 10% Pd/C (50% wet, 6.2 g, 2.9 mmol, 0.05 equiv) in THF (300 mL) was stirred under a hydrogen atmosphere (balloon) overnight. The solid was filtered through Celite and the filtrate was concentrated under reduced pressure to give a colorless solid, which was purified by silica gel chromatography (100% ethyl acetate) to give the desired product as a white solid (6.4 g, 67%). MS: (ES) m/z calculated for $C_8H_9FN_2O[M+H]^+$ 168.1. found 168.1.

Step e:

A mixture of 7-amino-6-difluoro-isoindolin-1-one (4.4 g, 26 mmol) and 3,4-dimethoxycyclobut-3-ene-1,2-dione (7.4 g, 52 mmol) in anhydrous methanol (30 mL) was stirred at 60° C. for overnight and then at 80° C. for 5 h. The reaction mixture was evaporated and the residue was stirred in ethyl acetate (200 mL) at 50° C. for 30 min, then cooled down to room temperature. The mixture was filtered and dried to give a light yellow color solid (5.0 g, 70%). MS: (ES) m/z calculated for $C_{13}H_{10}FN_2O_4[M+H]^+$ 277.2. found 277.2.

Step f:

Anhydrous ethanol (10 mL) was added to a mixture of 3-[(7-fluoro-3-oxo-isoindolin-4-yl)amino]-4-methoxy-cyclobut-3-ene-1,2-dione (1.5 g, 5.4 mmol) and (1R)-2,2-dimethyl-1-(5-methyl-2-furyl)propan-1-amine (1.1 g, 6.5 mmol) and this mixture was stirred at 60° C. overnight. The reaction was allowed to cool to room temperature, dissolved in minimal dichloromethane, and adsorbed onto silica gel. The product was purified by silica gel chromatography (40% ethyl acetate in dichloromethane) to give a white solid (800 mg, 45%). $^1H$ NMR (400 MHz, DMSO-$d_6$) δ 9.59 (s, 1H), 8.65 (s, 1H), 8.35 (d, J=10.4 Hz, 1H), 7.41 (dd, J=11.6, 8.4 Hz, 1H), 6.18 (dd, J=4.0, 8.4 Hz, 1H), 6.12 (d, J=3.2 Hz, 1H), 5.98 (d, J=2.0 Hz, 1H), 4.97 (d, J=4.10 Hz, 1H), 4.26 (s, 2H), 2.22 (s, 3H), 0.90 (s, 9H). MS: (ES) m/z calculated for $C_{22}H_{22}FN_3O_4[M-H]^-$ 410.0. found 410.0.

Example 4: Synthesis of 3-[(5,7-difluoro-3-oxo-isoindolin-4-yl)amino]-4-[[(1R)-2,2-dimethyl-1-(5-methyl-2-furyl)propyl]amino]cyclobut-3-ene-1,2-dione

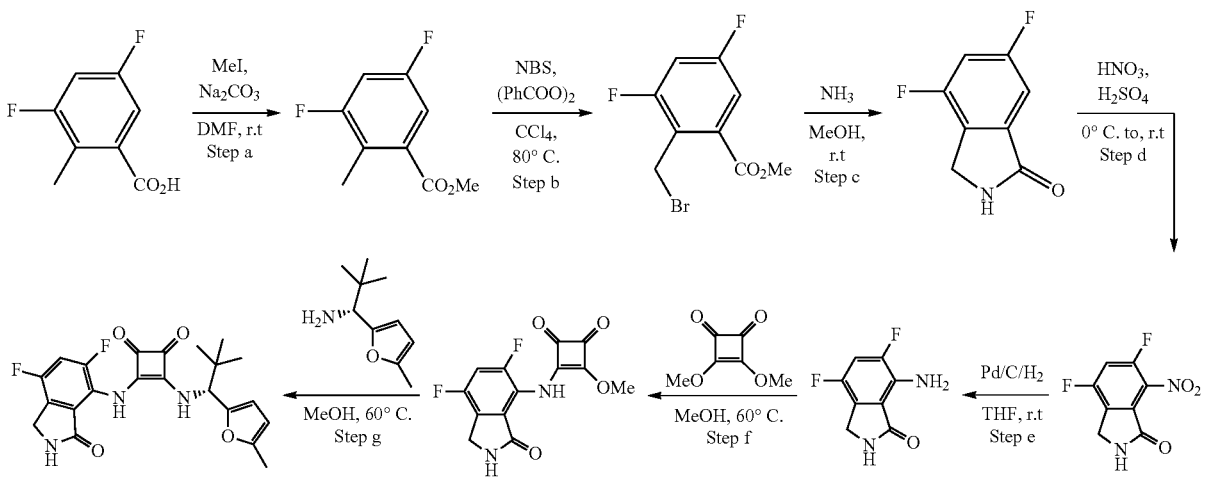

Step a:

3,5-Difluoro-2-methyl-benzoic acid (5.2 g, 30.2 mmol) was dissolved in anhydrous DMF (30 mL). Anhydrous $Na_2CO_3$ (3.5 g, 33.2 mmol, 1.1 equiv) was added and the reaction was stirred at room temperature for 30 minutes. Methyl iodide (2.1 mL, 33.2 mmol, 1.1 equiv) was added and the mixture was stirred at room temperature for 4 h, then the reaction was diluted with water (200 mL) and the product was extracted using $Et_2O$ (3×50 mL). The combined organic layers were washed with brine (4×30 mL), dried over $MgSO_4$, filtered and evaporated to give a yellow oil (5.4 g, 96%).

Step b:

The product from Step a (5.4 g, 29.0 mmol) was dissolved in carbon tetrachloride (60 mL) and N-bromosuccinimide (7.7 g, 43.5 mmol, 1.5 equiv) was added followed by benzoyl peroxide (1.4 g, 5.8 mmol, 0.20 equiv). The reaction mixture was stirred at reflux overnight then cooled to room temperature and filtered. The filtrate was evaporated and the residue was purified by column chromatography (silica gel, 100% hexanes to 9:1 hexanes: ethyl acetate) to give the product as a yellow oil (7.4 g, 96%).

Step c:

$NH_3$ in methanol (7 M, 45 mL, 6.4 mmol) was cooled to 0° C. and the product from Step b (6 g, 22.6 mmol) was added. The reaction mixture was stirred at 0° C. for 10 minutes and then at room temperature overnight. Excess solvent was evaporated and the residue was diluted with water (50 mL). The resulting solid was filtered and washed with water (2×20 mL), then hexanes (20 mL) to give the product (3.4 g, 89%). MS: (ES) m/z calculated for $C_8H_6F_2NO[M+H]^+$ 170.0. found 170.3.

Step d:

The 4,6-Difluoroisoindolin-1-one from Step c (3.4 g, 20.1 mmol) was dissolved in concentrated $H_2SO_4$ (40 mL) and cooled to 0° C. 70% $HNO_3$ (1.5 mL, 24.1 mmol, 1.2 equiv) was added drop-wise and the reaction mixture was stirred at 0° C. for 10 minutes, then allowed to warm to room temperature over a period of 1 hour and stirred overnight. Ice was added and the mixture was then diluted with cold water (100 mL). The resulting yellow solid was filtered, washed with water (2×50 mL), then hexanes (50 mL) and dried under vacuum (3.4 g, 79%). MS: (ES) m/z calculated for $C_8H_5F_2N_2O_3[M+H]^+$ 215.0. found 215.2.

Step e:

The 4,6-Difluoro-7-nitro-isoindolin-1-one from Step d (3.4 g, 15.9 mmol) was diluted with THF (50 mL) and 10% Pd/C, 50% wet, (1.7 g, 0.8 mmol, 5% mmol) was added under a nitrogen atmosphere. The reaction mixture was vigorously stirred under $H_2$ (balloon) for 1 day at room temperature, then filtered through Celite and evaporated to give the solid product (2.7 g, 92%). MS: (ES) m/z calculated for $C_8H_7F_2N_2O[M+H]^+$ 185.1. found 185.3.

Step f:

A mixture of 7-amino-4,6-difluoro-isoindolin-1-one from Step e (2.3 g, 12.5 mmol) and 3,4-dimethoxycyclobut-3-ene-1,2-dione (3.5 g, 25.0 mmol, 2.0 equiv) in anhydrous MeOH (15 mL) was stirred at 60° C. overnight. The reaction mixture was evaporated and the residue was diluted with MTBE:EtOAc (1:1, 200 mL) and stirred at 50° C. for 30 min, then cooled down to room temperature. The solid product was filtered, washed with MTBE, then dissolved in MeOH:DCM (1:1, 200 mL) and filtered through Celite. The filtrate was evaporated to give a gray solid (2.0 g, 54%). MS: (ES) m/z calculated for $C_{13}H_9F_2N_2O_4[M+H]^+$ 295.1. found 295.2.

Step g:

Anhydrous methanol (30 mL) was added to a mixture of the 3-[(5,7-difluoro-3-oxo-isoindolin-4-yl)amino]-4-methoxy-cyclobut-3-ene-1,2-dione from Step f (1.5 g, 5.1 mmol) and (1R)-2,2-dimethyl-1-(5-methyl-2-furyl)propan-1-amine (852 mg, 5.1 mmol) and this mixture was stirred at 60° C. for 1 day. The reaction was allowed to cool to room temperature, dissolved in a minimal amount of dichloromethane, and adsorbed on silica gel. The product was purified by silica gel chromatography (100:0 to 50:50 dichloromethane:ethyl acetate) to give a brown solid (1.4 g, 64%). $^1$H NMR (400 MHz, DMSO-$d_6$) δ 9.59 (s, 1H), 8.92 (s, 1H), 8.37 (d, J=10.2 Hz, 1H), 7.62 (dd, J=10.9, 8.6 Hz, 1H), 6.18 (d, J=3.1 Hz, 1H), 6.04 (d, J=3.1 Hz, 1H), 5.01 (d, J=10.2 Hz, 1H), 4.41 (s, 2H), 2.27 (s, 3H), 0.96 (s, 9H). MS: (ES) m/z calculated for $C_{22}H_{21}F_2N_3O_4[M-H]^-$ 428.1. found 428.1.

Example 5: 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]-4-methoxy-benzoic acid

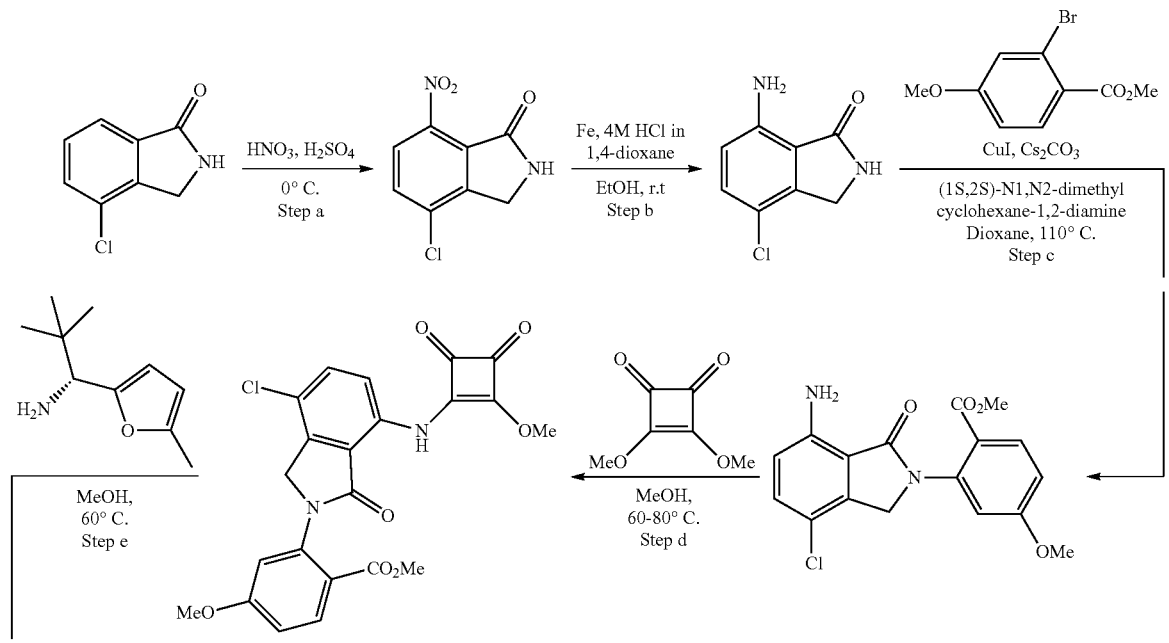

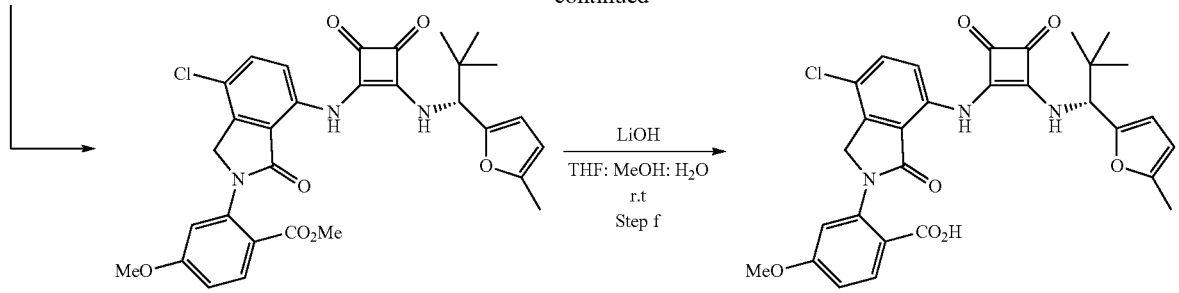

Step a:

A 1-L round bottom flask containing 4-chloroisoindolin-1-one (25.0 g, 0.149 mole) in concentrated $H_2SO_4$ (50 mL) was cooled in an ice-bath. A mixture of concentrated $H_2SO_4$ (50 mL) with 70% $HNO_3$ (10 mL, 0.16 mole, 1.05 equiv.) was added drop-wise and the reaction mixture was stirred at 0° C. for 2 h then carefully quenched with ice and diluted to 1 L with cold water. The solid was filtered, washed with water and dried under high vacuum to afford 4-chloro-7-nitro-isoindolin-1-one (23 g, 73%). MS: (ES) m/z calculated for $C_8H_5ClN_2O_3[M-H]^-$ 212.0. found 212.0.

Step b:

To a stirred mixture of 4-chloro-7-nitro-isoindolin-1-one (23 g, 108 mmol) in ethanol at room temperature was added iron powder (18.2 g, 324 mmol), followed by 4 M HCl in dioxane (162 mL, 648 mmol). The reaction mixture was stirred at room temperature for 1 h then concentrated in vacuo. The residue was diluted with ethyl acetate and neutralized with saturated sodium bicarbonate solution and extracted with ethyl acetate (2×500 mL). The combined organic layers were dried ($Na_2SO_4$), filtered, and concentrated in vacuo to afford 7-amino-4-chloro-isoindolin-1-one (16.5 g, 72%). MS: (ES) m/z calculated for $C_8H_7ClN_2O$ $[M+H]^+$ 183.2. found 183.2.

Step c:

To a reaction vial containing 7-amino-4-chloro-isoindolin-1-one (250 mg, 1.37 mmol) in dioxane (10 mL) was added methyl 2-bromo-5-methoxy-benzoate (502 mg, 2.05 mmol), cesium carbonate (893 mg, 2.74 mmol), copper iodide (104 mg, 0.55 mmol) and (1S,2S)—N1,N2-dimethylcyclohexane-1,2-diamine (156 mg, 1.1 mmol). The mixture was purged with nitrogen, then warmed to 110° C. The reaction was stirred at 110° C. for 1 h and the reaction was monitored by LC-MS. Following completion, the reaction was allowed to cool and was then filtered through Celite and rinsed with ethyl acetate. The crude was purified by silica gel chromatography (0-50% ethyl acetate/hexane) to give methyl 2-(7-amino-4-chloro-1-oxo-isoindolin-2-yl)-5-methoxy-benzoate as a white solid (284 mg, 60%). MS: (ES) m/z calculated for $C_{17}H_{15}ClN_2O_4[M+H]^+$ 347.1. found 347.1.

Step d:

A mixture of methyl 2-(7-amino-4-chloro-1-oxo-isoindolin-2-yl)-5-methoxy-benzoate (160 mg, 0.46 mmol) and 3,4-dimethoxycyclobutane-1,2-dione (131 mg, 0.92 mmol) in anhydrous methanol (5 mL) was stirred at 60° C. overnight. The reaction mixture was evaporated and the residue was stirred in ethyl acetate (5 mL) at 50° C. for 30 min, then allowed to cool to room temperature. The mixture was filtered and dried to give the product methyl 2-[4-chloro-7-[(2-methoxy-3,4-dioxo-cyclobutyl)amino]-1-oxo-isoindolin-2-yl]-5-methoxy-benzoate as a light yellow solid (170 mg, 81%). MS: (ES) m/z calculated for $C_{22}H_{17}ClN_2O_7[M+H]^+$ 457.1. found 457.1.

Step e:

Anhydrous methanol (10 mL) was added to a mixture of methyl 2-[4-chloro-7-[(2-methoxy-3,4-dioxo-cyclobutyl)amino]-1-oxo-isoindolin-2-yl]-5-methoxy-benzoate (170 mg, 0.37 mmol) and (1R)-2,2-dimethyl-1-(5-methyl-2-furyl)propan-1-amine (62 mg, 0.37 mmol) and this mixture was stirred at 60° C. overnight. The reaction was then concentrated and the crude methyl 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]-4-methoxy-benzoate (218 mg, 0.37 mmol) was used in the next step without further purification.

Step f:

To a solution of methyl 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]-4-methoxy-benzoate (218 mg, 0.37 mmol) in tetrahydrofuran (4.0 mL), methanol (0.5 mL) and water (0.5 mL) was added lithium hydroxide (78 mg, 1.85 mmol). The resulting mixture was stirred at 60° C. for 6 h. The reaction was acidified with a 5% hydrochloric acid solution and extracted with ethyl acetate. The organic layers were dried ($Na_2SO_4$), filtered, and concentrated in vacuo. The crude product was purified by reverse phase chromatography to afford 2-[4-chloro-7-[[2-[[(1R)-2,2-dimethyl-1-(5-methyl-2-furyl)propyl]amino]-3,4-dioxo-cyclobuten-1-yl]amino]-1-oxo-isoindolin-2-yl]-4-methoxy-benzoic acid as a yellow solid (37 mg, 17%). $^1$H NMR (400 MHz, DMSO-$d_6$) δ 9.94 (s, 1H), 9.12 (d, J=10 Hz, 1H), 7.90 (d, J=9.2, 1H), 7.66 (d, J=8.8, 1H), 7.49 (d, J=9.2, 1H), 7.19 (d, J=2.4, 1H), 7.04 (dd, J=8.8, 2.4, 1H), 6.16 (d, J=3.2 Hz, 1H), 6.02 (d, J=1.6 Hz, 1H), 5.09 (d, J=10 Hz, 1H), 4.78 (dd, J=23, 5.6 Hz, 2H), 3.83 (s, 3H), 2.24 (s, 3H), 0.87 (s, 9H). MS: (ES) m/z calculated for $C_{30}H_{28}ClN_3O_7[M-H]^-$ 576.0. found 576.0.

Example 6: 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-4-methoxy-benzoic acid

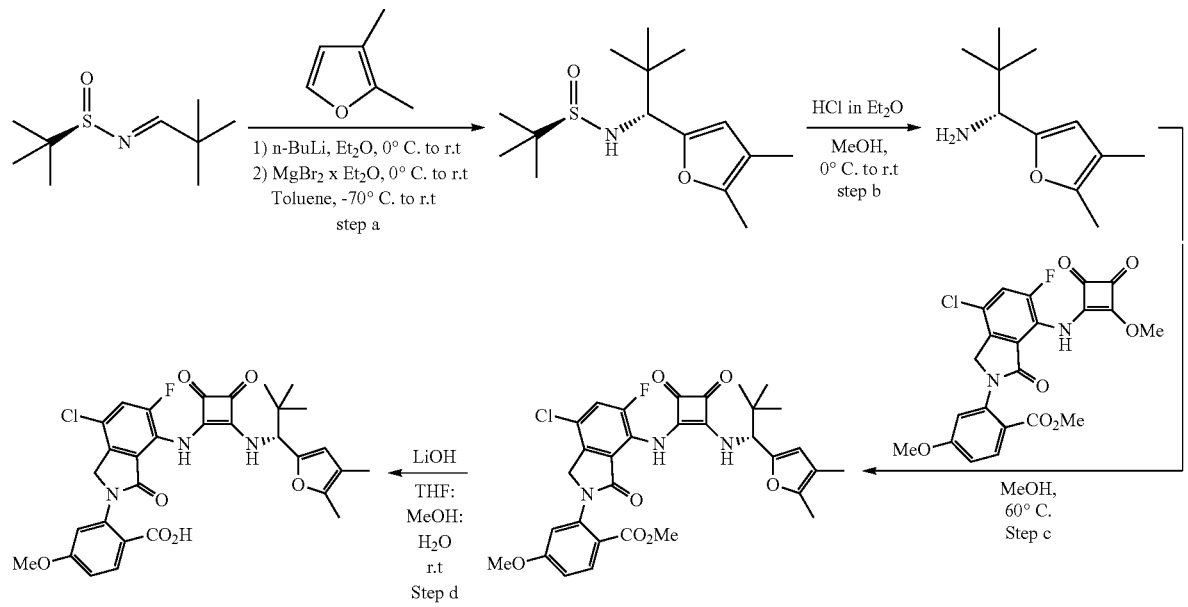

Step a:

A 1-L, 3 neck flask equipped with an addition funnel was charged with 2,3-dimethylfuran (30.0 g, 312.5 mmol, 1.3 equiv.) and anhydrous Et$_2$O (300 mL), then cooled in an ice bath. n-BuLi in hexanes (2.5 M, 125 mL, 312.5 mmol, 1.3 equiv) was added drop wise over approximately 35 min. The mixture was stirred at 0° C. for 30 min, then at room temperature for 40 min, then it was again cooled to 0° C. Solid MgBr$_2$×Et$_2$O (80.6 g, 312.5 mmol, 1.3 equiv) was added and the mixture was stirred at 0° C. for 30 min, then at room temperature for 20 min.

In 5-L 3 neck flask equipped with mechanical stirring and internal thermometer, the imine (45.4 g, 240.4 mmol) was dissolved in anhydrous toluene (1.2 L) and this was cooled to an internal temperature of −70° C. The lithium salt solution from the above paragraph was added over 56 minutes, keeping the internal temperature between −70 to −67.8° C. After the addition, the reaction mixture was stirred at −70° C. for 1 h then at room temperature overnight. The reaction mixture was slowly quenched with saturated aqueous NH$_4$Cl (400 mL) and water (400 mL), then stirred at room temperature for 15 min. The organic layer was then separated and washed with brine (200 mL). The combined aqueous layers were extracted with ethyl acetate (300 mL). The organics were dried over MgSO$_4$, filtered and concentrated to give a yellow oil. The crude product was purified by silica gel chromatography (0-10% MTBE/DCM) to give the product (18.0 g, 26%) as a single diastereomer. MS: (ES) m/z calculated for C$_{15}$H$_{28}$NO$_2$S[M+H]$^+$ 286.1. found 286.1.

Step b:

The N-[(1R)-2,2-dimethyl-1-(4,5-dimethyl-2-furyl)propyl]-2-methyl-propane-2-sulfinamide from the previous step (18 g, 63.1 mmol) was dissolved in methanol (200 mL) and cooled in an ice-bath, then 2M HCl in ether (31.5 mL, 126.2 mmol, 2 equiv) was added. The cooling bath was removed and the reaction mixture was stirred at room temperature for 2 h. Solvents were removed in vacuo, and anhydrous ether (100 mL) was added to the residue. The resulting mixture was filtered. To the solid was added water (100 mL) and 1M aqueous NaOH (100 mL). The product was extracted with dichloromethane (3×100 mL) and the combined organic layers were dried over MgSO$_4$, filtered and evaporated to give (1R)-1-(4,5-dimethyl-2-furyl)-2,2-dimethyl-propan-1-amine as a yellow oil (9.7 g, 85%). MS: (ES) m/z calculated for C$_{11}$H$_{17}$O[(M−NH$_3$)+H]$^+$ 165.1. found 165.1.

Step c:

Anhydrous methanol (1 mL) was added to a mixture of methyl 2-[4-chloro-7-[(2-methoxy-3,4-dioxo-cyclobutyl)amino]-1-oxo-isoindolin-2-yl]-5-methoxy-benzoate (60 mg, 0.13 mmol) and (1R)-1-(4,5-dimethyl-2-furyl)-2,2-dimethyl-propan-1-amine (24 mg, 0.13 mmol). This mixture was stirred at 60° C. 3 h. The reaction was concentrated to dryness and the crude methyl 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-4-methoxy-benzoate (78 mg, 0.13 mmol) was in the next step without further purification.

Step d:

To a solution of methyl 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-4-methoxy-benzoate (78 mg, 0.13 mmol) in tetrahydrofuran (1.0 mL), methanol (0.1 mL) and water (0.1 mL) was added lithium hydroxide (27 mg, 0.65 mmol). The resulting mixture was stirred at room temperature overnight. The reaction was acidified with a 5% hydrochloric acid solution and extracted with ethyl acetate. The organic layers were dried (Na$_2$SO$_4$), filtered, and concentrated in vacuo. The crude product was purified by reverse phase chromatography to afford 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-4-methoxy-benzoic acid as a yellow solid (12 mg, 15%). $^1$H NMR (400 MHz, DMSO-$d_6$) δ 9.93 (s, 1H), 9.09 (d, J=10 Hz, 1H), 7.90 (d, J=9.2, 1H), 7.66 (d, J=8.8, 1H), 7.49 (d, J=9.2, 1H), 7.19 (d, J=2.4, 1H), 7.04 (dd, J=8.8, 2.4, 1H), 6.06 (d, J=3.2 Hz, 1H), 5.04 (d, J=10 Hz, 1H), 4.83 (dd, J=23, 5.6 Hz, 2H), 3.83 (s, 3H), 2.15 (s, 3H), 1.85 (s, 3H), 0.87 (s, 9H). MS: (ES) m/z calculated for $C_{31}H_{30}ClN_3O_7[M-H]^-$ 590.2. found 590.2.

Example 7: 2-[4-chloro-7-[[2-[[(1R)-1-(4,5-dim-ethyl-2-furyl)-2,2-dimethyl-propyl]amino]-3,4-di-oxo-cyclobuten-1-yl]amino]-1-oxo-isoindolin-2-yl]-4-methyl-benzoic acid was added lithium hydroxide (874 mg, 20.83 mmol). The resulting mixture was stirred at 60° C. overnight. The reaction was then allowed to cool, then acidified with a 1N hydrochloric acid solution to pH=5 and extracted with ethyl acetate/MeOH (10:1). The organic layers were dried ($Na_2SO_4$), filtered, and concentrated in vacuo. Hexane was added to the crude product and the resulting solid was filtered and rinsed with hexane to afford 2-(7-amino-4-chloro-1-oxo-isoindolin-2-yl)-4-methyl-benzoic acid as a yellow solid (572 mg, 87%).

Step c:

A solution of 2-(7-amino-4-chloro-1-oxo-isoindolin-2-yl)-4-methyl-benzoic acid (570 mg, 1.80 mmol) and 3,4-dimethoxycyclobutane-1,2-dione (307 mg, 2.16 mmol) in anhydrous methanol (5 mL) was stirred at 60° C. overnight. The reaction mixture was then allowed to cool to room temperature and filtered. The solid was then washed with EtOAc and dried to give 2-[4-chloro-7-[(2-methoxy-3,4-

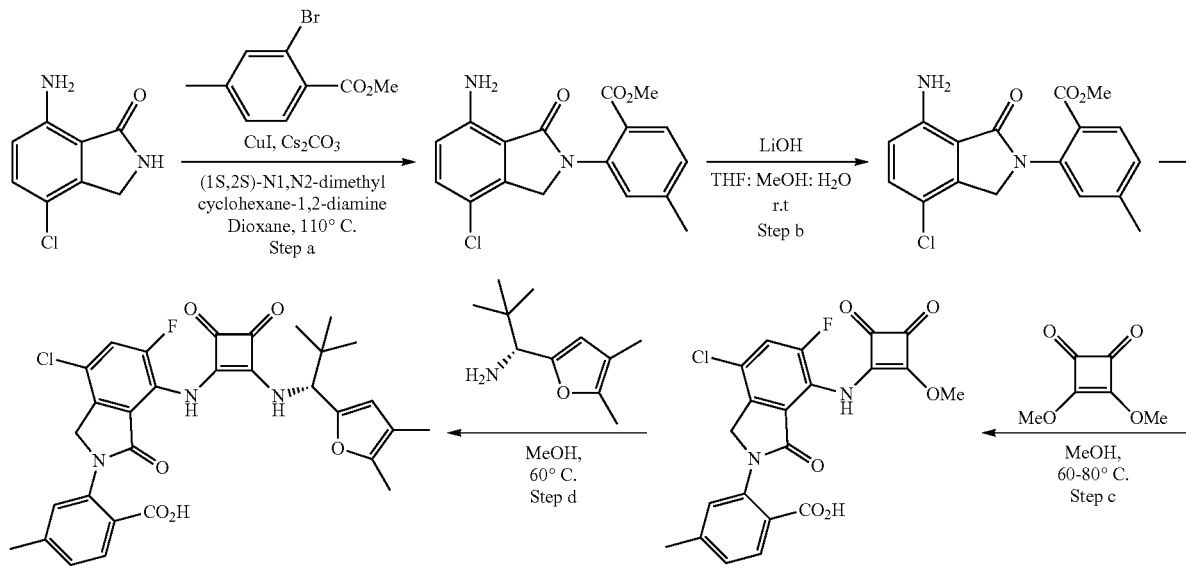

dioxo-cyclobuten-1-yl)amino]-1-oxo-isoindolin-2-yl]-4-methyl-benzoic acid as a yellow solid (565 mg, 71%). MS: (ES) m/z calculated for $C_{21}H_{15}ClN_2O_6$ $[M+H]^+$ 427.1. found 427.1.

Step d:

Anhydrous methanol (2 mL) was added to a mixture of 2-[4-chloro-7-[(2-methoxy-3,4-dioxo-cyclobuten-1-yl) amino]-1-oxo-isoindolin-2-yl]-4-methyl-benzoic acid (60 mg, 0.14 mmol) and (1R)-1-(4,5-dimethyl-2-furyl)-2,2-dimethyl-propan-1-amine (27 mg, 0.15 mmol) and this mixture was stirred at 60° C. overnight. The reaction was then concentrated and the crude was purified by reverse phase chromatography to afford 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-4-methyl-benzoic acid (30 mg, 37%). $^1$H NMR (400 MHz, DMSO-$d_6$) δ 9.94 (s, 1H), 9.09 (d, J=10 Hz, 1H), 7.81 (d, J=9.2, 1H), 7.66 (d, J=8.8, 1H), 7.49 (d, J=9.2, 1H), 7.42 (d, J=2.4, 1H), 7.30 (dd, J=8.8, 2.4, 1H), 6.07 (d, J=3.2 Hz, 1H), 5.04 (d, J=10 Hz, 1H), 4.83 (dd, J=23, 5.6 Hz, 2H), 2.38 (s, 3H), 2.15 (s, 3H), 1.85 (s, 3H), 0.87 (s, 9H). MS: (ES) m/z calculated for $C_{31}H_{30}ClN_3O_6[M-H]^-$ 574.0. found 574.0.

Step a:

To a reaction vial containing 7-amino-4-chloro-isoindo-lin-1-one (305 mg, 1.67 mmol) in dioxane (10 mL) was added methyl 2-bromo-5-methyl-benzoate (575 mg, 2.51 mmol), cesium carbonate (1.63 g, 5 mmol), copper iodide (190 mg, 1.0 mmol) and (1S,2S)—N1,N2-dimethylcyclo-hexane-1,2-diamine (285 mg, 2.0 mmol). The mixture was purged with nitrogen, and then warmed to 110° C. The reaction was stirred at 110° C. for 1 h and monitored by LC-MS. After completion, the reaction was allowed to cool and then filtered through Celite and rinsed with EtOAc. The crude was purified by silica gel chromatography (0-50% ethyl acetate/hexane) to give methyl 2-(7-amino-4-chloro-1-oxo-isoindolin-2-yl)-5-methyl-benzoate as a white solid (345 mg, 62%). MS: (ES) m/z calculated for $C_{17}H_{15}ClN_2O_3$ $[M+H]^+$ 331.1. found 331.1.

Step b:

To a solution of methyl 2-(7-amino-4-chloro-1-oxo-isoin-dolin-2-yl)-5-methyl-benzoate (689 mg, 2.08 mmol) in tet-rahydrofuran (10 mL), methanol (1 mL) and water (1 mL)

Example 8: Synthesis of 3-[[(1R)-2,2-dimethyl-1-(5-methyl-2-furyl)butyl]amino]-4-[(5-fluoro-3-oxo-isoindolin-4-yl)amino]cyclobut-3-ene-1,2-dione

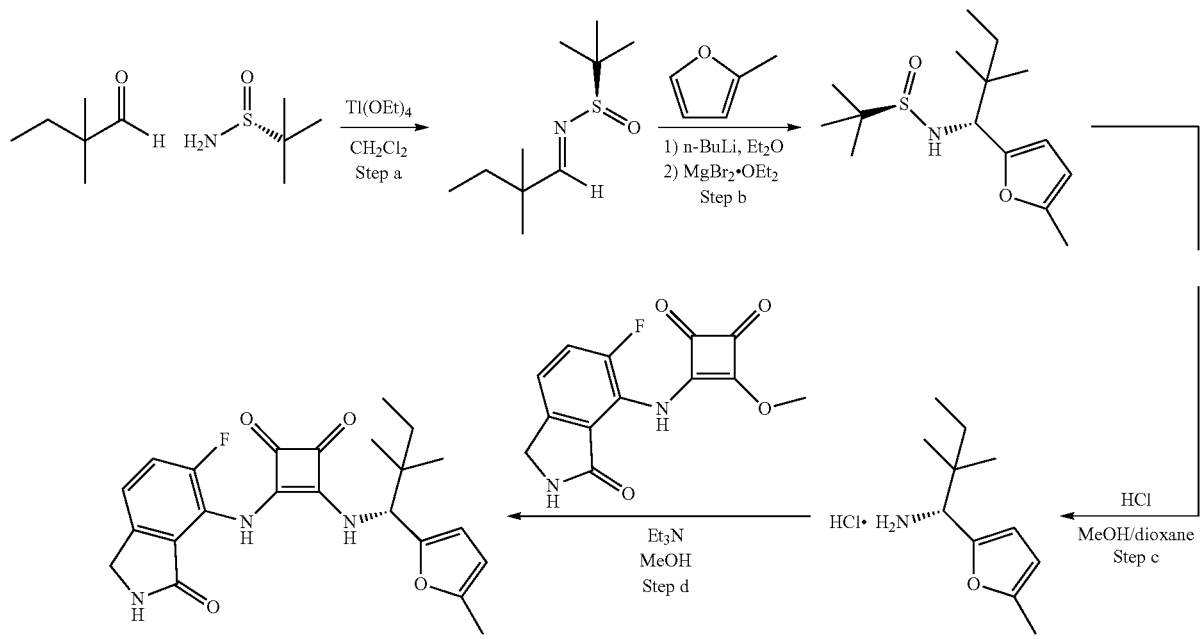

Step a:

2,2-Dimethylbutanal (5.0 g, 50 mmol) and (R)-tert-butanesulfinamide (6.36 g, 52.5 mmol) were dissolved in $CH_2Cl_2$ (100 mL) and $Ti(OEt)_4$ (85-95%, 22.81 g, ~90 mmol) was added. The reaction was stirred at room temperature overnight. The reaction was then diluted with $CH_2Cl_2$ (200 mL), then celite and $H_2O$ (90 mL) was added while vigorously stirring. The mixture was stirred for 5 h then filtered through celite, rinsing the filter cake with $CH_2Cl_2$. The filtrate was concentrated and purified on silica (1% to 30% EtOAc in hexanes) to give the product.

Step b:

2-Methylfuran (5.06 mL, 56.2 mmol) in $Et_2O$ (52 mL) was cooled on ice. N-BuLi (2.5 M, 22.5 mL, 56.3 mmol) was added dropwise and the reaction was stirred on ice for 15 min, then the bath was removed and stirring was continued at RT for 1 h. The reaction was then cooled on ice again, and $MgBr_2$ (14.5 g, 56.2 mmol) was added in one portion. The reaction was stirred on ice for 20 min, then the bath was removed and stirring was continued at RT for 50 min. The reaction was then cooled in a −78° C. bath, and (R,E)-N-(2,2-dimethylbutylidene)-2-methyl-propane-2-sulfinamide (7.6 g, 37.4 mmol) in $Et_2O$ (52 mL) was added dropwise. The reaction was allowed to slowly warm to room temperature overnight. Saturated aqueous $NH_4Cl$ was added to quench, and the mixture was stirred vigorously, then diluted with $H_2O$ and extracted with EtOAc (3×150 mL). The combined organic layers were dried over $MgSO_4$, filtered and concentrated to give the crude. This was then purified on silica (5% to 40% EtOAc in hexanes) to give the isomerically pure product.

Step c:

To N-[(1R)-2,2-dimethyl-1-(5-methyl-2-furyl)butyl]-2-methyl-propane-2-sulfinamide (6.0 g, 21 mmol) was added MeOH (60 mL) and HCl in dioxane (4M, 21 mL, 84 mmol). This was stirred at room temperature for 45 min. The reaction was then concentrated and dried under vacuum to give the product.

Step d:

$Et_3N$ (0.072 mL, 0.52 mmol) was added to a mixture of squarate (72 mg, 0.26 mmol) and (1R)-2,2-dimethyl-1-(5-methyl-2-furyl)butan-1-amine hydrochloride (57 mg, 0.26 mmol) in MeOH (1.3 mL). The reaction was stirred at 60° C. for 4 h, then at room temperature overnight. Silica gel was added to the reaction, the mixture was concentrated, and this was purified by silica gel chromatography (1% to 10% MeOH in $CH_2Cl_2$) to give the product. $^1$H NMR (400 MHz, DMSO-$d_6$) δ 9.65 (s, 1H), 8.71 (s, 1H), 8.39 (d, J=10.2 Hz, 1H), 7.47 (dd, J=11.2, 8.2 Hz, 1H), 7.33 (dd, J=8.3, 3.8 Hz, 1H), 6.17 (d, J=3.1 Hz, 1H), 6.06-6.02 (m, 1H), 5.11 (d, J=10.2 Hz, 1H), 4.32 (s, 2H), 2.27 (s, 3H), 1.36-1.21 (m, 2H), 0.94 (s, 3H), 0.88 (s, 3H), 0.83 (t, J=7.5 Hz, 3H). MS: (ES) m/z calculated for $C_{23}H_{25}FN_3O_4$ [M+H]$^+$ 426.2. found 426.0.

Example 9: Synthesis of 3-[[(1R)-1-(5-chloro-2-furyl)-2,2-dimethyl-propyl]amino]-4-[(7-chloro-3-oxo-isoindolin-4-yl)amino]cyclobut-3-ene-1,2-dione

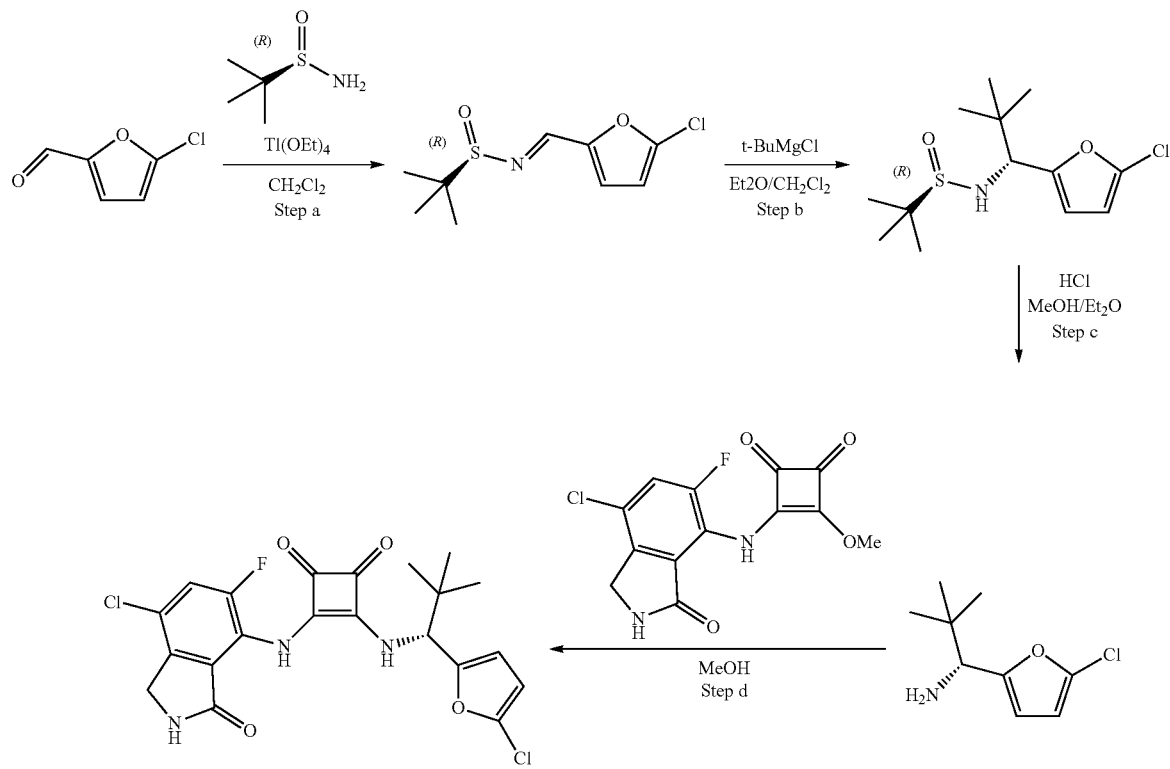

Step a:
5-chlorofuran-2-carbaldehyde (5.0 g, 38 mmol) and (R)-tert-butanesulfinamide (4.2 g, 35 mmol) were dissolved in CH$_2$Cl$_2$ (75 mL) and Ti(OEt)$_4$ (85-95%, 17.6 g, 77 mmol) was added. The reaction was stirred at room temperature overnight. The reaction was then diluted with CH$_2$Cl$_2$ (150 mL), Na$_2$SO$_4$.10H$_2$O (100 g) was added, and the mixture was stirred for 90 min. This was then filtered through celite, rinsing the filter cake with CH$_2$Cl$_2$ (200 mL). The filtrate was concentrated to give the product.

Step b:
(R,E)-N-[(5-chloro-2-furyl)methylene]-2-methyl-propane-2-sulfinamide (7.65 g, 32.7 mmol) was dissolved in CH$_2$Cl$_2$ (131 mL) and cooled in a −78° C. bath while under a nitrogen atmosphere. t-BuMgCl (2M in Et$_2$O, 33 mL, 66 mmol) was added via addition funnel over 30 min, and the reaction was then allowed to stir for 4 h. Saturated aqueous NH$_4$Cl was added, and the mixture was allowed to warm to room temperature. H$_2$O (50 mL) was then added and the mixture was extracted with CH$_2$Cl$_2$ (2×), dried over Na2SO4, filtered, and concentrated to give a mixture of diastereomers. The crude was adsorbed onto silica and purified by column chromatography (10% methyl tert-butyl ether in CH$_2$Cl$_2$). The early eluting diastereomer was collected and concentrated to give the product.

Step c:
N-[(1R)-1-(5-chloro-2-furyl)-2,2-dimethyl-propyl]-2-methyl-propane-2-sulfinamide (0.98 g, 3.4 mmol) was dissolved in MeOH (3.4 mL), and HCl (2M in Et$_2$O, 3.4 mL, 6.8 mmol) was added. The reaction was stirred overnight, and then concentrated. Et$_2$O (25 mL) was added and the mixture was stirred for 30 min, and then filtered. The solid was washed with Et$_2$O (2×), then aqueous KOH (3M, 5 mL) was added and the product was extracted with CH$_2$Cl$_2$ (3×). The combined organic layers were washed twice with aqueous KOH (1.5 M), dried over Na$_2$SO$_4$, filtered, and concentrated to give the product.

Step d:
3-[(7-chloro-3-oxo-isoindolin-4-yl)amino]-4-methoxy-cyclobut-3-ene-1,2-dione (59 mg, 0.2 mmol) and (1R)-1-(5-chloro-2-furyl)-2,2-dimethyl-propan-1-amine (38 mg, 0.2 mmol) were combined in MeOH (0.2 mL) and the mixture was stirred at room temperature overnight. The reaction was concentrated, then purified by reverse phase chromatography (MeCN:H$_2$O with 0.1% TFA as eluent) to give the product. $^1$H NMR (400 MHz, DMSO-d$_6$) δ 9.96 (s, 1H), 9.17 (d, J=10.0 Hz, 1H), 8.95 (s, 1H), 7.61 (d, J=8.7 Hz, 1H), 7.45 (d, J=8.7 Hz, 1H), 6.53-6.43 (m, 2H), 5.17 (d, J=9.9 Hz, 1H), 4.38 (s, 2H), 3.17 (s, 1H), 0.99 (s, 9H). MS: (ES) m/z calculated for C$_{21}$H$_{20}$Cl$_2$N$_3$O$_4$[M+H]$^+$ 448.1. found 448.1.

Example 10: (R)-3-((2,2-dimethyl-1-(5-methyl-furan-2-yl)propyl)amino)-4-((5-fluoro-7-methyl-3-oxoisoindolin-4-yl)amino)cyclobut-3-ene-1,2-dione

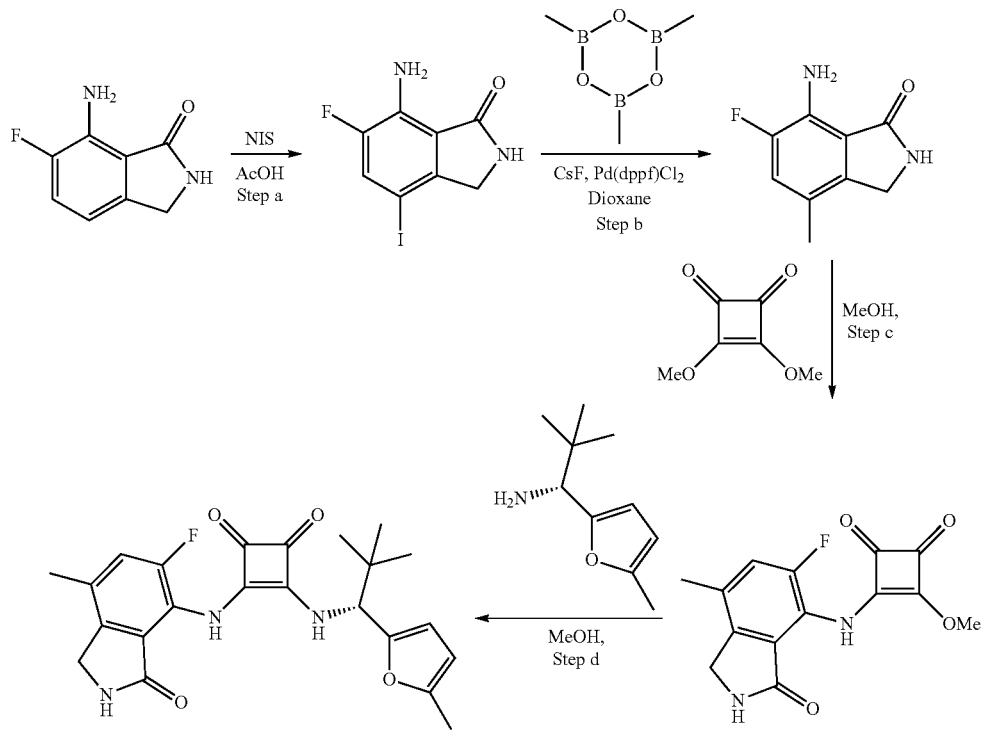

Step a:

To a solution of 7-amino-6-fluoroisoindolin-1-one (2.4 g, 14.4 mmol) in AcOH (30 mL) in a water bath, was added N-iodosuccinimide (4.55 g, 20.2 mmol) in portions at room temperature. The resulting mixture was stirred for 30 minutes in a water bath, quenched with water (20 mL), and extracted with ethyl acetate (100 mL). The organic layer was washed with brine (100 mL) and then dried over $MgSO_4$. The solvent was evaporated under reduced pressure to give an brown solid, which was purified by silica gel chromatography (0-60% ethyl acetate in hexanes) to give the product. MS: (ES) m/z calculated for $C_8H_6FIN_2O[M+H]^+$ 293.0. found 293.0.

Step b:

To a solution of 7-amino-6-fluoro-4-iodoisoindolin-1-one (2.2 g, 7.53 mmol) in dioxane (44 mL), was added CsF (4.57 g, 30.1 mmol), 2,4,6-trimethyl-1,3,5,2,4,6-trioxatriborinane (1.35 g, 22.6 mmol) and [1,1'-bis(diphenylphosphino)ferrocene]dichloropalladium(II) (551 mg, 0.753 mmol). The resulting mixture was stirred at 80° C. overnight. The reaction was then partitioned between water (100 mL) and ethyl acetate (100 mL), and the organic layer was washed with brine (80 mL) and then dried over $MgSO_4$. The solvent was evaporated under reduced pressure to give an brown solid, which was purified by silica gel chromatography (0-80% ethyl acetate in hexanes) to give the product. MS: (ES) m/z calculated for $C_9H_9FN_2O[M+H]^+$ 181.1. found 181.1.

Step c:

A mixture of 7-amino-6-fluoro-4-methylisoindolin-1-one (200 mg, 1.11 mmol) and 3,4-dimethoxycyclobut-3-ene-1,2-dione (189.3 mg, 1.33 mmol) in anhydrous methanol (3 mL) was stirred at 60° C. for overnight and then at 80° C. for 5 h. The reaction mixture was evaporated and purified by silica gel chromatography (0-100% ethyl acetate in hexanes) to give the product. MS: (ES) m/z calculated for $C_{14}H_{11}FN_2O_4[M+H]^+$ 291.1. found 291.1.

Step d:

Anhydrous methanol (2 mL) was added to a mixture of 3-((5-fluoro-7-methyl-3-oxoisoindolin-4-yl)amino)-4-methoxycyclobut-3-ene-1,2-dione (95 mg, 0.327 mmol) and (R)-2,2-dimethyl-1-(5-methylfuran-2-yl)propan-1-amine (55 mg, 0.329 mmol) and this mixture was stirred at 60° C. overnight. The reaction was allowed to cool to room temperature, dissolved in minimal dichloromethane, and adsorbed onto silica gel. The product was purified by silica gel chromatography (40% ethyl acetate in dichloromethane) to give the product. $^1$H NMR (400 MHz, DMSO-$d_6$) δ 9.46 (s, 1H), 8.61 (s, 1H), 8.24 (d, J=10.4 Hz, 1H), 7.21 (d, J=11.6 Hz, 1H), 6.07 (d, J=2.4 Hz, 1H), 5.94 (d, J=2.4 Hz, 1H), 4.90 (s, 2H), 2.16 (s, 3H), 2.15 (s, 3H), 0.90 (s, 9H). MS: (ES) m/z calculated for $C_{23}H_{24}FN_3O_4[M-H]^-$ 426.2. found 426.2.

Example 11: (R)-3-((1-(4,5-dimethylfuran-2-yl-2,2-dimethylbutyl)amino)-4-((5-fluoro-1,1,7-trimethyl-3-oxoisoindolin-4-yl)amino)cyclobut-3-ene-1,2-dione

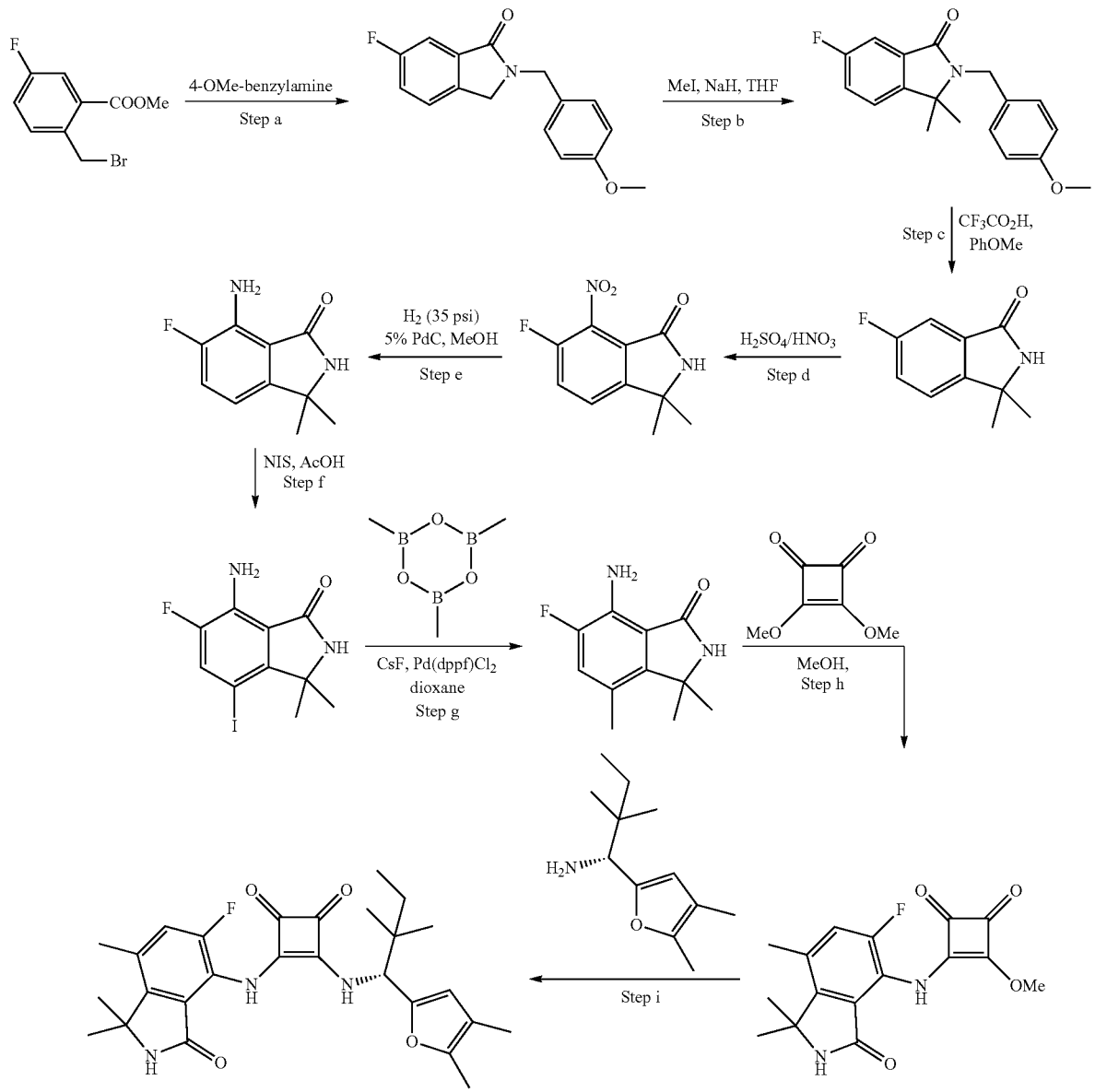

Step a:

To a 500 mL round-bottom flask charged with methyl 2-(bromomethyl)-5-fluorobenzoate (25 g, 101 mmol) and THF (300 mL) at 0° C. was slowly added 4-methoxybenzylamine (34.7 g, 253 mmol). The mixture was allowed to warm to room temperature overnight. The reaction was poured into a 2 L separatory funnel with ethyl acetate (300 mL) and HCl (1 N aqueous, 200 mL). The organic layer was washed with brine (2×200 mL) and then dried over MgSO$_4$, filtered, concentrated, and purified by silica gel chromatography (0-30% ethyl acetate in hexanes) to give 6-fluoro-2-(4-methoxybenzyl)isoindolin-1-one. MS: (ES) m/z calculated for $C_{16}H_{14}FNO_2$[M+H]$^+$ 272.1. found 272.1.

Step b:

To a solution of 6-fluoro-2-(4-methoxybenzyl)isoindolin-1-one (10 g, 36.9 mmol) in THF (50 mL) was added NaH (7.4 g, 184.5 mmol) at 0° C. The resulting mixture was stirred under nitrogen for 30 minutes. To the reaction mixture was added methyl iodide (31.4 g, 221.2 mmol) at 0° C., then this was heated at 70° C. overnight, allowed to cool to room temperature, quenched with water (40 mL), and extracted with ethyl acetate (100 mL). The organic layer was washed with brine (100 mL) and dried over MgSO$_4$. The solvent was concentrated to give the crude, which was purified by silica gel chromatography (0-80% ethyl acetate in hexanes) to give 6-fluoro-2-(4-methoxybenzyl)-3,3-dimethylisoindolin-1-one. MS: (ES) m/z calculated for $C_{18}H_{18}FNO_2$[M+H]$^+$ 300.1. found 300.1.

Step c:

A solution of 6-fluoro-2-(4-methoxybenzyl)-3,3-dimethylisoindolin-1-one (5 g, 16.7 mmol) in TFA (25 mL) and anisole (5 mL) was heated at 100° C. overnight. The reaction mixture was poured onto ice (20 g), neutralized with saturated aqueous NaHCO$_3$ (50 mL) and extracted with ethyl acetate (100 mL). The organic layer was washed with brine (100 mL) and then dried over MgSO$_4$. The solvent was evaporated under reduced pressure to give the crude, which was purified by silica gel chromatography (0-100% ethyl acetate in hexanes) to give 6-fluoro-3,3-dimethylisoindolin-1-one. MS: (ES) m/z calculated for C$_{10}$H$_{10}$FNO[M+H]$^+$ 180.1. found 180.1.

Step d:

To a 0° C. suspension of 6-fluoro-3,3-dimethylisoindolin-1-one (3.1 g, 17.3 mmol) in concentrated H$_2$SO$_4$ (12 mL) was added nitric acid (1.34 mL) dropwise while keeping the reaction mixture below 5° C. After addition, the reaction mixture was slowly allowed to warm to room temperature overnight. Ice (20 g) was added to the mixture and the solid was filtered, then washed with MTBE (50 mL) and ethyl acetate (50 mL) to give 6-fluoro-3,3-dimethyl-7-nitroisoindolin-1-one. MS: (ES) m/z calculated for C$_{10}$H$_9$FN$_2$O$_3$ [M+H]$^+$ 225.1. found 225.1.

Step e:

A solution of 6-fluoro-3,3-dimethyl-7-nitroisoindolin-1-one (2.0 g, 8.93 mmol) and 10% Pd/C (50% wet, 0.89 g, 0.45 mmol, 0.05 equiv) in MeOH (50 mL) was shaken under a hydrogen atmosphere (35 psi) for 2 hours. The solid was filtered through Celite and the filtrate was concentrated under reduced pressure to give the crude which was purified by silica gel chromatography (100% ethyl acetate) to give 7-amino-6-fluoro-3,3-dimethylisoindolin-1-one. MS: (ES) m/z calculated for C$_{10}$H$_{11}$FN$_2$O[M+H]$^+$ 195.1. found 195.1.

Step f:

To a solution of 7-amino-6-fluoro-3,3-dimethylisoindolin-1-one (150 mg, 0.77 mmol) in AcOH (2 mL) in a room temperature water bath was added N-iodosuccinimide (244 mg, 1.08 mmol) in potions at room temperature. The resulting mixture was stirred in a water bath for 30 minutes, quenched with water (1 mL) and extracted with ethyl acetate (10 mL). The organic layer was washed with brine (10 mL) and then dried over MgSO$_4$. The solvent was evaporated under reduced pressure to give the crude, which was purified by silica gel chromatography (0-60% ethyl acetate in hexanes) to give 7-amino-6-fluoro-4-iodo-3,3-dimethylisoindolin-1-one. MS: (ES) m/z calculated for C$_{10}$H$_{10}$FIN$_2$O [M+H]$^+$ 321.0. found 321.0.

Step g:

To a solution of 7-amino-6-fluoro-4-iodo-3,3-dimethylisoindolin-1-one (370 mg, 1.16 mmol) in dioxane (12 mL) was added CsF (705 mg, 4.64 mmol), 2,4,6-trimethyl-1,3,5,2,4,6-trioxatriborinane (435 mg, 3.47 mmol), and [1,1'-bis(diphenylphosphino)ferrocene]dichloropalladium(II) (95 mg, 0.116 mmol). The resulting mixture was stirred at 80° C. overnight, then allowed to cool to room temperature. The reaction was partitioned between water (20 mL) and ethyl acetate (30 mL). The organic layer was washed with brine (20 mL) and then dried over MgSO$_4$, filtered, and concentrated to give the crude, which was purified by silica gel chromatography (0-80% ethyl acetate in hexanes) to give 7-amino-6-fluoro-3,3,4-trimethylisoindolin-1-one. MS: (ES) m/z calculated for C$_{11}$H$_{13}$FN$_2$O[M+H]$^+$ 209.1. found 209.1.

Step h:

A mixture of 7-amino-6-fluoro-3,3,4-trimethylisoindolin-1-one (129 mg, 0.62 mmol) and 3,4-dimethoxycyclobut-3-ene-1,2-dione (176.3 mg, 1.24 mmol) in anhydrous methanol (2.5 mL) was stirred at 60° C. overnight and then at 80° C. for 5 h. The reaction mixture was concentrated, and the crude was purified by silica gel chromatography (0-100% ethyl acetate in hexanes) to give 3-((5-fluoro-1,1,7-trimethyl-3-oxoisoindolin-4-yl)amino)-4-methoxycyclobut-3-ene-1,2-dione. MS: (ES) m/z calculated for C$_{16}$H$_{15}$FN$_2$O$_4$ [M+H]$^+$ 319.1. found 319.1.

Step i:

Anhydrous methanol (2 mL) was added to a mixture of 3-((5-fluoro-1,1,7-trimethyl-3-oxoisoindolin-4-yl)amino)-4-methoxycyclobut-3-ene-1,2-dione (22 mg, 0.07 mmol) and (R)-1-(4,5-dimethylfuran-2-yl)-2,2-dimethylbutan-1-amine (15 mg, 0.077 mmol), and this mixture was stirred at 60° C. overnight. The reaction was allowed to cool to room temperature, dissolved in a minimal amount of dichloromethane, and adsorbed onto silica gel. This was purified by silica gel chromatography (40% ethyl acetate in dichloromethane) to give the title compound. $^1$H NMR (400 MHz, Cd$_3$OD) δ 7.21 (d, J=12 Hz, 1H), 6.04 (s, 1H), 5.16 (d, J=4.10 Hz, 1H), 2.47 (s, 3H), 2.19 (s, 3H), 1.92 (s, 3H), 1.60 (s, 6H), 1.40 (q, J=7.6 Hz, 2H), 1.03 (s, 3H), 0.97 (s, 3H), 0.91 (t, J=7.6 Hz, 3H). MS: (ES) m/z calculated for C$_{27}$H$_{32}$FN$_3$O$_4$[M−H]$^-$ 482.2. found 482.2.

Example 12: Synthesis of (R)-3-((7-chloro-2-(3-methyl-1H-pyrazol-5-yl)-3-oxoisoindolin-4-yl)amino)-4-((2,2-dimethyl-1-(5-methylfuran-2-yl)propyl)amino)cyclobut-3-ene-1,2-dione

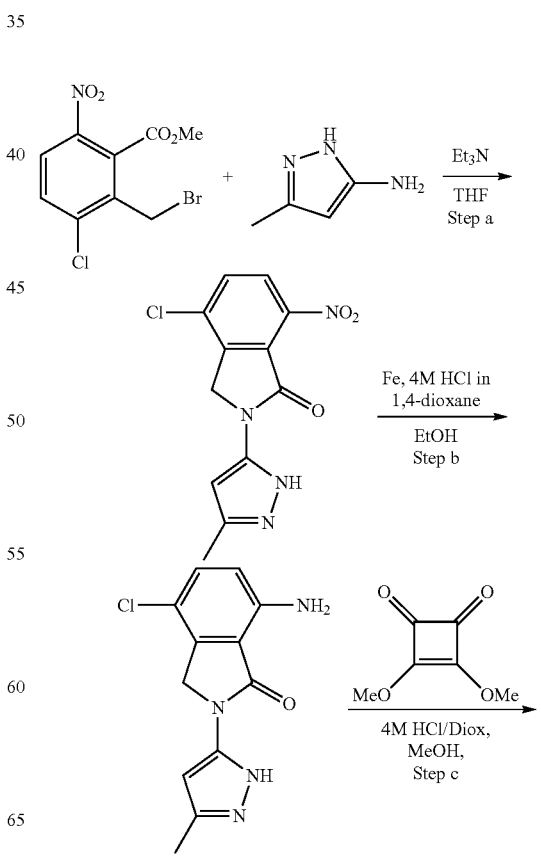

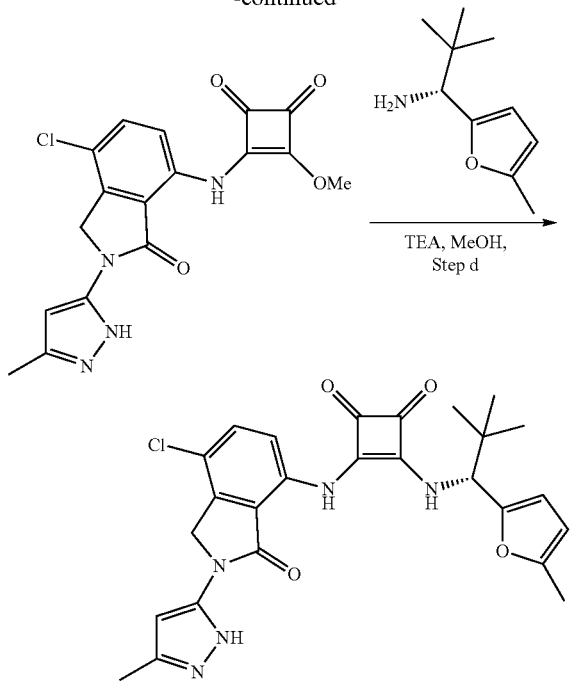

Step a:

To a solution of methyl 2-(bromomethyl)-3-chloro-6-nitrobenzoate (500 mg, 1.62 mmol) and 3-methyl-1H-pyrazol-5-amine (158 mg, 1.62 mmol) in anhydrous tetrahydrofuran (3 ml) was added triethylamine (0.5 ml, 3.56 mmol). The resulting reaction solution was heated to 60° C. in a closed 40 mL reaction vial for 1 h. A solid precipitated during the reaction. The reaction was then cooled to room temperature, and filtered. The solid was rinsed with dichloromethane to afford the product. MS: (ES) m/z calculated for $C_{12}H_9ClN_4O_3[M+H]^+$ 293.0. found 293.0.

Step b:

To a stirred mixture of 4-chloro-2-(3-methyl-1H-pyrazol-5-yl)-7-nitroisoindolin-1-one (266 mg, 0.91 mmol) in ethanol at room temperature was added iron powder (203 mg, 3.60 mmol), followed by 4 M HCl in dioxane (0.91 ml, 3.64 mmol). The reaction mixture was stirred at room temperature for 1 h then concentrated to dryness. The residue was diluted with ethyl acetate and neutralized with saturated sodium bicarbonate solution and extracted with ethyl acetate (2×5 ml). The combined organic layers were dried (Na$_2$SO$_4$), filtered, and concentrated in vacuo. The crude was purified by silica gel chromatography (0-100% ethyl acetate in hexanes) to afford the product. MS: (ES) m/z calculated for $C_{12}H_{11}ClN_4O[M+H]^+$ 263.0. found 263.0.

Step c:

To a slurry of 7-amino-4-chloro-2-(3-methyl-1H-pyrazol-5-yl)isoindolin-1-one (200 mg, 0.76 mmol) and 3,4-dimethoxycyclobut-3-ene-1,2-dione (130 mg, 0.91 mmol) in methanol (1 ml) was added 4 M HCl in dioxane (0.19 ml, 0.76 mmol). The reaction mixture was warmed to 60° C. and stirred for 1 hour. Then it was allowed to cool to room temperature, filtered and rinsed with methanol to give the product. MS: (ES) m/z calculated for $C_{17}H_{13}ClN_4O_4[M+H]^+$ 373.0. found 373.0.

Step d:

To a slurry of 3-((7-chloro-2-(3-methyl-1H-pyrazol-5-yl)-3-oxoisoindolin-4-yl)amino)-4-methoxycyclobut-3-ene-1,2-dione (100 mg, 0.27 mmol) in methanol (1 ml) was added (R)-2,2-dimethyl-1-(5-methylfuran-2-yl)propan-1-amine (45 mg, 0.27 mmol) and triethylamine (0.04 ml, 0.27 mmol). The resulting mixture was stirred at room temperature overnight and then diluted with dichloromethane. The solid was removed by filtration and the filtrate was concentrated to dryness. This was purified by reverse phase chromatography to afford the product. $^1$H NMR (400 MHz, DMSO-d$_6$) δ 12.33 (s, 1H), 10.00 (s, 1H), 9.13 (d, J=10 Hz, 1H), 7.63 (d, J=10 Hz, 1H), 7.46 (d, J=10 Hz, 1H), 6.56 (s, 1H), 6.20 (d, J=3.2 Hz, 1H), 6.04 (d, J=3.2 Hz, 1H), 5.12 (d, J=10 Hz, 1H), 4.85 (s, 2H), 2.28 (s, 3H), 2.25 (s, 3H), 0.97 (s, 9H). MS: (ES) m/z calculated for $C_{26}H_{26}ClN_5O_4[M-H]^-$ 506.1. found 506.1.

Example 13: Synthesis of (R)-3-((7-chloro-5-fluoro-1,1-dimethyl-3-oxoisoindolin-4-yl)amino)-4-((2,2-dimethyl-1-(5-methylfuran-2-yl)propyl)amino)cyclobut-3-ene-1,2-dione

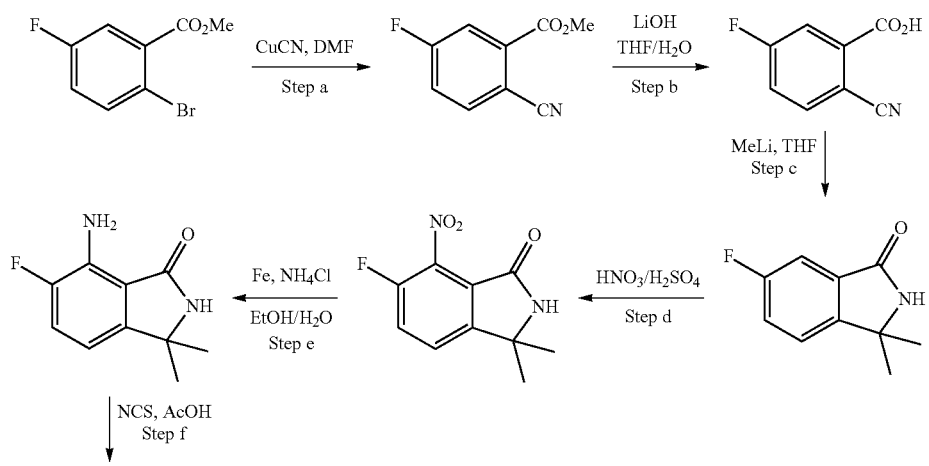

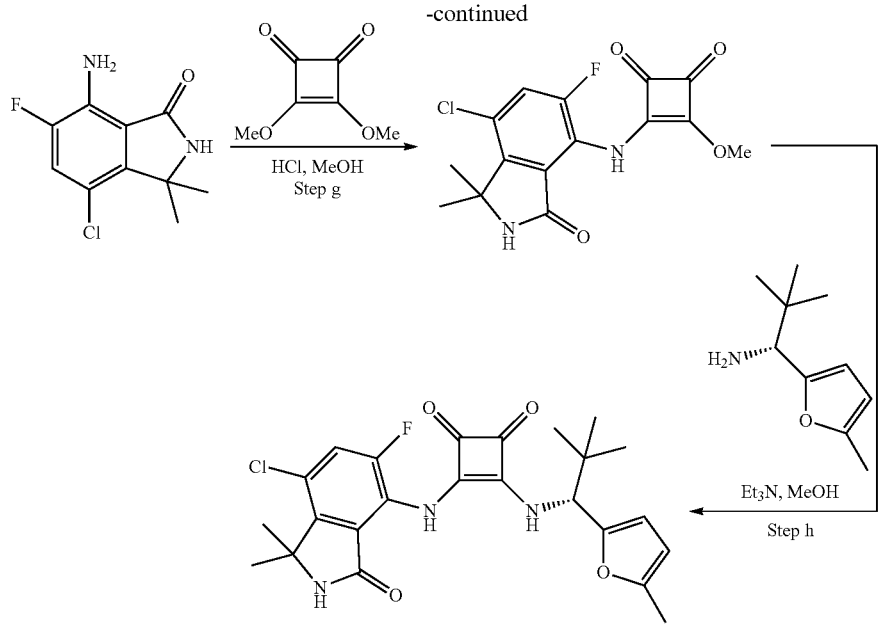

Step a:

A mixture of methyl 2-bromo-5-fluorobenzoate (5.00 g, 21.5 mmol) and copper cyanide (2.12 g, 23.6 mmol) in DMF was heated at 90° C. for 1 day, then allowed to cool to room temperature, diluted with ethyl acetate (300 mL), and filtered. The filtrate was washed with brine (5×50 mL) and then with sat. aqueous NaHCO$_3$ (50 mL). The organic layer was dried over MgSO$_4$, filtered, and concentrated in vacuo. This product was used in the next step without further purification. MS: (ES) m/z calculated for C$_9$H$_6$FNO$_2$[M+H]$^+$ 180.0. found 180.0.

Step b:

To a stirred solution of methyl 2-cyano-5-fluorobenzoate (3.85 g, 21.5 mmol) in tetrahydrofuran (30 mL) and water (3 mL) at 0° C. was added lithium hydroxide monohydrate (1.11 g, 26.5 mmol). The reaction was warmed to rt and stirred for 1 h. Then the solvent was evaporated and the residue was diluted with water (100 mL) and 2 M aqueous HCl (20 mL). The solid was collected by filtration and dried under vacuum to give the desired product. MS: (ES) m/z calculated for C$_8$H$_4$FNO$_2$[M+H]$^+$ 166.0. found 166.0.

Step c:

To a stirred solution of 2-cyano-5-fluorobenzoic acid (1.70 g, 10.3 mmol) in anhydrous tetrahydrofuran (105 mL) at −78° C. was added a 1.6 M solution of methyl lithium in ether (25.74 mL, 41.2 mmol) dropwise. The mixture was stirred at −78° C. for 1 h and then slowly warmed to rt, quenched with saturated aqueous ammonium chloride, and extracted with ethyl acetate. The organic layer was purified by silica gel chromatography (0-100% ethyl acetate in hexanes) to give 6-fluoro-3,3-dimethylisoindolin-1-one. MS: (ES) m/z calculated for C$_{10}$H$_{10}$FNO[M+H]$^+$ 180.0. found 180.0.

Step d:

A reaction vial containing 6-fluoro-3,3-dimethylisoindolin-1-one (620 mg, 3.46 mmol) in concentrated H$_2$SO$_4$ (1 mL) was cooled in an ice-bath. A mixture of concentrated H$_2$SO$_4$ (1 mL) with 70% HNO$_3$ (0.25 mL, 3.8 mmol) was added drop-wise and the reaction mixture was stirred at 0° C. for 2 h then carefully quenched with ice and diluted to 10 mL with cold water. The solid was filtered, washed with water and dried under vacuum to give 6-fluoro-3,3-dimethyl-7-nitroisoindolin-1-one. MS: (ES) m/z calculated for C$_{10}$H$_9$FN$_2$O$_3$[M+H]$^+$ 225.0. found 225.0.

Step e:

To a solution of 6-fluoro-3,3-dimethyl-7-nitroisoindolin-1-one (0.56 g, 2.50 mmol) in ethanol (10 mL) and water (1 mL) at room temperature was added iron powder (0.58 g, 10.38 mmol) and ammonium chloride (1.90 g, 34.6 mmol). The reaction mixture was warmed to 90° C. and stirred for 1 hour. Then the reaction was allowed to cool to room temperature, filtered through Celite and rinsed with methanol (20 ml). The filtrate was concentrated to dryness and the residue was diluted with ethyl acetate, then washed with water and brine. The combined organic layers were dried (Na$_2$SO$_4$), filtered, concentrated in vacuo, and purified by silica gel chromatography (0-100% ethyl acetate in hexanes) to provide 7-amino-6-fluoro-3,3-dimethylisoindolin-1-one. MS: (ES) m/z calculated for C$_{10}$H$_{11}$FN$_2$O[M+H]$^+$ 195.0. found 195.0.

Step f:

To a solution of 7-amino-6-fluoro-3,3-dimethylisoindolin-1-one (116 mg, 0.59 mmol) in acetic acid (1 mL) at room temperature was added N-chlorosuccinimide (80 mg, 0.59 mmol). The reaction mixture was warmed to 45° C. and stirred overnight. Then it was allowed to cool to room temperature, diluted with ethyl acetate, and washed with water and brine. The combined organic layers were dried (Na$_2$SO$_4$), filtered, and concentrated in vacuo. The crude was purified by silica gel chromatography (0-30% ethyl acetate in hexanes) to provide 7-amino-4-chloro-6-fluoro-3,3-dimethylisoindolin-1-one. MS: (ES) m/z calculated for C$_{10}$H$_{10}$ClFN$_2$O[M+H]$^+$ 229.0. found 229.0.

Step g:

To a slurry of 7-amino-4-chloro-6-fluoro-3,3-dimethylisoindolin-1-one (73 mg, 0.32 mmol) and 3,4-dimethoxycyclobut-3-ene-1,2-dione (54 mg, 0.38 mmol) in methanol (3 mL) was added 4 M HCl in dioxane (0.08 mL, 0.32 mmol). The reaction mixture was warmed to 60° C. and stirred for 1 hour. Then it was allowed to cool to room temperature and diluted with dichloromethane (2 ml) to generate a clear solution. This solution was concentrated in vacuo. The crude was purified by silica gel chromatography (0-10% methanol in dichloromethane) to provide the desired product. MS: (ES) m/z calculated for C$_{15}$H$_{12}$ClFN$_2$O$_4$[M+H]$^+$ 338.0. found 338.0.

Step h:

To a slurry of 3-((7-chloro-5-fluoro-1,1-dimethyl-3-oxoisoindolin-4-yl)amino)-4-methoxycyclobut-3-ene-1,2-dione (71 mg, 0.21 mmol) in methanol (2 mL) was added (R)-2,2-dimethyl-1-(5-methylfuran-2-yl)propan-1-amine (35 mg, 0.21 mmol) and triethylamine (0.03 mL, 0.21 mmol). The resulting mixture was stirred at room temperature overnight and then diluted with dichloromethane. This was then purified by silica gel chromatography (0-10% methanol in dichlormethane) to afford the title compound. $^1$H NMR (400 MHz, DMSO-$d_6$) δ 9.61 (s, 1H), 8.97 (s, 1H), 8.40 (d, J=10 Hz, 1H), 7.62 (d, J=10 Hz, 1H), 6.10 (d, J=2.6 Hz, 1H), 5.95 (d, J=2.6 Hz, 1H), 4.92 (d, J=10 Hz, 1H), 2.19 (s, 3H), 1.46 (s, 6H), 0.87 (s, 9H). MS: (ES) m/z calculated for $C_{24}H_{25}ClFN_3O_4$[M–H]$^-$ 472.0. found 472.0.

Example 14: Synthesis of 3-[(7-chloro-5-fluoro-1,1-dimethyl-3-oxo-isoindolin-4-yl)amino]-4-[[(1R)-1-(4,5-dimethyl-2-furyl)-2,2-dimethyl-propyl]amino]cyclobut-3-ene-1,2-dione

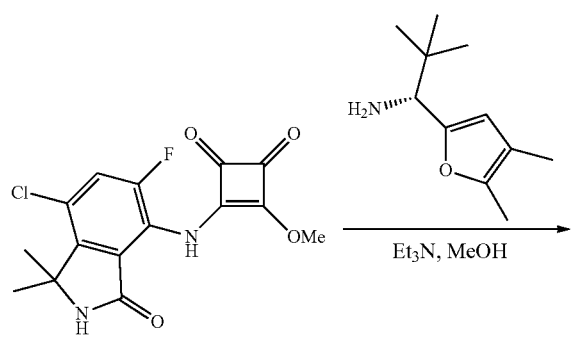

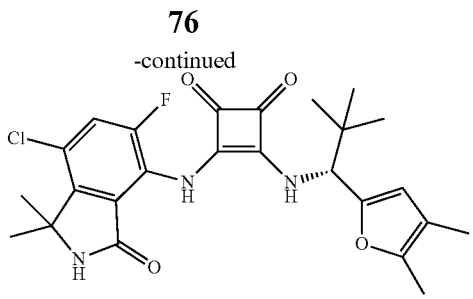

To a slurry of 3-((7-chloro-5-fluoro-1,1-dimethyl-3-oxoisoindolin-4-yl)amino)-4-methoxycyclobut-3-ene-1,2-dione (15 mg, 0.04 mmol) in methanol (2 ml) was added (R)-1-(4,5-dimethylfuran-2-yl)-2,2-dimethylpropan-1-amine (11 mg, 0.05 mmol) and triethylamine (0.01 ml, 0.05 mmol). The resulting mixture was stirred at room temperature overnight and concentrated to dryness. The crude was purified by reverse phase chromatography to afford the product. $^1$H NMR (400 MHz, DMSO-$d_6$) δ 9.68 (s, 1H), 9.06 (s, 1H), 8.44 (d, J=10 Hz, 1H), 7.70 (d, J=10 Hz, 1H), 6.08 (s, 1H), 4.94 (d, J=10 Hz, 1H), 2.17 (s, 3H), 1.87 (s, 3H), 1.54 (s, 6H), 0.94 (s, 9H). MS: (ES) m/z calculated for $C_{25}H_{27}ClFN_3O_4$[M–H]$^-$ 486.0. found 486.0.

Example 15: Synthesis of 3-[[7-chloro-3-oxo-2-[2-(5-oxo-1H-tetrazol-4-yl)ethyl]isoindolin-4-yl]amino]-4-[[1R)-2,2-dimethyl-1-(5-methyl-2-furyl)propyl]amino]cyclobut-3-ene-1,2-dione

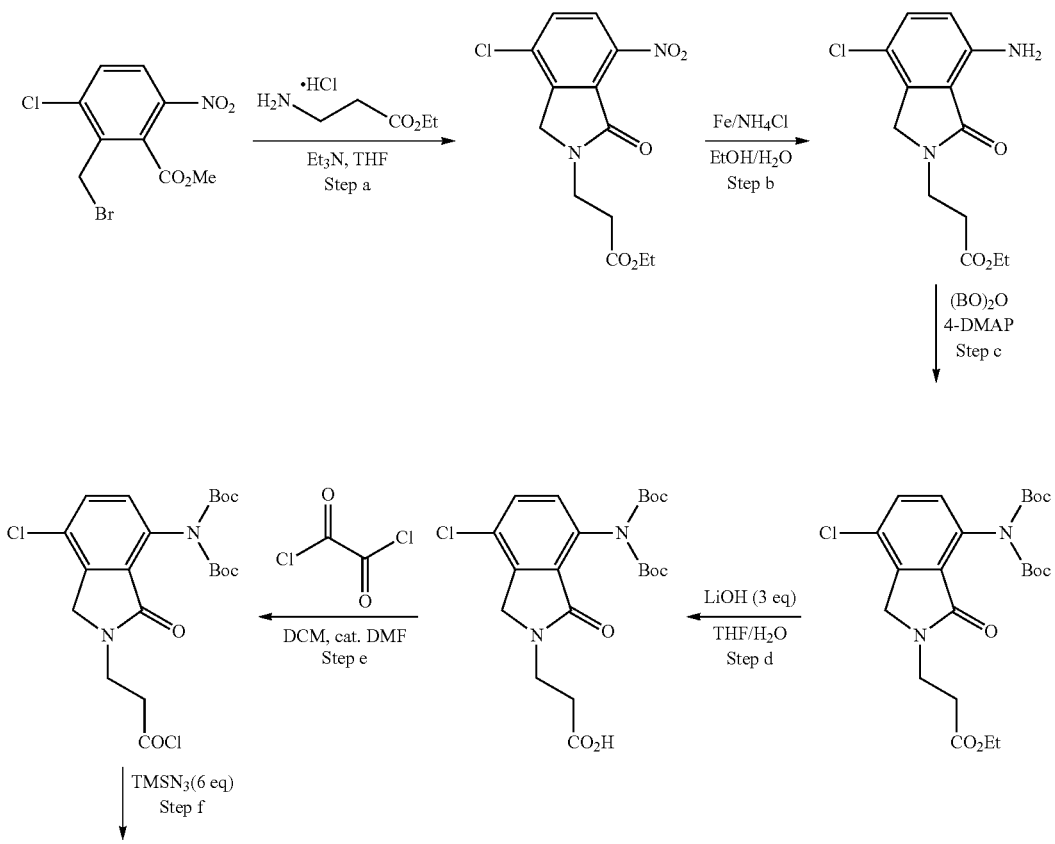

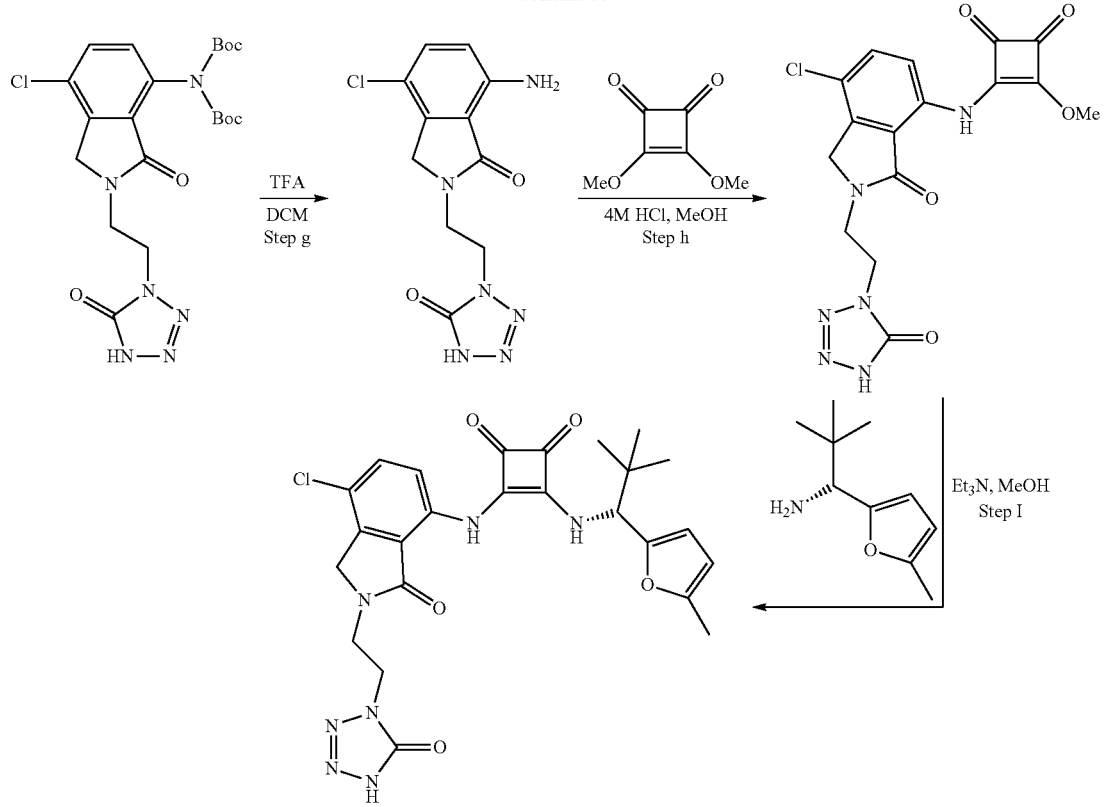

Step a:
To a mixture of methyl 2-(bromomethyl)-3-chloro-6-nitrobenzoate (10.0 g, 32.4 mmol) and ethyl 3-aminopropanoate hydrochloride salt (5.5 g, 35.6 mmol) in tetrahydrofuran (120 ml) was added triethylamine (10 ml, 71.3 mmol). The reaction mixture was stirred at room temperature overnight. The reaction was then diluted with ethyl acetate, and washed with water and brine. The combined organic layers were dried ($Na_2SO_4$), filtered, and concentrated in vacuo to give the product, which was used without further purification. MS: (ES) m/z calculated for $C_{13}H_{13}ClN_2O_5[M+H]^+$ 313.0. found 313.0.

Step b:
To a solution of ethyl 3-(4-chloro-7-nitro-1-oxoisoindolin-2-yl)propanoate (10.1 g, 32.4 mmol) in ethanol (90 ml) and water (10 ml) at room temperature was added iron powder (6.0 g, 97.2 mmol) and ammonium chloride (9.0 g, 162 mmol). The reaction mixture was warmed to 90° C. and stirred for 1 hour. It was then allowed to cool to room temperature, filtered through Celite and rinsed with methanol (120 ml). The filtrate was concentrated to dryness and the residue was diluted with ethyl acetate, washed with water, and then washed with brine. The combined organic layers were dried ($Na_2SO_4$), filtered, and concentrated in vacuo to give the product, which was used without further purification. MS: (ES) m/z calculated for $C_{13}H_{15}ClN_2O_3$ $[M+H]^+$ 283.0. found 283.0.

Step c:
To a solution of ethyl 3-(7-amino-4-chloro-1-oxoisoindolin-2-yl)propanoate (6.60 g, 23.2 mmol) in tetrahydrofuran (40 ml) at room temperature was added di tert-butyl dicarbonate (12.67 g, 58.0 mmol) and 4-di(methylamino)pyridine (142 mg, 1.16 mmol). The reaction mixture was warmed to 100° C. and stirred overnight. It was then allowed to cool to room temperature, diluted with saturated aqueous $NaHCO_3$ (100 ml) and stirred for 20 min. The reaction mixture was then diluted with ethyl acetate, and washed with water, then brine. The combined organic layers were dried ($Na_2SO_4$), filtered, and concentrated in vacuo. The crude product was purified by silica gel chromatography (0-40% ethyl acetate in hexanes) to provide the product. MS: (ES) m/z calculated for $C_{23}H_{31}ClN_2O_7[M+Na]^+$ 505.0. found 505.0.

Step d:
To a solution of ethyl 3-[7-[bis(tert-butoxycarbonyl)amino]-4-chloro-1-oxo-isoindolin-2-yl]propanoate (7.43 g, 15.4 mmol) in tetrahydrofuran (40 ml), methanol (4 ml) and water (4 ml) at room temperature was added lithium hydroxide monohydrate (1.9 g, 46.2 mmol). The reaction mixture was stirred overnight, then concentrated to dryness and the residue was acidified with 1 M HCl to pH=4. The mixture was then extracted with ethyl acetate, and washed with water and brine. The combined organic layers were dried ($Na_2SO_4$), filtered, and concentrated in vacuo to give the product, which was used without further purification. MS: (ES) m/z calculated for $C_{21}H_{27}ClN_2O_7[M+H]^+$ 455.0. found 455.0.

Step e:
To a slurry of 3-[7-[bis(tert-butoxycarbonyl)amino]-4-chloro-1-oxo-isoindolin-2-yl]propanoic acid (4.66 g, 10.2 mmol) in dichloromethane (40 ml) at 0° C. was added oxalyl chloride (1.3 ml, 15.4 mmol) drop wise. After addition, two drops of DMF were added. The reaction mixture was stirred at 0° C. for 10 min, then allowed to warm to room temperature for 3 h. The resulting solution was concentrated to dryness. The residue was dissolved in dichloromethane (40 ml) and concentrated to dryness once more to remove excess oxalyl chloride. The crude was used in the next step without further purification.

Step f:
Azidotrimethylsilane was added in one portion to the above acid chloride at room temperature while under a nitrogen atmosphere. The mixture was heated to 100° C. for 2 h and then allowed to cool to room temperature. The mixture was then concentrated to dryness to remove excess azidotrimethylsilane. The crude was diluted with ethyl acetate and acidified to pH=3 with 1 M aqueous HCl. The organic layer was washed with water, then brine. The combined organic layers were dried (Na$_2$SO$_4$), filtered, and concentrated in vacuo. The crude product was purified by silica gel chromatography (0-100% ethyl acetate in hexanes) to provide the product. MS: (ES) m/z calculated for C$_{21}$H$_{27}$ClN$_6$O$_6$[M+Na]$^+$ 517.0. found 517.0.

Step g:

To a solution of tert-butyl N-tert-butoxycarbonyl-N-[7-chloro-3-oxo-2-[2-(5-oxo-1H-tetrazol-4-yl)ethyl]isoindolin-4-yl]carbamate (135 mg, 0.27 mmol) in dichloromethane (1 ml) was added trifluoroacetic acid (0.25 ml) at room temperature. The reaction mixture was stirred at room temperature for 1 h, and then neutralized with saturated aqueous NaHCO$_3$. The mixture was extracted with dichloromethane, then the organic layer was washed with water and brine. The combined organic layers were dried (Na$_2$SO$_4$), filtered, and concentrated in vacuo. The crude product was purified by silica gel chromatography (0-100% ethyl acetate in hexanes) to provide the product. MS: (ES) m/z calculated for C$_{11}$H$_{11}$ClN$_6$O$_2$[M+H]$^+$ 295.0. found 295.0.

Step h:

To a slurry of 7-amino-4-chloro-2-(2-(5-oxo-4,5-dihydro-1H-tetrazol-1-yl)ethyl)isoindolin-1-one (60 mg, 0.21 mmol) and 3,4-dimethoxycyclobut-3-ene-1,2-dione (44 mg, 0.31 mmol) in methanol (1 ml) was added 4 M HCl in dioxane (0.05 ml, 0.21 mmol). The resulting clear solution was warmed to 60° C. and stirred for 1 hour, and during this time a solid precipitated. The reaction mixture was allowed to cool to room temperature and the solid was filtered and rinsed with ethyl acetate (2 ml) to provide the product. MS: (ES) m/z calculated for C$_{16}$H$_{13}$ClN$_6$O$_5$[M−H]$^−$ 403.0. found 403.0.

Step i:

To a slurry of 3-((7-chloro-3-oxo-2-(2-(5-oxo-4,5-dihydro-1H-tetrazol-1-yl)ethyl)isoindolin-4-yl)amino)-4-methoxycyclobut-3-ene-1,2-dione (40 mg, 0.10 mmol) in methanol (2 ml) was added (R)-2,2-dimethyl-1-(5-methylfuran-2-yl)propan-1-amine (20 mg, 0.12 mmol) and one drop of triethylamine. The resulting mixture was stirred at room temperature overnight, and then concentrated to dryness. The crude was purified by silica gel chromatography (0-100% ethyl acetate in hexanes) to afford the product. $^1$H NMR (400 MHz, DMSO-d$_6$) δ 9.84 (s, 1H), 9.11 (d, J=10 Hz, 1H), 7.58 (d, J=8 Hz, 1H), 7.42 (d, J=8 Hz, 1H), 6.18 (d, J=2.6 Hz, 1H), 6.03 (d, J=2.6 Hz, 1H), 5.10 (d, J=10.4 Hz, 1H), 4.54 (s, 2H), 4.22 (t, J=5.6, 5.6 Hz, 2H), 3.85 (t, J=5.6, 5.6 Hz, 2H), 2.27 (s, 3H), 0.95 (s, 9H). MS: (ES) m/z calculated for C$_{25}$H$_{26}$ClN$_7$O$_5$[M−H]$^−$ 538.0. found 538.0.

Example 16: Synthesis of (R)-3-((7-chloro-2-(2-(4-methyl-5-oxo-4,5-dihydro-1H-tetrazol-1-yl)ethyl)-3-oxoisoindolin-4-yl)amino)-4-((2,2-dimethyl-1-(5-methylfuran-2-yl)propyl)amino)cyclobut-3-ene-1,2-dione

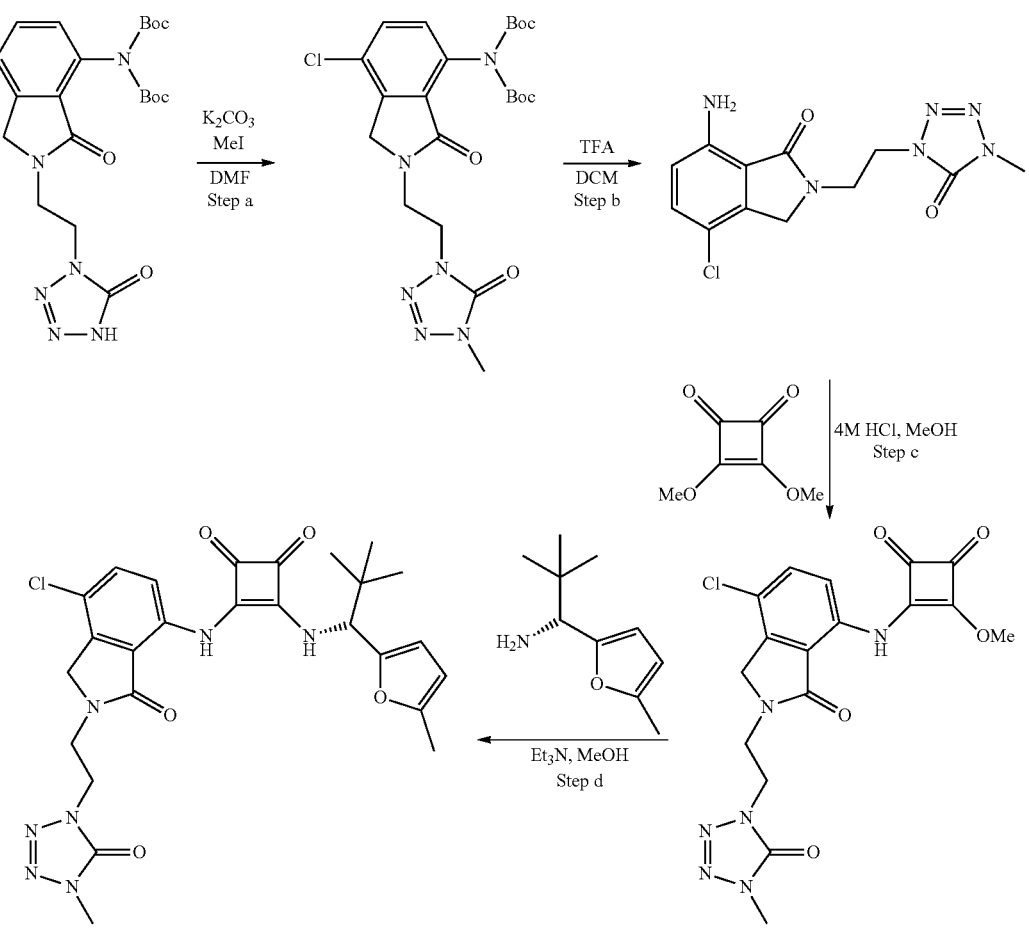

Step a:
To a solution of tert-butyl N-tert-butoxycarbonyl-N-[7-chloro-3-oxo-2-[2-(5-oxo-1H-tetrazol-4-yl)ethyl]isoindolin-4-yl] (100 mg, 0.20 mmol) in DMF (1 ml) was added potassium carbonate (70 mg, 0.51 mmol) and iodomethane at room temperature. The reaction mixture was stirred at room temperature for 2 h and then quenched with water. Solid precipitated and was filtered, and then rinsed with water and hexane. The collected solid was dried under vacuum to provide the product. MS: (ES) m/z calculated for $C_{22}H_{29}ClN_6O_6$ [M+H]$^+$ 509.0. found 509.0.

Step b:
To a solution of tert-butyl N-tert-butoxycarbonyl-N-[7-chloro-2-[2-(4-methyl-5-oxo-tetrazol-1-yl)ethyl]-3-oxo-isoindolin-4-yl]carbamate (80 mg, 0.16 mmol) in dichloromethane (1 ml) was added trifluoroacetic acid (0.25 mL) at room temperature. The reaction mixture was stirred at room temperature for 1 h, and then neutralized with saturated aqueous NaHCO$_3$. The mixture was extracted with dichloromethane, and the organic layer was washed with water and then brine. The combined organic layers were dried (Na$_2$SO$_4$), filtered, and concentrated in vacuo. The crude was purified by silica gel chromatography (0-100% ethyl acetate in hexanes) to provide the product. MS: (ES) m/z calculated for $C_{12}H_{13}ClN_6O_2$[M+H]$^+$ 309.0. found 309.0.

Step c:
To a slurry of 7-amino-4-chloro-2-(2-(4-methyl-5-oxo-4,5-dihydro-1H-tetrazol-1-yl)ethyl)isoindolin-1-one (31 mg, 0.10 mmol) and 3,4-dimethoxycyclobut-3-ene-1,2-dione (21 mg, 0.15 mmol) in methanol (1 ml) was added 4 M HCl in dioxane (0.025 ml, 0.10 mmol). The resulting clear solution was warmed to 60° C. and stirred for 1 hour. The reaction mixture was allowed to cool to room temperature and the solid precipitate was filtered and then rinsed with ethyl acetate (2 ml) to provide the product. MS: (ES) m/z calculated for $C_{17}H_{15}ClN_6O_5$[M−H]$^-$ 417.0. found 417.0.

Step d:
To a slurry of 3-((7-chloro-2-(2-(4-methyl-5-oxo-4,5-dihydro-1H-tetrazol-1-yl)ethyl)-3-oxoisoindolin-4-yl)-amino)-4-methoxycyclobut-3-ene-1,2-dione (32 mg, 0.076 mmol) in methanol (2 ml) was added (R)-2,2-dimethyl-1-(5-methylfuran-2-yl)propan-1-amine (15 mg, 0.09 mmol) and one drop of triethylamine. The resulting mixture was stirred at room temperature overnight and concentrated to dryness. The crude was purified by silica gel chromatography (0-100% ethyl acetate in hexanes) to afford the product. $^1$H NMR (400 MHz, DMSO-d$_6$) δ 9.85 (s, 1H), 9.10 (d, J=10 Hz, 1H), 7.59 (d, J=8.8 Hz, 1H), 7.44 (d, J=8.8 Hz, 1H), 6.18 (d, J=2.8 Hz, 1H), 6.03 (d, J=2.8 Hz, 1H), 5.10 (d, J=10.4 Hz, 1H), 4.54 (s, 2H), 4.22 (t, J=5.6, 5.6 Hz, 2H), 3.86 (t, J=5.6, 5.6 Hz, 2H), 2.27 (s, 3H), 0.95 (s, 9H). MS: (ES) m/z calculated for $C_{26}H_{28}ClN_7O_5$[M−H]$^-$ 552.0. found 552.0.

Example 17: Synthesis of 2-[4-chloro-7-[[2-[[(1R)-1-(5-chloro-2-furyl)-2,2-dimethyl-propyl]amino]-3,4-dioxo-cyclobuten-1-yl]amino]-1-oxo-isoindolin-2-yl]-6-methoxy-pyridine-3-carboxylic acid

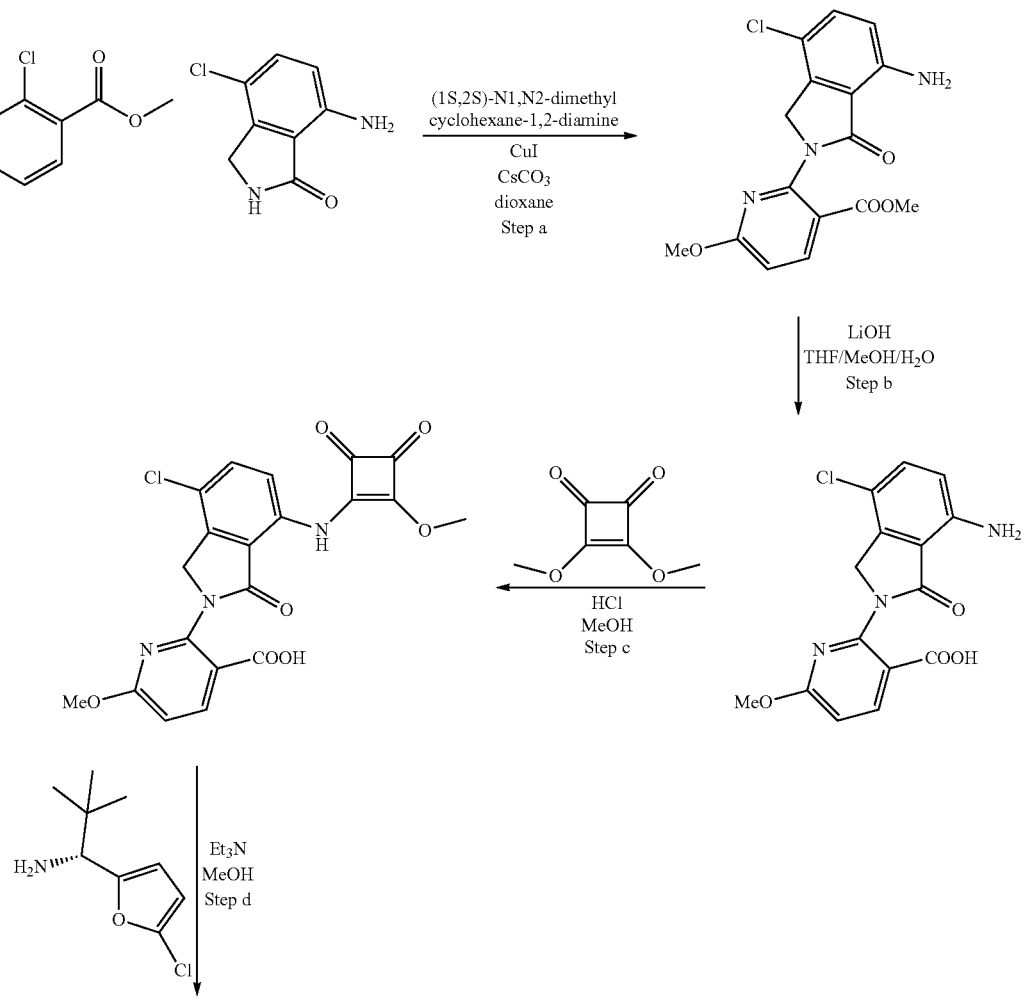

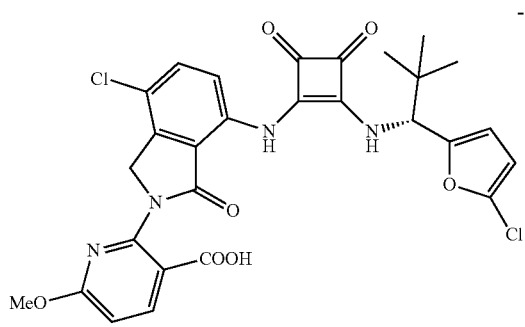

Step a:

To a reaction vial containing 7-amino-4-chloro-isoindolin-1-one (365 mg, 2.0 mmol) in dioxane (2.0 mL) was added methyl 2-chloro-6-methoxynicotinate (603 mg, 3.0 mmol), cesium carbonate (1.3 g, 4.0 mmol), copper iodide (152 mg, 80 mmol) and (1S,2S)—N1,N2-dimethylcyclohexane-1,2-diamine (227 mg, 1.6 mmol). The mixture was purged with nitrogen, then warmed to 110° C. The reaction was stirred at 110° C. and monitored by LC-MS. Following completion, the reaction was allowed to cool and was then filtered through Celite and rinsed with ethyl acetate. The crude was purified by silica gel chromatography (0-50% ethyl acetate/hexane) to give the product.

Step b:

To a solution of methyl 2-(7-amino-4-chloro-1-oxo-isoindolin-2-yl)-6-methoxy-pyridine-3-carboxylate (440 mg, 1.27 mmol) in tetrahydrofuran (5.0 mL), methanol (0.5 mL) and water (0.5 mL) was added lithium hydroxide (533 mg, 12.7 mmol). The resulting mixture was stirred at room temperature. Upon completion, the reaction was acidified to pH 5-7 using 1N aqueous HCl and extracted with ethyl acetate. The organic layer was washed with brine, dried ($Na_2SO_4$), filtered, and concentrated in vacuo to give the product.

Step c:

A mixture of 2-(7-amino-4-chloro-1-oxo-isoindolin-2-yl)-6-methoxy-pyridine-3-carboxylic acid (334 mg, 1.00 mmol) and 3,4-dimethoxycyclobut-3-ene-1,2-dione (156 mg, 1.10 mmol) in anhydrous methanol (5 mL) was stirred at 60° C. for 3 h. The reaction mixture was then filtered, and the solids were washed with ethyl acetate, then dried to give the product.

Step d:

$Et_3N$ (0.08 mL, 0.6 mmol) was added to a mixture of 2-[4-chloro-7-[(2-methoxy-3,4-dioxo-cyclobuten-1-yl)amino]-1-oxo-isoindolin-2-yl]-6-methoxy-pyridine-3-carboxylic acid (97 mg, 0.22 mmol) and (1R)-1-(5-chloro-2-furyl)-2,2-dimethyl-propan-1-amine (45 mg, 0.24 mmol) in MeOH (3.0 mL). The reaction was stirred at 60° C. for 4 h, and then concentrated. The resulting crude was purified by reverse phase chromatography ($MeCN:H_2O$ with 0.1% TFA as eluent) to give the product. $^1$H NMR (400 MHz, Methanol-$d_4$) δ 8.20 (d, J=8.5 Hz, 1H), 7.94 (d, J=8.9 Hz, 1H), 7.62 (d, J=8.8, 1H), 6.81 (d, J=8.6 Hz, 1H), 6.39 (s, 1H), 6.25 (d, J=3.5 Hz, 1H), 5.28 (s, 1H), 5.17 (s, 2H), 4.02 (s, 3H), 1.06 (s, 9H). MS: (ES) m/z calculated for $C_{28}H_{23}Cl_2N_4O_7$[M−H]$^-$ 597.1. found 597.1.

Example 18: Synthesis of 2-[4-chloro-7-[[2-[[(1R)-1-(4,5-dimethyl-2-furyl)-2,2-dimethyl-propyl]amino]-3,4-dioxo-cyclobuten-1-yl]amino]-1-oxo-isoindolin-2-yl]-6-methoxy-pyridine-3-carboxylic acid

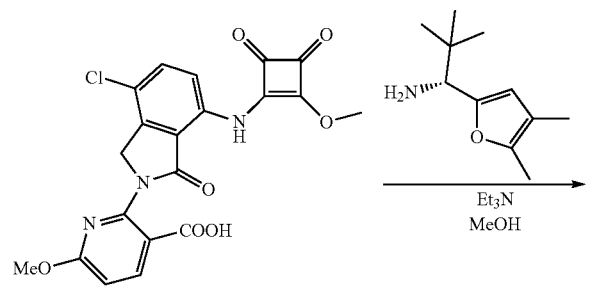

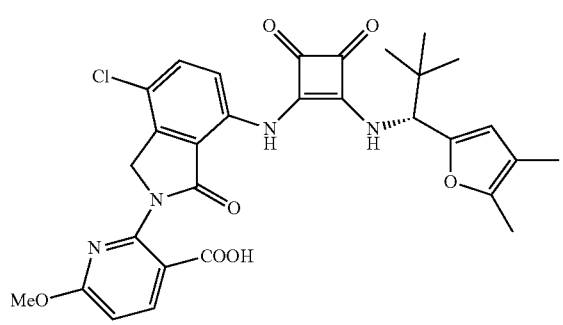

$Et_3N$ (0.08 mL, 0.6 mmol) was added to a mixture of 2-[4-chloro-7-[(2-methoxy-3,4-dioxo-cyclobuten-1-yl)amino]-1-oxo-isoindolin-2-yl]-6-methoxy-pyridine-3-carboxylic acid (90 mg, 0.15 mmol) and (1R)-1-(4,5-dimethyl-2-furyl)-2,2-dimethyl-propan-1-amine hydrochloride (45 mg, 0.23 mmol) in MeOH (3.0 mL). The reaction was stirred at 60° C. for 4 h, then concentrated. The resulting crude was purified by reverse phase chromatography (MeCN:H$_2$O with 0.1% TFA as eluent) to give the product. $^1$H NMR (400 MHz, Methanol-d$_4$) δ 8.19 (d, J=8.5 Hz, 1H), 7.92 (d, J=9.1 Hz, 1H), 7.61 (d, J=8.8 Hz, 1H), 6.80 (d, J=8.6 Hz, 1H), 6.06 (s, 1H), 5.24-5.09 (m, 3H), 4.02 (s, 3H), 2.18 (s, 3H), 1.91 (s, 3H), 1.04 (s, 9H). MS: (ES) m/z calculated for C$_{30}$H$_{28}$ClN$_4$O$_7$[M–H]$^-$ 591.2. found 591.1.

Example 19: Synthesis of 3-[[(1R)-1-(4,5-dimethyl-2-furyl)-2,2-dimethyl-propyl]amino]-4-[(5-fluoro-3-oxo-isoindolin-4-yl)amino]cyclobut-3-ene-1,2-dione

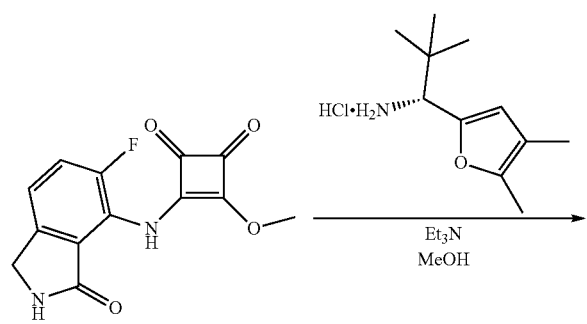

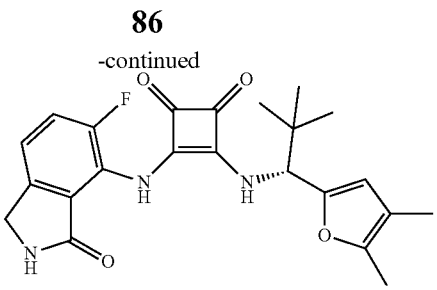

Et$_3$N (0.08 mL, 0.6 mmol) was added to a mixture of 3-[(5-fluoro-3-oxo-isoindolin-4-yl)amino]-4-methoxy-cyclobut-3-ene-1,2-dione (81 mg, 0.30 mmol) and (1R)-2,2-dimethyl-1-(5-methyl-2-furyl)butan-1-amine hydrochloride (72 mg, 0.33 mmol) in MeOH (3.0 mL). The reaction was stirred at 60° C. for 4 h. The reaction was concentrated and then purified by reverse phase chromatography (MeCN:H$_2$O with 0.1% TFA as eluent) to give the product. $^1$H NMR (400 MHz, DMSO-d$_6$) δ 9.64 (s, 1H), 8.72 (s, 1H), 8.39 (d, J=10.2 Hz, 1H), 7.47 (dd, J=11.2, 8.2 Hz, 1H), 7.33 (dd, J=8.3, 3.8 Hz, 1H), 6.07 (s, 1H), 4.97 (d, J=10.2 Hz, 1H), 4.32 (s, 2H), 2.18 (s, 3H), 1.87 (s, 3H), 0.95 (s, 9H).

Example 20: Synthesis of 3-[(7'-chloro-5'-fluoro-3'-oxo-spiro[cyclopentane-1,1'-isoindoline]-4'-yl)amino]-4-[[(1R)-2,2-dimethyl-1-(5-methyl-2-furyl)propyl]amino]cyclobut-3-ene-1,2-dione

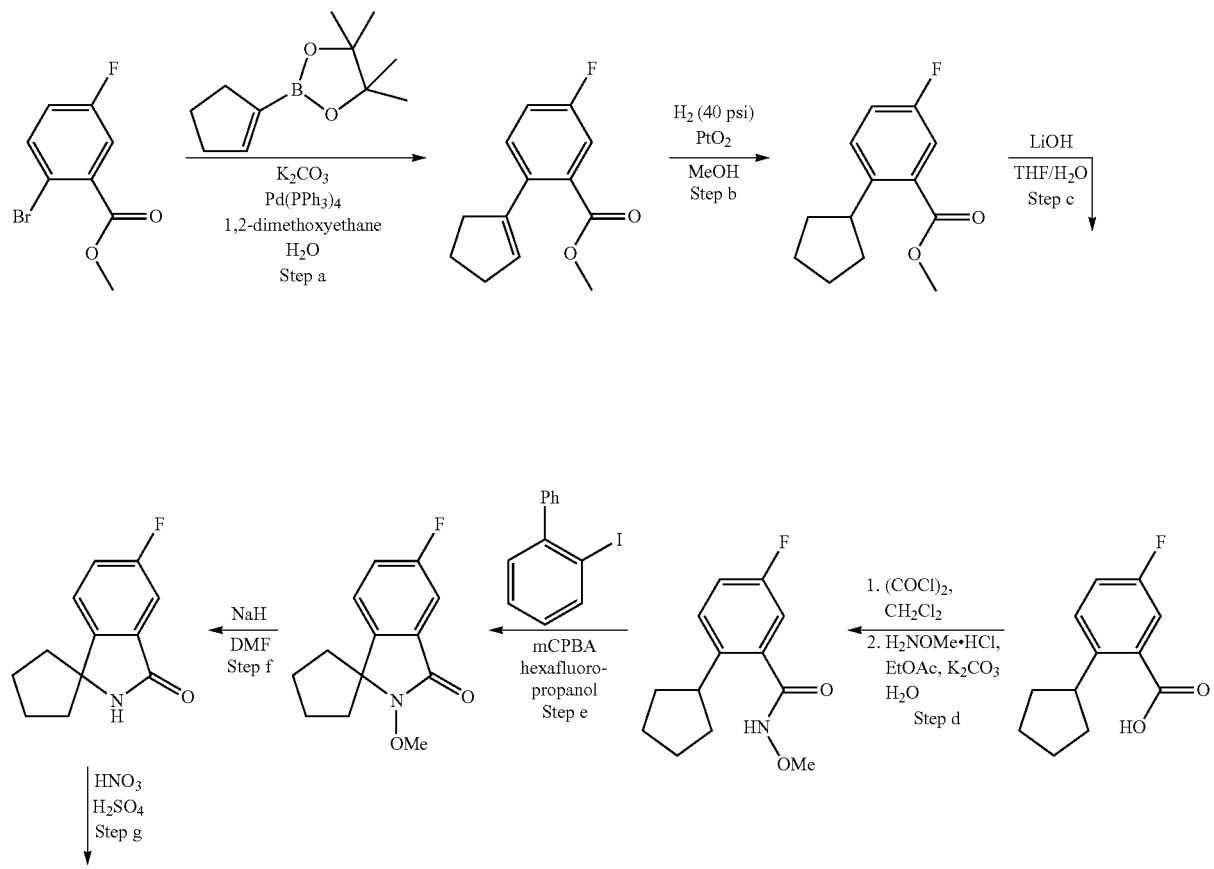

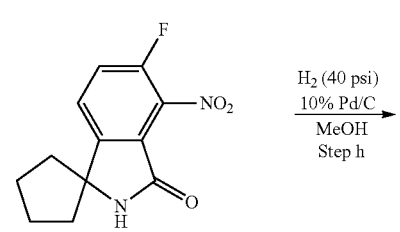 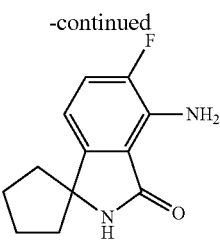 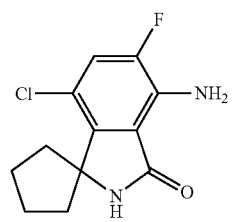

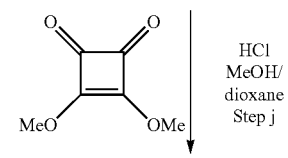

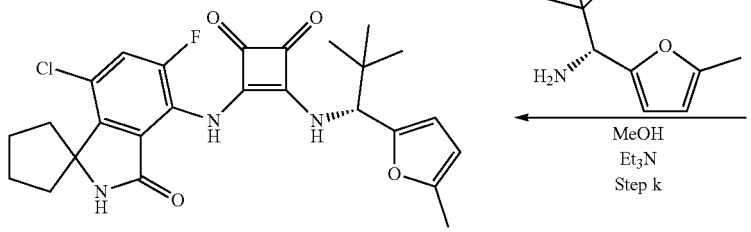 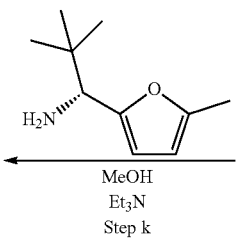

Step a:

A mixture of methyl 2-bromo-5-fluorobenzoate (2.5 g, 10.8 mmol), 2-cyclopentenyl-4,4,5,5-tetramethyl-1,3,2-dioxaborolane (2.3 g, 11.9 mmol), and K$_2$CO$_3$ (3.7 g, 27.0 mmol) in 1,2-dimethoxyethane (27 mL) and H$_2$O (3.0 mL) was purged with N$_2$ for 2 minutes. Pd(PPh$_3$)$_4$ (0.62 g, 0.54 mmol) was then added at room temperature. The resulting mixture was heated to 95° C. for 14 h, and after completion of the reaction, the mixture was allowed to cool to room temperature. The reaction mixture was diluted with EtOAc (100 mL), and the organic layer was washed with H$_2$O followed by brine, then dried over Na$_2$SO$_4$, filtered and concentrated. The crude compound was purified by silica gel chromatography (0-20% ethyl acetate in hexanes) to give methyl 2-cyclopentenyl-5-fluorobenzoate.

Step b:

To a solution of methyl 2-cyclopentenyl-5-fluorobenzoate (2.2 g, 10.0 mmol) in MeOH (25 mL) was added PtO$_2$ (448 mg, 2.0 mmol). This was shaken under H$_2$ (40 psi) for 3 h. The mixture was filtered through celite and washed with MeOH (40 mL), and the filtrate was concentrated under reduced pressure. The crude product was used directly in the next step without further purification.

Step c:

To a stirred solution of methyl 2-cyclopentyl-5-fluorobenzoate (2.0 g, 14.9 mmol) in THF/H$_2$O (20:6 mL) at room temperature was added LiOH.2H$_2$O (1.89 g, 61.0 mmol). The reaction mixture was stirred for 16 h. After completion, the reaction was quenched with 2N aqueous HCl (4 mL) to adjust to pH=7. The aqueous solution was extracted with ethyl acetate (2×75 mL) and the combined organic layers were washed with brine, dried over Na$_2$SO$_4$, filtered and concentrated. The crude product was used directly in the next step without further purification. MS: (ES) m/z calculated for C$_{12}$H$_{13}$FO$_2$[M+H]$^+$ 209.1. found 209.1.

Step d:

To a stirred solution of 2-cyclopentyl-5-fluorobenzoic acid (3.0 g, 14.4 mmol) in dichloromethane (30 mL) at 0° C. was added DMF (2 drops). Oxalyl chloride (2.27 g, 18.0 mmol) was then added dropwise over 5 minutes, and the reaction mixture was stirred at room temperature for 16 h. After completion of the reaction, the solvent was removed under reduced pressure and the residue was dried under vacuum for 2 h to give 2-cyclopentyl-5-fluorobenzoyl chloride.

The above obtained 2-cyclopentyl-5-fluorobenzoyl chloride (3.0 g, 13.2 mmol) in 5 ml of EtOAc was added to a cold solution of O-methylhydroxylamine hydrochloride (1.32 g, 15.8 mmol) and K$_2$CO$_3$ (3.6 g, 26.4 mmol) in EtOAc and H$_2$O (32:10 mL) at 0° C. The reaction mixture was then stirred at room temperature for 14 h. After completion of the reaction, the mixture was extracted with ethyl acetate (2×50 mL), and the combined organic layers were washed with brine solution, dried over Na$_2$SO$_4$, filtered, and concentrated in vacuo. The crude compound was purified by silica gel, chromatography (10-40% ethyl acetate in hexanes) to give 2-cyclopentyl-5-fluoro-N-methoxybenzamide. MS: (ES) m/z calculated for C$_{13}$H$_{16}$FNO$_2$[M+H]$^+$ 238.2. found 238.1.

Step e:

To a mixture of 2-cyclopentyl-5-fluoro-N-methoxybenzamide (2.0 g, 8.4 mmol) and mCPBA (2.16 g, 12.6 mmol) in hexafluoropropanol (3.5 mL) was added 2-iodobiphenyl (468 mg, 1.68 mmol) at room temperature. The reaction mixture was stirred at room temperature for 1 hour. After completion, the reaction mixture was quenched with saturated aqueous NaHCO$_3$, and diluted with ethyl acetate (100 mL). The organic layer was washed with H$_2$O then brine solution, dried over Na$_2$SO$_4$, filtered, and concentrated. The crude compound was purified by silica gel chromatography (10-60% ethyl acetate in hexanes) to give 5'-fluoro-2'-methoxyspiro[cyclopentane-1,1'-isoindolin]-3'-one. MS: (ES) m/z calculated for C$_{13}$H$_{14}$FNO$_2$[M+H]$^+$ 236.1. found 236.0.

Step f:

To a stirred solution of 5'-fluoro-2'-methoxyspiro-[cyclopentane-1,1'-isoindolin]-3'-one (0.95 g, 4.04 mmol), in DMF (3.5 mL) was added 60% NaH (185 mg, 8.08 mmol) at room temperature. The resulting mixture was heated to 95° C. for 3 h, and the mixture was then allowed to cool to room temperature. The reaction mixture was diluted with ethyl acetate (75 mL), and the organic layer was washed with H$_2$O, then brine, dried over Na$_2$SO$_4$, filtered, and concentrated. The crude product was used directly in the next step without further purification.

Step g:

The 5'-fluorospiro[cyclopentane-1,1'-isoindolin]-3'-one from Step f (0.75 g, 3.65 mmol) was dissolved in concentrated H$_2$SO$_4$. (5 mL) and cooled to 0° C. 70% HNO$_3$ (0.46 g, 7.31 mmol, 2.0 equiv) was added drop-wise and the reaction mixture was stirred at 0° C. for 10 minutes, then allowed to warm to room temperature and stirred overnight. Ice was added and the mixture was then diluted with cold water (10 mL). The reaction mixture was extracted with EtOAc (2×25 mL), washed with H$_2$O and then brine solution, dried over Na$_2$SO$_4$, filtered, and concentrated. The crude was used directly in the next step without further purification (0.55 g). MS: (ES) m/z calculated for C$_{12}$H$_{11}$FN$_2$O$_3$[M+H]$^+$ 251.1. found 251.0.

Step h:

5'-fluoro-4'-nitrospiro[cyclopentane-1,1'-isoindolin]-3'-one (0.55 g, 1.32 mmol) and 10% Pd/C (50% wet, 200 mg) in MeOH (20 mL) was stirred under a hydrogen atmosphere (40 psi) for 1 h. The mixture was filtered through celite and washed with MeOH (40 mL), and the filtrate was concentrated under reduced pressure to give the crude, which was purified by silica gel chromatography (20-100% ethyl acetate in hexanes) to give 4'-amino-5'-fluorospiro[cyclopentane-1,1'-isoindolin]-3'-one (0.45 g, 56%). MS: (ES) m/z calculated for C$_{12}$H$_{13}$FN$_2$O[M+H]$^+$ 221.1. found 221.0.

Step i:

To a stirred solution of 7'-amino-6'-fluoro-spiro[cyclopentane-1,3'-isoindoline]-1'-one (135 mg, 0.61 mmol) in AcOH (1.5 mL) was added N-chlorosuccinimide (89 mg, 0.67 mmol) at room temperature. The resulting mixture was heated to 45° C. for 16 h, and then allowed to cool to room temperature. The reaction mixture was diluted with EtOAc (50 mL). The organic layer was washed with H$_2$O and then brine solution, dried over Na$_2$SO$_4$, filtered, and concentrated. The crude product was used directly in the next step without further purification.

Step j:

To a mixture of 4'-amino-7'-chloro-5'-fluorospiro[cyclopentane-1,1'-isoindolin]-3'-one (125 mg, 0.490 mmol) and 3,4-dimethoxycyclobut-3-ene-1,2-dione (104 mg, 0.735 mmol) in anhydrous methanol (2 mL) was added 4N HCl in dioxane (0.12 µl, 0.490 mmol) at room temperature. The reaction mixture was stirred at 60° C. for 3 h, then concentrated. Ethyl acetate (5 mL) was added to the residue and this was stirred at 50° C. for 10 min, then allowed to cool to room temperature. The mixture was filtered and dried to give 3-((7'-chloro-5'-fluoro-3'-oxospiro-[cyclopentane-1,1'-isoindolin]-4'-yl)amino)-4-methoxycyclobut-3-ene-1,2-dione. MS: (ES) m/z calculated for C$_{17}$H$_{14}$ClFN$_2$O$_4$[M+H]$^+$ 365.1. found 365.0.

Step k:

To a mixture of 3-((7'-chloro-5'-fluoro-3'-oxospiro[cyclopentane-1,1'-isoindolin]-4'-yl)amino)-4-methoxycyclobut-3-ene-1,2-dione from step i (70 mg, 0.205 mmol) and (1R)-2,2-dimethyl-1-(5-methyl-2-furyl)propan-1-amine (32 mg, 0.205 mmol) in methanol (2.0 mL) was added triethylamine (114 mg, 0.41 mmol, 2.0 equiv.) at room temperature. The mixture was stirred at 60° C. for 3 hours, and was then allowed to cool to room temperature. The solvent was removed under reduced pressure and the crude compound was purified by silica gel chromatography (20-100% ethyl acetate in hexanes) to give (R)-3-((7'-chloro-5'-fluoro-3'-oxospiro[cyclopentane-1,1'-isoindolin]-4'-yl)amino)-4-((2,2-dimethyl-1-(5-methylfuran-2-yl)propyl)amino)cyclobut-3-ene-1,2-dione. $^1$H NMR (400 MHz, DMSO-d$_6$) δ 9.71 (s, 1H), 9.42 (s, 1H), 8.50 (d, J=10.2 Hz, 1H), 7.70 (d, J=8.6 Hz, 1H), 6.19 (d, J=4.2 Hz, 1H), 6.03-6.01 (m, 1H), 5.02 (d, J=10.2 Hz, 1H), 2.27 (s, 3H), 1.95-1.80 (m, 6H), 1.70-1.80 (m, 2H), 0.95 (s, 9H). MS: (ES) m/z calculated for C$_{26}$H$_{27}$ClFN$_3$O$_4$[M+H]$^+$ 500.2. found 500.2.

Example 21: Synthesis of 3-[(7-chloro-2-hydroxy-3-oxo-isoindolin-4-yl)amino]-4-[[(1R)-2,2-dimethyl-1-(5-methyl-2-furyl)propyl]amino]cyclobut-3-ene-1,2-dione

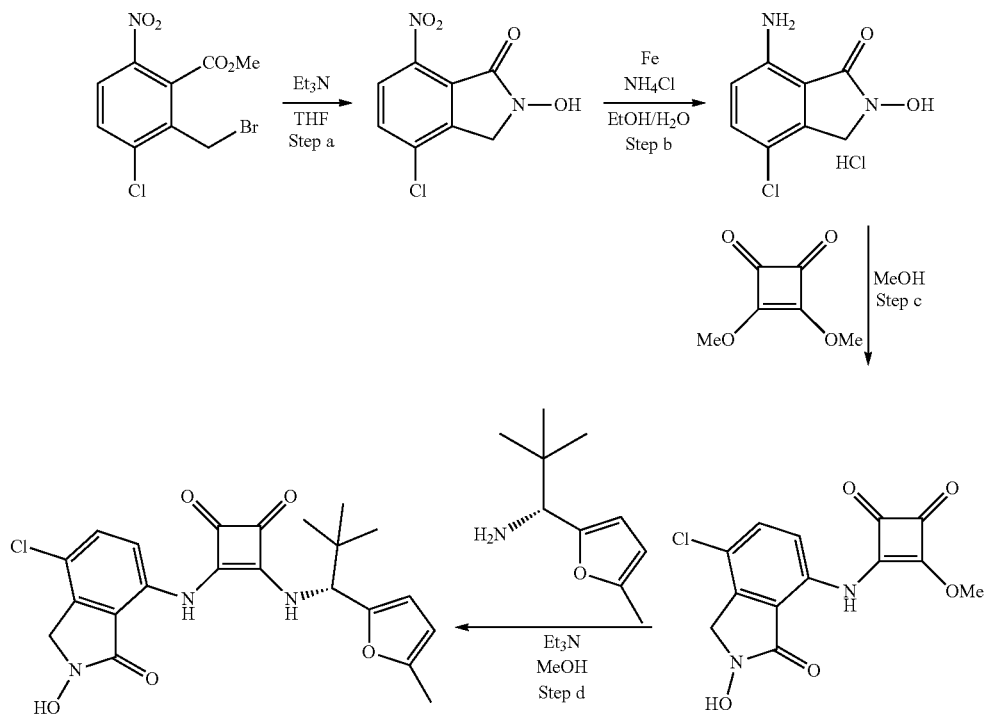

Step a:
Triethylamine (983 mg, 9.71 mmol) was added to a mixture of Methyl 2-(bromomethyl)-3-chloro-6-nitro-benzoate (1.5 g, 4.87 mmol) and tert-butyl N-hydroxycarbamate (710 mg, 5.35 mmol) in THF (10 mL), and this mixture was heated to 65° C. for 16 hours. After completion, the reaction was diluted with EtOAc and washed with H$_2$O (3×). The organic layer was dried with Na$_2$SO$_4$, filtered, and concentrated to give the product, which was used immediately in the next step.

Step b:
A mixture of 8:2 EtOH:H$_2$O (24 mL) was added to the crude 4-chloro-2-hydroxy-7-nitro-isoindolin-1-one from the previous step. To this solution was added NH$_4$Cl (2.67 g, 49.9 mmol) and iron powder (800 mg, 14.3 mmol). The reaction was heated to 85° C. Once complete, the reaction was concentrated to remove the EtOH, and EtOAc and H$_2$O were added. The mixture was filtered to remove the iron, then washed with H$_2$O, dried over Na$_2$SO$_4$, filtered, and concentrated. HCl in MeOH (4M, 2.0 mL) was added to the crude, and the solid was collected by filtration to give the product.

Step c:
A mixture of (75 mg, 0.38 mmol) and 3,4-dimethoxycyclobut-3-ene-1,2-dione (80 mg, 0.56 mmol) in anhydrous methanol (2.5 mL) was stirred at 60° C. overnight. The reaction mixture was filtered and the solid was rinsed with MeOH then dried under vacuum to give the crude.

Step d:
The crude 3-[(7-chloro-2-hydroxy-3-oxo-isoindolin-4-yl)amino]-4-methoxy-cyclobut-3-ene-1,2-dione from the previous step and (1R)-2,2-dimethyl-1-(5-methyl-2-furyl)propan-1-amine hydrochloride (66 mg, 0.40 mmol) were combined in MeOH (2.0 mL) and triethylamine (76 mg, 0.76 mmol) was added. The mixture was stirred at room temperature overnight. The reaction was concentrated and purified by silica gel chromatography, followed by reverse phase chromatography (MeCN:H2O with 0.1% TFA as eluent) to give the product. $^1$H NMR (400 MHz, DMSO-d$_6$) δ 11.76 (s, 1H), 10.42 (s, 1H), 9.19 (d, J=9.7 Hz, 1H), 7.65 (d, J=9.0 Hz, 1H), 7.39 (d, J=9.0 Hz, 1H), 6.22-6.18 (m, 1H), 6.05-6.03 (m, 1H), 5.09-5.15 (m, 3H), 2.26 (s, 3H), 0.95 (s, 9H). MS: (ES) m/z calculated for C$_{22}$H$_{22}$ClN$_3$O$_5$[M+Na]$^+$ 464.1. found 464.0.

Example 22: Synthesis of 3-[(2-amino-7-chloro-3-oxo-isoindolin-4-yl)amino]-4-[[(1R)-1-(4,5-dimethyl-2-furyl)-2,2-dimethyl-propyl]amino]cyclobut-3-ene-1,2-dione

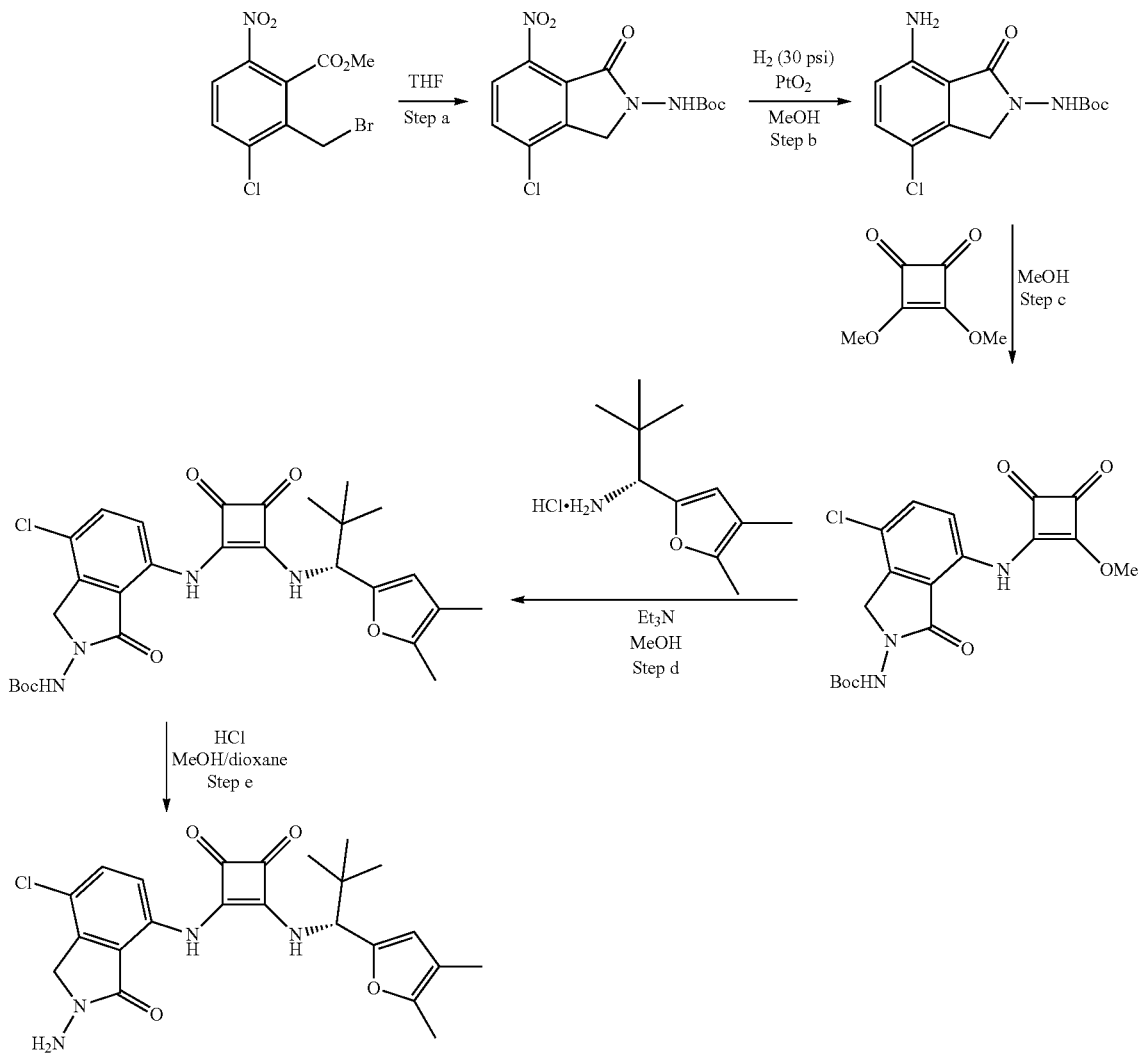

Step a:

A mixture of methyl 2-(bromomethyl)-3-chloro-6-nitrobenzoate (1.5 g, 4.87 mmol) and tert-butyl N-aminocarbamate (670 mg, 5.11 mmol) in THF (10 mL) was heated to 65° C. for 3 hours. After completion, the reaction was diluted with EtOAc and washed with $H_2O$ (3×). The organic layer was dried with $Na_2SO_4$, filtered, and concentrated to give the crude, which was purified by silica gel chromatography to give the product.

Step b:

MeOH (15 mL) was added to the tert-butyl N-(4-chloro-7-nitro-1-oxo-isoindolin-2-yl)carbamate (1.6 g, 4.9 mmol) from the previous step. To this solution was added $PtO_2$ (221 mg, 0.97 mmol) and this mixture was shaken in a hydrogenation apparatus under $H_2$ (30 psi). After completion of the reaction, the mixture was filtered and dried under vacuum to give the product.

Step e:

The crude from the previous step was dissolved in MeOH (2.0 mL) and HCl in dioxane (4M, 10 drops) was added and the reaction was stirred at room temperature. After completion, the reaction was concentrated and purified by reverse phase chromatography (MeCN:$H_2O$ with 0.1% TFA as eluent) to give the product. $^1$H NMR (400 MHz, DMSO-$d_6$) δ 9.87 (s, 1H), 9.01 (d, J=10.2 Hz, 1H), 8.05 (d, J=6.0 Hz, 2H), 7.43 (d, J=9.0 Hz, 1H), 7.23 (d, J=9.0 Hz, 1H), 6.1 (d, J=3.2 Hz, 1H), 5.04 (d, J=4.2 Hz, 1H), 4.40 (d, J=11.2 Hz, 2H), 2.09 (s, 3H), 1.79 (s, 3H), 0.86 (s, 9H). MS: (ES) m/z calculated for $C_{23}H_{25}ClN_4O_4[M+H]^+$ 457.2. found 457.0.

Example 23: Synthesis of 3-[(7-chloro-2-methoxy-3-oxo-isoindolin-4-yl)amino]-4-[[(1R)-1-(4,5-dimethyl-2-furyl)-2,2-dimethyl-propyl]amino]cyclobut-3-ene-1,2-dione

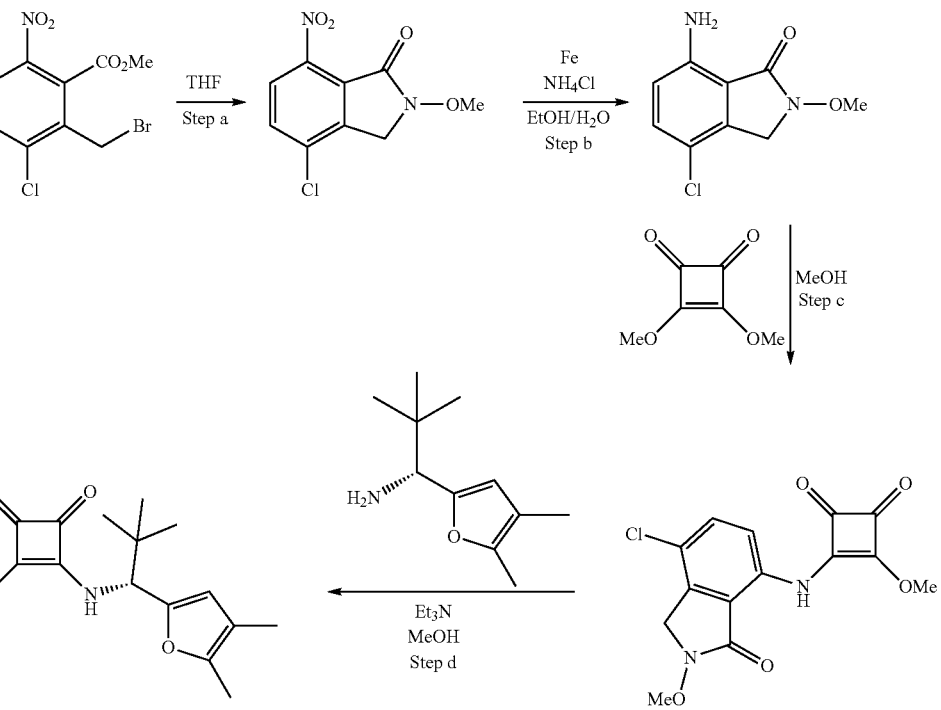

Step c:

A mixture of tert-butyl N-(7-amino-4-chloro-1-oxo-isoindolin-2-yl)carbamate (420 mg, 1.84 mmol) and 3,4-dimethoxycyclobut-3-ene-1,2-dione (392 mg, 2.7 mmol) in anhydrous methanol (5.0 mL) was stirred at 60° C. for 12 hours. The reaction mixture was filtered and the solid purified by silica gel chromatography to give the product.

Step d:

tert-Butyl N-[4-chloro-7-[(2-methoxy-3,4-dioxo-cyclobuten-1-yl)amino]-1-oxo-isoindolin-2-yl]carbamate (50 mg, 0.12 mmol) and (1R)-1-(4,5-dimethyl-2-furyl)-2,2-dimethyl-propan-1-amine hydrochloride (27 mg, 0.13 mmol) were combined in MeOH (4.0 mL), and triethylamine (24 mg, 0.244 mmol) was added. The mixture was stirred at 65° C. overnight. The reaction was then concentrated to give the crude, which was used in the next step without further purification.

Step a:

A mixture of methyl 2-(bromomethyl)-3-chloro-6-nitrobenzoate (5.0 g, 16.2 mmol) and O-methylhydroxylamine hydrochloride (2.12 g, 17.9 mmol) in THF (30 mL) was heated to 65° C. for 2 hours. After completion, the reaction was diluted with EtOAc and washed with $H_2O$ (3×). The organic layer was dried with $Na_2SO_4$, filtered, and concentrated to give the product, which was used in the next step without further purification.

Step b:

A mixture of 8:2 EtOH:$H_2O$ (26 mL) was added to the product from the previous step. To this solution was added $NH_4Cl$ (9.0 g, 170 mmol) and iron powder (2.27 g, 40.6 mmol), and the mixture was heated to 85° C. Once complete, the reaction was concentrated to remove the EtOH, and then EtOAc and $H_2O$ were added. The mixture was filtered to remove the iron, then washed with $H_2O$, dried over $Na_2SO_4$, filtered, and concentrated. The crude was purified by silica gel chromatography (10% to 80% EtOAc in hexanes) to give the product.

Step c:

A mixture of 7-amino-4-chloro-2-methoxy-isoindolin-1-one (1.0 g, 4.1 mmol) and 3,4-dimethoxycyclobut-3-ene-1,2-dione (0.88 g, 6.2 mmol) in anhydrous methanol (10 mL) was stirred at 60° C. overnight. This was then filtered and the solid was rinsed with MeOH and dried under vacuum to give the product.

Step d:

3-[(7-Chloro-2-methoxy-3-oxo-isoindolin-4-yl)amino]-4-methoxy-cyclobut-3-ene-1,2-dione (125 mg, 0.39 mmol) and (1R)-1-(4,5-dimethyl-2-furyl)-2,2-dimethyl-propan-1-amine hydrochloride (87 mg, 0.41 mmol) were combined in MeOH (4.0 mL) and triethylamine (117 mg, 1.15 mmol) was added. The mixture was stirred at 60° C. overnight. The reaction was then concentrated to give the crude, which was purified by silica gel chromatography (CH$_2$Cl$_2$:MeOH) to give the product. $^1$H NMR (400 MHz, DMSO-d$_6$) δ 9.87 (s, 1H), 9.01 (d, J=10.2 Hz, 1H), 7.63 (d, J=9.0 Hz, 1H), 7.42 (d, J=9.0 Hz, 1H), 6.09 (s, 1H), 5.04 (d, J=10.1 Hz, 1H), 4.73 (s, 2H), 3.86 (s, 3H), 2.18 (s, 3H), 1.87 (s, 3H), 0.95 (s, 9H). MS: (ES) m/z calculated for C$_{24}$H$_{26}$ClN$_3$O$_5$[M−H]$^−$ 470.2. found 470.1.

Example 24: Synthesis of 3-((((R)-1-(4,5-dimethyl-furan-2-yl)-2,2-dimethylpropyl)amino)-4-(((S)-5-fluoro-1-methyl-3-oxoisoindolin-4-yl)amino)cyclobut-3-ene-1,2-dione and 3-(((R)-1-(4,5-dimethylfuran-2-yl)-2,2-dimethylpropyl)amino)-4-((((R)-5-fluoro-1-methyl-3-oxoisoindolin-4-yl)amino)cyclobut-3-ene-1,2-dione

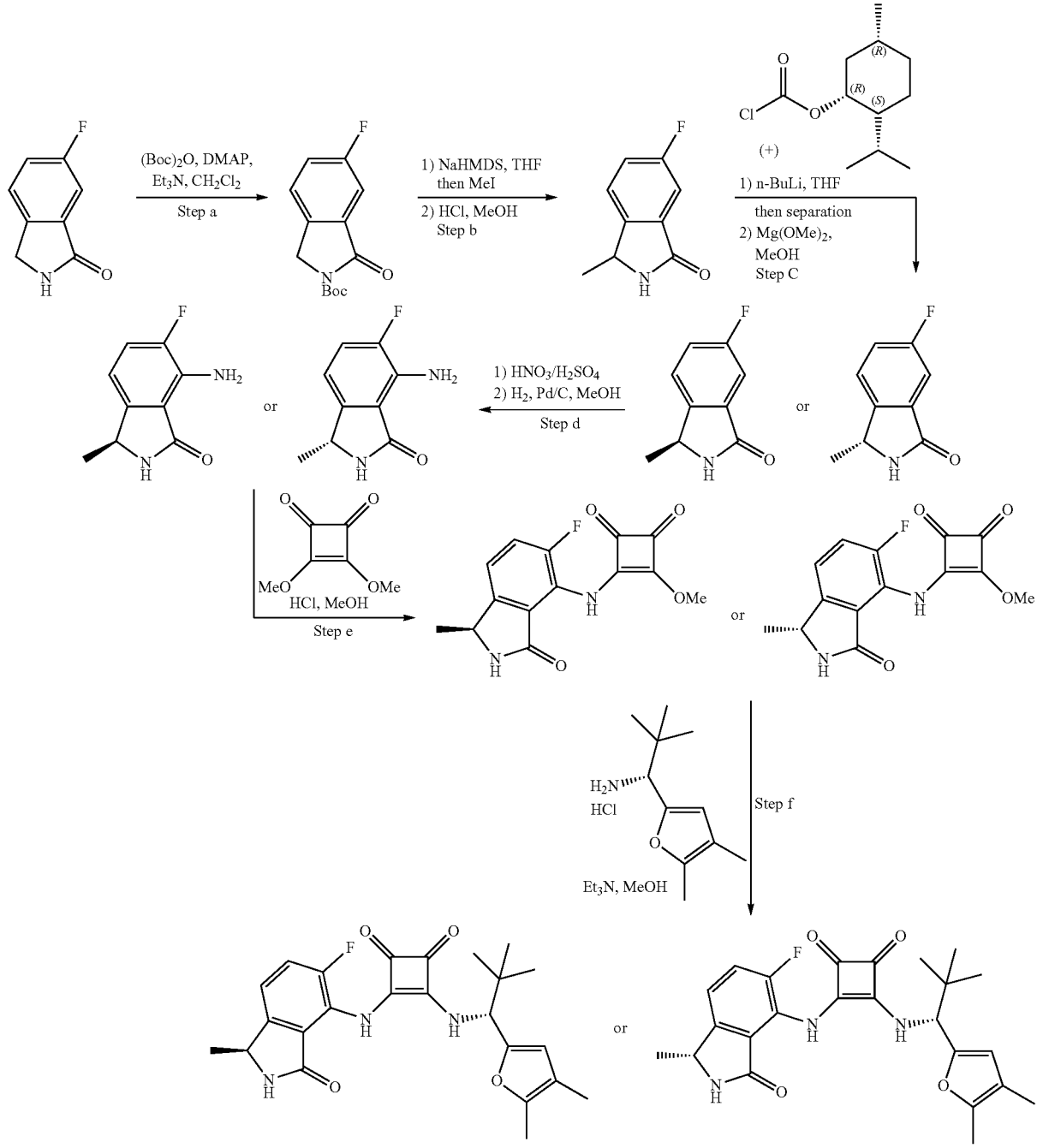

Step a:

To a stirred solution of 6-fluoroisoindolin-1-one (10 g, 66.2 mmol) in anhydrous dichloromethane (100 mL) were added triethylamine (16.72, 165.5 mmol, 21.8 mL), di-tert-butyl dicarbonate (17.3 g, 79.4 mmol) and catalytic DMAP (100 mg) at room temperature. The reaction mixture was stirred at room temperature for 16 h. After completion, this was diluted with $CH_2Cl_2$, washed with $H_2O$, and then washed with saturated aqueous $NaHCO_3$. The organic layer was dried over $Na_2SO_4$, filtered and concentrated in vacuo. The crude compound was purified by silica gel, chromatography (0-30% ethyl acetate in hexanes) to give the product. MS: (ES) m/z calculated for $C_{13}H_{14}FNO_3[M+H]^+$ 252.3. found 252.3.

Step b:

1) To a stirred solution of tert-butyl-6-fluoro-1-oxoisoindoline-2-carboxylate (5.0 g, 19.9 mmol) in anhydrous THF (40 mL) at −78° C. under $N_2$ atmosphere was added LiH-MDS (21.89 mL, 21.89 mmol) dropwise. After stirring for 30 min, a solution of methyl iodide (2.82 g, 19.92 mmol) in THF (5 mL) was added to the mixture. The reaction mixture was stirred at −78° C. for 1 h, and then allowed to warm to room temperature and stirred for 2 h. After completion, the reaction mixture was quenched with saturated aqueous $NH_4Cl$, diluted with EtOAc (100 mL), and the organic layer was washed with $H_2O$ and then brine solution. The organic layer was then dried over $Na_2SO_4$, filtered and concentrated in vacuo. The crude was used directly in the next step without any further purification. 2) To a stirred solution of tert-butyl-5-fluoro-1-methyl-3-oxoisoindoline-2-carboxylate (6.2 g, 66.2 mmol) in MeOH (60 mL) was added 4N HCl in dioxane (79.6 mmol, 20 mL). This was stirred at room temperature for 3 h. After completion of the reaction, the solvent was removed and the reaction mixture was diluted with EtOAc (3×50 mL). This was washed with $H_2O$, and then saturated aqueous $NaHCO_3$. The organic layer was then dried over $Na_2SO_4$, filtered, and concentrated. The crude compound was purified by silica gel chromatography (10-80% ethyl acetate in hexanes) to give the product. MS: (ES) m/z calculated for $C_9H_8FNO[M+H]^+$ 166.2. found 166.2.

Step c:

1) To a stirred solution of 6-fluoro-3-methylisoindolin-1-one (2.5 g, 15.1 mmol) in anhydrous THF (25 mL) at −78° C. under $N_2$ atmosphere was added n-BuLi (6.64 mL, 16.61 mmol, 2.5 M in hexane) dropwise and the reaction mixture was stirred at −78° C. for 30 min. A solution of (1R,2S,5R)-2-isopropyl-5-methylcyclohexyl chloroformate (3.96 g, 18.18 mmol) in THF (5 mL) was then added to the mixture, and this was stirred at −78° C. for 30 min. The reaction mixture was then allowed to warm to room temperature and stirred for 3 h. After completion of the reaction, the reaction mixture was quenched with saturated aqueous $NH_4Cl$, extracted with EtOAc (2×75 mL), and the combined organic layer was then washed with $H_2O$, then brine solution, dried over $Na_2SO_4$, filtered, and concentrated in vacuo. The crude compound was purified by silica gel chromatography to give (1S)-(1R,2S,5R)-2-isopropyl-5-methylcyclohexyl 5-fluoro-1-methyl-3-oxoisoindoline-2-carboxylate and (1R)-(1R,2S,5R)-2-isopropyl-5-methylcyclohexyl 5-fluoro-1-methyl-3-oxoisoindoline-2-carboxylate separately. 2) To a stirred solution of one diastereomer obtained above (1.2 g, 3.45 mmol) in MeOH (10 mL) was added $Mg(OMe)_2$ (10-12% wt) in MeOH (17.2 mmol, 10 mL) at room temperature. The reaction mixture was stirred at room temperature for 2 h. After completion of the reaction, the solvent was removed and the reaction mixture was quenched with saturated aqueous $NH_4Cl$, and extracted with EtOAc (2×75 mL). The combined organic layer was washed with $H_2O$, then brine solution, dried over $Na_2SO_4$, filtered, and concentrated in vacuo. The crude compound was purified by silica gel chromatography (20-60% ethyl acetate in hexanes) to give the desired product. MS: (ES) m/z calculated for $C_9H_8FNO$ $[M+H]^+$ 166.2. found 166.2. The other diastereomer was treated similarly to give the other desired product.

Step d:

1) One of the compounds obtained from Step c (0.45 g, 2.72 mmol) was dissolved in concentrated $H_2SO_4$ (5 mL) and cooled to 0° C. 70% $HNO_3$ (0.34 g, 24.1 mmol, 2.0 equiv) was added drop-wise and the reaction mixture was stirred at 0° C. for 10 minutes, then allowed to warm to room temperature and stirred overnight. Ice was added and the mixture was then diluted with cold water (10 mL) and extracted with EtOAc (2×25 mL). The combined organic layers were washed with $H_2O$, then brine solution, and were then dried over $Na_2SO_4$, filtered and concentrated. The crude was used directly in the next step without any further purification. MS: (ES) m/z calculated for $C_9H_7F_2N_2O_3[M+H]^+$ 211.0. found 211.2. The other enantiomer was treated similarly to give the other desired product. 2) One of the compounds obtained above (0.35 g, 1.32 mmol) and 10% Pd/C (50% wet, 100 mg) in MeOH (25 mL) was stirred under a hydrogen atmosphere (40 psi) for 1 h. The mixture was filtered through Celite and washed with MeOH (40 mL). The filtrate was concentrated under reduced pressure to give the crude, which was purified by silica gel chromatography (20-100% ethyl acetate/hexanes) to give the desired product. MS: (ES) m/z calculated for $C_9H_9FN_2O[M+H]^+$ 181.1. found 181.2. The other enantiomer was treated similarly to give the other desired product.

Step e:

A mixture of one of the compounds obtained in Step d (170 mg, 0.939 mmol) and 3,4-dimethoxycyclobut-3-ene-1,2-dione (200 mg, 1.40 mmol) in anhydrous methanol (4 mL) was stirred at 60° C. for 3 h. The reaction mixture was evaporated and the residue was stirred in ethyl acetate (10 mL) at 50° C. for 30 min, then allowed to cool to room temperature. The mixture was filtered and dried to give the desired product. MS: (ES) m/z calculated for $C_{14}H_{11}FN_2O_4$ $[M+H]^+$ 291.1. found 291.2. The other enantiomer was treated similarly to give the other desired product.

Step f:

To a solution of the hydrochloride salt of (1R)-1-(4,5-dimethyl-2-furyl)-2,2-dimethyl-propan-1-amine (62 mg, 0.288 mmol, 1.05 equiv.) in methanol (2.5 mL) was added triethylamine (75 mg, 0.687 mmol, 2.5 equiv). The mixture was stirred at room temperature for 10 min to become a clear solution, and then one of the compounds obtained above was added at room temperature. The resulting solution was stirred at 60° C. for 3 hours. After completion, the reaction was allowed to cool to room temperature. The solvent was removed under reduced pressure and the crude product was purified by preparative HPLC (acetonitrile-water with 0.1% TFA) to give the desired product. $^1$H NMR (400 MHz, DMSO-$d_6$) δ 9.64 (s, 1H), 8.79 (s, 1H), 8.38 (d, J=10.2 Hz, 1H), 7.46 (dd, J=11.4, 8.2 Hz, 1H), 7.34 (dd, J=3.9, 8.2 Hz, 1H), 6.07 (s, 1H), 4.95 (d, J=10.1 Hz, 1H), 4.58 (q, J=6.6 Hz, 1H), 2.18 (s, 3H), 1.87 (s, 3H), 1.33 (d, J=6.6 Hz, 3H), 0.95 (s, 9H). MS: (ES) m/z calculated for $C_{24}H_{26}FN_3O_4[M-H]^-$ 438.2. found 438.0. The other diastereomer was obtained similarly. $^1$H NMR (400 MHz, DMSO-$d_6$) δ 9.64 (s, 1H), 8.79 (s, 1H), 8.37 (d, J=10.2 Hz, 1H), 7.44 (dd, J=11.0, 8.2 Hz, 1H), 7.33 (dd, J=3.9, 8.8 Hz, 1H), 6.07 (s, 1H), 4.95 (d, J=10.1 Hz, 1H), 4.56 (q, J=6.3 Hz, 1H), 2.18 (s, 3H), 1.87 (s, 3H), 1.33 (d, J=6.6 Hz, 3H), 0.95 (s, 9H). MS: (ES) m/z calculated for $C_{24}H_{26}FN_3O_4[M-H]$ 438.2. found 438.0.

Example 25: 3-(((R)-1-(4,5-dimethylfuran-2-yl)-2,2-dimethylbutyl)amino)-4-(((S)-5-fluoro-1,7-dimethyl-3-oxoisoindolin-4-yl)amino)cyclobut-3-ene-1,2-dione and 3-(((R)-1-(4,5-dimethylfuran-2-yl)-2,2-dimethylbutyl)amino)-4-(((R)-5-fluoro-1,7-dimethyl-3-oxoisoindolin-4-yl)amino)cyclobut-3-ene-1,2-dione
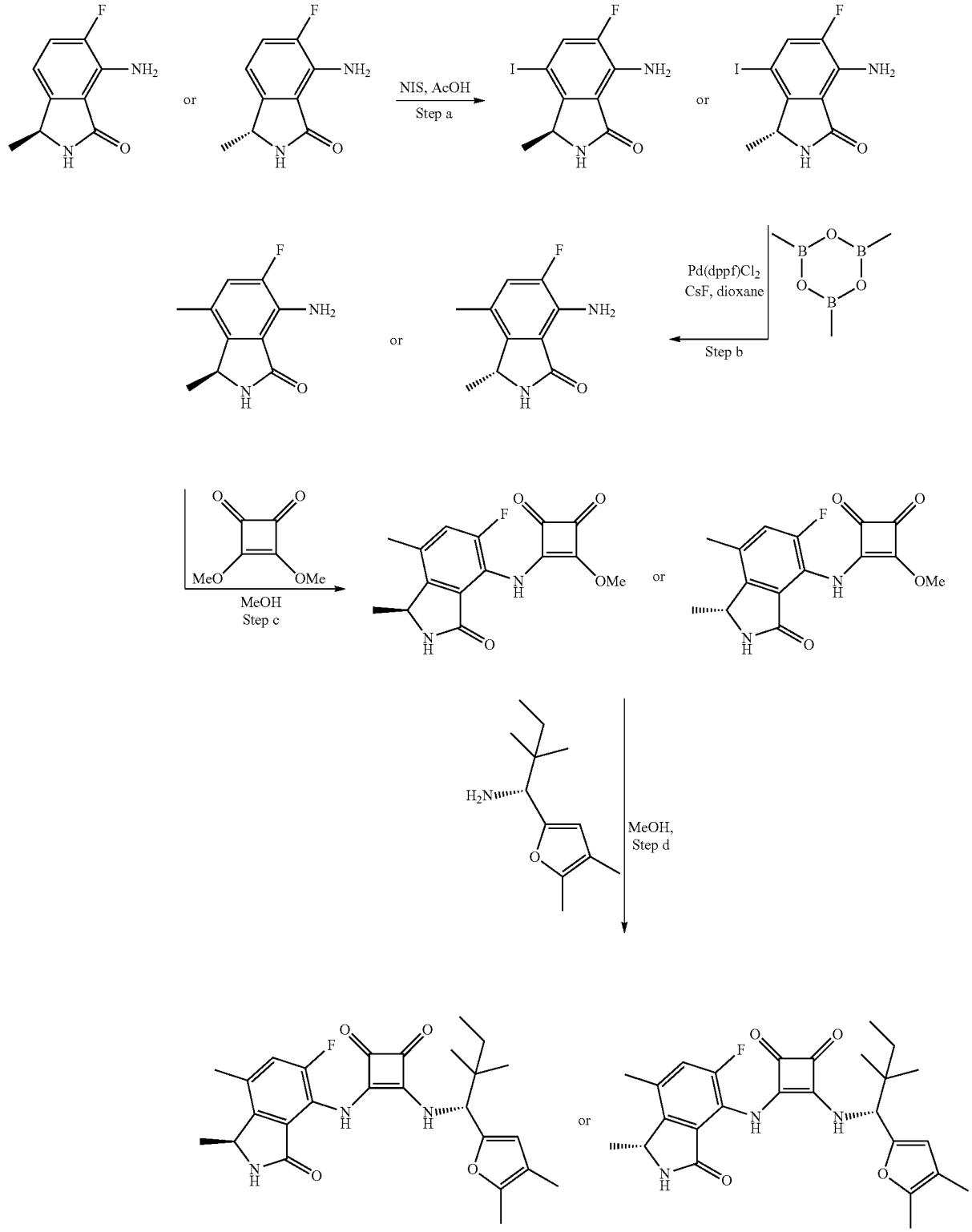

Step a:

To a solution of one of the enantiomers of 7-amino-6-fluoro-3-methylisoindolin-1-one (200 mg, 1.11 mmol) in AcOH (2.2 mL) in a room temperature water bath was added N-iodosuccinimide (350 mg, 1.56 mmol) in portions at room temperature. The resulting mixture was stirred for 30 minutes in the water bath, quenched with water (1 mL), and then extracted with ethyl acetate (10 mL). The organic layer was washed with brine (10 mL), and then dried over $MgSO_4$, filtered, and concentrated. The crude was purified by silica gel chromatography (0-60% ethyl acetate in hexanes) to give the desired product. MS: (ES) m/z calculated for $C_9H_8FIN_2O[M+H]^+$ 307.0. found 307.0. The other enantiomer was treated similarly to give the other desired product.

Step b:

To a solution of one of the compounds obtained in step a (248 mg, 0.81 mmol) in dioxane (8.1 mL) was added CsF (493 mg, 3.24 mmol), 2,4,6-trimethyl-1,3,5,2,4,6-trioxatriborinane (305 mg, 2.43 mmol) and [1,1'-bis(diphenylphosphino)ferrocene]-dichloropalladium(II) (66 mg, 0.08 mmol). The resulting mixture was stirred at 80° C. overnight. The reaction was partitioned between water (20 mL) and ethyl acetate (30 mL). The organic layer was washed with brine (20 mL) and then dried over $MgSO_4$, filtered, and concentrated. The crude was purified by silica gel chromatography (0-80% ethyl acetate in hexanes) to give the desired product. MS: (ES) m/z calculated for $C_{10}H_{11}FN_2O$ $[M+H]^+$ 195.1. found 195.1. The other enantiomer was treated similarly to give the other desired product.

Step c:

A mixture of one of the compounds obtained in step b (127 mg, 0.65 mmol) and 3,4-dimethoxycyclobut-3-ene-1,2-dione (186 mg, 1.3 mmol) in anhydrous methanol (3 mL) was stirred at 60° C. overnight and then at 80° C. for 5 h. The reaction mixture was concentrated and purified by silica gel chromatography (0-100% ethyl acetate in hexanes) to give the desired product. MS: (ES) m/z calculated for $C_{15}H_{13}FN_2O_4[M+H]^+$ 305.1. found 305.1. The other enantiomer was treated similarly to give the other desired product.

Step d:

Anhydrous methanol (2 mL) was added to a mixture of one of the compounds obtained in Step c (40 mg, 0.13 mmol) and (R)-1-(4,5-dimethylfuran-2-yl)-2,2-dimethylbutan-1-amine (33.6 mg, 0.145 mmol), and this mixture was stirred at 60° C. overnight. The reaction was allowed to cool to room temperature, dissolved in minimal dichloromethane, and adsorbed onto silica gel. This was purified by silica gel chromatography (40% ethyl acetate in dichloromethane) to give the desired product. $^1H$ NMR (400 MHz, DMSO-$d_6$) δ 9.55 (s, 1H), 8.78 (s, 1H), 8.32 (d, J=10.0 Hz, 1H), 7.29 (d, J=11.6 Hz, 1H), 6.06 (s, 1H), 5.05 (d, J=10.4 Hz, 1H), 4.63 (q, J=6.8 Hz, 1H), 2.31 (s, 3H), 2.18 (s, 3H), 1.87 (s, 3H), 1.34 (d, J=6.8 Hz, 3H), 1.26 (q, J=7.2 Hz, 2H), 0.93 (s, 3H), 0.88 (s, 3H), 0.82 (t, J=7.2 Hz, 3H). MS: (ES) m/z calculated for $C_{26}H_{30}FN_3O_4$ $[M-H]^-$ 468.2. found 468.2. The other diastereomer was obtained similarly.

Example 26: 3-(((R)-1-(4,5-dimethylfuran-2-yl)-2,2-dimethylpropyl)amino)-4-(((S)-5-fluoro-1,7-dimethyl-3-oxoisoindolin-4-yl)amino)cyclobut-3-ene-1,2-dione and 3-(((R)-1-(4,5-dimethylfuran-2-yl)-2,2-dimethylpropyl)amino)-4-(((R)-5-fluoro-1,7-dimethyl-3-oxoisoindolin-4-yl)amino)cyclobut-3-ene-1,2-dione

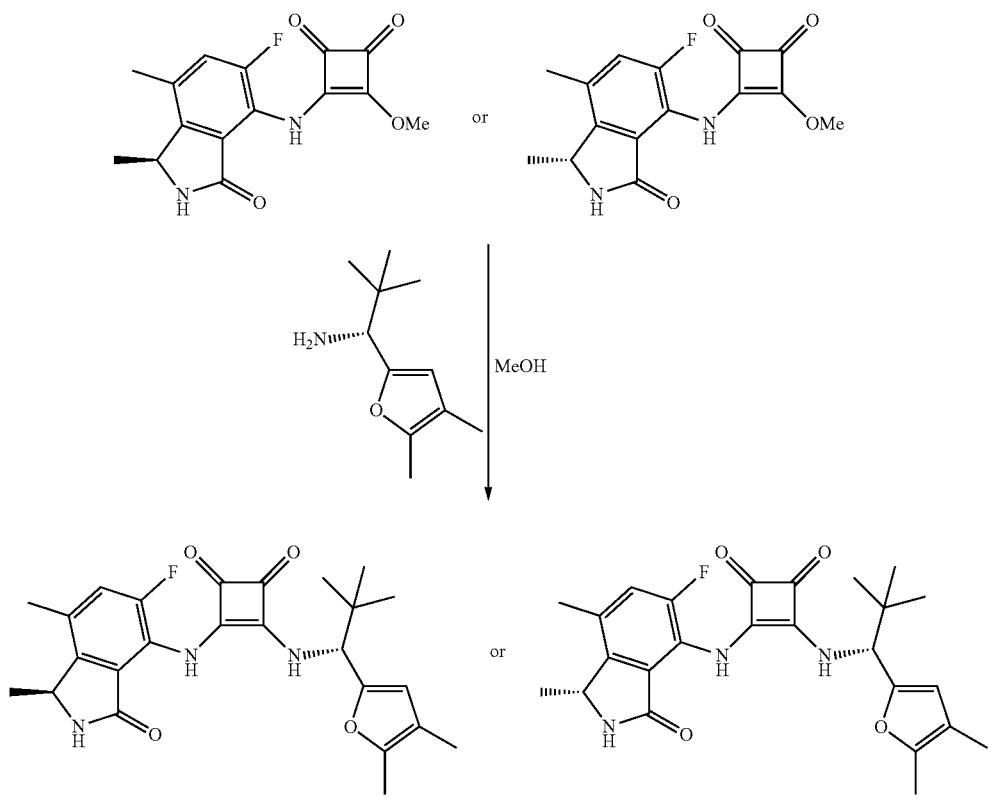

Anhydrous methanol (2 mL) was added to a mixture of one of the enantiomers of 3-((5-fluoro-1,7-dimethyl-3-oxoisoindolin-4-yl)amino)-4-methoxycyclobut-3-ene-1,2-dione (40 mg, 0.13 mmol) and (R)-1-(4,5-dimethylfuran-2-yl)-2,2-dimethylbutan-1-amine (31.6 mg, 0.145 mmol) and this mixture was stirred at 60° C. overnight. The reaction was allowed to cool to room temperature, dissolved in minimal dichloromethane, and adsorbed onto silica gel. This was purified by silica gel chromatography (40% ethyl acetate in dichloromethane) to give the desired product. $^1$H NMR (400 MHz, DMSO-$d_6$) δ 9.55 (s, 1H), 8.74 (s, 1H), 8.34 (d, J=10.4 Hz, 1H), 7.28 (d, J=11.6 Hz, 1H), 6.06 (s, 1H), 4.95 (d, J=10.0 Hz, 1H), 4.61 (q, J=6.8 Hz, 1H), 2.31 (s, 3H), 2.16 (s, 3H), 1.86 (s, 3H), 1.33 (d, J=6.8 Hz, 3H), 0.94 (s, 9H). MS: (ES) m/z calculated for $C_{25}H_{28}FN_3O_4$ [M−H]$^−$ 454.2. found 454.2. The other diastereomer was obtained similarly.

Example 27: Synthesis of 3-(((R)-2,2-dimethyl-1-(5-methylfuran-2-yl)propyl)amino)-4-(((S)-5-fluoro-1-methyl-3-oxoisoindolin-4-yl)amino)cyclobut-3-ene-1,2-dione and 3-(((R)-2,2-dimethyl-1-(5-methylfuran-2-yl)propyl)amino)-4-(((R)-5-fluoro-1-methyl-3-oxoisoindolin-4-yl)amino)cyclobut-3-ene-1,2-dione

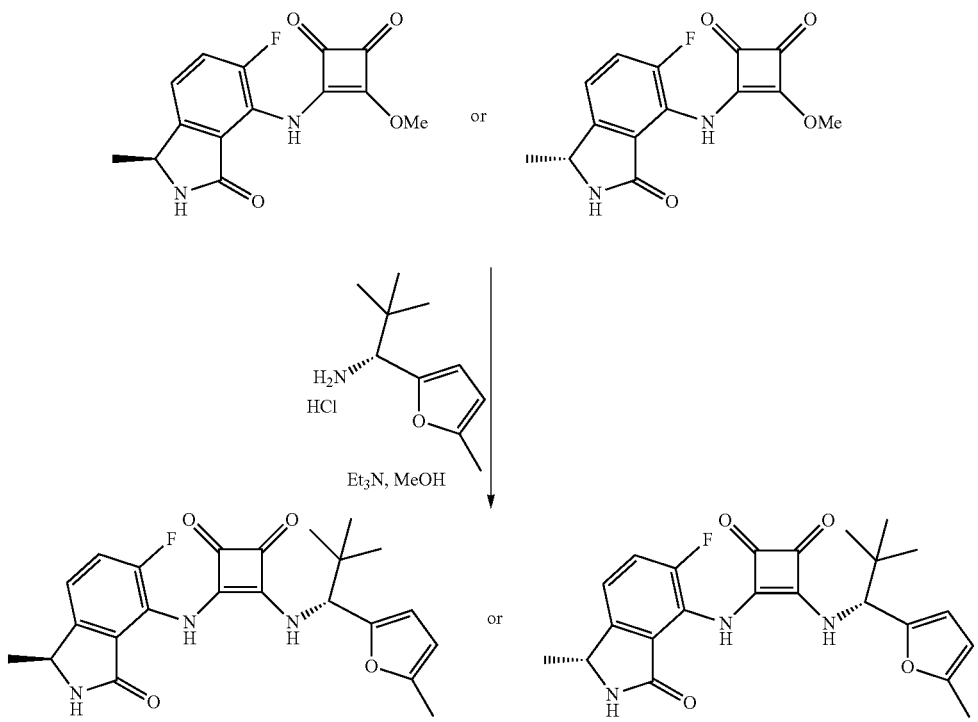

To a mixture of one of the enantiomers of 3-((5-fluoro-1-methyl-3-oxoisoindolin-4-yl)amino)-4-methoxycyclobut-3-ene-1,2-dione (50 mg, 0.171 mmol) and (1R)-2,2-dimethyl-1-(5-methyl-2-furyl)propan-1-amine (30 mg, 0.180 mmol) in methanol (3.0 mL) was added triethylamine (43 mg, 0.42 mmol, 2.5 equiv.) at room temperature. The mixture was stirred at 60° C. for 3 hours, and was then allowed to cool to room temperature. The solvent was removed under reduced pressure and the crude product was purified by preparative HPLC (acetonitrile-water with 0.1% TFA) to give the desired product. $^1$H NMR (400 MHz, DMSO-$d_6$) δ 9.65 (s, 1H), 8.80 (s, 1H), 8.42 (d, J=10.1 Hz, 1H), 7.46 (dd, J=3.1, 8.4 Hz, 1H), 7.36 (dd, J=3.9, 8.2 Hz, 1H), 6.18 (d, J=3.2, Hz, 1H), 6.03 (d, J=2.4 Hz, 1H), 5.00 (d, J=10.5 Hz, 1H), 4.56 (q, J=7.1 Hz, 1H), 2.27 (s, 3H), 1.33 (d, J=6.6 Hz, 3H), 0.95 (s, 9H). MS: (ES) m/z calculated for $C_{23}H_{24}FN_3O_4$[M−H]$^−$ 424.2. found 424.0. The other diastereomer was obtained similarly. $^1$H NMR (400 MHz, DMSO-$d_6$) δ 9.64 (s, 1H), 8.79 (s, 1H), 8.40 (d, J=10.5 Hz, 1H), 7.46 (dd, J=11.3, 8.6 Hz, 1H), 7.34 (dd, J=3.9, 8.2 Hz, 1H), 6.17 (d, J=3.2, Hz, 1H), 6.04-6.03 (m, 1H), 5.00 (d, J=10.1 Hz, 1H), 4.56 (q, J=6.6 Hz, 1H), 2.27 (s, 3H), 1.33 (d, J=6.6 Hz, 3H), 0.95 (s, 9H). MS: (ES) m/z calculated for $C_{23}H_{24}FN_3O_4$[M+H]$^+$ 426.2. found 426.0.

Example 28: Synthesis of 3-[[(1R)-2,2-dimethyl-1-(5-methyl-2-furyl)butyl]amino]-4-]](1S)-5-fluoro-1-methyl-3-oxo-isoindolin-4-yl]amino]cyclobut-3-ene-1,2-dione and 3-[[(1R)-2,2-dimethyl-1-(5-methyl-2-furyl)butyl]amino]-4-[[(1R)-5-fluoro-1-methyl-3-oxo-isoindolin-4-yl]amino]cyclobut-3-ene-1,2-dione

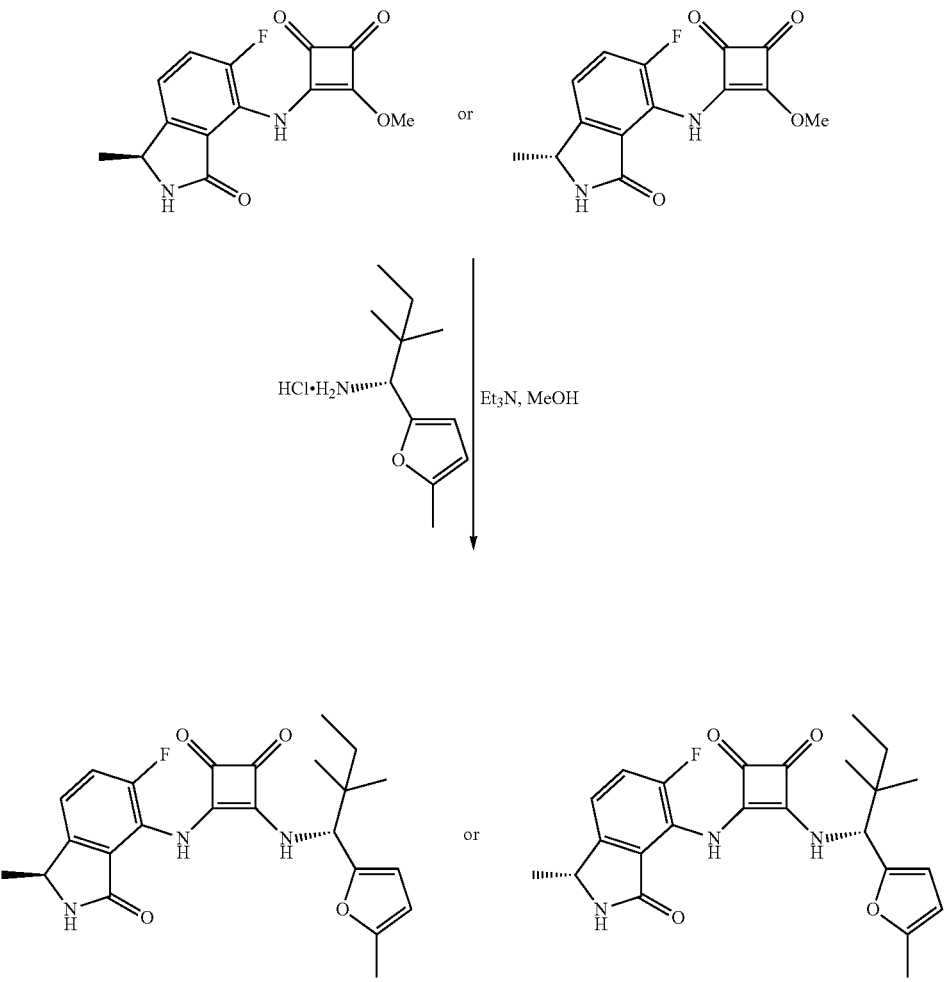

Triethylamine (0.025 mL, 0.18 mmol) was added to a mixture of one of the enantiomers of 3-((5-fluoro-1-methyl-3-oxoisoindolin-4-yl)amino)-4-methoxycyclobut-3-ene-1,2-dione (26 mg, 0.09 mmol) and (1R)-2,2-dimethyl-1-(5-methyl-2-furyl)butan-1-amine hydrochloride (20 mg, 0.09 mmol) in MeOH (1.0 mL). The reaction was stirred at room temperature for 18 h. Silica gel was then added to the reaction, the mixture was concentrated, and this was purified by silica gel chromatography (1% to 10% MeOH in CH$_2$Cl$_2$). The product was then purified by reverse phase chromatography (MeCN:H$_2$O with 0.1% TFA as eluent) to give the final product. $^1$H NMR (400 MHz, DMSO-d$_6$) δ 9.65 (s, 1H), 8.79 (s, 1H), 8.40 (d, J=10.2 Hz, 1H), 7.47 (dd, J=11.1, 8.2 Hz, 1H), 7.35 (dd, J=8.3, 3.8 Hz, 1H), 6.17 (d, J=3.1 Hz, 1H), 6.06-6.01 (m, 1H), 5.10 (d, J=10.2 Hz, 1H), 4.58 (q, J=6.6 Hz, 1H), 2.27 (s, 3H), 1.34 (d, J=6.7 Hz, 3H), 1.32-1.24 (m, 2H), 0.94 (s, 3H), 0.88 (s, 3H), 0.83 (t, J=7.4 Hz, 3H). MS: (ES) m/z calculated for C$_{24}$H$_{27}$FN$_3$O$_4$[M+H]$^+$ 440.2. found 440.4. The other diastereomer was obtained similarly.

The following compounds were made using similar synthetic methods as described herein with the appropriate reagents and were characterized by MS (Mass spectrometry) and/or NMR as illustrated in Table 1.

TABLE 1

Characterization of compounds

| Structure | NMR | MS |
|---|---|---|
| | ¹H NMR (400 MHz, DMSO-d₆) δ 9.88 (s, 1 H), 9.06 (d, J = 9.6 Hz, 1 H), 7.79 (d, J = 8.0 Hz, 1 H), 7.40-7.37 (m, 3 H), 7.29 (d, J = 8.0 Hz, 1 H), 6.16 (d, J = 3.2 Hz, 1 H), 6.02 (d, J = 3.2 Hz, 1 H), 5.12 (d, J = 10.4 Hz, 1 H), 4.82 (s, 2 H), 2.39 (s, 3 H), 2.27 (s, 3 H), 2.25 (s, 3 H), 0.96 (s, 9H). | MS: (ES) m/z calculated for $C_{31}H_{31}N_3O_6$ [M − H]⁻ 542.2, found 542.2. |
| | ¹H NMR (400 MHz, DMSO-d₆) δ 9.86 (s, 1 H), 9.04 (d, J = 10.4 Hz, 1 H), 7.5 (m, 1 H), 7.44 (s, 1 H), 7.42 (s, 1 H), 7.19 (m, 1 H), 6.18 (d, J = 2.8 Hz, 1 H), 6.03 (d, J = 2.8 Hz, 1 H), 5.11 (d, J = 10.4 Hz, 1 H), 4.56 (s, 2 H), 4.11 (s, 2 H), 2.27 (s, 3 H), 0.96 (s, 9 H). | MS: (ES) m/z calculated for $C_{24}H_{25}FN_4O_5$ [M − H]⁻ 469.2, found 469.2. |
| | ¹H NMR (400 MHz, DMSO-d₆) δ 10.00 (s, 1 H), 9.18 (s, 1 H), 7.56 (d, J = 8.4 Hz, 1 H), 7.45 (d, J = 8.4 Hz, 1 H), 6.19 (d, J = 3.2 Hz, 1 H), 6.04 (d, J = 3.2 Hz, 1 H), 2.94 (s, 3 H), 2.27 (s, 3 H), 1.56 (s, 6 H), 0.95 (s, 9 H). | MS: (ES) m/z calculated for $C_{25}H_{27}DClN_3O_4$ [M − H]⁻ 471.2, found 471.2. |
| | ¹H NMR (400 MHz, DMSO-d₆) δ 9.84 (s, 1 H), 8.98 (d, J = 10.0 Hz, 1 H), 8.94 (s, 1 H), 7.57 (d, J = 8.4 Hz, 1 H), 7.40 (d, J = 8.4 Hz, 1 H), 7.33 (d, J = 8.0 Hz, 1 H), 7.29-7.25 (m, 1 H), 7.19-7.17 (m, 2 H), 5.52 (d, J = 10.4 Hz, 1 H), 4.36 (s, 2H), 2.40 (s, 3 H), 0.96 (s, 9 H). | MS: (ES) m/z calculated for $C_{24}H_{24}ClN_3O_3$ [M − H]⁻ 438.2, found 438.2. |
| | ¹H NMR (400 MHz, DMSO-d₆) δ 9.87 (s, 1 H), 9.04 (d, J = 10.4 Hz, 1 H), 8.95 (s, 1 H), 7.57 (d, J = 8.8 Hz, 1 H), 7.42-7.36 (m, 3 H), 7.31-7.29 (m, 3 H), 5.12 (d, J = 10.4 Hz, 1 H), 4.37 (s, 2 H), 0.93 (s, 9 H). | MS: (ES) m/z calculated for $C_{23}H_{22}ClN_3O_3$ [M − H]⁻ 424.1, found 424.1. |
| | ¹H NMR (400 MHz, DMSO-d₆) δ 9.86 (s, 1 H), 8.93 (m, 1 H), 8.87 (d, J = 10.4 Hz, 1 H), 7.57 (d, J = 8.4 Hz, 1 H), 7.39 (d, J = 8.4 Hz, 1 H), 7.31-7.25 (m, 2 H), 7.03-7.00 (m, 2 H), 5.52 (d, J = 10.4 Hz, 1 H), 4.36 (s, 2 H), 3.79 (s, 3 H), 0.92 (s, 9 H). | MS: (ES) m/z calculated for $C_{24}H_{24}ClN_3O_4$ [M − H]⁻ 454.2, found 454.2. |

TABLE 1-continued

Characterization of compounds

| Structure | NMR | MS |
|---|---|---|
| 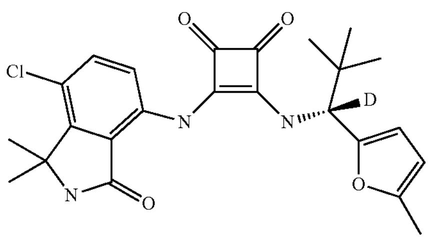 | $^1$H NMR (400 MHz, DMSO-d$_6$) δ 10.02 (s, 1 H), 9.22 (s, 1 H), 9.09 (s, 1 H), 7.59 (d, J = 8.8 Hz, 1 H), 7.47 (d, J = 8.8 Hz, 1 H), 6.24 (d, J = 3.2 Hz, 1 H), 6.09 (d, J = 3.2 Hz, 1 H), 2.32 (s, 3 H), 1.61 (s, 6H), 1.01 (s, 9H). | MS: (ES) m/z calculated for C$_{24}$H$_{25}$DClN$_3$O$_4$ [M − H]$^-$ 457.2, found 457.2. |
| 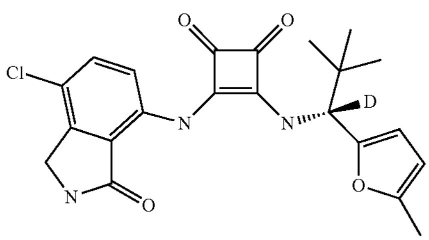 | $^1$H NMR (400 MHz, DMSO-d$_6$) δ 9.99 (s, 1 H), 9.18 (s, 1 H), 8.98 (s, 1 H), 7.63 (d, J = 8.4 Hz, 1 H), 7.47 (d, J = 8.4 Hz, 1 H), 6.24 (d, J = 3.2 Hz, 1 H), 6.09 (d, J = 3.2 Hz, 1 H), 4.42 (s, 2 H), 2.32 (s, 3H), 1.01 (s, 9H). | MS: (ES) m/z calculated for C$_{22}$H$_{21}$DClN$_3$O$_4$ [M − H]$^-$ 429.1, found 429.1. |
| 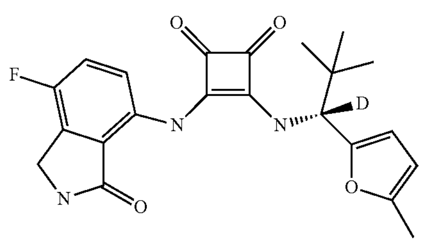 | $^1$H NMR (400 MHz, DMSO-d$_6$) δ 9.93 (s, 1 H), 9.12 (s, 1 H), 8.96 (s, 1 H), 7.46 (d, J = 7.2 Hz, 2 H), 6.25 (d, J = 2.8 Hz, 1 H), 6.09 (d, J = 2.8 Hz, 1 H), 4.51 (s, 2 H), 2.33 (s, 3 H), 1.02 (s, 9 H). | MS: (ES) m/z calculated for C$_{22}$H$_{21}$DFN$_3$O$_4$ [M − H]$^-$ 413.2, found 413.2. |
| | | MS: (ES) m/z calculated for C$_{30}$H$_{27}$ClN$_4$O$_6$ [M + Na]$^+$ 581.2, found 581.5. |
| | | MS: (ES) m/z calculated for C$_{30}$H$_{29}$ClN$_4$O$_6$ [M − H]$^-$ 575.2, found 575.2. |

TABLE 1-continued

Characterization of compounds

| Structure | NMR | MS |
|---|---|---|
| | | MS: (ES) m/z calculated for $C_{30}H_{27}ClN_4O_4$ [M + Na]$^+$ 565.2, found 565.4. |
| | | MS: (ES) m/z calculated for $C_{29}H_{25}ClN_4O_4$ [M − H]$^-$ 527.2, found 527.1. |
| | | MS: (ES) m/z calculated for $C_{29}H_{24}ClF_2N_3O_6$ [M − H]$^-$ 582.1, found 582.3. |
| | | MS: (ES) m/z calculated for $C_{28}H_{25}ClN_4O_6$ [M + H]$^+$ 549.2, found 549.5. |

TABLE 1-continued

Characterization of compounds

| Structure | NMR | MS |
|---|---|---|
| | | MS: (ES) m/z calculated for $C_{29}H_{27}ClFN_3O_3$ [M − H]⁻ 550.2, found 550.2. |
| | | MS: (ES) m/z calculated for $C_{31}H_{30}ClN_3O_8$ [M − H]⁻ 606.2, found 606.2. |
| | | MS: (ES) m/z calculated for $C_{30}H_{25}ClN_4O_6$ [M + H]⁺ 573.2, found 573.2. |
| | ¹H NMR (400 MHz, DMSO-d₆) δ 9.95 (s, 1 H), 9.14 (d, J = 9.7 Hz, 1 H), 7.89 (d, J = 8.6 Hz, 1 H), 7.67 (d, J = 8.6 Hz, 1 H), 7.50 (d, J = 8.6 Hz, 1 H), 7.18 (d, J = 2.4 Hz, 1 H), 7.04 (dd, J = 2.4, 8.4 Hz, 1 H), 6.50-.44 (m, 2 H), 6.35 (d, J = 2.4 Hz, 1 H), 5.12 (d, J = 10.2 Hz, 1 H), 4.84 (d, J = 4.7 Hz, 2 H), 3.83 (s, 3 H), 0.95 (s, 9 H). | MS: (ES) m/z calculated for $C_{29}H_{25}Cl_2N_3O_7$ [M − H] 596.1, found 596.4. |

TABLE 1-continued

Characterization of compounds

| Structure | NMR | MS |
|---|---|---|
| | | MS: (ES) m/z calculated for $C_{27}H_{24}ClN_5O_6$ $[M + H]^+$ 550.1, found 550.5. |
| | | MS: (ES) m/z calculated for $C_{28}H_{25}ClN_4O_6$ $[M + H]^+$ 549.2, found 549.5. |
| | | MS: (ES) m/z calculated for $C_{28}H_{25}ClN_4O_6$ $[M + H]^+$ 549.2, found 549.5. |
| 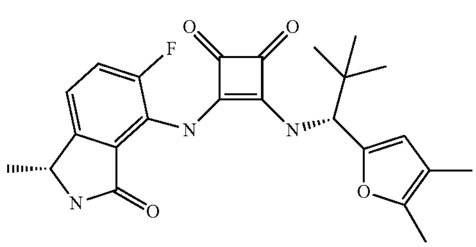 | $^1$H NMR (400 MHz, DMSO-d$_6$) δ 9.64 (s, 1 H), 8.79 (s, 1 H), 8.37 (d, J = 10.2 Hz, 1 H), 7.44 (dd, J = 11.0, 8.2 Hz, 1 H), 7.33 (dd, J = 3.9, 8.8 Hz, 1 H), 6.07 (s, 1 H), 4.95 (d, J = 10.1 Hz, 1 H), 4.56 (q, J = 6.3 Hz, 1 H), 2.18 (s, 3 H), 1.87 (s, 3 H), 1.33 (d, J = 6.6 Hz, 3 H), 0.95 (s, 9 H). | MS: (ES) m/z calculated for $C_{24}H_{26}FN_3O_4$ $[M - H]^-$ 438.2, found 438.0. |
| | $^1$H NMR (400 MHz, DMSO-d$_6$) δ 9.65 (s, 1 H), 8.88 (s, 1 H), 8.40 (d, J = 10.2 Hz, 1 H), 7.46 (d, J = 8.2 Hz, 1 H), 7.33 (dd, J = 3.9, 8.6 Hz, 1 H), 6.17 (d, J = 3.2 Hz, 1 H), 6.03 (d, J = 3.2 Hz, 1 H), 5.00 (d, J = 10.2 Hz, 1 H), 4.50-4.40 (m, 1 H), 2.27 (s, 3 H), 1.95-1.80 (m, 1 H), 1.60-1.50 (m, 1 H), 0.90 (s, 9 H) 0.82-0.79 (m, 3 H). | MS: (ES) m/z calculated for $C_{24}H_{26}ClFN_3O_4$ $[M + H]^+$ 440.2, found 440.1. |

TABLE 1-continued

Characterization of compounds

| Structure | NMR | MS |
|---|---|---|
| | ¹H NMR (400 MHz, DMSO-d₆) δ 9.64 (s, 1 H), 8.87 (s, 1 H), 8.36 (d, J = 10.1 Hz, 1 H), 7.45 (dd, J = 8.6, 11.3 Hz, 1 H), 7.33 (dd, J = 3.9, 8.6, Hz, 1 H), 6.16 (d, J = 3.2 Hz, 1 H), 6.04-6.03 (m, 1 H), 5.09 (d, J = 10.2 Hz, 1 H), 4.55-4.45 (m, 1 H), 2.27 (s, 3 H), 1.98-1.85 (m, 1 H), 1.60-.50 (m, 1 H), 1.35-1.25 (m, 2 H), 0.94 (s, 3 H), 0.88 (s, 3 H), 0.85-0.79 (m, 6 H). | MS: (ES) m/z calculated for $C_{25}H_{28}ClFN_3O_4$ $[M + H]^+$ 454.2, found 454.0. |
| | ¹H NMR (400 MHz, DMSO-d₆) δ 9.67 (s, 1 H), 9.01 (s, 1 H), 8.40 (d, J = 10.2 Hz, 1 H), 7.72 (d, J = 10.6 Hz, 1 H), 6.07 (s, 1 H), 4.94 (d, J = 10.2 Hz, 1 H), 4.65 (q, J = 6.2 Hz, 1 H), 2.18 (s, 3 H), 1.87 (s, 3 H), 1.42 (d, J = 6.6 Hz, 3 H), 0.95 (s, 9 H). | MS: (ES) m/z calculated for $C_{24}H_{25}ClFN_3O_4$ $[M - H]^-$ 472.1, found 471.9. |
| | ¹H NMR (400 MHz, DMSO-d₆) δ 9.68 (s, 1 H), 9.01 (s, 1 H), 8.43 (d, J = 10.1 Hz, 1 H), 7.72 (d, J = 11.0 Hz, 1 H), 6.17 (d, J = 2.8 Hz, 1 H), 6.03 (d, J = 2.8 Hz, 1 H), 5.00 (d, J = 10.2 Hz, 1 H), 4.65 (q, J = 6.6 Hz, 1 H), 2.22 (s, 3 H), 1.42 (d, J = 6.6 Hz, 3 H), 0.95 (s, 9 H). | MS: (ES) m/z calculated for $C_{23}H_{23}ClFN_3O_4$ $[M + H]^+$ 460.1, found 460.0. |
| | ¹H NMR (400 MHz, DMSO-d₆) δ 9.91 (s, 1 H), 9.0 (d, J = 10.2 Hz, 1 H), 8.59 (d, J = 10.2 Hz, 1 H), 8.40-8.18 (m, 1 H), 7.60 (d, J = 8.6 Hz, 1 H), 7.42 (d, J = 9.0 Hz, 1 H), 6.09 (s, 1 H), 5.04 (d, J = 10.1 Hz, 1 H), 4.48 (s, 2 H), 4.35-4.20 (m, 1 H), 3.20-3.0 (m, 4 H), 2.18 (s, 3 H), 2.25-1.85 (m, 4 H), 1.87 (s, 3 H), 0.95 (s, 9 H). | MS: (ES) m/z calculated for $C_{28}H_{33}ClN_4O_4$ $[M + H]^+$ 525.2, found 525.2. |
| | ¹H NMR (400 MHz, DMSO-d₆) δ 9.92 (s, 1 H), 9.25 (bs, 1 H), 9.04 (d, J = 2.6 Hz, 1 H), 7.61 (d, J = 8.6 Hz, 1 H), 7.42 (d, J = 8.6 Hz, 1 H), 6.19 (d, J = 3.1 Hz, 1 H), 6.04 (d, J = 2.3 Hz, 1 H), 5.09 (d, J = 9.8 Hz, 1 H), 4.48 (s, 3 H), 4.35-4.15 (m, 2 H), 3.60-3.45 (m, 2 H), 3.20-3.10 (m, 2 H), 2.78 (d, J = 3.2 Hz, 2 H), 2.27 (s, 3 H), 2.10-1.95 (m, 3 H), 0.95 s, 9 H). | MS: (ES) m/z calculated for $C_{28}H_{33}ClN_4O_4$ $[M + H]^+$ 525.2, found 525.2. |

TABLE 1-continued

Characterization of compounds

| Structure | NMR | MS |
|---|---|---|
| | | MS: (ES) m/z calculated for $C_{29}H_{32}ClN_3O_6$ [M + H]$^+$ 554.2, found 554.2. |
| | | MS: (ES) m/z calculated for C30H29FN3O6 [M + H]$^+$ 546.2, found 546.5. |
| | $^1$H NMR (400 MHz, DMSO-d$_6$) δ 9.94 (s, 1 H), 9.10 (d, J = 10 Hz, 1 H), 7.81 (d, J = 8.4 Hz, 1 H), 7.66 (d, J = 8.4 Hz, 1 H), 7.49 (d, J = 8.8 Hz, 1 H), 7.42 (s, 1 H), 7.31 (d, J = 6.8 Hz, 1 H), 6.17 (d, J = 3.2 Hz, 1 H), 6.02 (d, J = 3.2 Hz, 1 H), 5.11 (d, J = 10 Hz, 1 H), 4.90-4.78 (m, 2H), 2.58 (q, J = 7.2 Hz, 2H), 2.38 (s, 3H), 1.12 (t, J = 7.2 Hz, 3H), 0.94 (s, 9 H). | MS: (ES) m/z calculated for $C_{31}H_{30}ClN_3O_6$ [M − H]$^−$ 574.1, found 574.1. |
| | | MS: (ES) m/z calculated for $C_{29}H_{25}Cl_2N_3O_6$ [M − H]$^−$ 580.1, found 580.3. |

TABLE 1-continued

Characterization of compounds

| Structure | NMR | MS |
|---|---|---|
| 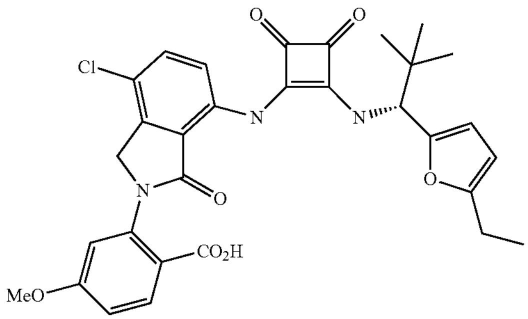 [SMILES: CCc1ccc([C@H](Nc2c(Nc3ccc(Cl)c4c3C(=O)N(c3cc(OC)ccc3C(=O)O)C4)c(=O)c2=O)C(C)(C)C)o1] | $^1$H NMR (400 MHz, DMSO-d$_6$) δ 9.94 (s, 1 H), 9.09 (d, J = 10 Hz, 1 H), 7.90 (d, J = 8.8 Hz, 1 H), 7.66 (d, J = 8.8 Hz, 1 H), 7.49 (d, J = 8.8 Hz, 1 H), 7.19 (d, J = 2.8 Hz, 1 H), 7.04 (dd, J = 2.8, 8.8 Hz, 1 H), 6.17 (d, J = 3.2 Hz, 1 H), 6.02 (d, J = 3.2 Hz, 1 H), 5.11 (d, J = 10 Hz, 1 H), 4.90-4.78 (m, 2H), 3.83 (s, 3H), 2.56 (q, J = 7.6 Hz, 2 H), 1.12 (t, J = 7.6 Hz, 3H), 0.94 (s, 9 H). | MS: (ES) m/z calculated for C$_{31}$H$_{30}$ClN$_3$O$_7$ [M − H]$^-$ 590.0, found 590.0. |
| | | MS: (ES) m/z calculated for C$_{29}$H$_{28}$ClN$_3$O$_5$ [M − H]$^-$ 532.1, found 532.4. |
| 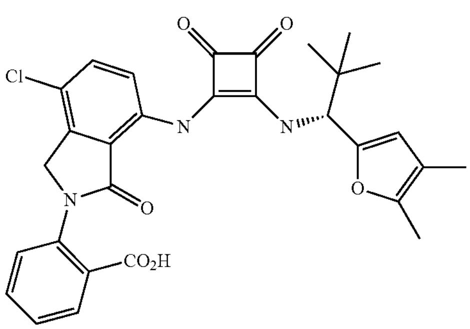 [SMILES: Cc1cc([C@H](Nc2c(Nc3ccc(Cl)c4c3C(=O)N(c3ccccc3C(=O)O)C4)c(=O)c2=O)C(C)(C)C)oc1C] | $^1$H NMR (400 MHz, DMSO-d$_6$) δ 9.94 (s, 1 H), 9.09 (dd, J = 1.6, 8 Hz, 1 H), 7.72-7.67 (m, 2 H), 7.60 (d, J = 7.2 Hz, 1 H), 7.53-7.48 (m, 2 H), 6.07 (s, 1 H), 5.04 (d, J = 10 Hz, 1 H), 4.94-4.81 (m, 2H), 2.15 (s, 3H), 1.85 (s, 3 H), 0.94 (s, 9 H). | MS: (ES) m/z calculated for C$_{30}$H$_{28}$ClN$_3$O$_6$ [M − H]$^-$ 560.1, found 560.1. |
| | | MS: (ES) m/z calculated for C$_{29}$H$_{25}$ClFN$_3$O$_6$ [M − H]$^-$ 564.1, found 564.3. |

TABLE 1-continued

Characterization of compounds

| Structure | NMR | MS |
|---|---|---|
| | | MS: (ES) m/z calculated for $C_{30}H_{28}ClN_3O_6$ [M − H]− 560.1, found 560.4. |
| | | MS: (ES) m/z calculated for $C_{31}H_{31}N_3O_6$ [M − H]− 540.2, found 540.2. |
| | | MS: (ES) m/z calculated for $C_{29}H_{27}N_3O_6$ [M − H]− 513.2, found 513.2. |
| | | MS: (ES) m/z calculated for $C_{30}H_{28}FN_3O_7$ [M − H]− 560.2, found 560.2. |

TABLE 1-continued

Characterization of compounds

| Structure | NMR | MS |
|---|---|---|
| | ¹H NMR (400 MHz, DMSO-d₆) δ 9.81 (s, 1 H), 8.97 (d, J = 10 Hz, 1 H), 7.64-7.38 (m, 5 H), 6.09 (d, J = 2.8 Hz, 1 H), 5.94 (d, J = 2.8 Hz, 1 H), 5.02 (d, J = 12 Hz, 1 H), 4.92-4.81 (m, 2 H), 2.17 (s, 3H), 0.87 (s, 9 H). | MS: (ES) m/z calculated for $C_{29}H_{25}F_2N_3O_6$ $[M - H]^-$ 548.1, found 548.1. |
| | ¹H NMR (400 MHz, DMSO-d₆) δ 9.83 (s, 1 H), 8.95 (d, J = 10 Hz, 1 H), 7.84 (dd, J = 1.6, 8.0 Hz, 1 H), 7.62 (dt, J = 1.6, 8 Hz, 1 H), 7.51 (d, J = 6.8 Hz, 1 H), 7.48-7.41 (m, 3 H), 6.00 (s, 1 H), 4.98 (d, J = 10 Hz, 1 H), 4.97-4.84 (m, 2 H), 2.09 (s, 3 H), 1.80 (s, 3 H), 0.88 (s, 9 H). | MS: (ES) m/z calculated for $C_{30}H_{28}FN_3O_6$ $[M - H]^-$ 544.1, found 544.1. |
| | ¹H NMR (400 MHz, DMSO-d₆) δ 9.84 (s, 1 H), 9.01 (d, J = 10 Hz, 1 H), 7.84 (dd, J = 1.6, 8.0 Hz, 1 H), 7.62 (dt, J = 1.6, 10 Hz, 1 H), 7.51 (d, J = 6.8 Hz, 1 H), 7.48-7.43 (m, 2 H), 6.39 (s, 2 H), 5.06 (d, J = 10 Hz, 1 H), 4.97-4.85 (m, 2 H), 0.89 (s, 9 H). | MS: (ES) m/z calculated for $C_{28}H_{23}ClFN_3O_6$ $[M - H]^-$ 550.1, found 550.1. |
| | | MS: (ES) m/z calculated for $C_{30}H_{28}FN_3O_6$ $[M - H]^-$ 544.2, found 544.2. |

TABLE 1-continued

Characterization of compounds

| Structure | NMR | MS |
|---|---|---|
| | | MS: (ES) m/z calculated for $C_{29}H_{25}ClFN_3O_6$ [M − H]⁻ 564.1, found 564.1. |
| | | MS: (ES) m/z calculated for $C_{29}H_{25}ClFN_3O_6$ [M − H]⁻ 564.1, found 564.1. |
| | ¹H NMR (400 MHz, DMSO-d₆) δ 9.83 (s, 1 H), 8.99 (d, J = 10 Hz, 1 H), 7.84 (dd, J = 1.6, 8.0 Hz, 1 H), 7.62 (dt, J = 1.6, 8 Hz, 1 H), 7.51 (d, J = 6.8 Hz, 1 H), 7.48-7.42 (m, 3 H), 6.10 (d, J = 3.2 Hz, 1 H), 5.96 (d, J = 3.2 Hz, 1 H), 5.04 (d, J = 10 Hz, 1 H), 4.97-4.85 (m, 2 H), 2.18 (s, 3 H), 0.88 (s, 9 H). | MS: (ES) m/z calculated for $C_{29}H_{26}FN_3O_6$ [M − H]⁻ 530.1, found 530.1. |
| | | MS: (ES) m/z calculated for $C_{29}H_{26}ClN_3O_6$ [M − H]⁻ 546.1, found 546.1. |

TABLE 1-continued

Characterization of compounds

| Structure | NMR | MS |
|---|---|---|
| | | MS: (ES) m/z calculated for $C_{29}H_{26}ClN_3O_6$ [M − H]⁻ 546.1, found 546.1. |
| | | MS: (ES) m/z calculated for $C_{30}H_{28}ClN_3O_6$ [M − H]⁻ 560.2, found 560.2. |
| | | MS: (ES) m/z calculated for $C_{26}H_{26}ClN_5O_4$ [M − H]⁻ 506.2, found 506.2. |
| | | MS: (ES) m/z calculated for $C_{25}H_{24}ClN_5O_4$ [M − H]⁻ 492.1, found 492.1. |

TABLE 1-continued

Characterization of compounds

| Structure | NMR | MS |
|---|---|---|
| | | MS: (ES) m/z calculated for $C_{25}H_{24}ClN_5O_4$ [M − H]⁻ 492.1, found 492.1. |
| | | MS: (ES) m/z calculated for $C_{25}H_{28}ClN_3O_5$ [M − H]⁻ 484.2, found 484.2. |
| | | MS: (ES) m/z calculated for $C_{32}H_{32}ClN_3O_7$ [M − H]⁻ 604.2, found 604.2. |
| | ¹H NMR (400 MHz, DMSO-d₆) δ 9.57 (s, 1 H), 8.72 (s, 1 H), 8.37 (d, J = 10 Hz, 1 H), 7.32 (d, J = 12 Hz, 1 H), 6.17 (d, J = 2.8 Hz, 1 H), 6.03 (d, J = 2.8 Hz, 1 H), 5.00 (d, J = 12 Hz, 1 H), 4.31 (s, 1 H), 2.56 (q, J = 7.2 Hz, 2H), 2.27 (s, 3H), 1.17 (t, J = 7.2 Hz, 3H), 0.95 (s, 9 H). | MS: (ES) m/z calculated for $C_{24}H_{26}ClN_3O_4$ [M − H]⁻ 438.1, found 438.1. |
| | ¹H NMR (400 MHz, DMSO-d₆) δ 9.52 (s, 1 H), 8.68 (s, 1 H), 8.26 (d, J = 10.4 Hz, 1 H), 7.38-7.28 (m, 2 H), 5.96 (s, 1 H), 4.85 (d, J = 10.4 Hz, 1 H), 2.07 (s, 3H), 1.77 (s, 3H), 1.31 (s, 6H), 0.84 (s, 9 H). | MS: (ES) m/z calculated for $C_{25}H_{28}FN_3O_4$ [M − H]⁻ 452.2, found 452.2. |

TABLE 1-continued

Characterization of compounds

| Structure | NMR | MS |
|---|---|---|
| | | MS: (ES) m/z calculated for C₂₈H₂₈ClN₅O₄ [M − H]⁻ 533.2, found 533.2. |
| | ¹H NMR (400 MHz, DMSO-d₆) δ 10.07 (s, 1 H), 9.20 (d, J = 10 Hz, 1 H), 8.77 (d, J = 4.8 Hz, 2 H), 7.69 (d, J = 8.8 Hz, 1 H), 7.57 (d, J = 8.8 Hz, 1 H), 7.29 (t, J = 4.8 Hz, 1 H), 6.20 (d, J = 3.2 Hz, 1 H), 6.04 (d, J = 3.2 Hz, 1 H), 5.12 (d, J = 10 Hz, 1 H), 5.04 (s, 2H), 2.28 (s, 3H), 0.97 (s, 9 H). | MS: (ES) m/z calculated for C₂₆H₂₄ClN₅O₄ [M − H]⁻ 504.1, found 504.1. |
| | | MS: (ES) m/z calculated for C₂₄H₂₆FN₃NaO₄ [M + Na]⁻ 462.2, found 462.5. |
| | | MS: (ES) m/z calculated for C₂₂H₂₀F₄N₃O₄ [M + H]⁻ 466.2, found 466.4. |
| | | MS: (ES) m/z calculated for C₂₃H₂₁F₂N₃O₄ [M + H]⁻ 422.2, found 422.0. |

TABLE 1-continued

Characterization of compounds

| Structure | NMR | MS |
|---|---|---|
| | | MS: (ES) m/z calculated for C28H26Cl2N4O6 [M + H]− 579.2, found 549.4. |
| | | MS: (ES) m/z calculated for C30H27ClN3O6 [M − H]− 560.2, found 560.3. |
| | ¹H NMR (400 MHz, DMSO-d₆) δ 9.97 (s, 1H), 9.13 (d, J = 10.1 Hz, 1H), 7.94 (dd, J = 7.8, 1.6 Hz, 1H), 7.79-7.67 (m, 2H), 7.63 (dd, J = 8.0, 1.3 Hz, 1H), 7.57-7.46 (m, 2H), 6.20 (d, J = 3.1 Hz, 1H), 6.05 (d, J = 3.1 Hz, 1H), 5.14 (d, J = 10.0 Hz, 1H), 4.93 (d, J = 17.5 Hz, 1H), 4.86 (d, J = 17.5 Hz, 1H), 2.61 (q, J = 7.5 Hz, 2H), 1.16 (t, J = 7.5 Hz, 3H), 0.96 (s, 9H). | MS: (ES) m/z calculated for C30H27ClN3O6 [M − H]− 560.2, found 560.0. |
| | | MS: (ES) m/z calculated for C31H30N3O6 [M − H]− 540.2, found 540.3. |

TABLE 1-continued

Characterization of compounds

| Structure | NMR | MS |
|---|---|---|
| | | MS: (ES) m/z calculated for C32H33N3NaO7 [M + Na]+ 594.2, found 594.3. |
| | | MS: (ES) m/z calculated for C31H30N3O7 [M − H]− 556.2, found 556.2. |
| | | MS: (ES) m/z calculated for C31H30N3O6 [M − H]− 540.2, found 540.2. |
| | | MS: (ES) m/z calculated for C30H28N3O6 [M − H]− 526.2, found 526.2. |

TABLE 1-continued

Characterization of compounds

| Structure | NMR | MS |
|---|---|---|
| | | MS: (ES) m/z calculated for C29H24F2N3O6 [M − H]⁻ 548.2, found 548.4. |
| | | MS: (ES) m/z calculated for C26H28F2N3O6 [M + H]⁺ 516.2, found 516.1. |
| | | MS: (ES) m/z calculated for C24H24ClN7NaO4 [M + Na]⁺ 532.2, found 532.2. |
| | | MS: (ES) m/z calculated for C27H30ClN4O6 [M − H]⁻ 541.2, found 541.2. |

TABLE 1-continued

Characterization of compounds

| Structure | NMR | MS |
|---|---|---|
| | | MS: (ES) m/z calculated for C27H29ClN3O6 [M − H]⁻ 526.2, found 526.3. |
| | ¹H NMR (400 MHz, DMSO-d₆) δ 13.12 (s, 1H), 9.95 (s, 1H), 9.13 (d, J = 10.1 Hz, 1H), 7.66 (d, J = 8.7 Hz, 1H), 7.49 (d, J = 8.8 Hz, 1H), 6.21 (d, J = 3.1 Hz, 1H), 6.05 (dd, J = 3.1, 1.3 Hz, 1H), 5.12 (d, J = 10.0 Hz, 1H), 4.65 (dd, J = 10.9, 4.8 Hz, 1H), 4.49 (s, 2H), 2.29 (s, 3H), 2.13-1.87 (m, 2H), 0.97 (s, 9H), 0.90 (t, J = 7.3 Hz, 3H). | MS: (ES) m/z calculated for C26H29ClN3O6 [M + H]⁺ 514.2, found 514.0. |
| | | MS: (ES) m/z calculated for C26H28ClN4O5 [M − H]⁻ 511.2, found 511.1. |
| | | MS: (ES) m/z calculated for C25H28ClN4O6S [M − H]⁻ 547.1, found 547.1. |

TABLE 1-continued

Characterization of compounds

| Structure | NMR | MS |
|---|---|---|
| | | MS: (ES) m/z calculated for C26H29ClN4NaO5 [M + H]+ 535.2, found 535.2. |
| | | MS: (ES) m/z calculated for C24H28ClN4O4 [M + H]+ 471.2, found 471.1. |
| | | MS: (ES) m/z calculated for C25H26ClN4O5 [M − H]− 497.2, found 497.1. |
| | | MS: (ES) m/z calculated for C26H27ClF3N4O5 [M + H]+ 567.2, found 567.0. |

TABLE 1-continued

Characterization of compounds

| Structure | NMR | MS |
|---|---|---|
| | | MS: (ES) m/z calculated for C25H26ClN4O5 [M − H]⁻ 497.2, found 497.1. |
| | | MS: (ES) m/z calculated for C25H26ClN4O5 [M − H]⁻ 497.2, found 497.1. |
| | | MS: (ES) m/z calculated for C25H26ClN4O5 [M − H]⁻ 497.2, found 497.1. |
| | | MS: (ES) m/z calculated for C26H27ClN3O6 [M − H]⁻ 512.2, found 512.1. |
| | | MS: (ES) m/z calculated for C25H27ClN3O6 [M + H]⁺ 500.2, found 500.1. |

TABLE 1-continued

Characterization of compounds

| Structure | NMR | MS |
|---|---|---|
| | | MS: (ES) m/z calculated for C25H27ClN3O6 [M + H]+ 500.2, found 500.1. |
| | | MS: (ES) m/z calculated for C25H25ClN3O6 [M − H]− 498.1, found 498.1. |
| | | MS: (ES) m/z calculated for C24H24ClN4O5 [M + H]+ 485.2, found 485.1. |
| | | MS: (ES) m/z calculated for C22H19ClN3O5 [M − H]− 440.1, found 440.1. |
| | | MS: (ES) m/z calculated for C26H32ClN4O4 [M + H]+ 499.2, found 499.2. |

TABLE 1-continued

Characterization of compounds

| Structure | NMR | MS |
|---|---|---|
| | | MS: (ES) m/z calculated for C24H25ClN3O6 [M + H]+ 486.1, found 486.1. |
| | | MS: (ES) m/z calculated for C26H29ClN3O6 [M + H]+ 514.2, found 514.1. |
| | | MS: (ES) m/z calculated for C22H22ClN3O5 [M + H]+ 408.2, found 408.1. |
| | | MS: (ES) m/z calculated for C24H25ClN3O5 [M − H]− 470.1, found 470.1. |
| | | MS: (ES) m/z calculated for C25H27ClN3O4 [M − H]− 468.2, found 468.1. |

TABLE 1-continued

Characterization of compounds

| Structure | NMR | MS |
|---|---|---|
| | | MS: (ES) m/z calculated for C23H25ClN3O4 [M + H]+ 442.2, found 442.1. |
| | ¹H NMR (400 MHz, DMSO-d₆) δ 9.88 (s, 1H), 9.06 (d, J = 10.1 Hz, 1H), 8.70 (s, 1H), 7.37-7.25 (m, 2H), 6.20 (d, J = 3.1 Hz, 1H), 6.05 (d, J = 2.3 Hz, 1H), 5.15 (d, J = 10.0 Hz, 1H), 4.32 (s, 2H), 2.29 (s, 3H), 2.24 (s, 3H), 0.98 (s, 9H). | MS: (ES) m/z calculated for C23H24N3O4 [M − H]− 406.2, found 406.1. |
| | ¹H NMR (400 MHz, DMSO-d₆) δ 9.97 (s, 1H), 9.16 (d, J = 10.0 Hz, 1H), 9.04 (s, 1H), 7.54 (d, J = 8.7 Hz, 1H), 7.40 (d, J = 8.7 Hz, 1H), 6.19 (d, J = 3.1 Hz, 1H), 6.04 (d, J = 3.1 Hz, 1H), 5.13 (d, J = 10.0 Hz, 1H), 2.27 (s, 3H), 1.56 (s, 6H), 0.96 (s, 9H). | MS: (ES) m/z calculated for C24H25ClN3O4 [M − H]− 454.2, found 454.2. |
| | ¹H NMR (400 MHz, DMSO-d₆) δ 9.87 (s, 1H), 9.05 (d, J = 10.1 Hz, 1H), 8.90 (s, 1H), 7.46-7.36 (m, 2H), 6.19 (d, J = 3.1 Hz, 1H), 6.04 (d, J = 3.2 Hz, 1H), 5.13 (d, J = 10.0 Hz, 1H), 4.45 (s, 2H), 2.27 (s, 3H), 0.96 (s, 9H). | MS: (ES) m/z calculated for C22H23FN3O4 [M + H]+ 412.2, found 412.2. |
| | ¹H NMR (400 MHz, DMSO-d₆) δ 11.04 (s, 1H), 9.21 (d, J = 10.0 Hz, 1H), 8.26 (s, 1H), 7.40 (t, J = 7.9 Hz, 1H), 7.27 (d, J = 8.3 Hz, 1H), 6.97 (d, J = 7.3 Hz, 1H), 6.21 (s, 1H), 6.05 (d, J = 2.5 Hz, 1H), 5.18 (d, J = 9.9 Hz, 1H), 3.39-3.31 (m, 2H), 2.90 (t, J = 6.6 Hz, 2H), 2.28 (s, 3H), 0.97 (s, 9H). | MS: (ES) m/z calculated for C23H26N3O4 [M + H]+ 408.2, found 408.1. |
| | ¹H NMR (400 MHz, DMSO-d₆) δ 9.95 (s, 1H), 9.15 (d, J = 10.1 Hz, 1H), 8.94 (s, 1H), 7.60 (d, J = 8.7 Hz, 1H), 7.44 (d, J = 8.7 Hz, 1H), 6.21 (d, J = 3.1 Hz, 1H), 6.06 (d, J = 3.0 Hz, 1H), 5.14 (d, J = 10.0 Hz, 1H), 4.38 (s, 2H), 2.29 (s, 3H), 0.98 (s, 9H). | MS: (ES) m/z calculated for C22H23ClN3O4 [M + H]+ 428.1, found 428.1. |

TABLE 1-continued

Characterization of compounds

| Structure | NMR | MS |
|---|---|---|
| | | MS: (ES) m/z calculated for C22H21BrN3O4 [M − H]− 470.1, found 470.0. |
| | | MS: (ES) m/z calculated for C24H28N3O4 [M + H]+ 422.2, found 422.1. |
| | | MS: (ES) m/z calculated for C22H24N3O4 [M + H]+ 394.2, found 394.1. |
| | | MS: (ES) m/z calculated for C23H26N3O4 [M + H]+ 408.2, found 408.2. |
| | | MS: (ES) m/z calculated for C33H33ClN3O7 [M − H]− 618.2, found 618.1. |

TABLE 1-continued

Characterization of compounds

| Structure | NMR | MS |
|---|---|---|
| | | MS: (ES) m/z calculated for C32H31ClN3O6 [M − H]⁻ 588.2, found 588.4. |
| | ¹H NMR (400 MHz, DMSO-d₆) δ 9.96 (s, 1H), 9.15 (d, J = 10.1 Hz, 1H), 7.90 (d, J = 8.8 Hz, 1H), 7.69 (d, J = 8.7 Hz, 1H), 7.51 (d, J = 8.8 Hz, 1H), 7.18 (d, J = 2.5 Hz, 1H), 7.04 (dd, J = 8.8, 2.6 Hz, 1H), 6.19 (d, J = 3.1 Hz, 1H), 6.04 (dd, J = 3.1, 1.2 Hz, 1H), 5.13 (d, J = 10.1 Hz, 1H), 4.88 (d, J = 17.8 Hz, 1H), 4.82 (d, J = 17.4 Hz, 1H), 4.74 (p, J = 6.1 Hz, 1H), 2.26 (s, 3H), 1.31 (d, J = 6.0 Hz, 6H), 0.96 (s, 9H). | MS: (ES) m/z calculated for C32H31ClN3O7 [M − H]⁻ 604.2, found 604.1. |
| | ¹H NMR (400 MHz, DMSO-d₆) δ 9.96 (s, 1H), 9.16 (d, J = 10.2 Hz, 1H), 7.91 (d, J = 8.8 Hz, 1H), 7.69 (d, J = 8.7 Hz, 1H), 7.51 (d, J = 8.8 Hz, 1H), 7.19 (d, J = 2.5 Hz, 1H), 7.06 (dd, J = 8.8, 2.6 Hz, 1H), 6.19 (d, J = 3.1 Hz, 1H), 6.04 (d, J = 3.1 Hz, 1H), 5.12 (d, J = 10.1 Hz, 1H), 4.88 (d, J = 17.4 Hz, 1H), 4.82 (d, J = 17.3 Hz, 1H), 4.13 (q, J = 7.0 Hz, 2H), 2.26 (s, 3H), 1.36 (t, J = 7.0 Hz, 3H), 0.96 (s, 9H). | MS: (ES) m/z calculated for C31H31ClN3O7 [M + H]⁺ 592.2, found 592.1. |
| | | MS: (ES) m/z calculated for C31H30ClN3NaO6 [M + Na]⁺ 598.2, found 598.1. |

TABLE 1-continued

Characterization of compounds

| Structure | NMR | MS |
|---|---|---|
| | | MS: (ES) m/z calculated for C30H24ClF3N3O6 [M − H]⁻ 614.1, found 614.4. |
| | | MS: (ES) m/z calculated for C30H24ClF3N3O7 [M − H]⁻ 630.1, found 630.4. |
| | | MS: (ES) m/z calculated for C29H24ClFN3O6 [M − H]⁻ 564.1, found 564.3. |
| | | MS: (ES) m/z calculated for C29H24Cl2N3O6 [M − H]⁻ 580.1, found 580.3. |

TABLE 1-continued

Characterization of compounds

| Structure | NMR | MS |
|---|---|---|
| | | MS: (ES) m/z calculated for C30H27ClN3O7 [M − H]⁻ 576.2, found 576.4. |
| | | MS: (ES) m/z calculated for C30H28N3O7 [M − H]⁻ 542.2, found 542.4. |
| | ¹H NMR (400 MHz, DMSO-d₆) δ 9.91 (s, 1H), 9.08 (d, J = 10.1 Hz, 1H), 7.85 (d, J = 7.9 Hz, 1H), 7.57-7.47 (m, 2H), 7.42 (s, 1H), 7.34 (d, J = 7.7 Hz, 1H), 6.19 (d, J = 3.1 Hz, 1H), 6.04 (d, J = 2.9 Hz, 1H), 5.13 (d, J = 10.1 Hz, 1H), 4.98 (d, J = 17.2 Hz, 1H), 4.91 (d, J = 17.3 Hz, 1H), 2.40 (s, 3H), 2.26 (s, 3H), 0.96 (s, 9H). | MS: (ES) m/z calculated for C30H29FN3O6 [M + H]⁺ 546.2, found 546.6. |
| | | MS: (ES) m/z calculated for C29H26ClFN3O6 [M + H]⁺ 566.1, found 566.5. |

TABLE 1-continued

Characterization of compounds

| Structure | NMR | MS |
|---|---|---|
| | ¹H NMR (400 MHz, DMSO-d₆) δ 9.91 (s, 1H), 9.08 (d, J = 10.1 Hz, 1H), 7.93 (d, J = 8.8 Hz, 1H), 7.57-7.43 (m, 2H), 7.18 (d, J = 2.6 Hz, 1H), 7.08 (dd, J = 8.8, 2.6 Hz, 1H), 6.19 (d, J = 3.1 Hz, 1H), 6.04 (dd, J = 3.1, 1.3 Hz, 1H), 5.13 (d, J = 10.1 Hz, 1H), 4.97 (d, J = 17.2 Hz, 1H), 4.91 (d, J = 17.3 Hz, 1H), 3.85 (s, 3H), 2.26 (s, 3H), 0.96 (s, 9H). | MS: (ES) m/z calculated for C30H28FN3NaO7 [M + Na]⁺ 584.2, found 584.2. |
| | ¹H NMR (400 MHz, DMSO-d₆) δ 9.91 (s, 1H), 9.08 (d, J = 10.1 Hz, 1H), 7.99 (dd, J = 8.8, 6.5 Hz, 1H), 7.66-7.44 (m, 3H), 7.38 (td, J = 8.5, 2.7 Hz, 1H), 6.19 (d, J = 3.1 Hz, 1H), 6.05 (d, J = 3.1 Hz, 1H), 5.13 (d, J = 10.1 Hz, 1H), 5.05 (d, J = 17.2 Hz, 1H), 4.98 (d, J = 17.2 Hz, 1H), 2.27 (s, 3H), 0.97 (s, 9H). | MS: (ES) m/z calculated for C29H24F2N3O6 [M − H]⁻ 548.2, found 548.5. |
| | | MS: (ES) m/z calculated for C29H25FN3O6 [M − H]⁻ 530.2, found 530.2. |
| | | MS: (ES) m/z calculated for C22H21ClN3O4 [M − H]⁻ 426.1, found 426.1. |
| | | MS: (ES) m/z calculated for C24H26N3O6 [M + H]⁺ 452.2, found 452.5. |

TABLE 1-continued

Characterization of compounds

| Structure | NMR | MS |
|---|---|---|
| | ¹H NMR (400 MHz, Methanol-d₄) δ 7.54 (d, J = 10.3 Hz, 1H), 6.15 (d, J = 3.1 Hz, 1H), 5.97 (dd, J = 3.1, 1.1 Hz, 1H), 5.12 (s, 1H), 4.38 (d, J = 1.4 Hz, 2H), 2.28 (s, 3H), 1.05 (s, 9H). | MS: (ES) m/z calculated for C22H22ClFN3O4 [M + H]⁺ 446.1, found 446.4. |
| | | MS: (ES) m/z calculated for C22H22Cl2N3O4 [M + H]⁺ 462.1, found 462.0. |
| | | MS: (ES) m/z calculated for C24H23N4O4 [M − H]⁻ 431.2, found 431.1. |
| | | MS: (ES) m/z calculated for C22H21ClN3O4 [M − H]⁻ 426.1, found 426.1. |
| | | MS: (ES) m/z calculated for C24H22ClFN3O3 [M − H]⁻ 454.1, found 454.1. |
| | | MS: (ES) m/z calculated for C24H20ClF3N3O3 [M − H]⁻ 490.1, found 490.0. |

TABLE 1-continued
Characterization of compounds
| Structure | NMR | MS |
|---|---|---|
| 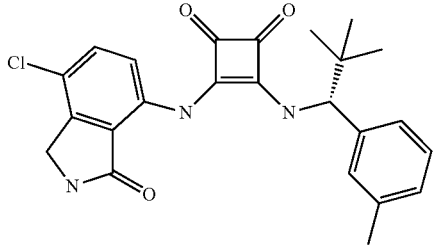 | | MS: (ES) m/z calculated for C24H23ClN3O3 [M − H]− 436.1, found 436.1. |
| 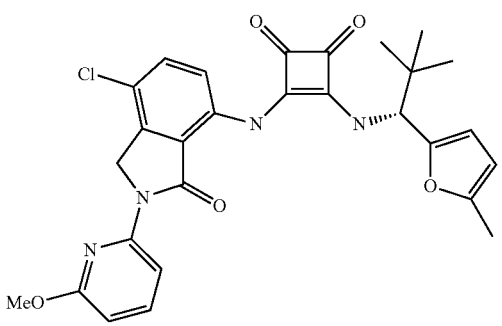 | | MS: (ES) m/z calculated for C29H26ClN4O7 [M − H]− 577.2, found 577.1. |
| 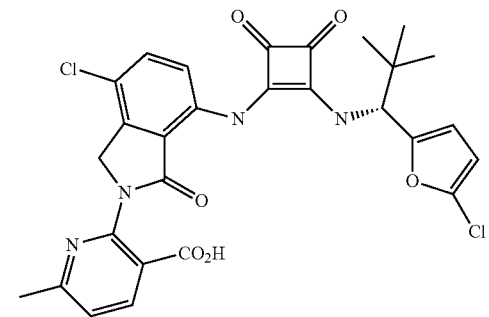 | | MS: (ES) m/z calculated for C28H23Cl2N4O6 [M − H]− 581.1, found 581.1. |
| 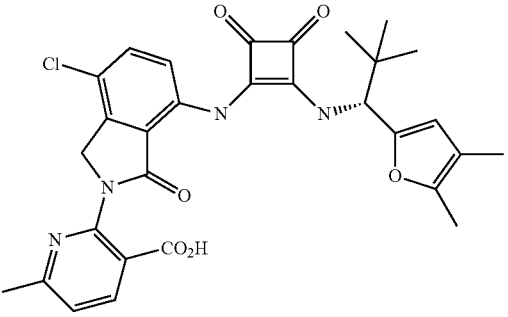 | | MS: (ES) m/z calculated for C30H28ClN4O6 [M − H]− 575.2, found 575.2. |
| 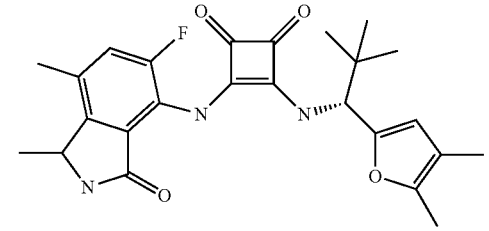 | | MS: (ES) m/z calculated for C25H27FN3O4 [M − H]− 452.2, found 452.0. |

TABLE 1-continued

Characterization of compounds

| Structure | NMR | MS |
|---|---|---|
| | | MS: (ES) m/z calculated for C24H27FN3O4 [M + H]+ 440.2, found 440.0. |
| | | MS: (ES) m/z calculated for C27H25ClN5O5 [M − H]− 534.2, found 534.1. |
| | | MS: (ES) m/z calculated for C21H22FN4O4 [M + H]+ 413.2, found 413.5. |
| | | MS: (ES) m/z calculated for C26H26ClN4O5 [M − H]− 509.2, found 509.2. |
| | | MS: (ES) m/z calculated for C26H27ClN5O4 [M + H]+ 508.2, found 508.1. |

TABLE 1-continued

Characterization of compounds

| Structure | NMR | MS |
|---|---|---|
| | | MS: (ES) m/z calculated for C26H27ClN5O4 [M + H]+ 508.2, found 508.1. |
| | | MS: (ES) m/z calculated for C23H24Cl2N3O4 [M + H]+ 476.1, found 476.0. |
| | | MS: (ES) m/z calculated for C23H24ClN4O3 [M + H]+ 439.2, found 439.1. |
| | ¹H NMR (400 MHz, DMSO-d₆) δ 9.88 (s, 1H), 9.04 (d, J = 10.1 Hz, 1H), 8.91 (s, 1H), 7.47-7.35 (m, 2H), 6.10 (s, 1H), 5.09 (d, J = 10.0 Hz, 1H), 4.46 (s, 2H), 2.20 (s, 3H), 1.89 (s, 3H), 0.97 (s, 9H). | MS: (ES) m/z calculated for C23H25FN3O4 [M + H]+ 426.2, found 426.1. |
| | | MS: (ES) m/z calculated for C21H20ClFN3O4 [M + H]+ 432.1, found 432.1. |
| | ¹H NMR (400 MHz, DMSO-d₆) δ 9.94 (s, 1H), 9.11 (d, J = 10.1 Hz, 1H), 8.94 (s, 1H), 7.60 (d, J = 8.7 Hz, 1H), 7.43 (d, J = 8.8 Hz, 1H), 6.11 (s, 1H), 5.09 (d, J = 9.9 Hz, 1H), 4.38 (s, 2H), 2.20 (s, 3H), 1.89 (s, 3H), 0.97 (s, 9H). | MS: (ES) m/z calculated for C23H25ClN3O4 [M + H]+ 442.2, found 442.1. |

TABLE 1-continued

Characterization of compounds

| Structure | NMR | MS |
|---|---|---|
| | | MS: (ES) m/z calculated for C22H20ClFN3O4 [M + H]+ 482.1, found 482.1. |
| | | MS: (ES) m/z calculated for C21H21ClN3O4 [M + H]+ 414.1, found 414.1. |
| | ¹H NMR (400 MHz, DMSO-d₆) δ 9.60 (s, 1H), 8.74 (s, 1H), 8.30 (d, J = 10.2 Hz, 1H), 7.49 (dd, J = 11.2, 8.2 Hz, 1H), 7.35 (dd, J = 8.2, 3.8 Hz, 1H), 6.79 (d, J = 3.4 Hz, 1H), 6.71 (m, 1H), 5.25 (d, J = 10.1 Hz, 1H), 4.34 (s, 2H), 2.43 (s, 3H), 1.01 (s, 9H). | MS: (ES) m/z calculated for C22H22FN3O3S [M + H]+ 428.1, found 428.4. |
| | | MS: (ES) m/z calculated for C26H29ClN7O5 [M + H]+ 554.3, found 554.3. |
| | | MS: (ES) m/z calculated for C25H29FN3O4 [M + H]+ 454.2, found 554.0. |

TABLE 1-continued

Characterization of compounds

| Structure | NMR | MS |
|---|---|---|
| | | MS: (ES) m/z calculated for C26H30FN3NaO4 [M + Na]+ 490.2, found 490.0. |
| | | MS: (ES) m/z calculated for C27H30ClN7NaO6 [M + Na]+ 606.2, found 606.4. |
| | | MS: (ES) m/z calculated for C28H32ClN7NaO6 [M + Na]+ 620.2, found 620.4. |

Biological Activity

Biological Example 1—Ligand Binding Assay for CXCR2 Activity

A ligand binding assay was used to determine the ability of potential CXCR2 antagonists to block the interaction between CXCR2 and any of its ligands. HEK-293 cells stably expressing CXCR2 or Human Neutrophils expressing CXCR2, were centrifuged and resuspended in assay buffer (20 mM HEPES pH 7.1, 140 mM NaCl, 1 mM CaCl$_2$, 5 mM MgCl$_2$, 0.1% sodium azide and with 0.1% bovine serum albumin) to a concentration of 5×10$^5$ cells/mL. Binding assays were set up as follows: Compounds for screening were serially diluted from a maximum of 20 μM, and 0.1 mL of cells containing 5×10$^4$ cells (for the HEK-293 cells) or 3×10$^4$ cells (for the human neutrophils) was added to each well containing compound. Then 0.1 mL of $^{125}$I labeled CXCL8 (obtained from PerkinElmer; Waltham, Mass.) diluted in assay buffer to a final concentration of ~50 pM, yielding ~1 ~Ci per well was added, and the plates were sealed and incubated for approximately 3 hours at 25° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 uL; Microscint 20, Packard Instruments) was added to each well, the plates were sealed and radioactivity measured in a Top Count scintillation counter (Packard Instruments). Control wells containing either diluent only (for total counts) or 20 μM compound were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled CXCR8 to the receptor by 50%. Compounds in FIG. 1 having an $IC_{50}$ value in the binding assay of less than 100 nM are labeled (+++); from 100-1000 nM are labeled (++); and less than or equal to 20 µM but above 1000 nM are labeled (+).

Biological Example 2—Migration/Chemotaxis Assay for CXCR2 Activity

A serum chemotaxis assay can be used to determine the efficacy of potential receptor antagonists at blocking the migration mediated through chemokine receptors, such as CXCR2. This assay is routinely performed using the ChemoTX® microchamber system with a 5-µm pore-sized polycarbonate membrane. To begin such an assay, chemokine-receptor expressing cells (in this case neutrophils isolated from human whole blood) are collected by centrifugation at 400×g at room temperature, then suspended at 4 million/ml in human serum. The compound being tested is serially diluted from a maximum final concentration of 10 µM (or an equivalent volume of its solvent (DMSO)) and is then added to the cell/serum mixture. Separately, recombinant human CXCL5 (ENA-78) at its $EC_{50}$ concentration (10 nM) is placed in the lower wells of the ChemoTX® plate. The 5-µm (pore size) polycarbonate membrane is placed onto the plate, and 20 µL of the cell/compound mixture is transferred onto each well of the membrane. The plates are incubated at 37° C. for 45 minutes, after which the polycarbonate membranes are removed and 5 µl of the DNA-intercalating agent CyQUANT (Invitrogen, Carlsbad, Calif.) is added to the lower wells. The amount of fluorescence, corresponding to the number of migrated cells, is measured using a Spectrafluor Plus plate reader (TECAN, San Jose, Calif.).

Biological Example 3—Migration/Chemotaxis Assay for CCR6 Activity

A serum chemotaxis assay was used to determine the efficacy of potential receptor antagonists at blocking the migration mediated through chemokine receptors, such as CCR6. This assay was routinely performed using the ChemoTX® microchamber system with a 5-µm pore-sized polycarbonate membrane. To begin such an assay, chemokine-receptor expressing cells (in this case KHYG-1 cells, Yagita et al., *Leukemia*, 14:922, 2000) were collected by centrifugation at 400×g at room temperature, then suspended at 4 million/ml in human serum. The compound being tested was serially diluted from a maximum final concentration of 10 µM (or an equivalent volume of its solvent (DMSO)) and was then added to the cell/serum mixture. Separately, recombinant human CCL20 (MIP-3α/LARC) at its $EC_{50}$ concentration (10 nM) was placed in the lower wells of the ChemoTX® plate. The 5-µm (pore size) polycarbonate membrane was placed onto the plate, and 20 µL of the cell/compound mixture was transferred onto each well of the membrane. The plates were incubated at 37° C. for 45 minutes, after which the polycarbonate membranes were removed and 5 µl of the DNA-intercalating agent CyQUANT (Invitrogen, Carlsbad, Calif.) was added to the lower wells. The amount of fluorescence, corresponding to the number of migrated cells, was measured using a Spectrafluor Plus plate reader (TECAN, San Jose, Calif.). Compounds in FIG. 1 having an $IC_{50}$ value in the chemotaxis assay of less than 100 nM are labeled (+++); from 100-1000 nM are labeled (++); and less than or equal to 20 µM but above 1000 nM are labeled (+).

Figure 2:
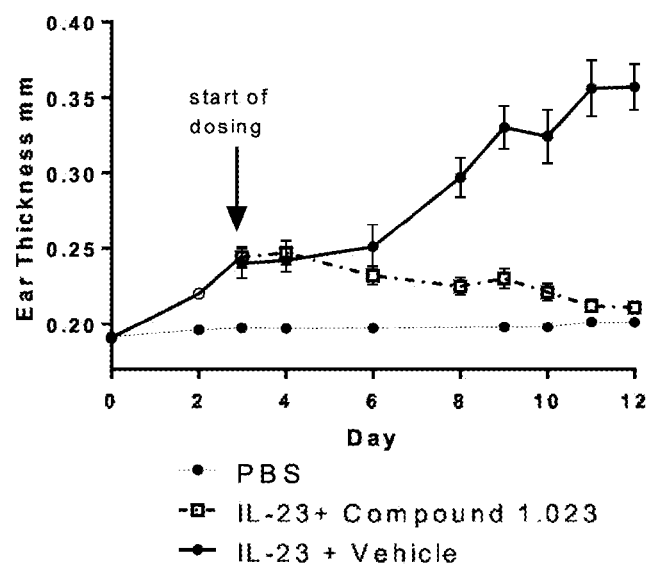
FIG. 2 provides compound 1.023 in the IL-23 Induced ear swelling model.

Biological Example 4—In Vivo Efficacy in IL-23 Induced Ear Swelling Model for Psoriasis An intradermal injection of IL-23 into the ear of mice can cause a swelling of the ear which is CCR6 dependent (Hedrick M. N et. al. J. Clinical Investigation. 2009. 119: 2317-2329). C57Bl/6 mice were given intradermal injections of IL-23 in the right ear. PBS was given by intradermal injection into the left ear as a control. Compound 1.023 (synthesized in example 6) was dosed by sub-cutaneous route. The compound was dosed in a therapeutic manner, after 3 intradermal injections of IL-23 and upon initiation of moderate ear swelling. The degree of swelling was measured using calipers. Compound 1.023 was able to completely inhibit IL-23 induced ear swelling and was capable of reducing the swelling back to baseline levels (FIG. 2).

Figure 3:
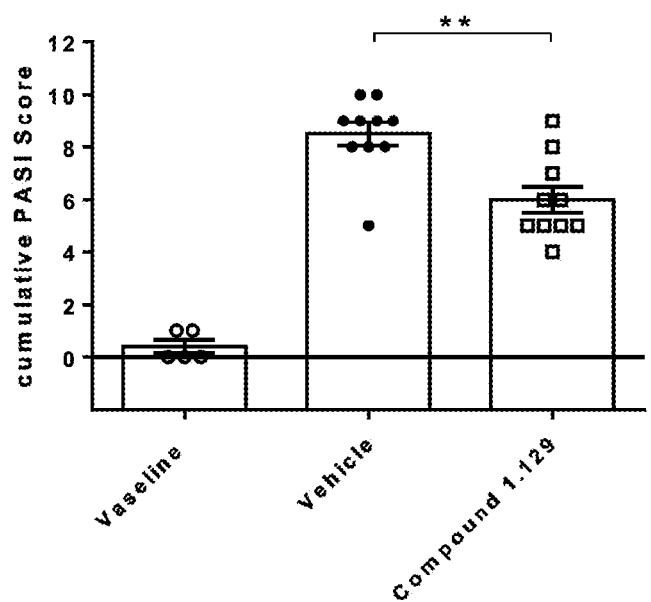
FIG. 3 provides a PASI score in mice treated with Compound 1.129 in the imiquimod induced psoriasis model.
Figure 4:
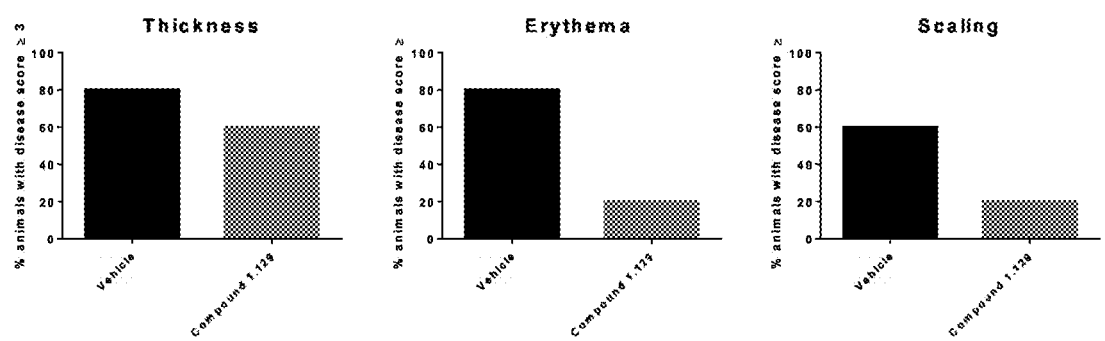
FIG. 4 provides thickness, erythema and scaling scores≥3 in mice treated with Compound 1.129 compared to vehicle treated mice in the imiquimod induced psoriasis model.

Biological Example 5—In Vivo Efficacy in the Imiquimod Induced Psoriasis-Like Model Topical application of imiquimod cream to the shaved back of a mouse causes the development of psoriasis like lesions with characteristics similar to that of human psoriasis i.e. skin erythema, skin thickness and scaling. (Van Der Fits L. et. al. 2009. J Immunology 182: 5836-5845). Balb/c mice were treated with imiquimod cream applied topically to the shaved back skin. Compound 1.129 was dosed prophylactically by the oral route to achieve appropriate plasma concentrations throughout the study. The development of psoriasis-like lesions was determined in a blinded manner by measuring 3 aspects of the skin disease, i.e. the degree of erythema, the percentage of skin affected by scaling and skin thickness as measured by calipers. Each measurement was assigned a disease score between 0 (no disease) and 4 (maximum disease) such that a cumulative PASI (Psoriasis Activity Severity Index) score was calculated, the maximum being a score of 12. Compound 1.129 was able to reduce the severity of the cumulative PASI score by inhibiting erythema, scaling and skin thickness. The percentage of mice exhibiting severe symptoms (score of ≥3 for each readout) was reduced in groups dosed with compound 1.129 compared with vehicle treated mice (FIG. 3).

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the Formula (A):

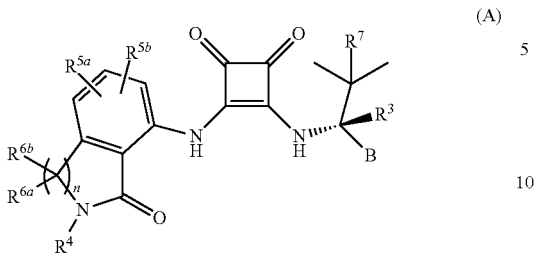

wherein
- B is selected from the group consisting of furanyl, thiophenyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;
- $R^3$ is a member selected from the group consisting of H and D;
- $R^4$ is a member selected from the group consisting of H, $C_{1-8}$ alkyl, OH, —$NR^aR^b$, —$C_{1-4}$ alkoxy, and Y; wherein the $C_{1-8}$ alkyl is optionally substituted with halogen, —CN, —$CO_2R^a$, —$CONR^aR^b$, —$C(O)R^a$, $OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$ and Y, wherein Y is a 4 to 8 membered cycloheteroalkyl group or a 3 to 8 membered cycloalkyl group or a 5- or 6-membered aryl or heteroaryl group any of which is optionally substituted with from 1 to four substituents selected from halogen, oxo, —CN, —$C_{1-6}$ alkyl, —$C_{1-6}$ alkoxy, —$C_{1-6}$ hydroxyalkyl, —$C_{1-6}$ haloalkyl, O—$C_{1-6}$ haloalkyl, —$C_{1-4}$alkyl-O—$C_{1-4}$ alkyl, —$C_{1-6}$ alkyl-$NR^aR^b$, —$C_{1-6}$ alkyl-$CO_2H$, —$C_{1-6}$ alkyl-$CO_2R^a$, —$C_{1-6}$ alkyl-$CONR^aR^b$, —$C_{1-6}$ alkyl-$C(O)R^a$, —$C_{1-6}$ alkyl-$OC(O)NR^aR^b$, —$C_{1-6}$ alkyl-$NR^aC(O)R^b$, —$C_{1-6}$ alkyl-$NR^aC(O)_2R^c$, —$C_{1-6}$ alkyl-$NR^aC(O)NR^aR^b$, —$C_{1-6}$ alkyl-$OR^a$, —$C_{1-6}$ alkyl-$S(O)_2NR^aR^b$, —$C_{1-6}$ alkyl-$NR^aS(O)_2R^b$, —$CO_2R^a$, —$CONR^aR^b$, —$C(O)R^a$, —$OC(O)NR^aR^b$, —$NR^aC(O)R^b$, —$NR^aC(O)_2R^b$, —$NR^aC(O)NR^aR^b$, —$NR^aR^b$, —$OR^a$, —$S(O)_2NR^aR^b$, —$NR^aS(O)_2R^b$, —$CH_2CO_2R^a$; each $R^a$ and $R^b$ is independently selected from hydrogen, $C_{1-4}$ alkyl, $C_{1-4}$ hydroxyalkyl and $C_{1-4}$ haloalkyl, and R is selected from $C_{1-4}$ alkyl, $C_{1-4}$ hydroxyalkyl and $C_{1-4}$ haloalkyl; and wherein the 4 to 8 membered cycloheteroalkyl group and the 3 to 8 membered cycloalkyl group may additionally be optionally substituted with oxo;
- $R^{5a}$ and $R^{5b}$ are each members independently selected from the group consisting of H, halogen, $C_{1-4}$ alkyl, —$C_{1-4}$ haloalkyl, O—$C_{1-4}$ haloalkyl, $C_{1-4}$ alkoxy, $CO_2H$ and CN;
- $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O) or a 4 to 6 membered cycloheteroalkyl group or a 3 to 6 membered cycloalkyl group;
- $R^7$ is a member selected from the group consisting of methyl, ethyl and $C_{1-2}$ haloalkyl; and
- the subscript n is 1 or 2;
- or a pharmaceutically acceptable salt, solvate, hydrate, N-oxide, tautomer or rotamer thereof.

2. A compound of claim 1 having the Formula (I):

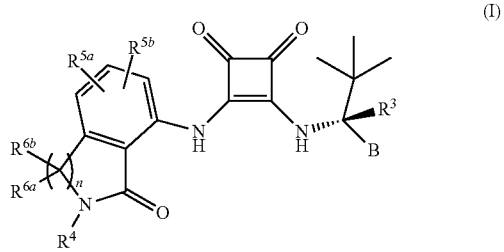

wherein
- B is selected from the group consisting of furanyl, oxazolyl, phenyl, pyridyl, pyrimidinyl and pyrazinyl, each of which is optionally substituted with $R^{1a}$, $R^{1b}$, and $R^2$ which are independently selected from the group consisting of halogen, CN, $C_{1-4}$ alkyl, $C_{1-4}$ alkoxy and $C_{1-4}$ haloalkyl;
- $R^3$ is a member selected from the group consisting of H and D;
- $R^4$ is a member selected from the group consisting of H, $C_{1-8}$ alkyl, and Y; wherein the $C_{1-8}$ alkyl is optionally substituted with halogen, —CN, —$CO_2R^a$, —$CONR^aR^b$, —$C(O)R^a$, $OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$ and Y, wherein Y is a 5- or 6-membered aryl or heteroaryl group with from one to four substituents selected from halogen, —CN, —$C_{1-4}$ alkyl, —$C_{1-4}$ alkoxy, —$C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$; and each $R^a$ and $R^b$ is independently selected from hydrogen, $C_{1-4}$ alkyl, $C_{1-4}$ hydroxyalkyl and $C_{1-4}$ haloalkyl, and R is selected from $C_{1-4}$ alkyl, $C_{1-4}$ hydroxyalkyl and $C_{1-4}$ haloalkyl;
- $R^{5a}$ and $R^{5b}$ are each members independently selected from the group consisting of H, halogen, $C_{1-4}$ alkyl, $C_{1-4}$ alkoxy, $CO_2H$ and CN;
- $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O); and
- the subscript n is 1 or 2;
- or a pharmaceutically acceptable salt, solvate, hydrate, N-oxide, tautomer or rotamer thereof.

3. A compound of claim 1, or a pharmaceutically acceptable salt, solvate, hydrate, N-oxide, tautomer or rotamer thereof, wherein B is selected from the group consisting of:

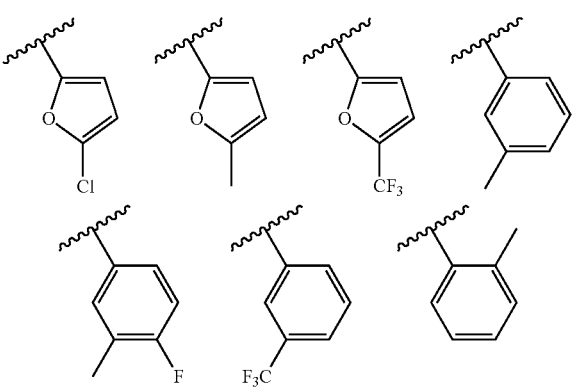

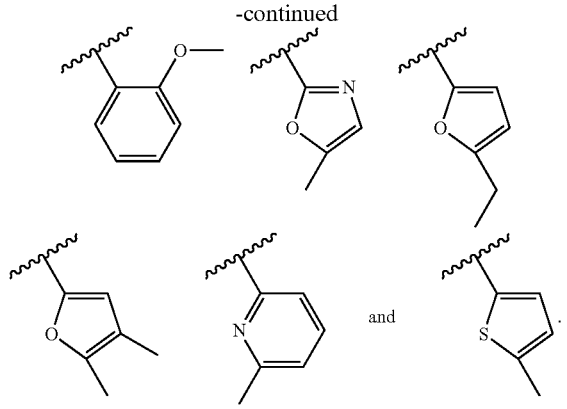

4. A compound of claim 3, or a pharmaceutically acceptable salt, solvate, hydrate, N-oxide, tautomer or rotamer thereof, wherein B is selected from the group consisting of:

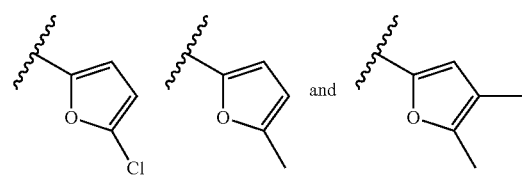

5. A compound of claim 1, or a pharmaceutically acceptable salt, solvate, hydrate, N-oxide, tautomer or rotamer thereof, wherein B is furanyl or oxazolyl, each of which is optionally substituted with $R^{1a}$ and $R^{1b}$, which are independently selected from the group consisting of halogen, CN, $C_{1-4}$ alkyl, $C_{1-4}$ alkoxy and $C_{1-4}$ haloalkyl.

6. A compound of claim 5 or a pharmaceutically acceptable salt, solvate, hydrate, N-oxide, tautomer or rotamer thereof, wherein B is furanyl substituted with $R^{1a}$ which is $CH_3$ or Cl and optionally substituted with $R^{1b}$ which is $CH_3$.

7. A compound of claim 1, or a pharmaceutically acceptable salt, solvate, hydrate, N-oxide, tautomer or rotamer thereof, wherein $R^3$ is H.

8. A compound of claim 1, or a pharmaceutically acceptable salt, solvate, hydrate, N-oxide, tautomer or rotamer thereof, wherein each of $R^{5a}$ and $R^{5b}$ is independently selected from the group consisting of H, $CH_3$, Cl and F.

9. A compound of claim 1, or a pharmaceutically acceptable salt, solvate, hydrate, N-oxide, tautomer or rotamer thereof, wherein

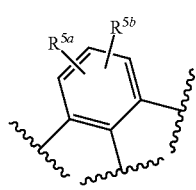

is selected from the group consisting of:

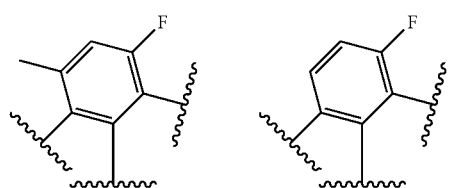

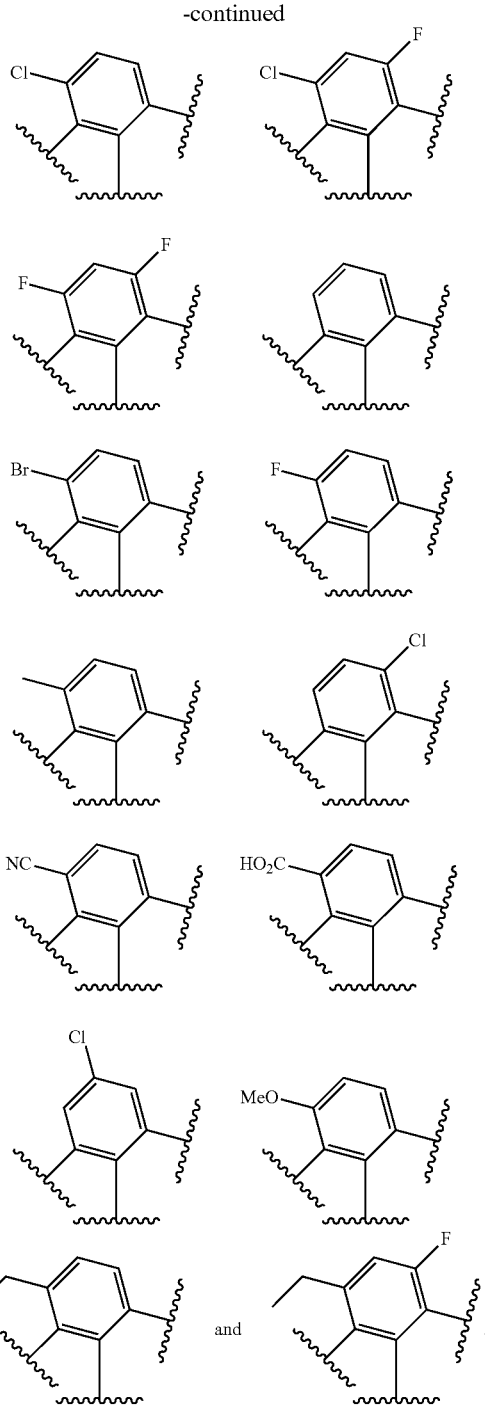

10. A compound of claim 9, or a pharmaceutically acceptable salt, solvate, hydrate, N-oxide, tautomer or rotamer thereof, wherein

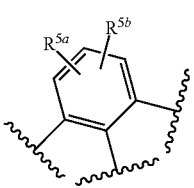

is selected from the group consisting of:

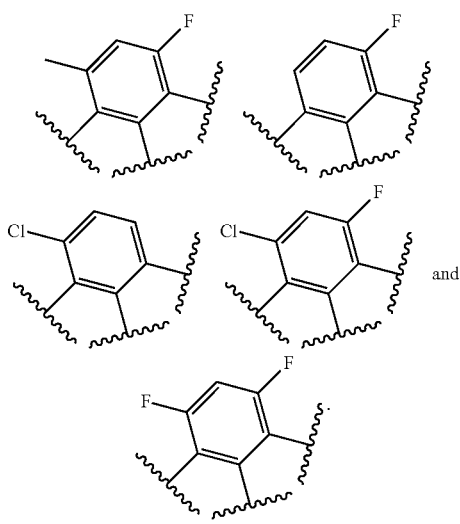

and

11. A compound of claim 1, or a pharmaceutically acceptable salt, solvate, hydrate, N-oxide, tautomer or rotamer thereof, wherein each of $R^{6a}$ and $R^{6b}$ is independently selected from the group consisting of H and $C_{1-2}$ alkyl.

12. A compound of claim 1, or a pharmaceutically acceptable salt, solvate, hydrate, N-oxide, tautomer or rotamer thereof, wherein

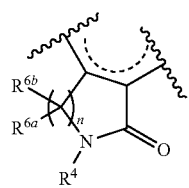

is independently selected from the group consisting of

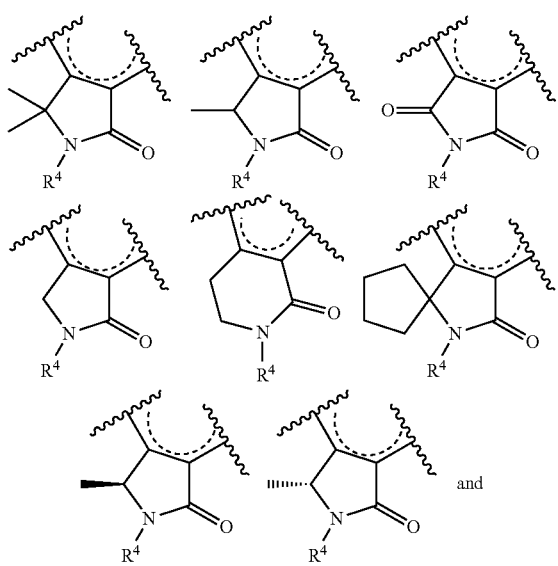

and

-continued

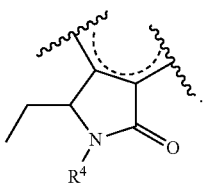

13. A compound of claim 12, or a pharmaceutically acceptable salt, solvate, hydrate, N-oxide, tautomer or rotamer thereof, wherein

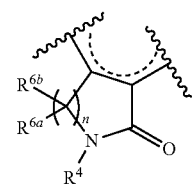

is independently selected from the group consisting of

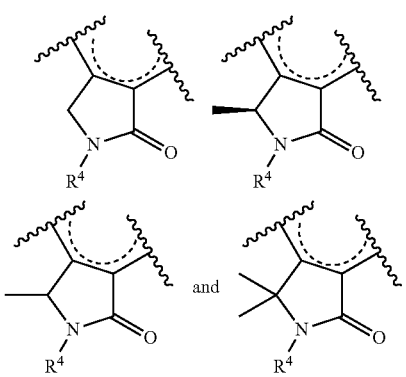

14. A compound of claim 1, or a pharmaceutically acceptable salt, solvate, hydrate, N-oxide, tautomer or rotamer thereof, wherein $R^4$ is H, $C_{1-3}$ alkyl or Y, wherein the $C_{1-3}$ alkyl is substituted with tetrazolyl or tetrazolonyl, wherein the tetrazolyl or tetrazolonyl is optionally substituted with $C_{1-6}$ alkyl, $C_{1-6}$ hydroxyalkyl, or $C_{1-4}$alkyl-O—$C_{1-4}$alkyl wherein Y is selected from the group consisting of pyridinyl, pyrazolyl, and phenyl wherein the pyridinyl, pyrazolyl, and phenyl have from one to three substituents each of which is independently selected from —$C_{1-4}$ alkyl, —$C_{1-4}$ alkoxy and —$CO_2H$.

15. A compound of claim 14, or a pharmaceutically acceptable salt, solvate, hydrate, N-oxide, tautomer or rotamer thereof, wherein $R^4$ is selected from the group consisting of:

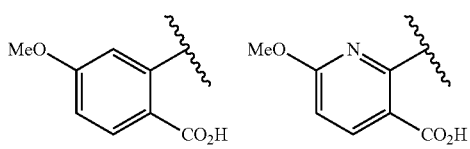

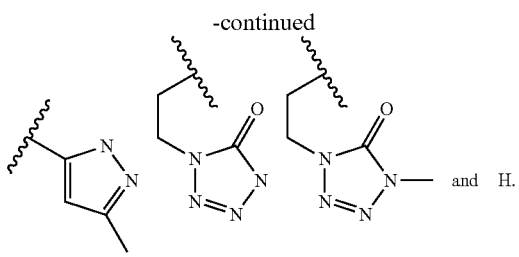 and H.

16. A compound of claim 1, or a pharmaceutically acceptable salt, solvate, hydrate, N-oxide, tautomer or rotamer thereof, wherein $R^7$ is selected from the group consisting of methyl, ethyl and $CF_3$.

17. A compound of claim 1, having the formula (A1):

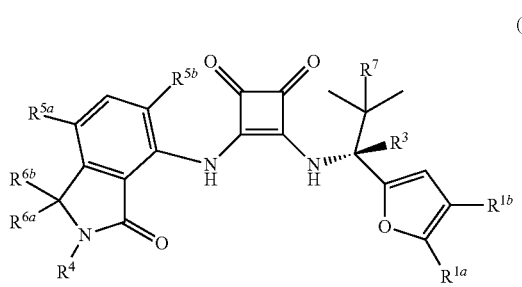

(A1)

wherein $R^{1a}$ is selected from $CH_3$ and Cl; $R^{1b}$ is absent or is $CH_3$; $R^3$ is H or D; $R^4$ is H or Y; $R^{5a}$ and $R^{5b}$ are each independently selected from H, F, Cl, Br and $CH_3$; $R^{6a}$ and $R^{6b}$ are each independently selected from H and $CH_3$; and $R^7$ is methyl or ethyl; or a pharmaceutically acceptable salt, solvate or hydrate thereof.

18. A compound of claim 17, or a pharmaceutically acceptable salt, solvate, or hydrate thereof, wherein $R^{1a}$ is $CH_3$; $R^{1b}$ is absent or is $CH_3$; $R^3$ is H or D; $R^4$ is H; $R^{5a}$ is H, F, Me or Cl or Br; $R^{5b}$ is H or F; $R^{6a}$ and $R^{6b}$ are each H; and $R^7$ is methyl or ethyl.

19. A compound of claim 17, or a pharmaceutically acceptable salt, solvate, or hydrate thereof, which compound is substantially free of other isomers at the carbon atom bearing $R^3$.

20. A compound of claim 17, or a pharmaceutically acceptable salt, solvate, or hydrate thereof, wherein $R^4$ is Y.

21. A compound of claim 1, having the formula (A2):

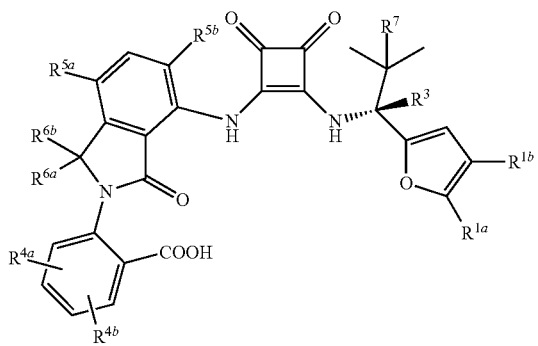

(A2)

wherein $R^{1a}$ is selected from $CH_3$ and Cl; $R^{1b}$ is H or $CH_3$; $R^3$ is H or D; $R^{4a}$ and $R^{4b}$ are independently selected from halogen, —CN, —$C_{1-4}$ alkyl, —$C_{1-4}$ alkoxy, —$C_{1-4}$ hydroxyalkyl, —$C_{1-4}$ haloalkyl, $OCF_3$, —$CO_2R^a$, —$CONR^aR^b$, —$C(O)R^a$, —$OC(O)NR^aR^b$, —$NR^aC(O)R^b$, —$CH_2CO_2R^a$, and $R^a$ and $R^b$ are independently selected from hydrogen, $C_{1-4}$ alkyl, $C_{1-4}$ hydroxyalkyl and $C_{1-4}$ haloalkyl; $R^{5a}$ and $R^{5b}$ are each independently selected from H, F, Cl, Br and $CH_3$; $R^{6a}$ and $R^{6b}$ are each independently selected from H and $CH_3$; and $R^7$ is selected from the group consisting of methyl, ethyl and $C_{1-2}$ haloalkyl; or a pharmaceutically acceptable salt, solvate or hydrate thereof.

22. The compound of claim 1, or a pharmaceutically acceptable salt thereof, selected from the group consisting of

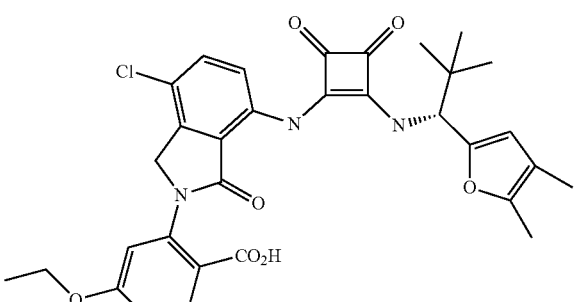

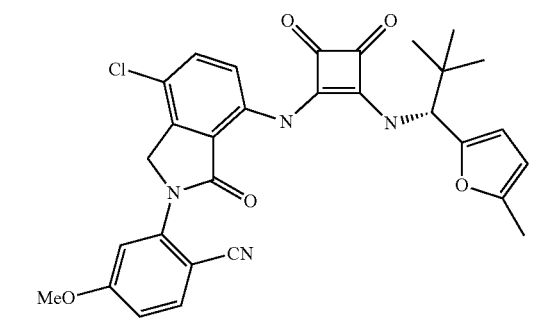

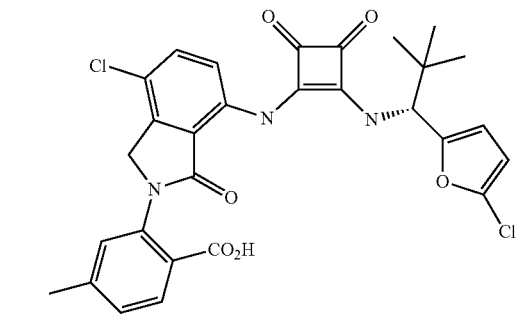

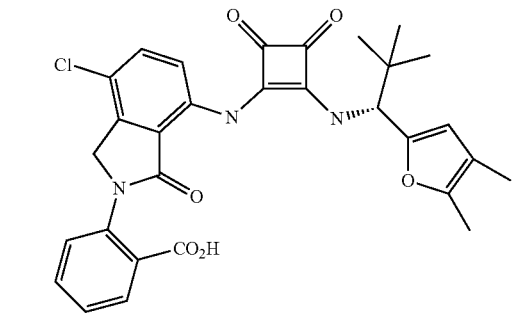

185
-continued
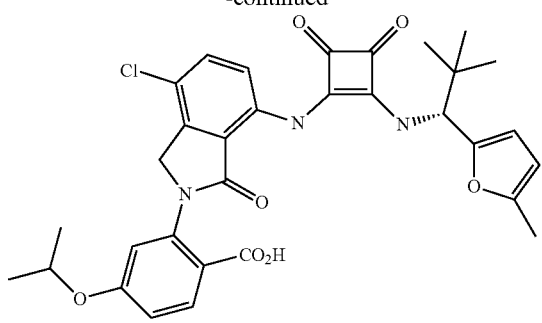
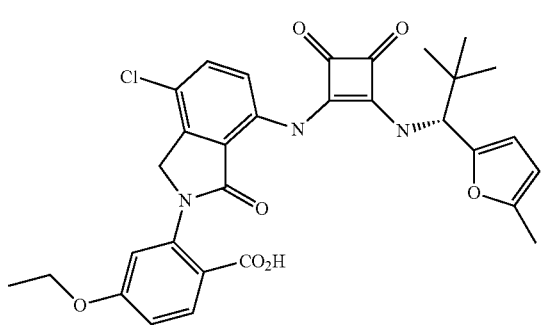
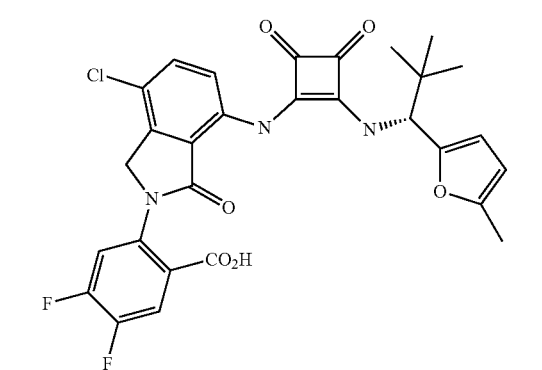
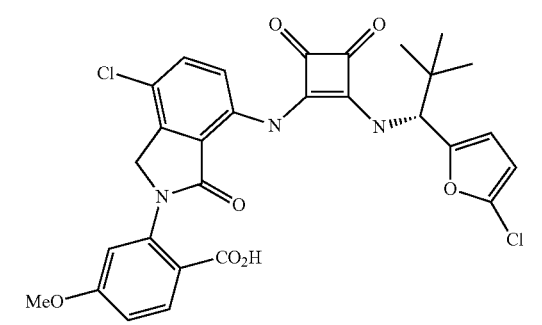
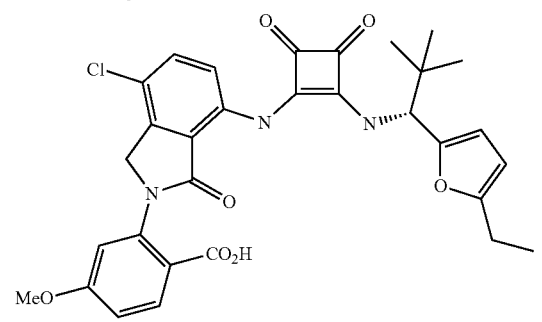
186
-continued
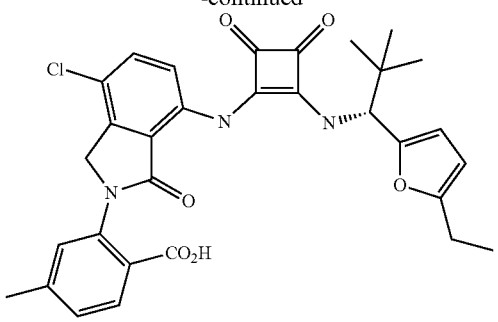
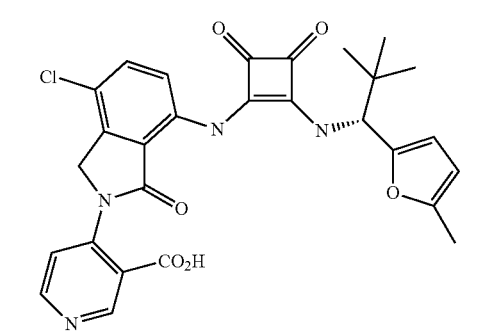
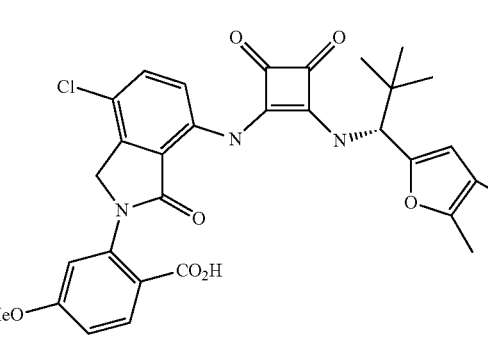
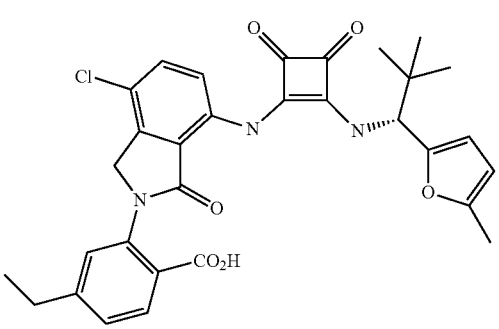
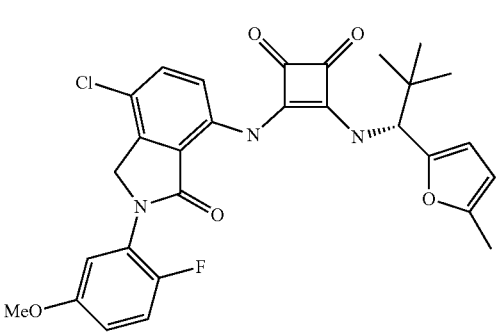

187
-continued
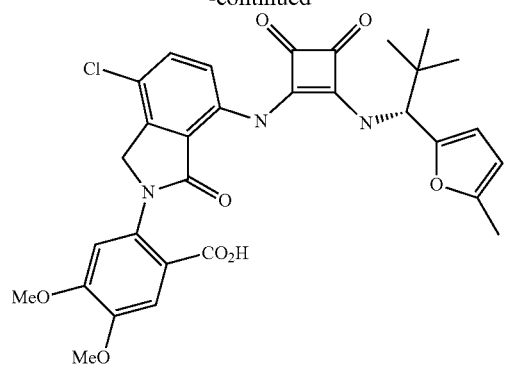
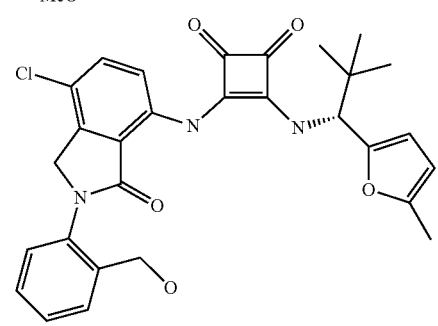
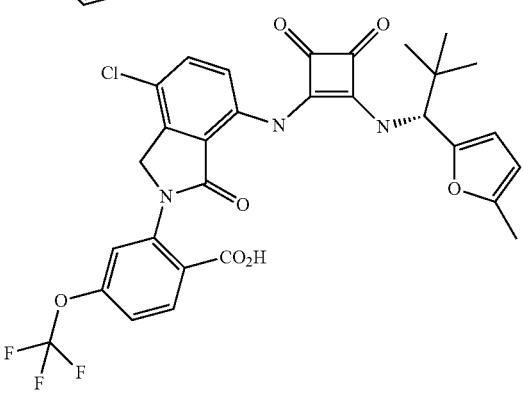
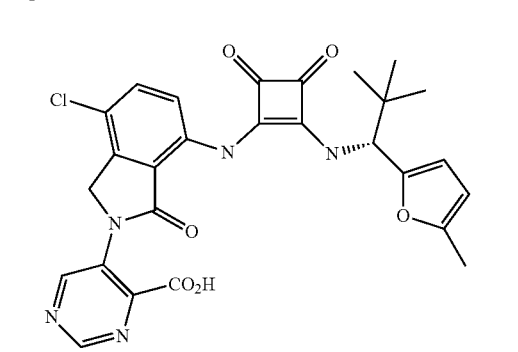
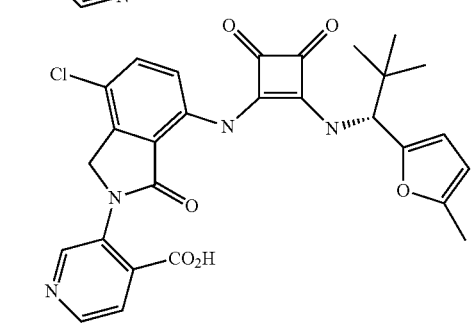
188
-continued
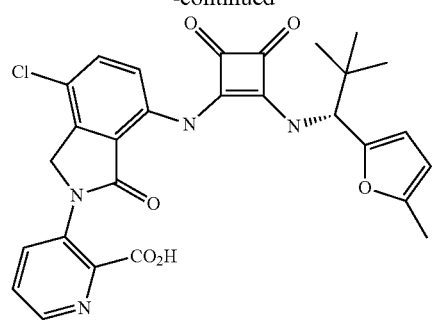
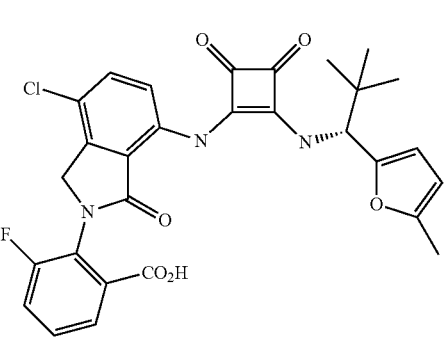 [SMILES: Cc1ccc([C@H](Nc2c(Nc3ccc(Cl)c4c3C(=O)N(c3c(F)cccc3C(=O)O)C4)c(=O)c2=O)C(C)(C)C)o1]
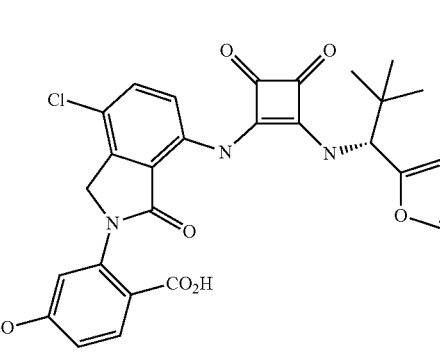
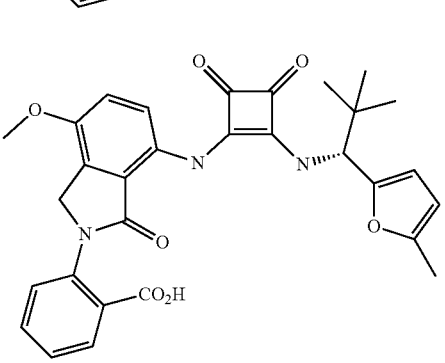
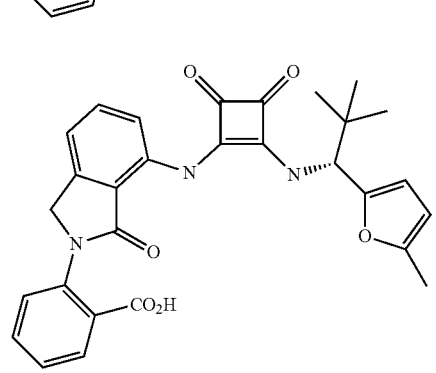

189
-continued
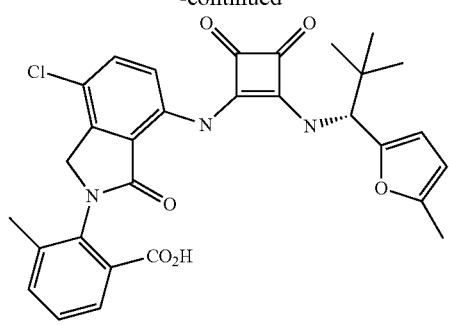
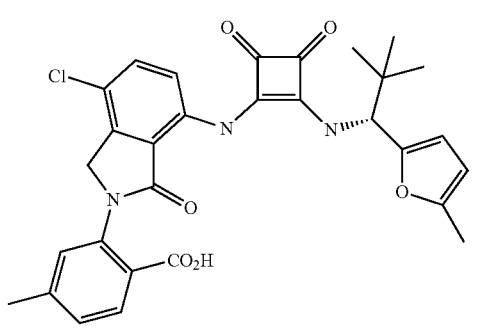
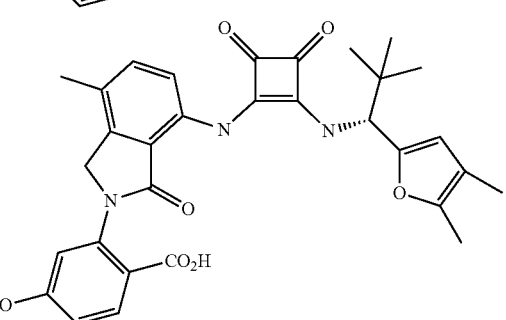
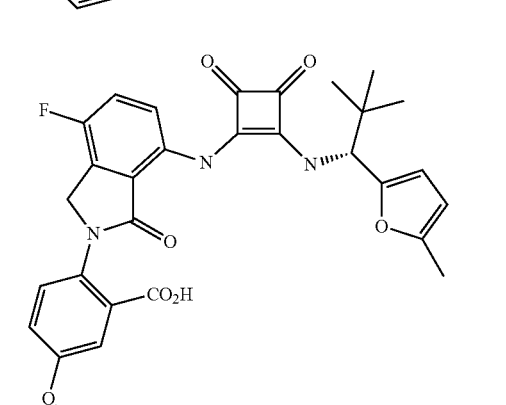
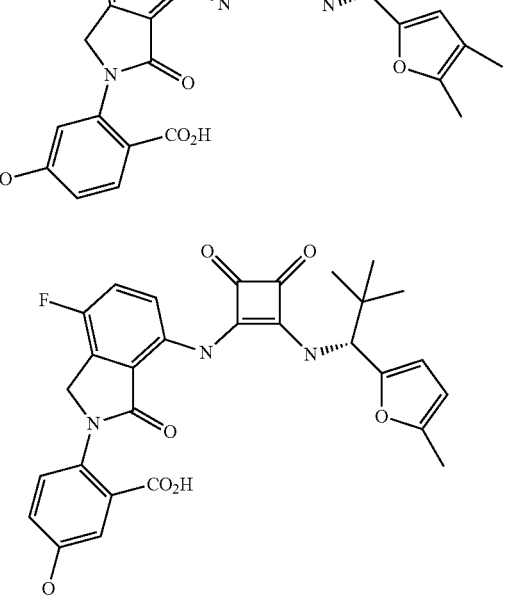
190
-continued
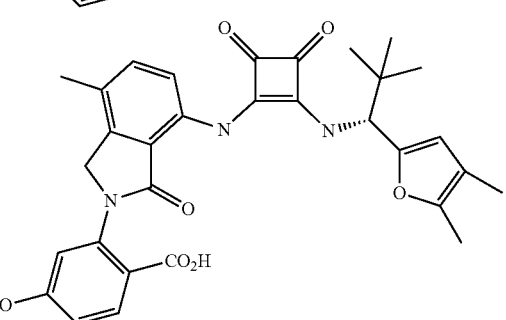
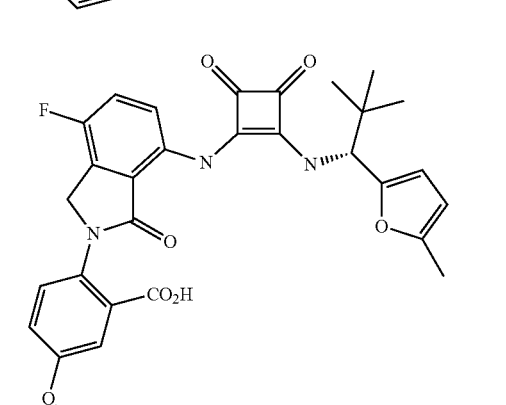
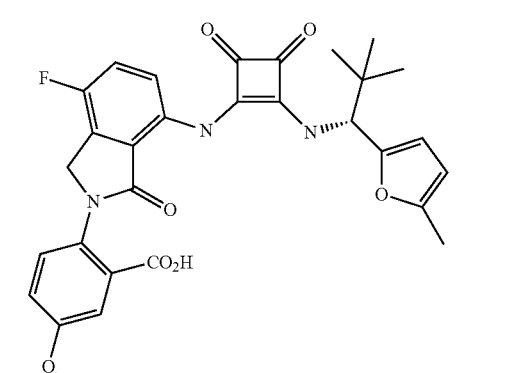 [SMILES: Cc1ccc([C@H](Nc2c(Nc3ccc(F)c4c3C(=O)N(c3ccc(F)cc3C(=O)O)C4)c(=O)c2=O)C(C)(C)C)o1]
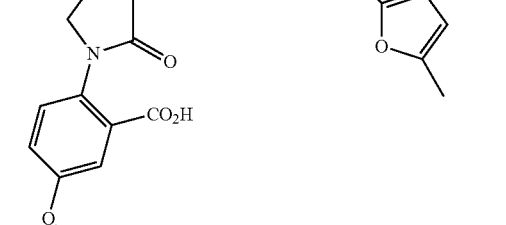

191
-continued
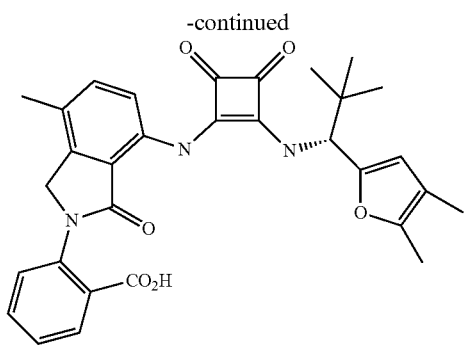
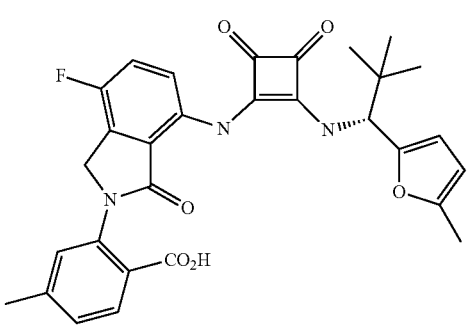
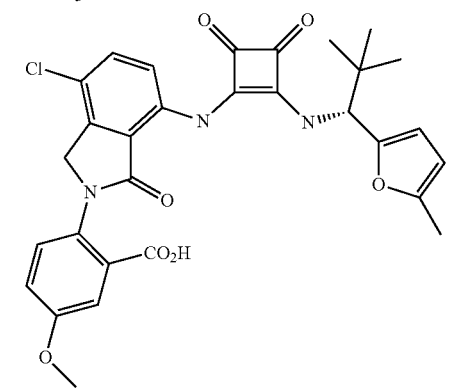
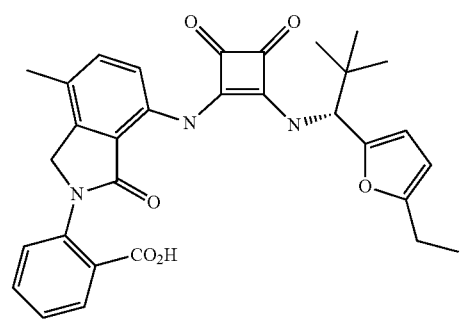
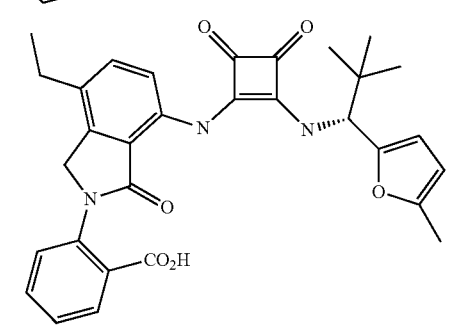
192
-continued
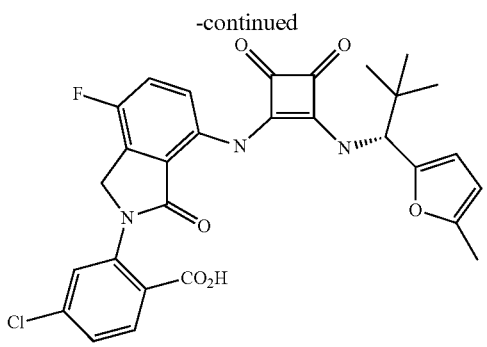
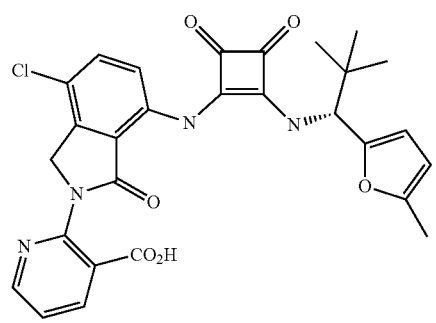
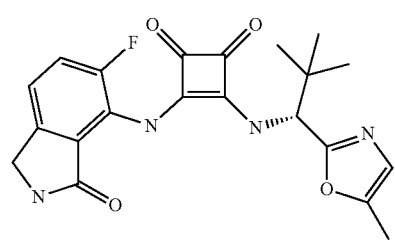
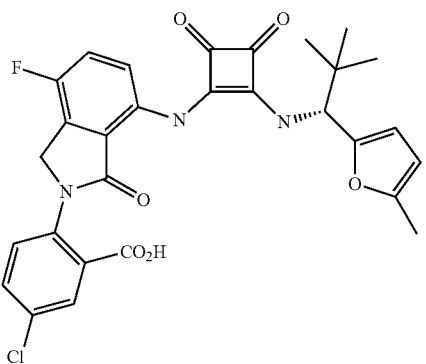 [SMILES: Cc1ccc([C@H](Nc2c(Nc3ccc(F)c4c3C(=O)N(c3ccc(Cl)cc3C(=O)O)C4)c(=O)c2=O)C(C)(C)C)o1]
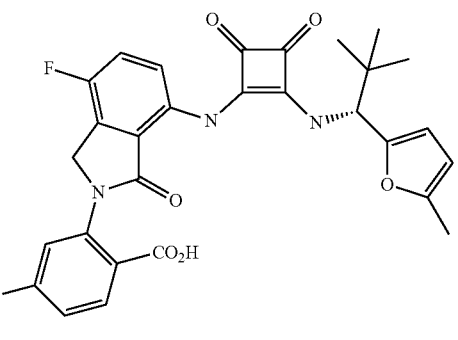

193
-continued
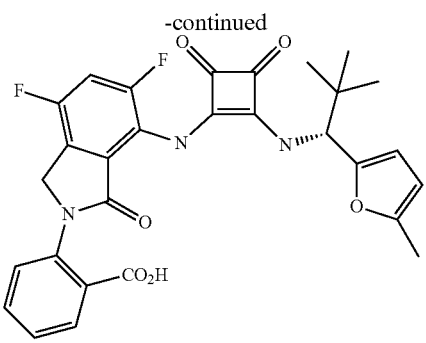
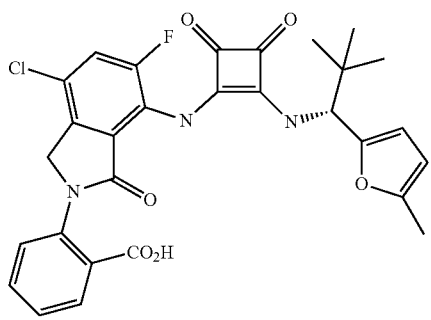 [SMILES: Cc1ccc([C@H](Nc2c(Nc3c(F)cc(Cl)c4c3C(=O)N(c3ccccc3C(=O)O)C4)c(=O)c2=O)C(C)(C)C)o1]
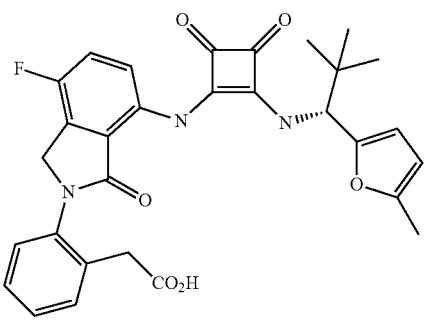
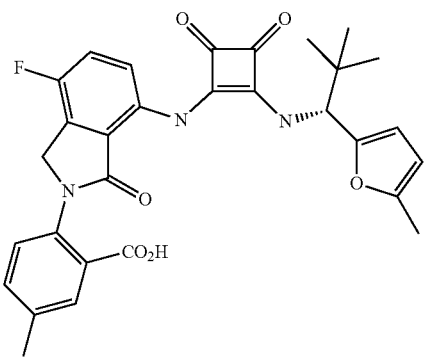
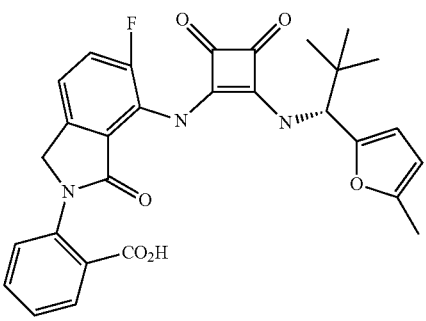
194
-continued
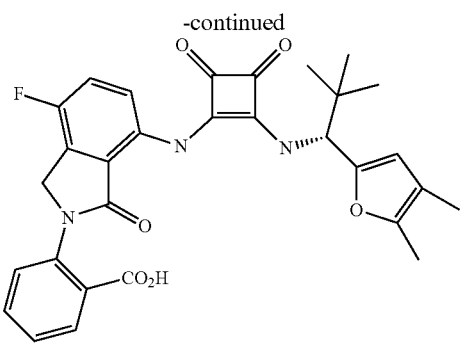
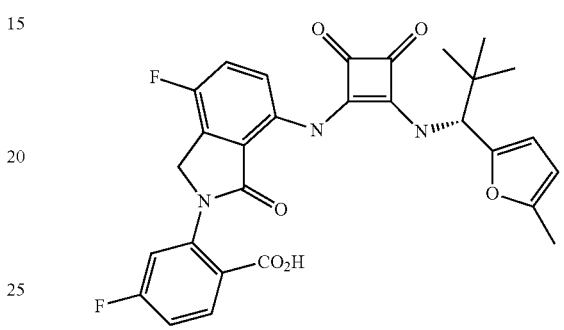
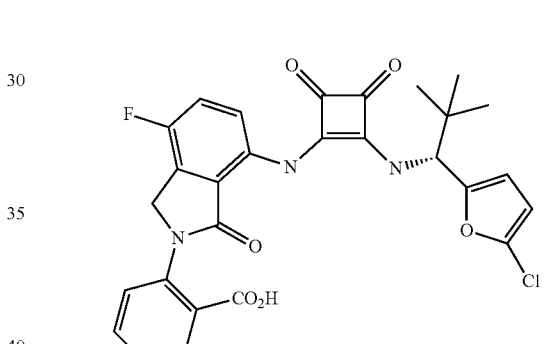
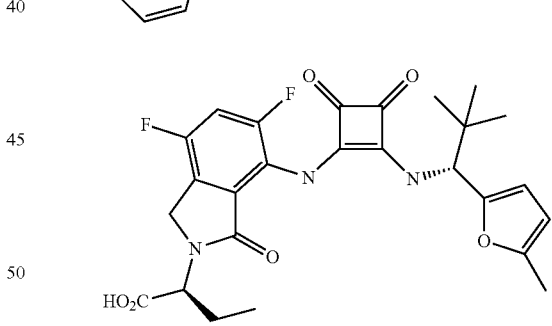
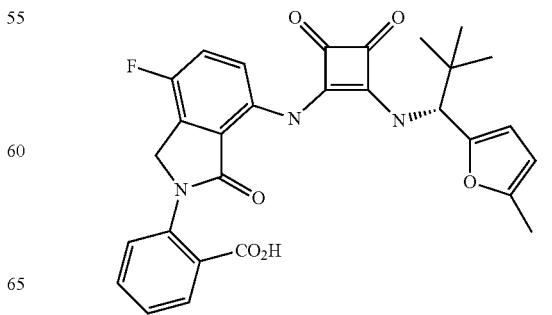

195
-continued
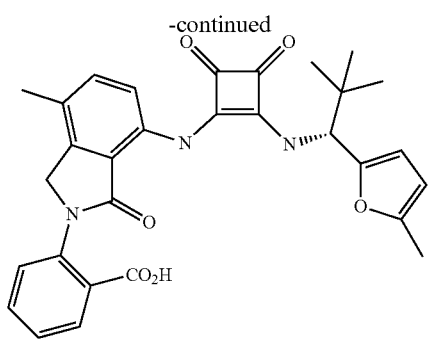
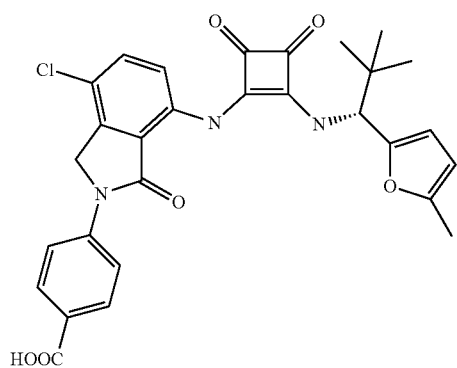 [SMILES: Cc1ccc([C@H](Nc2c(Nc3ccc(Cl)c4c3C(=O)N(c3ccc(C(=O)O)cc3)C4)c(=O)c2=O)C(C)(C)C)o1]
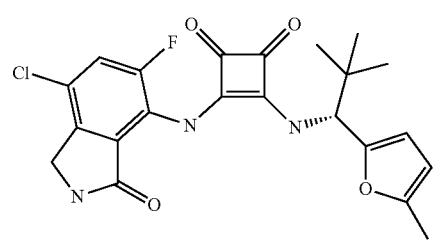
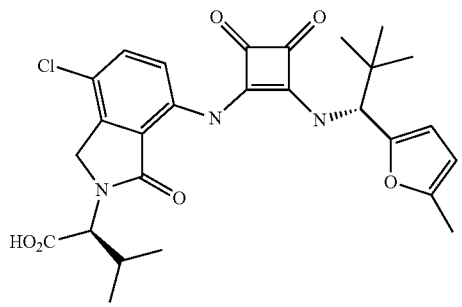
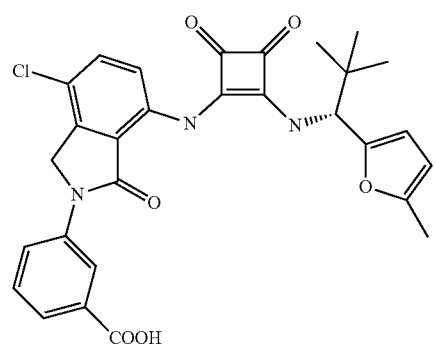 [SMILES: Cc1ccc([C@H](Nc2c(Nc3ccc(Cl)c4c3C(=O)N(c3cccc(C(=O)O)c3)C4)c(=O)c2=O)C(C)(C)C)o1]
196
-continued
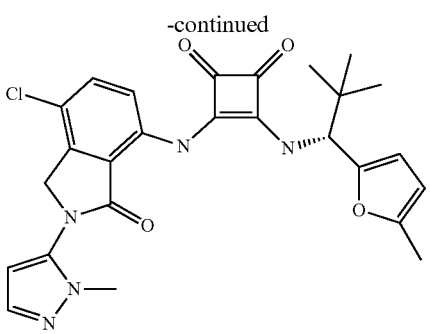
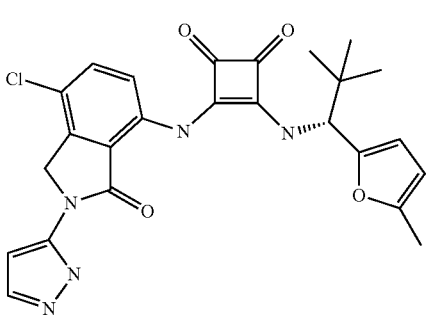
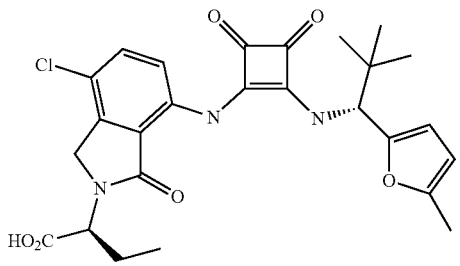
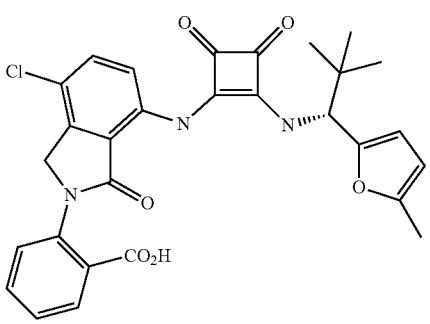 [SMILES: Cc1ccc([C@H](Nc2c(Nc3ccc(Cl)c4c3C(=O)N(c3ncccc3C(=O)O)C4)c(=O)c2=O)C(C)(C)C)o1]
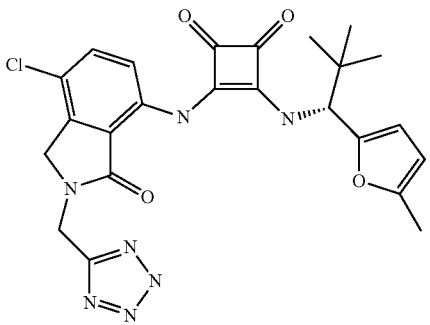 [SMILES: Cc1ccc([C@H](Nc2c(Nc3ccc(Cl)c4c3C(=O)N(Cc3nn[nH]n3)C4)c(=O)c2=O)C(C)(C)C)o1]

197
-continued
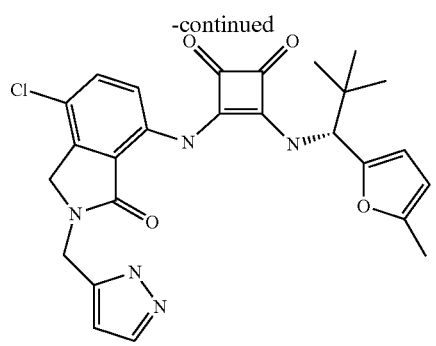
198
-continued
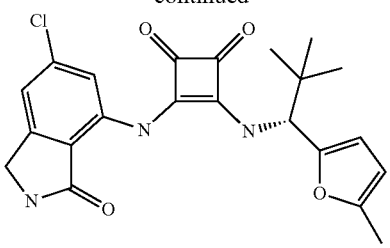
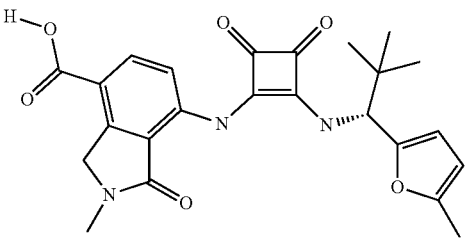
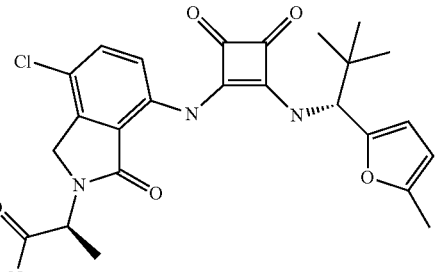
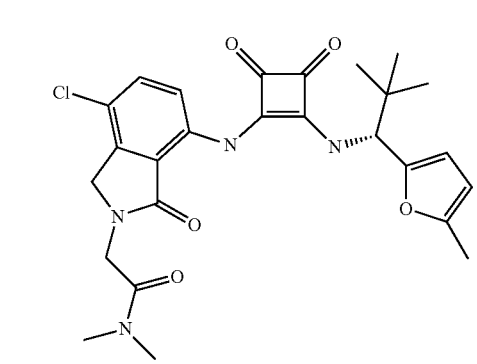 [SMILES: Cc1ccc([C@H](Nc2c(Nc3ccc(Cl)c4c3C(=O)N(CC(=O)N(C)C)C4)c(=O)c2=O)C(C)(C)C)o1]
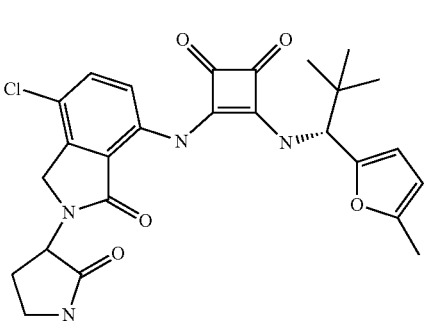

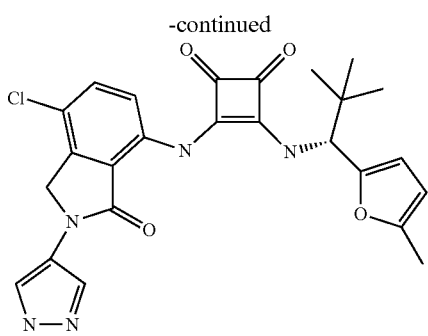
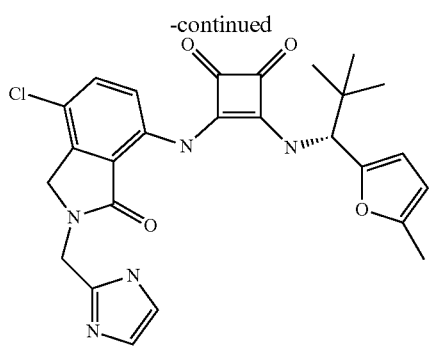
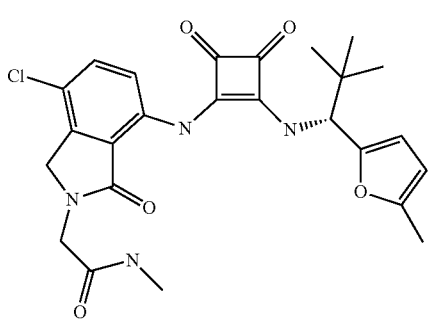 [SMILES: CNC(=O)CN1Cc2c(Cl)ccc(Nc3c(N[C@@H](c4ccc(C)o4)C(C)(C)C)c(=O)c3=O)c2C1=O]
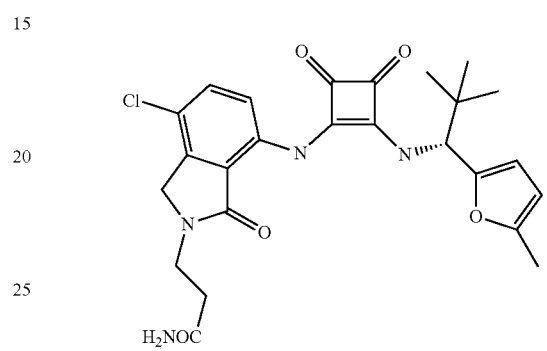
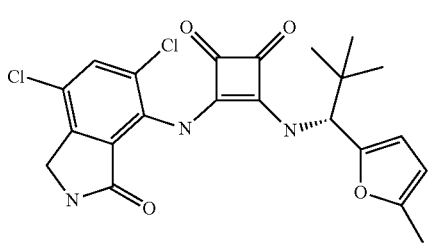
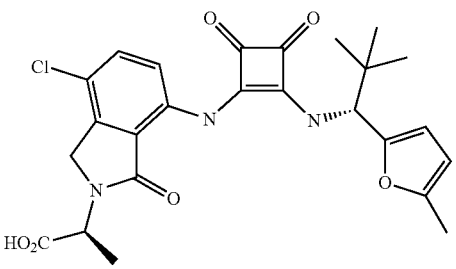
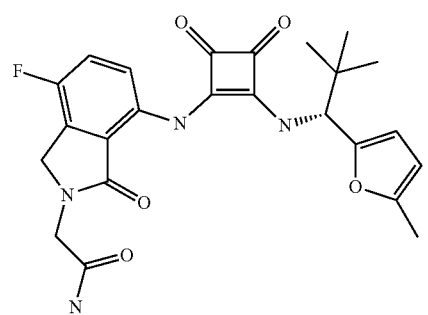
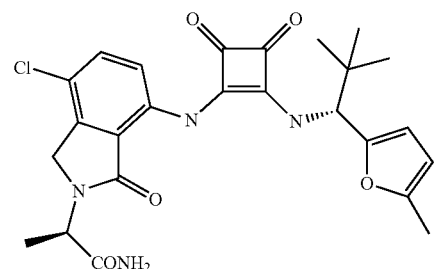
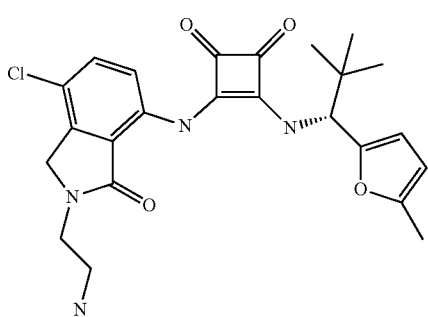
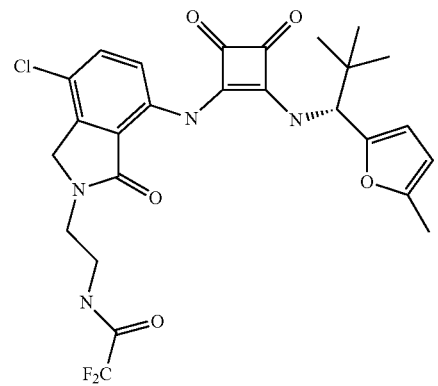 [SMILES: Cc1ccc([C@H](Nc2c(Nc3ccc(Cl)c4c3C(=O)N(CCNC(=O)C(F)(F)F)C4)c(=O)c2=O)C(C)(C)C)o1]

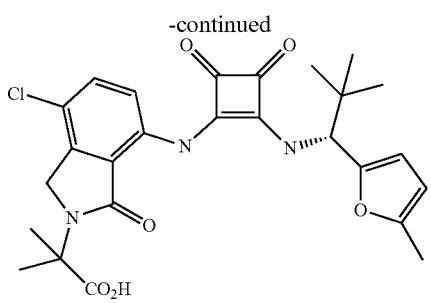
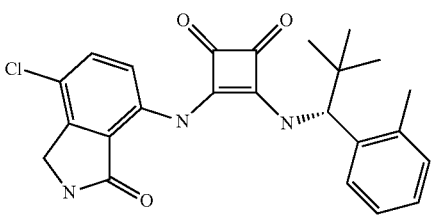
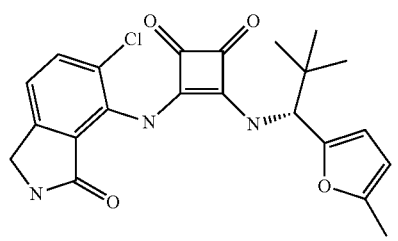
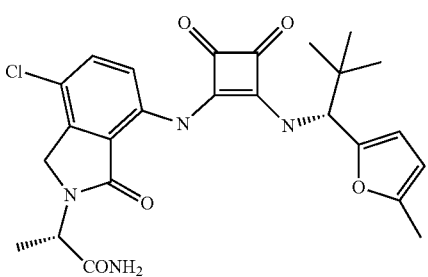 [SMILES: Cc1ccc([C@H](Nc2c(Nc3ccc(Cl)c4c3C(=O)N([C@@H](C)C(N)=O)C4)c(=O)c2=O)C(C)(C)C)o1]
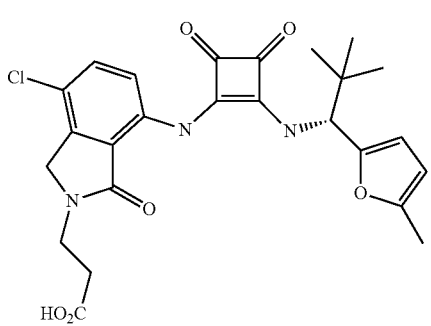 [SMILES: Cc1ccc([C@H](Nc2c(Nc3ccc(Cl)c4c3C(=O)N(CCC(=O)O)C4)c(=O)c2=O)C(C)(C)C)o1]
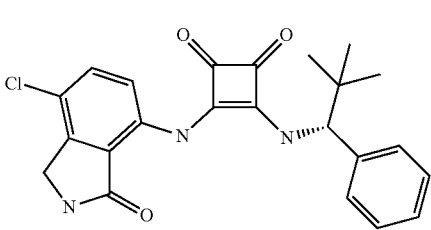
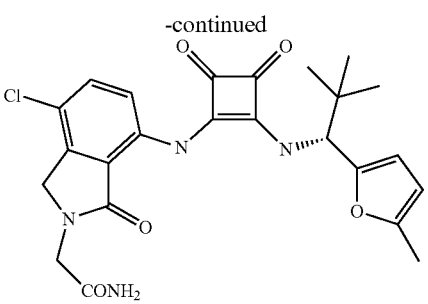
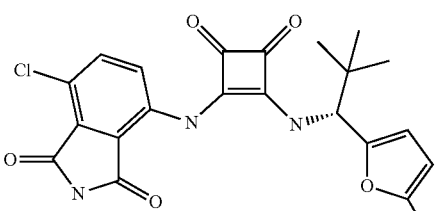
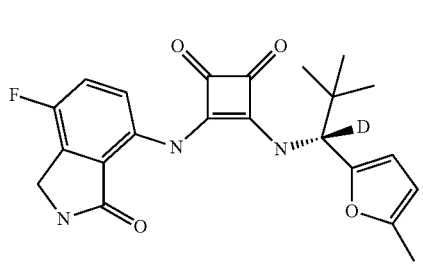
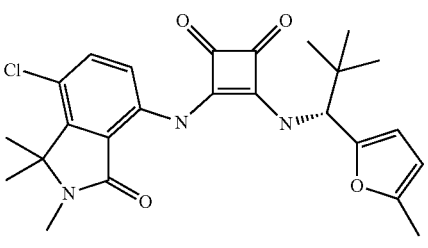
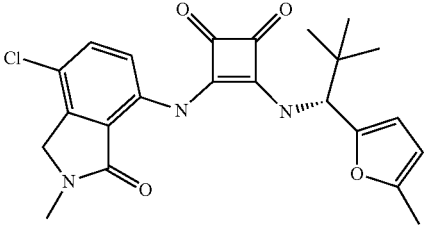
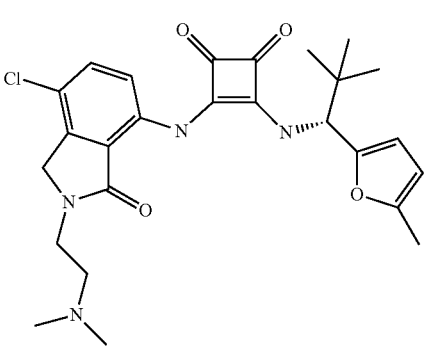

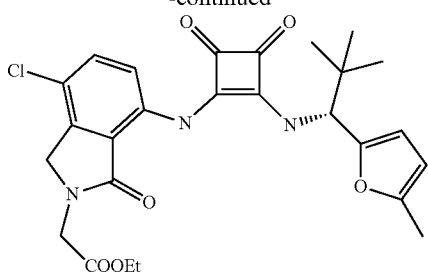
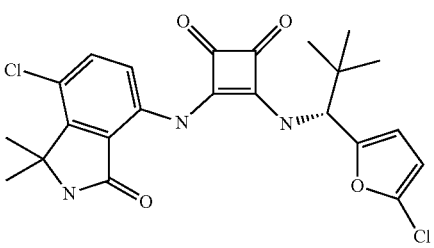
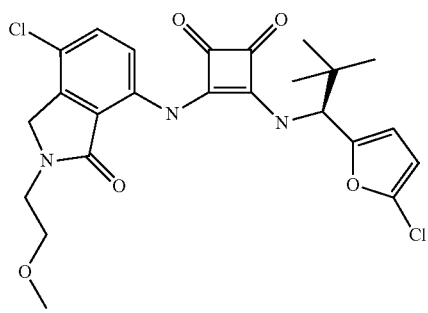
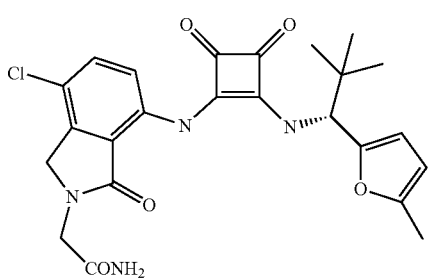 [SMILES: Cc1ccc([C@H](Nc2c(Nc3ccc(Cl)c4c3C(=O)N(CC(N)=O)C4)c(=O)c2=O)C(C)(C)C)o1]
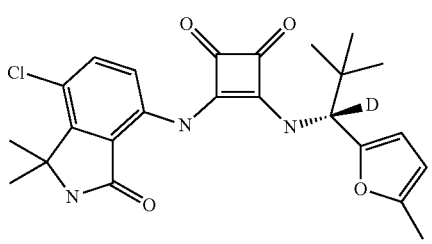
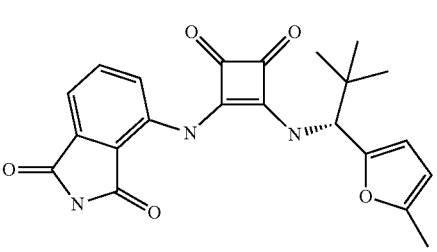
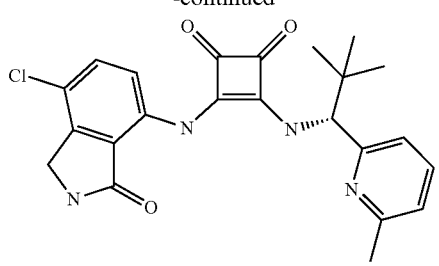
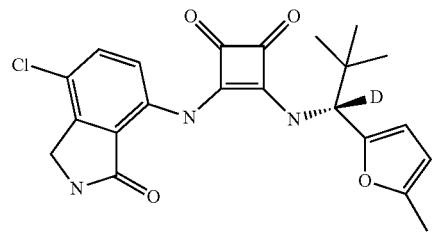
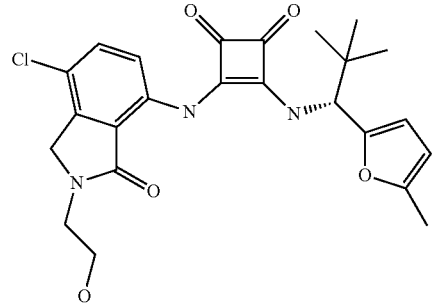 [SMILES: Cc1ccc([C@H](Nc2c(Nc3ccc(Cl)c4c3C(=O)N(CCO)C4)c(=O)c2=O)C(C)(C)C)o1]
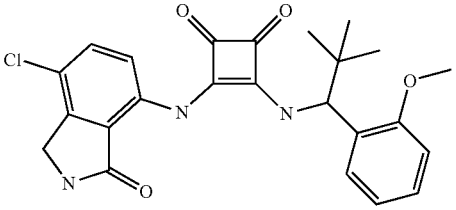
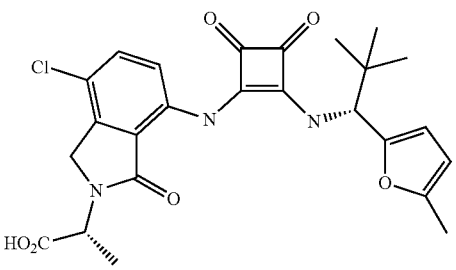

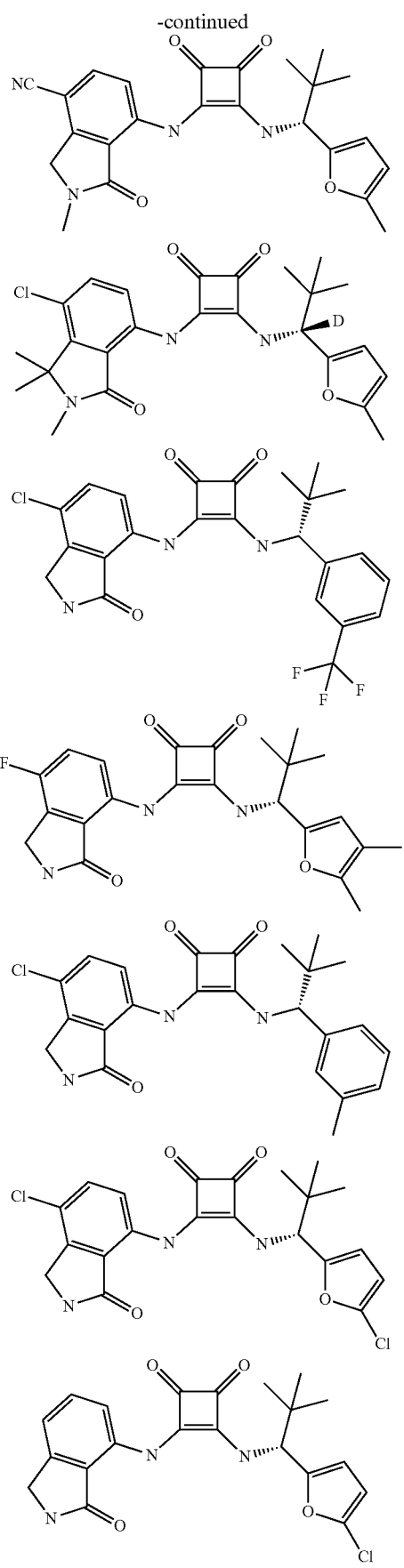
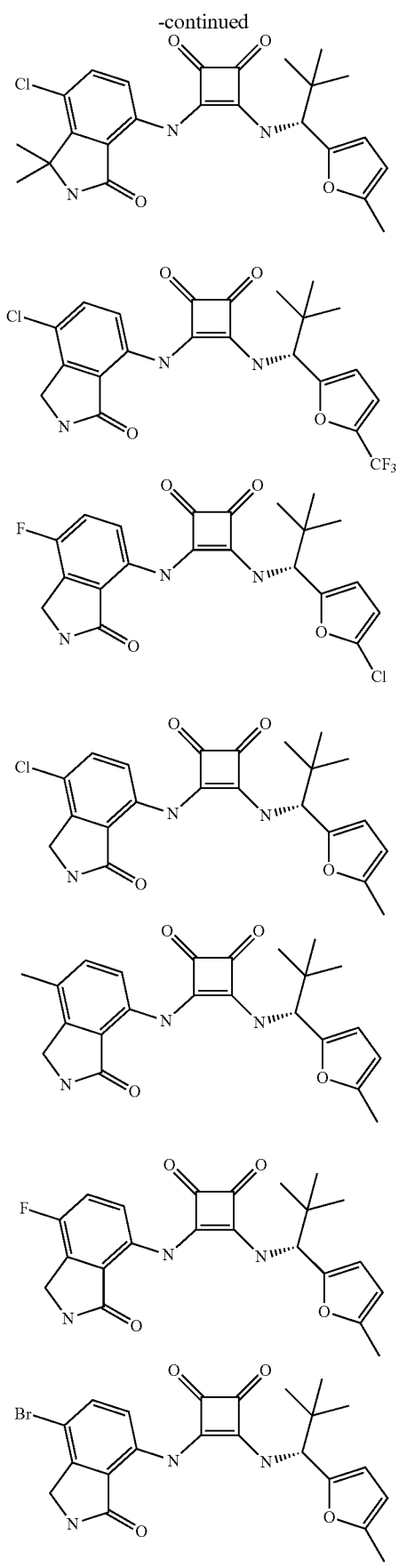

207
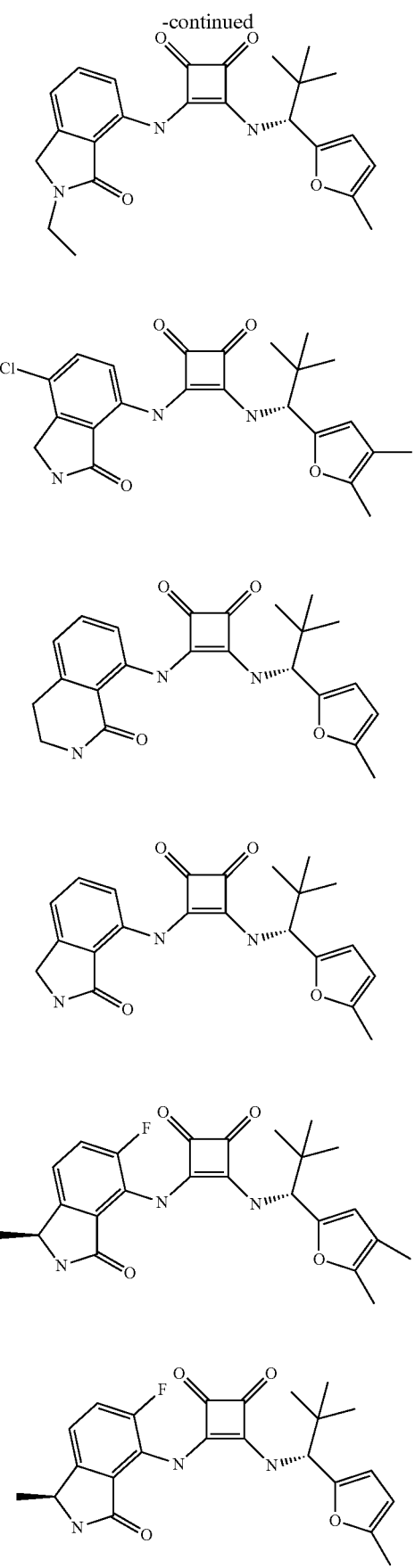
208
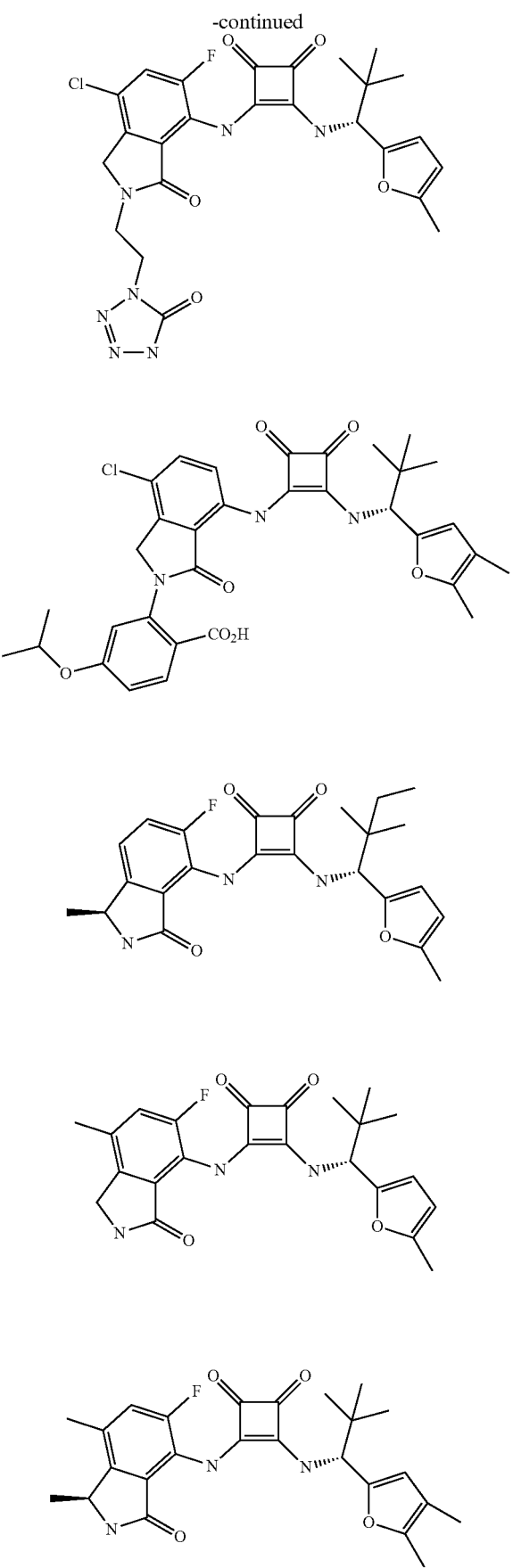

209
-continued
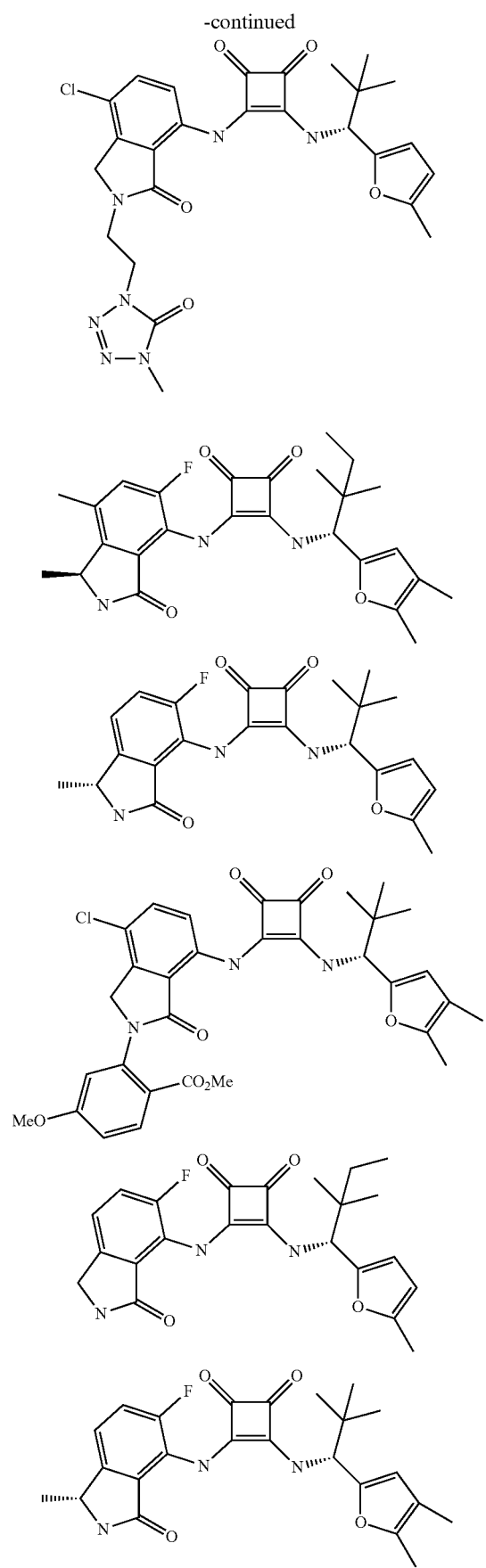
210
-continued
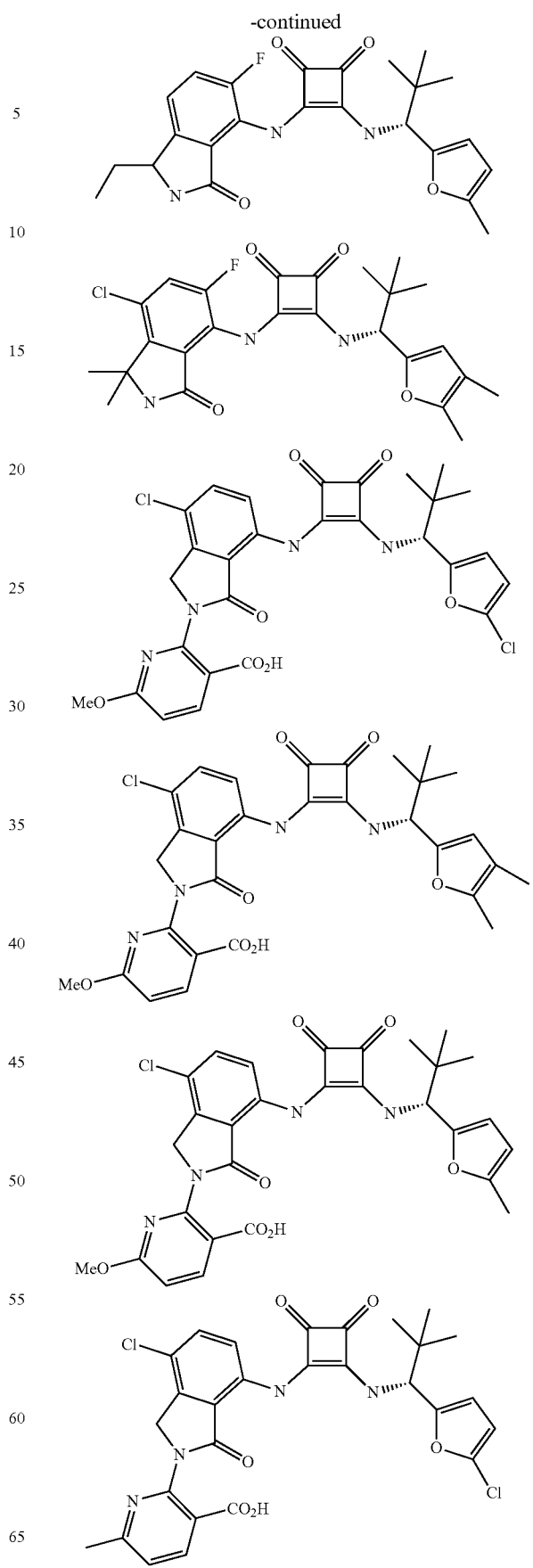

211
-continued
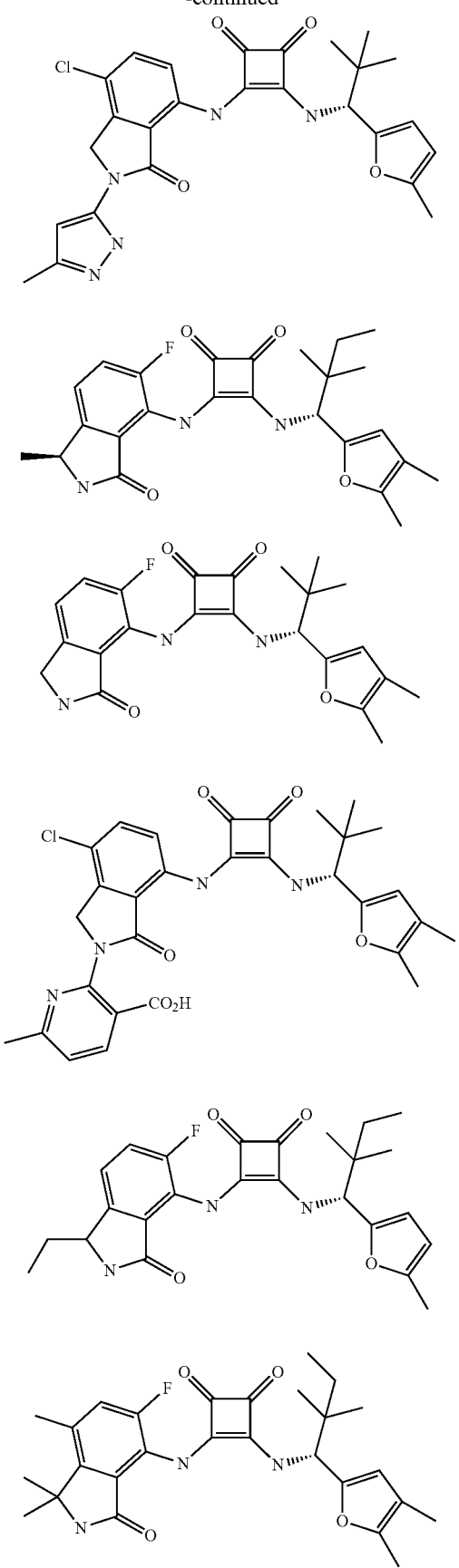
212
-continued
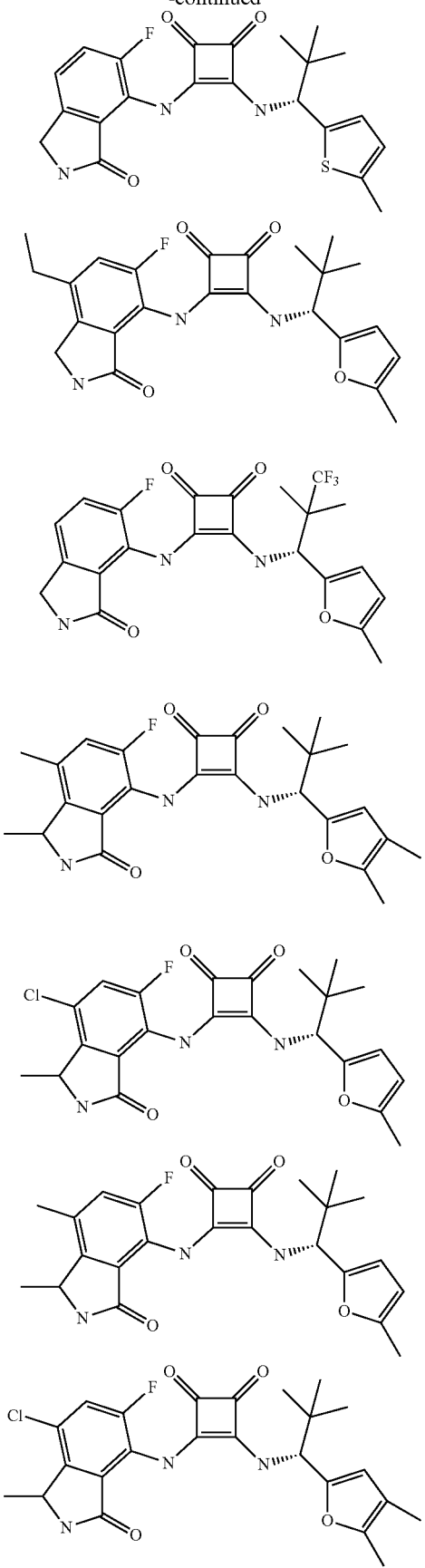

213
-continued
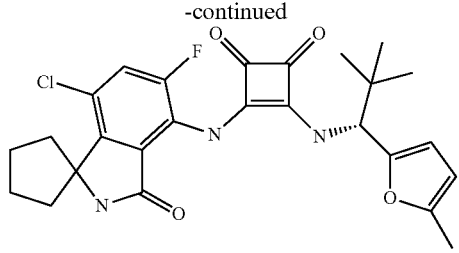
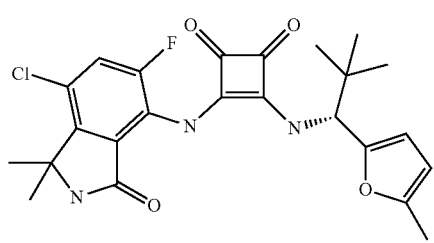
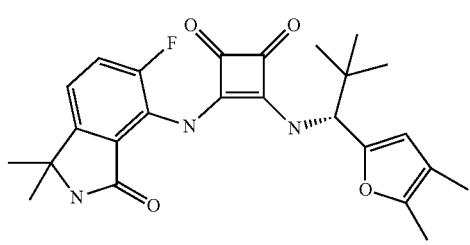
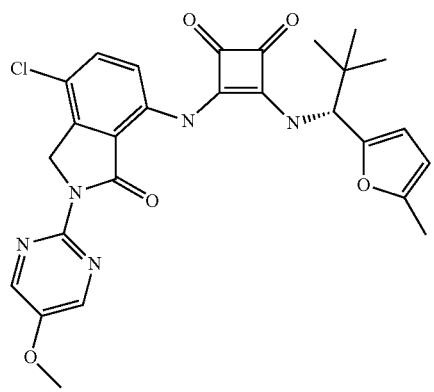
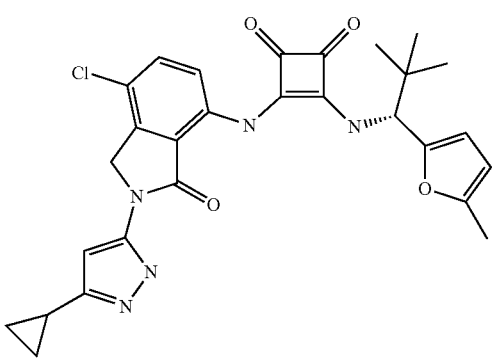
214
-continued
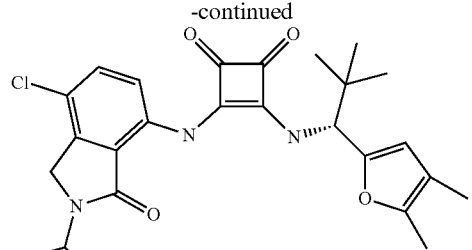
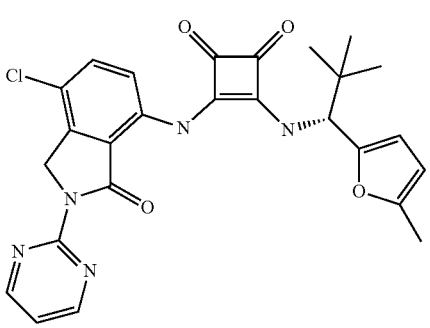
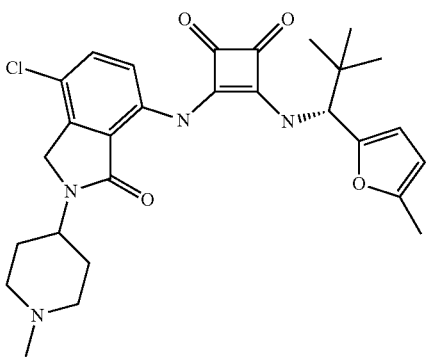
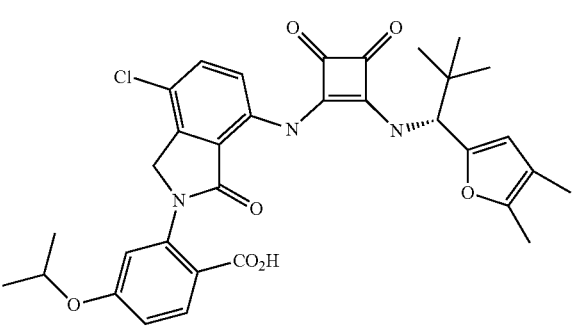
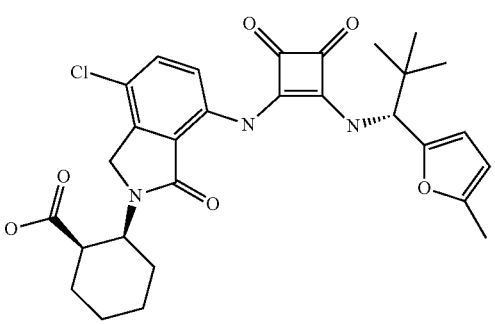

215
-continued
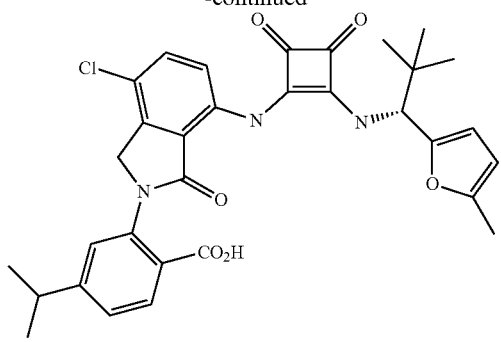
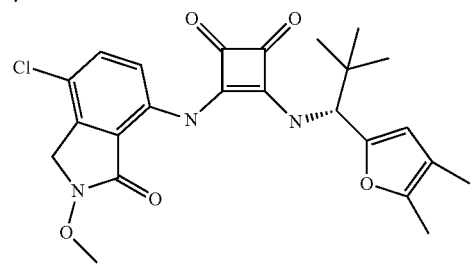
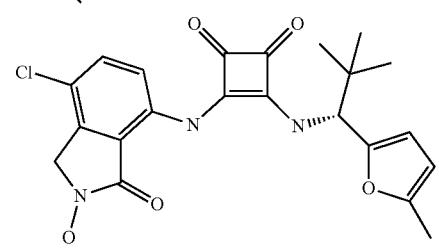
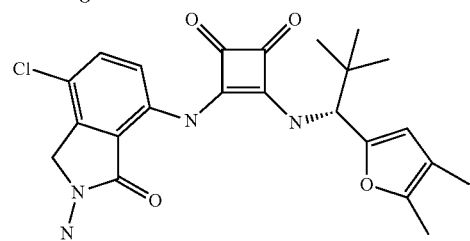
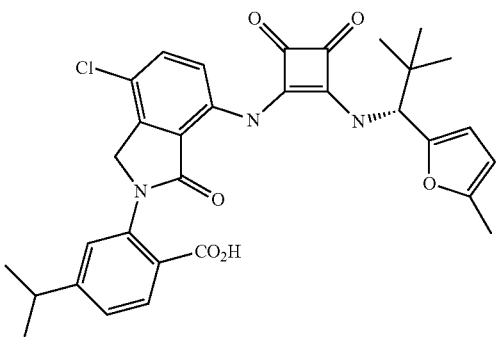 [SMILES: Cc1ccc([C@H](Nc2c(Nc3ccc(Cl)c4c3C(=O)N(c3cc(C(C)C)ccc3C(=O)O)C4)c(=O)c2=O)C(C)(C)C)o1]
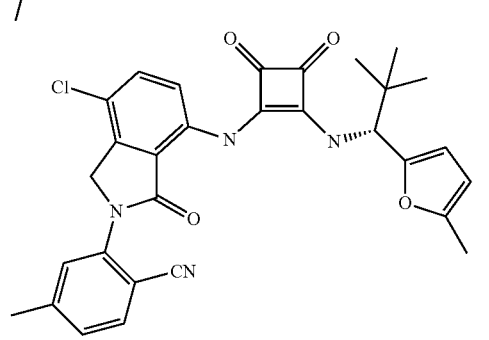
216
-continued
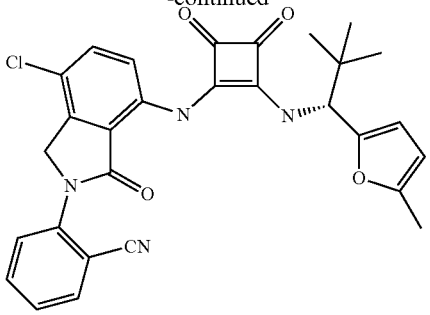
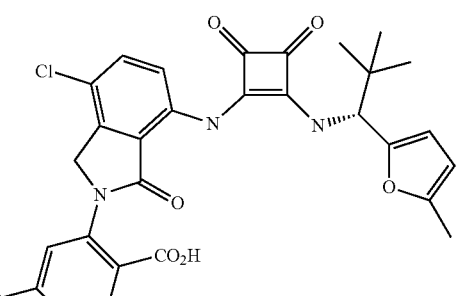
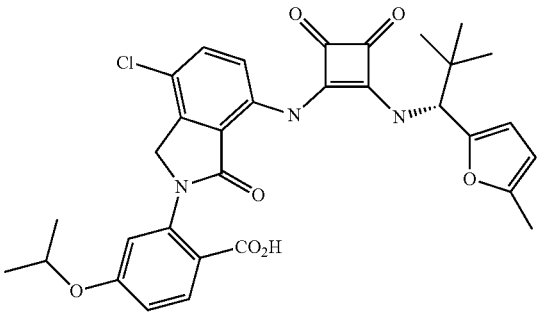 [SMILES: Cc1ccc([C@H](Nc2c(Nc3ccc(Cl)c4c3C(=O)N(c3cc(OC(C)C)ccc3C(=O)O)C4)c(=O)c2=O)C(C)(C)C)o1]
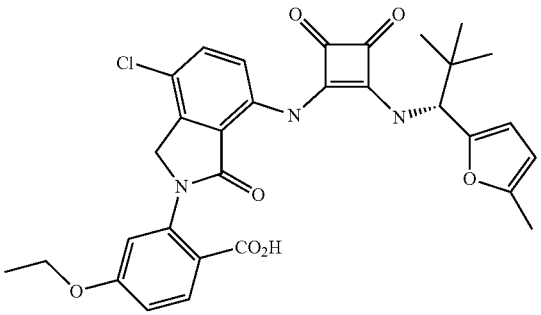 [SMILES: CCOc1ccc(C(=O)O)c(N2Cc3c(Cl)ccc(Nc4c(N[C@@H](c5ccc(C)o5)C(C)(C)C)c(=O)c4=O)c3C2=O)c1]
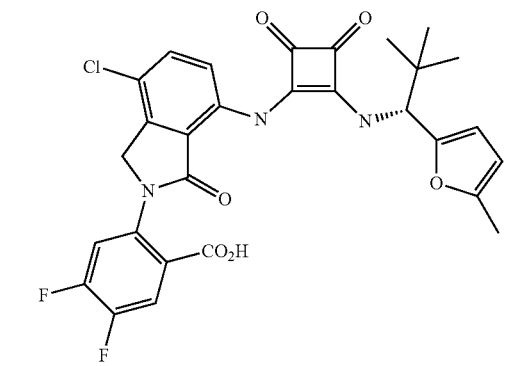

217
-continued
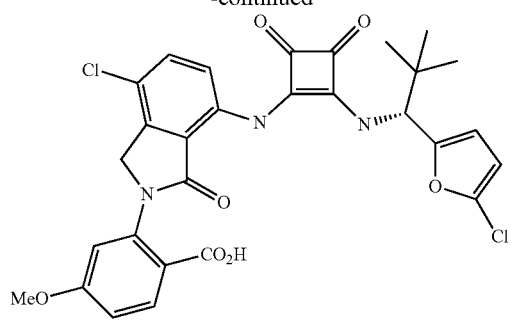
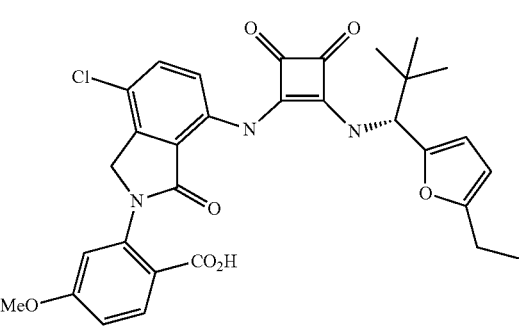
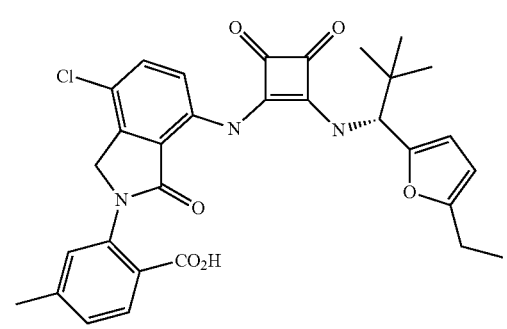
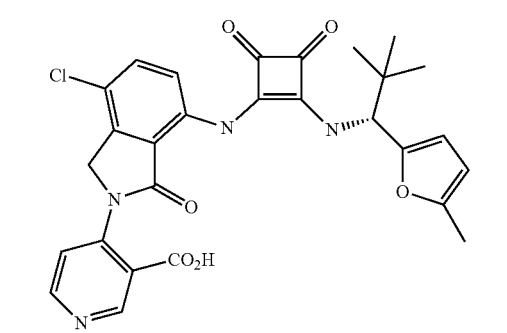
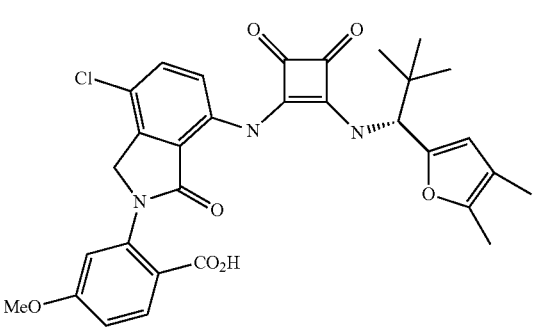
218
-continued
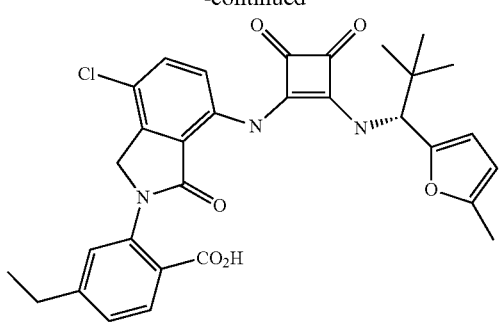
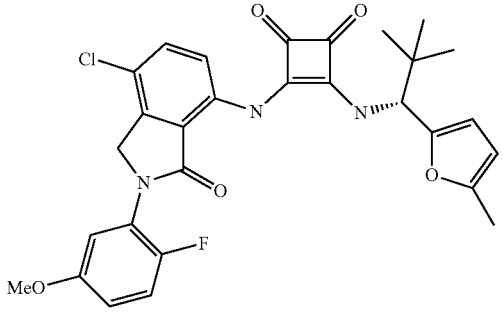
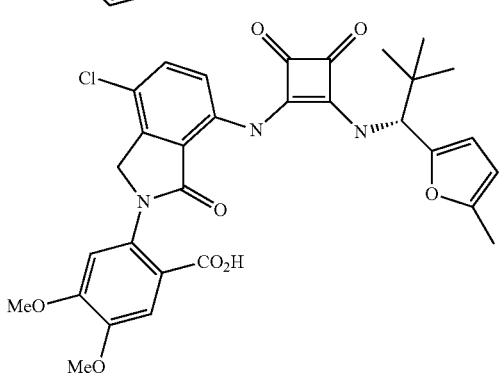
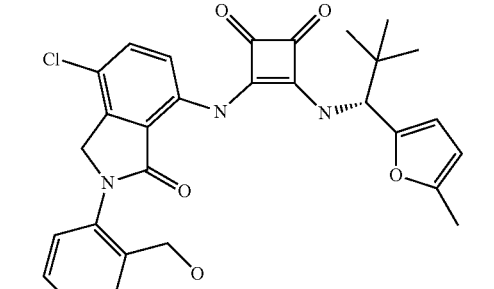
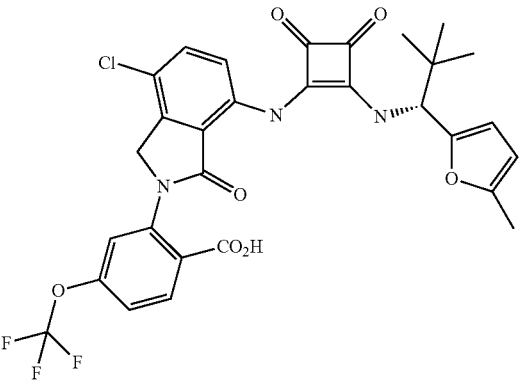 [SMILES: Cc1ccc([C@H](Nc2c(Nc3ccc(Cl)c4c3C(=O)N(c3cc(CC(F)(F)F)ccc3C(=O)O)C4)c(=O)c2=O)C(C)(C)C)o1]

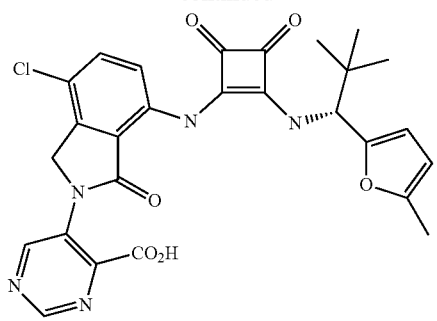
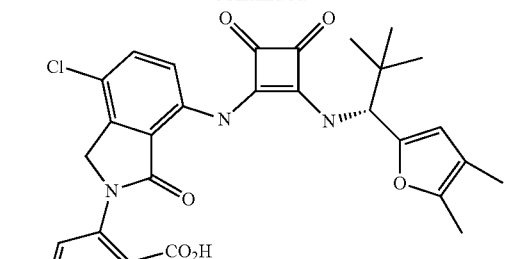
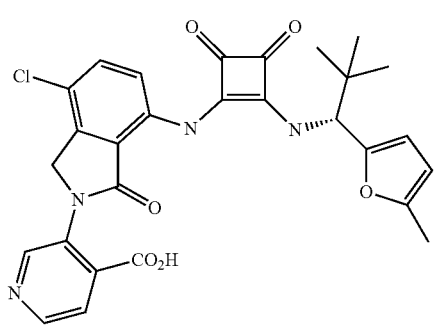
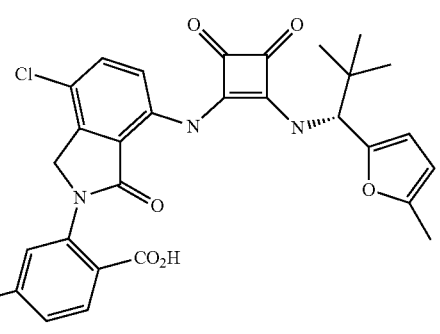 [SMILES: COc1ccc(Nc2c(N[C@@H](c3ccc(C)o3)C(C)(C)C)c(=O)c2=O)c2c1CN(c1ccccc1C(=O)O)C2=O]
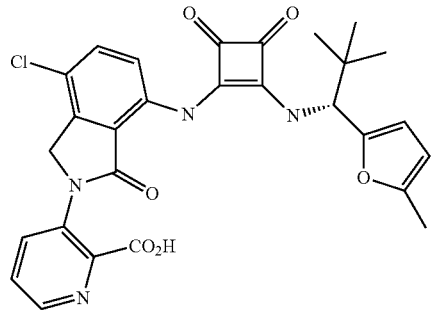
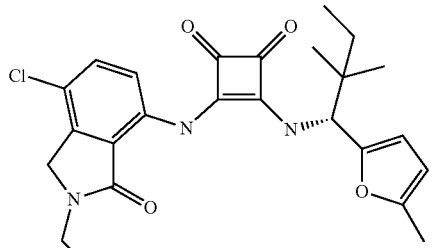
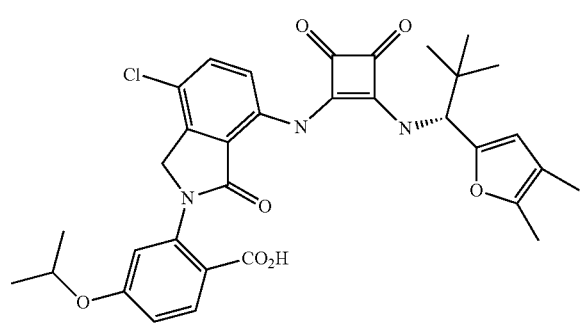
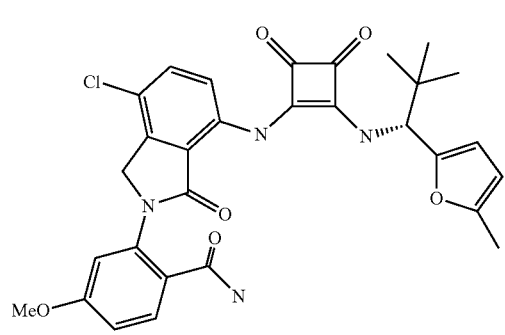
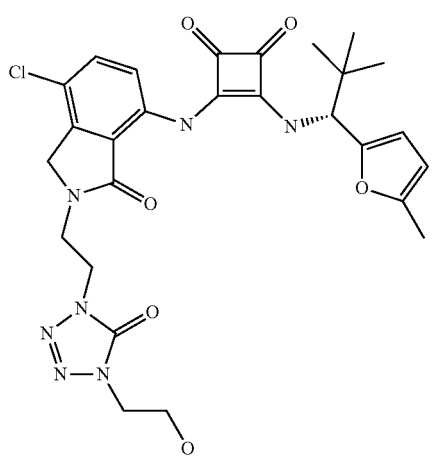

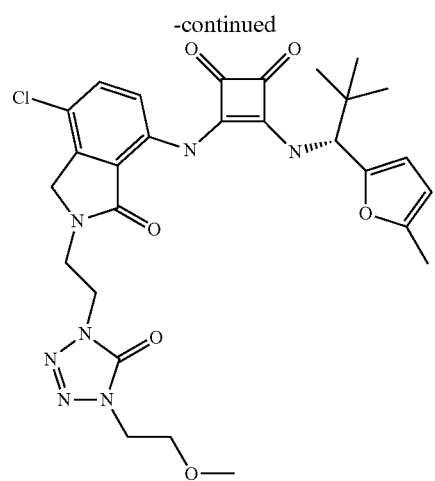
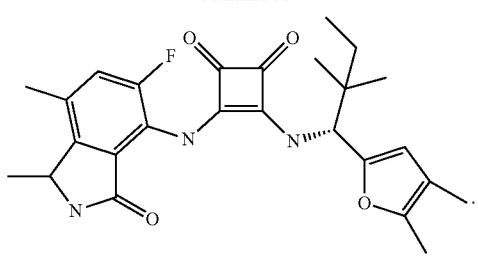
23. The compound of claim 1, or a pharmaceutically acceptable salt thereof, selected from the group consisting of:
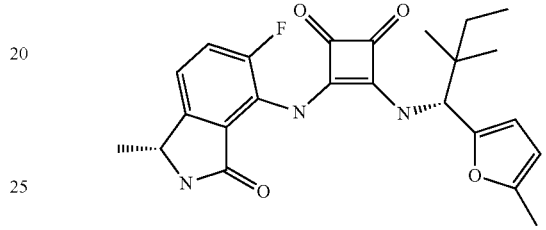
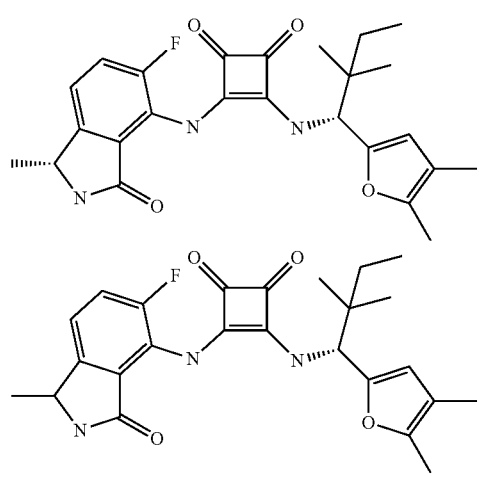
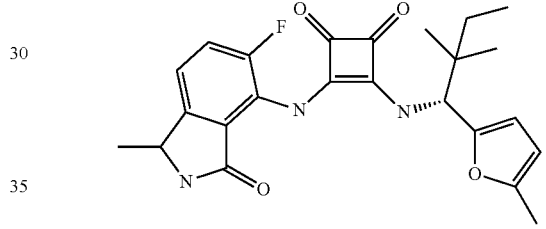
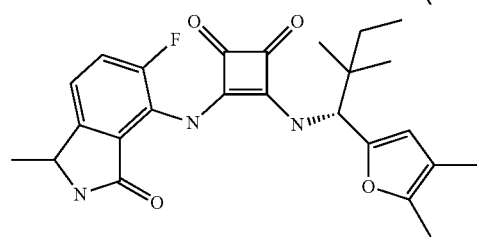
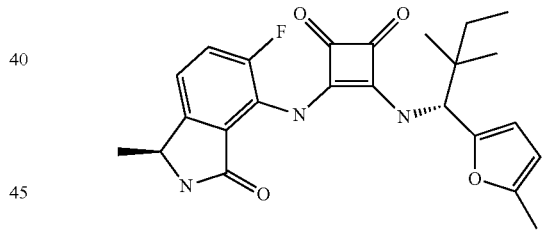
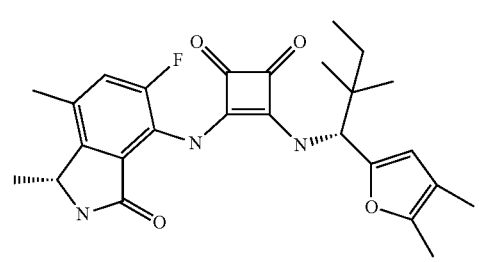
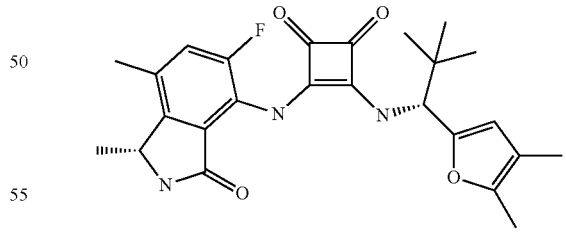
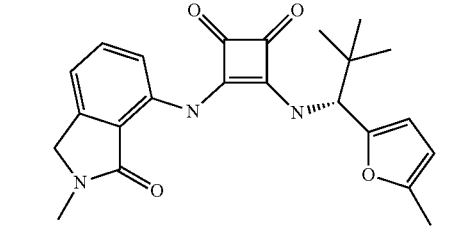
and
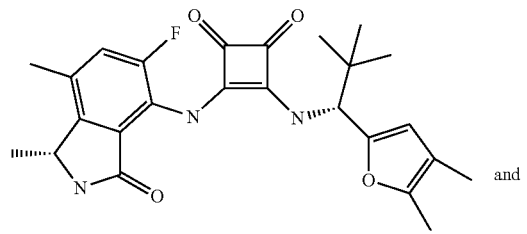

-continued

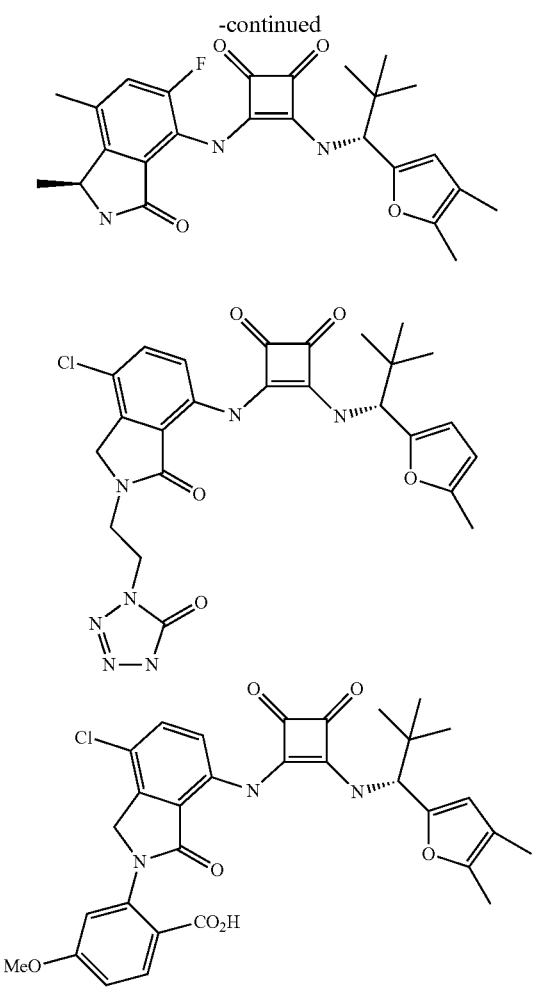

-continued

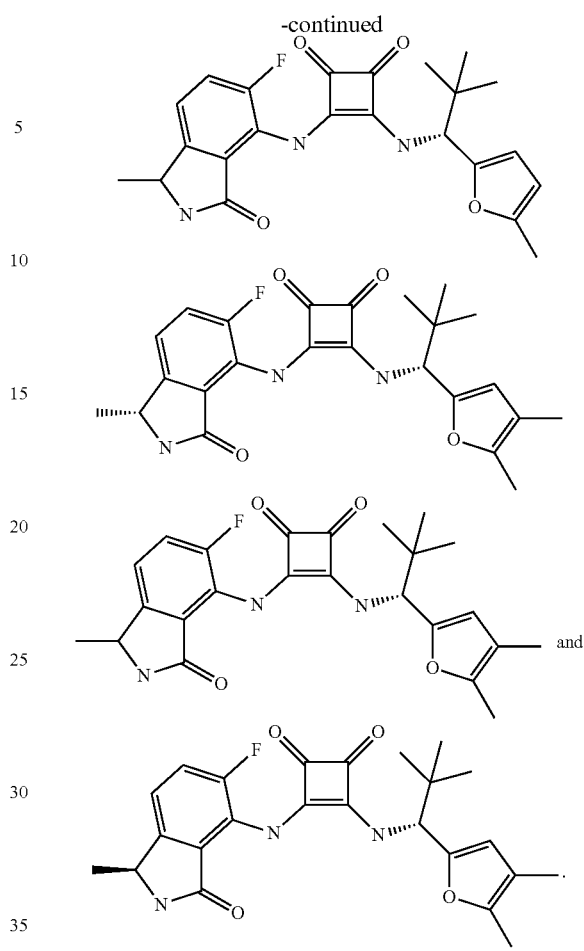

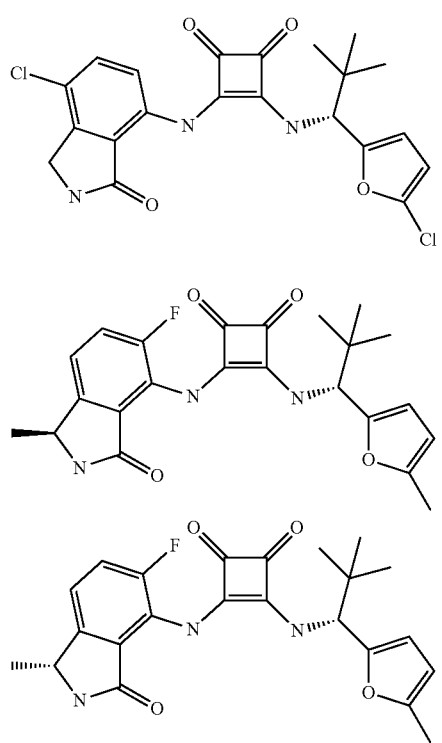

24. A pharmaceutical composition comprising a compound of claim 1.

25. A method of treating a CXCR2- and/or CCR6-mediated disease or condition in a subject in need thereof, said method comprising administering an effective amount of a compound of claim 1 to said subject.

26. A method of claim 25, wherein the disease or condition is an acute or chronic inflammatory disorder.

27. A method of claim 26, wherein the acute or chronic inflammatory disorder is psoriasis, dry eye disease, atherosclerosis, discoid lupus erythematosus, rheumatoid arthritis, lupus, radiation induced fibrotic lung disease, autoimmune bullous dermatosis (AIBD), chronic obstructive pulmonary disease, or ozone-induced airway inflammation.

28. A method of claim 25, wherein the disease is a cancer selected from the group consisting of cutaneous T-cell lymphoma, non-Hodgkin lymphoma, Mycosis fungoides, Pagetoid reticulosis, Sézary syndrome, Granulomatous slack skin, Lymphomatoid papulosis, Pityriasis lichenoides chronica, Pityriasis lichenoides et varioliformis acuta, CD30+ cutaneous T-cell lymphoma, Secondary cutaneous CD30+ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins Lymphoma (HL), Head and neck tumor; Squamous cell carcinoma, rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma.

29. A method of claim 28, wherein the compound is used alone or in combination with one or more other anti-cancer therapies.

30. A method of claim 29, wherein the compound is used in combination with one or more other anti-cancer therapies, wherein said one or more other anticancer therapies are selected from the group consisting of a cytotoxic chemotherapy, an anti-cancer vaccine, an anti-tumor vaccine, an anti-immunocytokine therapy, an immunocytokine therapy, a checkpoint inhibitor, and a chimeric antigen receptor (CAR) T cell immunotherapeutic agent, and gene transfer therapy.

31. A method of claim 29, wherein the one or more other anti-cancer therapy is selected from the group consisting of: drugs that block the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

32. A method of claim 27 wherein the compound is used alone or in combination with one or more other therapeutic agents.

33. A method of claim 32, wherein the compound is used in combination with one or more of a corticosteroid, a retinoid-like agent, an antineoplastics, and interferons analogs, TNF alpha ligand inhibitor, a TNF binding agent, an IL-1 ligand inhibitor; an IL-6 ligand inhibitor, an IL-8 ligand inhibitor; an IL-17 antagonist, a TNF antagonist, a Retinoic acid receptor gamma antagonist, an IL-17A ligand inhibitor; an IL-17F ligand inhibitor, a sphingosine-1-phosphate receptor-1 antagonist, a sphingosine-1-phosphate receptor-1 modulator, an IL-12 antagonist; an IL-23 antagonist, a type II TNF receptor modulator, an IL-23A inhibitor, a PDE 4 inhibitor, a JAK tyrosine kinase inhibitor, a Jak1 tyrosine kinase inhibitor; a Jak3 tyrosine kinase inhibitor, a Retinoic acid receptor agonist, a Sphingosine-1-phosphate receptor-1 modulator, a TLR-7 antagonist, a TLR-8 antagonist a TLR-9 antagonist, or an IL-8 antagonist.

* * * * *